(12) United States Patent
Appleby et al.

(10) Patent No.: US 8,513,184 B2
(45) Date of Patent: Aug. 20, 2013

(54) MACROCYCLIC INHIBITORS OF FLAVIVIRIDAE VIRUSES

(75) Inventors: Todd Appleby, San Francisco, CA (US); Hans G. Fliri, Essex (GB); Andrew J. Keats, Essex (GB); Linos Lazarides, London (GB); Richard L. Mackman, Millbrae, CA (US); Simon N. Pettit, Essex (GB); Karine G. Poullennec, Essex (GB); Jonathan Sanvoisin, Essex (GB); Victoria A. Steadman, Essex (GB); Gregory M. Watt, Bristol (GB)

(73) Assignees: Gilead Sciences, Inc., Foster City, CA (US); Selcia Limited, Essex (GB)

( * ) Notice: Subject to any disclaimer, the term of this patent is extended or adjusted under 35 U.S.C. 154(b) by 0 days.

(21) Appl. No.: 13/315,069

(22) Filed: Dec. 8, 2011

(65) Prior Publication Data

US 2013/0022573 A1    Jan. 24, 2013

Related U.S. Application Data

(60) Provisional application No. 61/422,071, filed on Dec. 10, 2010.

(51) Int. Cl.
| | |
|---|---|
| *A61K 38/00* | (2006.01) |
| *A61K 38/12* | (2006.01) |
| *A01N 37/18* | (2006.01) |
| *A61P 31/10* | (2006.01) |
| *C07K 5/00* | (2006.01) |
| *C07K 7/00* | (2006.01) |
| *C07K 16/00* | (2006.01) |
| *C07K 17/00* | (2006.01) |

(52) U.S. Cl.
USPC ............... 514/1.1; 514/2.9; 514/3.6; 530/317

(58) Field of Classification Search
None
See application file for complete search history.

(56) References Cited

FOREIGN PATENT DOCUMENTS

| | | | |
|---|---|---|---|
| WO | WO-2006138507 A1 | 12/2006 | |
| WO | WO 2006138507 A1 * | 12/2006 | |

OTHER PUBLICATIONS

International Search Report for International Application No. PCT/US2011/064009, mailed Feb. 8, 2012.
Sedrani, R. et al. (2003) "Sanglifehrin-Cyclophilin Interaction: Degradation Work, Synthetic Macrocyclic Analogues, X-ray Crystal Structure, and Binding Data", Journal of American Chemistry Society, vol. 125, pp. 3849-3859.

* cited by examiner

*Primary Examiner* — Marcela M Cordero Garcia
*Assistant Examiner* — Kaipeen Yang
(74) *Attorney, Agent, or Firm* — Foley & Lardner LLP

(57) ABSTRACT

Provided are compounds of Formula I:

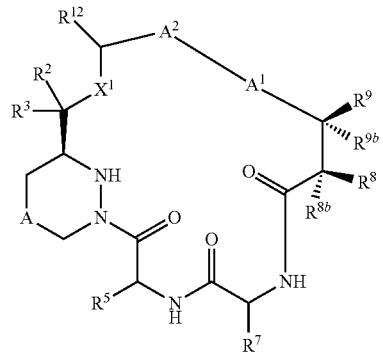

Formula I and pharmaceutically acceptable salts and esters thereof. The compounds, compositions, and methods provided are useful for the treatment of Flaviviridae virus infections, particularly hepatitis C infections.

27 Claims, No Drawings

MACROCYCLIC INHIBITORS OF FLAVIVIRIDAE VIRUSES

The present application claims the benefit of U.S. Provisional Application No. 61/422,071, filed Dec. 10, 2010.

FIELD OF THE INVENTION

The present application provides novel inhibitors Flaviviridae viruses, compositions containing such compounds, and therapeutic methods that include the administration of such compounds.

BACKGROUND OF THE INVENTION

RNA viruses comprising the Flaviviridae family include at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., J. Med. Chem. 2005, 48, 1-20; Maradpour, D., et al., Nat. Rev. Micro. 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene, 1985, 40, 1-8; Martell, et al., J. Virol. 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit. Therefore, there is a need to develop more effective anti-HCV therapies.

The macrocycle sanglifehrin and derivatives are immunomodulatory and bind peptidyl-prolyl cis/trans isomerase (PPIase) cyclophilins in a unique manner (WO 97/02285; WO 98/07743; J. Am. Chem. Soc 2003, 125, 3849-3859; J. Org. Chem. 2000, 65, 9255-9260; Angew. Chem. Int. Ed. 1999, 38, 2443-2446). The cyclophilins are peptidyl-prolyl cis/trans isomerases (PPIase) that regulate protein folding in vivo and inhibit hepatitis C virus (Lin et al., WO2006/138507). However, none of the sanglifehrins or their derivatives has become available for human anti-viral therapy. Therefore, there is a continuing need to develop macrocyclic sanglifehrins with anti-Flaviviridae virus activity and particularly anti-HCV activity.

SUMMARY OF INVENTION

In one embodiment, provided is a compound useful for the treatment of Flaviviridae infections represented by Formula I:

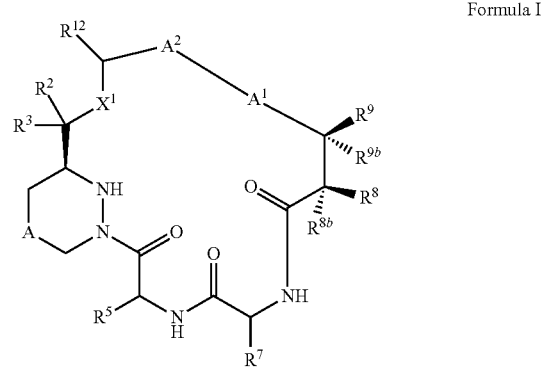

Formula I or a pharmaceutically acceptable salt or ester thereof, wherein:

$X^1$ is O, S, or $NR^1$;

each $R^1$ is independently H, optionally substituted $(C_1\text{-}C_4)$ alkyl, optionally substituted $(C_2\text{-}C_4)$alkenyl or optionally substituted $(C_2\text{-}C_4)$alkynyl;

each $R^2$ or $R^3$ is independently H, optionally substituted $(C_1\text{-}C_4)$alkyl, optionally substituted $(C_2\text{-}C_4)$ alkenyl, optionally substituted $(C_2\text{-}C_4)$ alkynyl, halogen, cyano, $C(O)R^1$, $C(O)OR^1$ or $CON(R^1)_2$; or $R^2$ and $R^3$ when taken together with the carbon to which they are both attached form —C(=O)—, —C(=S)— or —C(=$NR^1$)—;

A is O, $S(O)_n$, $NR^4$ or optionally substituted $(C_1\text{-}C_2)$alkylene;

each n is independently 0, 1 or 2;

each $R^4$ is independently H, optionally substituted $(C_1\text{-}C_4)$ alkyl, optionally substituted $(C_2\text{-}C_4)$alkenyl, optionally substituted $(C_2\text{-}C_4)$alkynyl, cyano, $C(O)R^7$, $C(O)OR^7$, CON $(R^7)_2$, $S(O)R^{16}$, $S(O)_2R^{16}$, $S(O)_2OR^7$ or $S(O)_2N(R^7)_2$;

$R^5$ is optionally substituted aryl$(C_0\text{-}C_4)$alkyl, optionally substituted heterocyclyl$(C_0\text{-}C_4)$alkyl, optionally substituted cycloalkyl$(C_0\text{-}C_4)$alkyl or optionally substituted $(C_1\text{-}C_8)$ alkyl wherein each optionally substituted aryl$(C_0\text{-}C_4)$alkyl, optionally substituted cycloalkyl$(C_0\text{-}C_4)$alkyl or optionally substituted $(C_1\text{-}C_8)$alkyl is substituted with one or more $R^6$;

each $R^6$ is independently halo, $CF_3$, $OR^4$, $CH_2OR^4$, $SR^4$, $S(O)R^{16}$, $S(O)_2R^{16}$, $N(R^1)_2$, $NHCOR^1$, $NHC(O)OR^1$, NHC $(O)N(R^1)_2$, $NHC(NR^1)R^1$, $NHC(NR^1)N(R^1)_2$, $C(O)R^1$, $C(O)$ $N(R^1)_2$, $CO_2R^1$, $S(O)_2OR^1$, $S(O)_2N(R^1)_2$, $NHS(O)_2OR^1$, $NHS(O)_2R^{16}$, $NHS(O)_2N(R^1)_2$, $P(O)(OR^1)_2$, $P(O)(OR^1)(N(R^1)_2)$, $P(O)(R^7)(OR^1)$, $OP(O)(OR^1)_2$, $OP(O)(OR^1)(N(R^1)_2)$, $NHP(O)(OR^1)_2$ or $NHP(O)(OR^1)(N(R^1)_2)$;

each $R^7$ is H, optionally substituted $(C_1\text{-}C_8)$alkyl, optionally substituted $(C_2\text{-}C_8)$alkenyl, optionally substituted $(C_2\text{-}C_8)$alkynyl, optionally substituted aryl, optionally substituted heterocyclyl, optionally substituted cycloalkyl, optionally substituted aryl$(C_1\text{-}C_4)$alkyl, optionally substituted cycloalkyl$(C_1\text{-}C_4)$alkyl or optionally substituted heterocyclyl $(C_1\text{-}C_4)$alkyl;

each $R^{16}$ is optionally substituted $(C_1$-$C_8)$alkyl, optionally substituted $(C_2$-$C_8)$alkenyl, optionally substituted $(C_2$-$C_8)$alkynyl, optionally substituted aryl, optionally substituted heterocyclyl, optionally substituted cycloalkyl, optionally substituted aryl$(C_1$-$C_4)$alkyl, optionally substituted cycloalkyl$(C_1$-$C_4)$alkyl or optionally substituted heterocyclyl $(C_1$-$C_4)$alkyl;

each $R^8$, $R^{8b}$, $R^9$, or $R^{9b}$ are each independently H, optionally substituted $(C_1$-$C_8)$alkyl, optionally substituted $(C_2$-$C_8)$alkenyl, optionally substituted $(C_2$-$C_8)$alkynyl, optionally substituted aryl, optionally substituted heterocyclyl, optionally substituted cycloalkyl, optionally substituted aryl$(C_1$-$C_4)$alkyl, optionally substituted cycloalkyl$(C_1$-$C_4)$alkyl, optionally substituted heterocyclyl$(C_1$-$C_4)$alkyl, $OR^4$, $SR^4$, $S(O)R^{16}$, $S(O)_2R^{16}$ or $N(R^4)_2$;

provided that each $R^8$, $R^{8b}$, $R^9$ and $R^{9b}$ is not H; and provided that when $R^9$ is OH and each $R^{8b}$ and $R^{9b}$ are H, then $R^8$ is not

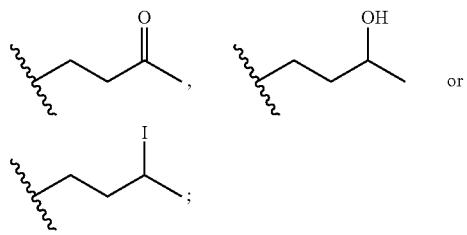

$A^1$ is optionally substituted $(C_2$-$C_5)$alkylene, optionally substituted $(C_2$-$C_5)$alkenylene or optionally substituted $(C_2$-$C_5)$alkynylene, optionally substituted aryl$(C_0$-$C_2)$alkylene, optionally substituted cycloalkyl$(C_0$-$C_2)$alkylene or optionally substituted heterocyclyl$(C_0$-$C_2)$alkylene; wherein a sp$^3$ carbon atom of said optionally substituted $(C_2$-$C_5)$alkylene, optionally substituted $(C_2$-$C_5)$alkenylene, optionally substituted $(C_2$-$C_5)$alkynylene, optionally substituted aryl$(C_0$-$C_2)$alkylene, optionally substituted cycloalkyl$(C_0$-$C_2)$alkylene or optionally substituted heterocyclyl$(C_0$-$C_2)$alkylene is optionally replaced by O, S(O), or $NR^4$;

$A^2$ is optionally substituted arylene, optionally substituted heteroarylene, optionally substituted heterocyclene, optionally substituted cycloalkylene, optionally substituted $(C_1$-$C_3)$alkylene, optionally substituted $(C_2$-$C_3)$alkenylene or optionally substituted $(C_2$-$C_3)$alkynylene;

$R^{12}$ is H, optionally substituted $(C_1$-$C_4)$alkyl, optionally substituted $(C_2$-$C_4)$alkenyl or optionally substituted $(C_2$-$C_4)$alkynyl;

each $R^a$ is independently H, $(C_1$-$C_8)$alkyl, $(C_2$-$C_8)$alkenyl, $(C_2$-$C_8)$alkynyl, aryl, heterocyclyl, aryl$(C_1$-$C_8)$alkyl, cycloalkyl or cycloalkyl$(C_1$-$C_8)$alkyl and wherein when $R^1$, $R^2$, $R^3$, $R^4$, $R^5$, $R^6$, $R^7$, $R^8$, $R^9$, $R^{8b}$, $R^{9b}$, $R^{10}$, $R^{11}$, $R^{12}$, $R^{13}$, $R^{14}$, $R^{15}$, $R^{16}$, A, $A^1$ or $A^2$ is substituted, the substitutent is, independently, one or more substituents selected from the group consisting of halo, CN, $CF_3$, $N_3$, $N(R^a)_2$, $SR^a$, $OR^a$, $R^a$, $NHCOR^a$, $NHC(O)OR^a$, $NHC(O)N(R^a)_2$, $NHC(NR^a)R^a$, $NHC(NR^a)N(R^a)_2$, $C(O)R^a$, $C(O)N(R^a)_2$, $CO_2R^a$, $S(O)_2OR^a$, $S(O)_2N(R^a)_2$, $NHS(O)_2OR^a$, $NHS(O)_2N(R^a)_2$, $OP(O)(OR^a)_2$, $OP(O)(OR^a)(N(R^a)_2)$, $NHP(O)(OR^a)_2$ and $NHP(O)(OR^a)(N(R^a)_2)$.

In another aspect, a method for treating Flaviviridae viral infection is provided comprising administering a therapeutically effective amount of a compound of Formula I to a mammal in need thereof. The compound of Formula I is administered to a human subject in need thereof, such as a human being who is infected with viruses of the Flaviviridae family. In another embodiment, the compound of Formula I is administered to a human subject in need thereof, such as a human being who is infected with a HCV virus. In one embodiment, the treatment results in the reduction of the in viral load or clearance of viral RNA in a patient.

In another embodiment, provided is a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral disarrhea virus, Zika virus and Hepatitis C virus; by administering to a subject in need thereof a therapeutically effective amount of a compound of Formula I, or a pharmaceutically acceptable salt or ester thereof.

In another aspect, provided is the use of a compound of Formula I for the manufacture of a medicament for the treatment of a Flaviviridae viral infection. In another aspect, provided is a compound of Formula I for use in treating a Flaviviridae viral infection. In one embodiment, the Flaviviridae viral infection is an acute or chronic HCV infection. In one embodiment of each aspect of use and compound, the treatment results in the reduction of one or more of the viral loads or clearance of viral RNA in the patient.

In another aspect, provided is a method for treating or preventing HCV comprising administering an effective amount of a compound of Formula I to a patient in need thereof. In another aspect, provided is the use of a compound of the present invention for the manufacture of a medicament for the treatment or prevention of HCV.

In another aspect, provided is a use of a compound of Formula I for the treatment of a Flaviviridae viral infection or a Hepatitis C virus infection.

In another aspect, provided is a pharmaceutical composition comprising a compound of Formula I or a pharmaceutically acceptable salt or ester thereof and one or more pharmaceutically acceptable carriers or excipients. The pharmaceutical composition of Formula I may further comprise one or more additional therapeutic agents. The one or more additional therapeutic agent may be, without limitation, selected from: interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof. In another aspect, the one or more additional therapeutic agent may be, without limitation, from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, and CCR5 inhibitors.

In another aspect, provided is a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another embodiment, provided are compounds of Formula I and pharmaceutically acceptable salts and esters thereof and all racemates, enantiomers, diastereomers, tautomers, polymorphs, pseudopolymorphs and amorphous forms thereof.

In another aspect, provided are processes and novel intermediates disclosed herein which are useful for preparing Formula I compounds.

In other aspects, novel methods for synthesis, analysis, separation, isolation, purification, characterization, and testing of the compounds of Formula I are provided.

The present invention includes combinations of aspects and embodiments, as well as preferences, as herein described throughout the present specification.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined herein.

In one embodiment of the compound of Formula I, $A^1$ is optionally substituted $(C_2)$alkylene, optionally substituted $(C_2)$alkenylene or optionally substituted $(C_2)$alkynylene. In another aspect of this embodiment, $A^1$ is optionally substituted $(C_2)$alkylene. In another aspect of this embodiment, $A^1$ is optionally substituted $(C_2)$alkenylene. In another aspect of this embodiment, $A^1$ is optionally substituted $(C_2)$alkynylene. In another aspect of this embodiment, $A^1$ is

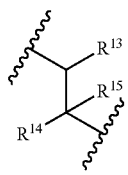

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$.

In one embodiment of the compound of Formula I, $A^1$ is optionally substituted $(C_4)$alkylene, optionally substituted $(C_4)$alkenylene or optionally substituted $(C_4)$alkynylene. In another aspect of this embodiment, $A^1$ is optionally substituted $(C_4)$alkylene. In another aspect of this embodiment, $A^1$ is optionally substituted $(C_4)$alkenylene. In another aspect of this embodiment, $A^1$ is optionally substituted $(C_4)$alkynylene. In another aspect of this embodiment, $A^1$ is

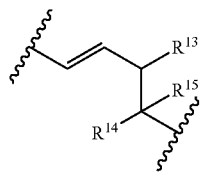

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$.

In one embodiment of the compound of Formula I, $A^2$ is optionally substituted arylene. In another aspect of this embodiment, $A^1$ is optionally substituted $(C_4)$alkylene, optionally substituted $(C_4)$alkenylene or optionally substituted $(C_4)$alkynylene. In another aspect of this embodiment, $A^1$ is optionally substituted $(C_4)$alkylene. In another aspect of this embodiment, $A^1$ is optionally substituted $(C_4)$alkenylene. In another aspect of this embodiment, $A^1$ is optionally substituted $(C_4)$alkynylene. In another aspect of this embodiment, $R^2$ and $R^3$ taken together with the carbon atom to which they are both attached form —C(O)—. In another aspect of this embodiment, $A^1$ is

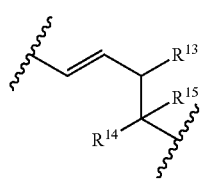

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$. In another aspect of this embodiment, $A^1$ is optionally substituted $(C_2)$alkylene, optionally substituted $(C_2)$alkenylene or optionally substituted $(C_2)$alkynylene. In another aspect of this embodiment, $A^1$ is optionally substituted $(C_2)$alkylene. In another aspect of this embodiment, $A^1$ is optionally substituted $(C_2)$alkenylene. In another aspect of this embodiment, $A^1$ is optionally substituted $(C_2)$alkynylene. In another aspect of this embodiment, $A^1$ is

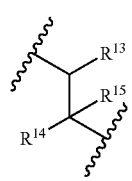

wherein each $R^{13}$, $R^{14}$ or $R^{15}$ is independently H, optionally substituted $(C_1-C_8)$alkyl, optionally substituted $(C_2-C_8)$alkenyl, optionally substituted (C$_2$-C$_8$)alkynyl, optionally substituted aryl, optionally substituted heterocyclyl, optionally substituted cycloalkyl, optionally substituted aryl(C$_1$-C$_4$)alkyl, optionally substituted cycloalkyl(C$_1$-C$_4$)alkyl, optionally substituted heterocyclyl(C$_1$-C$_4$)alkyl, OR$^4$, SR$^4$, S(O)R$^{16}$, S(O)$_2$R$^{16}$ or N(R$^4$)$_2$.

In one embodiment of the compound of Formula I, A$^2$ is optionally substituted heteroarylene. In another aspect of this embodiment, A$^1$ is optionally substituted (C$_4$)alkylene, optionally substituted (C$_4$)alkenylene or optionally substituted (C$_4$)alkynylene. In another aspect of this embodiment, A$^1$ is optionally substituted (C$_4$)alkylene. In another aspect of this embodiment, A$^1$ is optionally substituted (C$_4$)alkenylene. In another aspect of this embodiment, A$^1$ is optionally substituted (C$_4$)alkynylene. In another aspect of this embodiment, R$^2$ and R$^3$ taken together with the carbon atom to which they are both attached form —C(O)—. In another aspect of this embodiment, A$^1$ is

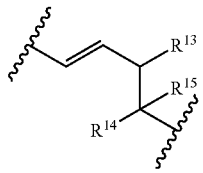

wherein each R$^{13}$, R$^{14}$ or R$^{15}$ is independently H, optionally substituted (C$_1$-C$_8$)alkyl, optionally substituted (C$_2$-C$_8$)alkenyl, optionally substituted (C$_2$-C$_8$)alkynyl, optionally substituted aryl, optionally substituted heterocyclyl, optionally substituted cycloalkyl, optionally substituted aryl(C$_1$-C$_4$)alkyl, optionally substituted cycloalkyl(C$_1$-C$_4$)alkyl, optionally substituted heterocyclyl(C$_1$-C$_4$)alkyl, OR$^4$, SR$^4$, S(O)R$^{16}$, S(O)$_2$R$^{16}$ or N(R$^4$)$_2$. In another aspect of this embodiment, A$^1$ is optionally substituted (C$_2$)alkylene, optionally substituted (C$_2$)alkenylene or optionally substituted (C$_2$)alkynylene. In another aspect of this embodiment, A$^1$ is optionally substituted (C$_2$)alkylene. In another aspect of this embodiment, A$^1$ is optionally substituted (C$_2$)alkenylene. In another aspect of this embodiment, A$^1$ is optionally substituted (C$_2$)alkynylene. In another aspect of this embodiment, A$^1$ is

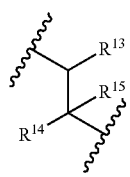

wherein each R$^{13}$, R$^{14}$ or R$^{15}$ is independently H, optionally substituted (C$_1$-C$_8$)alkyl, optionally substituted (C$_2$-C$_8$)alkenyl, optionally substituted (C$_2$-C$_8$)alkynyl, optionally substituted aryl, optionally substituted heterocyclyl, optionally substituted cycloalkyl, optionally substituted aryl(C$_1$-C$_4$)alkyl, optionally substituted cycloalkyl(C$_1$-C$_4$)alkyl, optionally substituted heterocyclyl(C$_1$-C$_4$)alkyl, OR$^4$, SR$^4$, S(O)R$^{16}$, S(O)$_2$R$^{16}$ or N(R$^4$)$_2$.

In another embodiment of the compound of Formula I, A$^2$ is

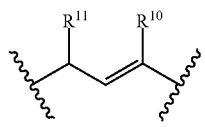

wherein each R$^{10}$ or R$^{11}$, independently, is H, optionally substituted (C$_1$-C$_4$)alkyl, optionally substituted (C$_2$-C$_4$)alkenyl, optionally substituted (C$_2$-C$_4$)alkynyl, halogen, cyano, C(O)R$^1$, C(O)OR$^1$ or CON(R$^1$)$_2$; or R$^{11}$ and R$^{10}$ taken together with the atoms to which they are attached form an optionally substituted (C$_5$-C$_7$)cycloalkyl ring wherein a sp$^3$ carbon atom of said optionally substituted (C$_5$-C$_7$)cycloalkyl ring is optionally replaced by O, S(O), or NR$^4$. In another aspect of this embodiment, A$^1$ is optionally substituted (C$_4$)alkylene, optionally substituted (C$_4$)alkenylene or optionally substituted (C$_4$)alkynylene. In another aspect of this embodiment, A$^1$ is optionally substituted (C$_4$)alkylene. In another aspect of this embodiment, A$^1$ is optionally substituted (C$_4$)alkenylene. In another aspect of this embodiment, A$^1$ is optionally substituted (C$_4$)alkynylene. In another aspect of this embodiment, R$^2$ and R$^3$ taken together with the carbon atom to which they are both attached form —C(O)—. In another aspect of this embodiment, A$^1$ is

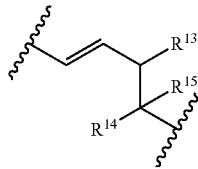

wherein each R$^{13}$, R$^{14}$ or R$^{15}$ is independently H, optionally substituted (C$_1$-C$_8$)alkyl, optionally substituted (C$_2$-C$_8$)alkenyl, optionally substituted (C$_2$-C$_8$)alkynyl, optionally substituted aryl, optionally substituted heterocyclyl, optionally substituted cycloalkyl, optionally substituted aryl(C$_1$-C$_4$)alkyl, optionally substituted cycloalkyl(C$_1$-C$_4$)alkyl, optionally substituted heterocyclyl(C$_1$-C$_4$)alkyl, OR$^4$, SR$^4$, S(O)R$^{16}$, S(O)$_2$R$^{16}$ or N(R$^4$)$_2$.

In one embodiment of the compound of Formula I, R$^2$ and R$^3$ taken together with the carbon atom to which they are both attached form —C(O)—.

In another embodiment of the compound of Formula I, R$^5$ is optionally substituted aryl(C$_1$-C$_4$)alkyl. In another aspect of this embodiment, R$^5$ is optionally substituted benzyl. In another aspect of this embodiment, R$^5$ is optionally substituted

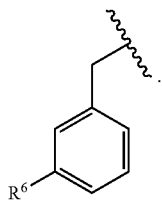

In one embodiment, the compound of Formula I is represented by Formula II:

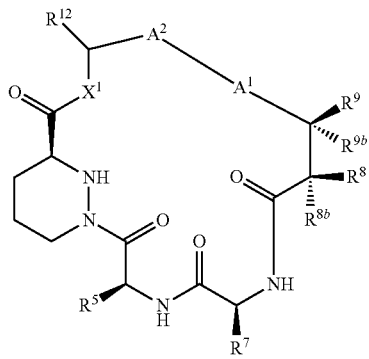

Formula II or a pharmaceutically acceptable salt of ester thereof; wherein all variables are defined as for Formula I.

In one embodiment of the compound of Formula II, $A^1$ is optionally substituted $(C_2)$alkylene, optionally substituted $(C_2)$alkenylene or optionally substituted $(C_2)$alkynylene. In another aspect of this embodiment, $A^1$ is optionally substituted $(C_2)$alkylene. In another aspect of this embodiment, $A^1$ is optionally substituted $(C_2)$alkenylene. In another aspect of this embodiment, $A^1$ is optionally substituted $(C_2)$alkynylene. In another aspect of this embodiment, $A^1$ is

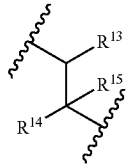

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$.

In one embodiment of the compound of Formula II, $A^1$ is optionally substituted $(C_4)$alkylene, optionally substituted $(C_4)$alkenylene or optionally substituted $(C_4)$alkynylene. In another aspect of this embodiment, $A^1$ is optionally substituted $(C_4)$alkylene. In another aspect of this embodiment, $A^1$ is optionally substituted $(C_4)$alkenylene. In another aspect of this embodiment, $A^1$ is optionally substituted $(C_4)$alkynylene. In another aspect of this embodiment, $A^1$ is

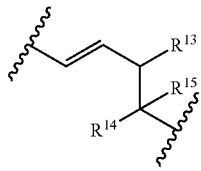

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$. In another aspect of this embodiment, $A^1$ is

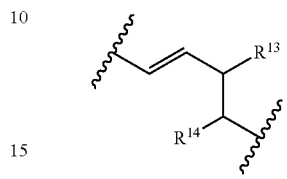

wherein each $R^{13}$ or $R^{14}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H.

In one embodiment of the compound of Formula II, $A^2$ is optionally substituted arylene. In another aspect of this embodiment, $A^1$ is optionally substituted $(C_4)$alkylene, optionally substituted $(C_4)$alkenylene or optionally substituted $(C_4)$alkynylene. In another aspect of this embodiment, $A^1$ is optionally substituted $(C_4)$alkylene. In another aspect of this embodiment, $A^1$ is optionally substituted $(C_4)$alkenylene. In another aspect of this embodiment, $A^1$ is optionally substituted $(C_4)$alkynylene. In another aspect of this embodiment, $A^1$ is

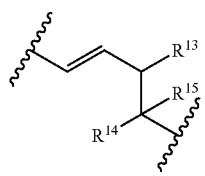

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$. In another aspect of this embodiment, $A^1$ is

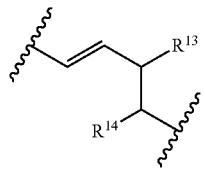

wherein each $R^{13}$ or $R^{14}$ is independently H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$)alkyl, optionally substituted heterocyclyl($C_1$-$C_4$)alkyl, $OR^4$, $SR^4$, $S(O)R^{16}$, $S(O)_2R^{16}$ or $N(R^4)_2$ and each $R^{8b}$ and $R^{9b}$ is H. In another aspect of this embodiment, $A^1$ is optionally substituted ($C_2$)alkylene, optionally substituted ($C_2$)alkenylene or optionally substituted ($C_2$)alkynylene. In another aspect of this embodiment, $A^1$ is optionally substituted ($C_2$)alkylene. In another aspect of this embodiment, $A^1$ is optionally substituted ($C_2$)alkenylene. In another aspect of this embodiment, $A^1$ is optionally substituted ($C_2$)alkynylene. In another aspect of this embodiment, $A^1$ is

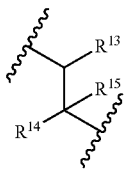

wherein each $R^{13}$, $R^{14}$ or $R^{15}$ is independently H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$)alkyl, optionally substituted heterocyclyl($C_1$-$C_4$)alkyl, $OR^4$, $SR^4$, $S(O)R^{16}$, $S(O)_2R^{16}$ or $N(R^4)_2$. In another aspect of this embodiment, $A^1$ is

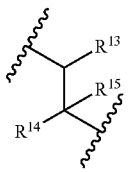

wherein each $R^{13}$, $R^{14}$ or $R^{15}$ is independently H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$)alkyl, optionally substituted heterocyclyl($C_1$-$C_4$)alkyl, $OR^4$, $SR^4$, $S(O)R^{16}$, $S(O)_2R^{16}$ or $N(R^4)_2$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H.

In one embodiment of the compound of Formula II, $A^2$ is optionally substituted heteroarylene. In another aspect of this embodiment, $A^1$ is optionally substituted ($C_4$)alkylene, optionally substituted ($C_4$)alkenylene or optionally substituted ($C_4$)alkynylene. In another aspect of this embodiment, $A^1$ is optionally substituted ($C_4$)alkylene. In another aspect of this embodiment, $A^1$ is optionally substituted ($C_4$)alkenylene. In another aspect of this embodiment, $A^1$ is optionally substituted ($C_4$)alkynylene. In another aspect of this embodiment, $A^1$ is

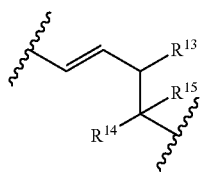

wherein each $R^{13}$, $R^{14}$ or $R^{15}$ is independently H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$)alkyl, optionally substituted heterocyclyl($C_1$-$C_4$)alkyl, $OR^4$, $SR^4$, $S(O)R^{16}$, $S(O)_2R^{16}$ or $N(R^4)_2$. In another aspect of this embodiment, $A^1$ is

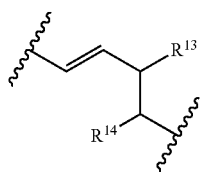

wherein each $R^{13}$ or $R^{14}$ is independently H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$)alkyl, optionally substituted heterocyclyl($C_1$-$C_4$)alkyl, $OR^4$, $SR^4$, $S(O)R^{16}$, $S(O)_2R^{16}$ or $N(R^4)_2$ and each $R^{8b}$ and $R^{9b}$ is H. In another aspect of this embodiment, $A^1$ is optionally substituted ($C_2$)alkylene, optionally substituted ($C_2$)alkenylene or optionally substituted ($C_2$)alkynylene. In another aspect of this embodiment, $A^1$ is optionally substituted ($C_2$)alkylene. In another aspect of this embodiment, $A^1$ is optionally substituted ($C_2$)alkenylene. In another aspect of this embodiment, $A^1$ is optionally substituted ($C_2$)alkynylene. In another aspect of this embodiment, $A^1$ is

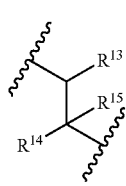

wherein each $R^{13}$, $R^{14}$ or $R^{15}$ is independently H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$)alkyl, optionally substituted heterocyclyl($C_1$-$C_4$)alkyl, $OR^4$, $SR^4$, $S(O)R^{16}$, $S(O)_2R^{16}$ or $N(R^4)_2$. In another aspect of this embodiment, $A^1$ is

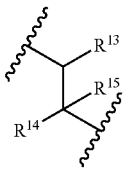

wherein each $R^{13}$, $R^{14}$ or $R^{15}$ is independently H, optionally substituted $(C_1\text{-}C_8)$alkyl, optionally substituted $(C_2\text{-}C_8)$alkenyl, optionally substituted $(C_2\text{-}C_8)$alkynyl, optionally substituted aryl, optionally substituted heterocyclyl, optionally substituted cycloalkyl, optionally substituted aryl$(C_1\text{-}C_4)$alkyl, optionally substituted cycloalkyl$(C_1\text{-}C_4)$alkyl, optionally substituted heterocyclyl$(C_1\text{-}C_4)$alkyl, $OR^4$, $SR^4$, $S(O)R^{16}$, $S(O)_2R^{16}$ or $N(R^4)_2$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H.

In one embodiment of the compound of Formula II, $A^2$ is optionally substituted bicyclic arylene or bicyclic heteroarylene and $A^1$ is optionally substituted $(C_2)$alkylene or optionally substituted $(C_2)$alkenylene. In another aspect of this embodiment, $R^7$ is optionally substituted $(C_1\text{-}C_8)$alkyl, optionally substituted aryl, or optionally substituted aryl$(C_1\text{-}C_4)$alkyl. In another aspect of this embodiment, $R^5$ is optionally substituted aryl$(C_1\text{-}C_4)$alkyl. In another aspect of this embodiment, $R^9$ is $OR^4$. In another aspect of this embodiment, $R^8$ is optionally substituted $(C_1\text{-}C_8)$alkyl. In another aspect of this embodiment, $A^1$ is

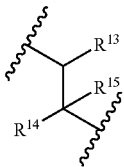

wherein each $R^{13}$, $R^{14}$ or $R^{15}$ is independently H, optionally substituted $(C_1\text{-}C_8)$alkyl or $OR^4$. In another aspect of this embodiment, $A^1$ is

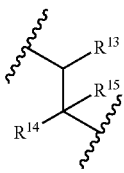

wherein each $R^{13}$ or $R^{14}$ is independently H, optionally substituted $(C_1\text{-}C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1\text{-}C_4)$alkyl. In another aspect of this embodiment, $R^{12}$ is H or methyl.

In one embodiment of the compound of Formula II, $A^2$ is optionally substituted arylene and $A^1$ is optionally substituted $(C_4)$alkylene or optionally substituted $(C_4)$alkenylene. In another aspect of this embodiment, $A^2$ is

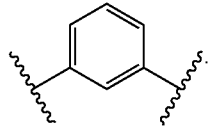 [SMILES: *c1cccc(*)c1]

In another aspect of this embodiment, $R^7$ is optionally substituted $(C_1\text{-}C_8)$alkyl, optionally substituted aryl, or optionally substituted aryl$(C_1\text{-}C_4)$alkyl. In another aspect of this embodiment, $R^5$ is optionally substituted aryl$(C_1\text{-}C_4)$alkyl. In another aspect of this embodiment, $R^9$ is $OR^4$. In another aspect of this embodiment, $R^8$ is optionally substituted $(C_1\text{-}C_8)$alkyl. In another aspect of this embodiment, $A^1$ is

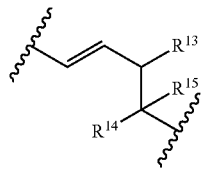

wherein each $R^{13}$, $R^{14}$ or $R^{15}$ is independently H, optionally substituted $(C_1\text{-}C_8)$alkyl or $OR^4$. In another aspect of this embodiment, $A^1$ is

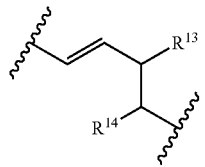

wherein each $R^{13}$ or $R^{14}$ is independently H, optionally substituted $(C_1\text{-}C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1\text{-}C_4)$alkyl. In another aspect of this embodiment, $R^{12}$ is H or methyl.

In one embodiment of the compound of Formula II, $A^2$ is optionally substituted arylene, $A^1$ is optionally substituted $(C_4)$alkylene or optionally substituted $(C_4)$alkenylene and $R^7$ is optionally substituted $(C_1\text{-}C_8)$alkyl. In another aspect of this embodiment, $A^2$ is

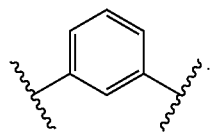 [SMILES: *c1cccc(*)c1]

In another aspect of this embodiment, $R^5$ is optionally substituted aryl$(C_1\text{-}C_4)$alkyl. In another aspect of this embodiment, $R^5$ is optionally substituted benzyl. In another aspect of this embodiment, $R^9$ is $OR^4$. In another aspect of this embodiment, $R^8$ is optionally substituted $(C_1\text{-}C_8)$alkyl. In another aspect of this embodiment, $R^9$ is $OR^4$ and $R^8$ is optionally substituted $(C_1\text{-}C_8)$alkyl. In another aspect of this embodiment, $R^{12}$ is H. In another aspect of this embodiment, $A^1$ is

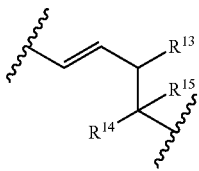

wherein each $R^{13}$, $R^{14}$ or $R^{15}$ is independently H, optionally substituted $(C_1-C_8)$alkyl or $OR^4$. In another aspect of this embodiment, $A^1$ is

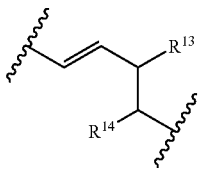

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In one embodiment of the compound of Formula II, $A^2$ is

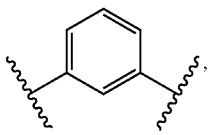

$A^1$ is optionally substituted $(C_4)$alkylene or optionally substituted $(C_4)$alkenylene, $R^7$ is optionally substituted $(C_1-C_8)$ alkyl and $X^1$ is O or $NR^1$. In another aspect of this embodiment, $R^5$ is optionally substituted aryl$(C_1-C_4)$alkyl. In another aspect of this embodiment, $R^5$ is optionally substituted benzyl. In another aspect of this embodiment, $R^5$ is optionally substituted

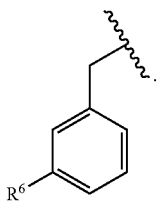

In another aspect of this embodiment, $R^9$ is $OR^4$. In another aspect of this embodiment, $R^8$ is optionally substituted $(C_1$-$C_8)$alkyl. In another aspect of this embodiment, $R^9$ is $OR^4$ and $R^8$ is optionally substituted $(C_1-C_8)$alkyl. In another aspect of this embodiment, $R^{12}$ is H. In another aspect of this embodiment, $A^1$ is

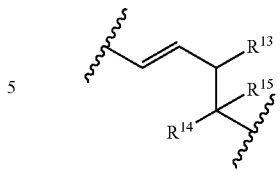

wherein each $R^{13}$, $R^{14}$ or $R^{15}$ is independently H, optionally substituted $(C_1-C_8)$alkyl or $OR^4$. In another aspect of this embodiment, $A^1$ is

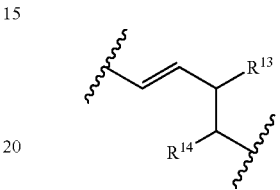

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In one embodiment of the compound of Formula II, $A^2$ is

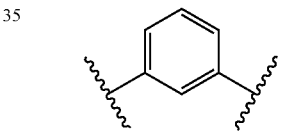

$A^1$ is optionally substituted $(C_4)$alkylene or optionally substituted $(C_4)$alkenylene, $R^7$ is optionally substituted $(C_1-C_8)$ alkyl, $X^1$ is O or $NR^1$ and $R^5$ is optionally substituted

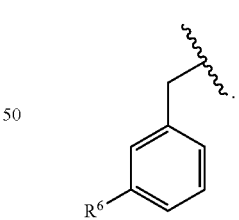

In another aspect of this embodiment, $R^6$ is $OR^4$, $CH_2OR^4$, $N(R^1)_2$, $NHCOR^1$, $NHC(O)OR^1$, $NHC(O)N(R^1)_2$, $NHC(NR^1)R^1$, $NHC(NR^1)N(R^1)_2$, $C(O)N(R^1)_2$, $S(O)_2N(R^1)_2$, $NHS(O)_2OR^1$, $NHS(O)_2R^{16}$ or $NHS(O)_2N(R^1)_2$. In another aspect of this embodiment, $R^6$ is OH. In another aspect of this embodiment, $R^9$ is $OR^4$. In another aspect of this embodiment, $R^8$ is optionally substituted $(C_1-C_8)$alkyl. In another aspect of this embodiment, $R^9$ is $OR^4$ and $R^8$ is optionally substituted $(C_1-C_8)$alkyl. In another aspect of this embodiment, $R^{12}$ is H. In another aspect of this embodiment, $A^1$ is

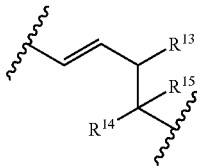

wherein each $R^{13}$, $R^{14}$ or $R^{15}$ is independently H, optionally substituted $(C_1-C_8)$alkyl or $OR^4$. In another aspect of this embodiment, $A^1$ is

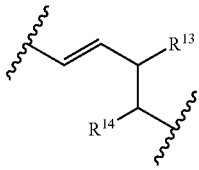

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In another embodiment of the compound of Formula II, $A^2$ is

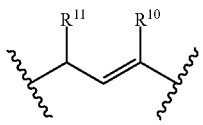

wherein $R^{11}$ and $R^{10}$ are defined as above for Formula I. In another aspect of this embodiment, $A^1$ is optionally substituted $(C_4)$alkylene, optionally substituted $(C_4)$alkenylene or optionally substituted $(C_4)$alkynylene. In another aspect of this embodiment, $A^1$ is optionally substituted $(C_4)$alkylene. In another aspect of this embodiment, $A^1$ is optionally substituted $(C_4)$alkenylene. In another aspect of this embodiment, $A^1$ is optionally substituted $(C_4)$alkynylene. In another aspect of this embodiment, $A^1$ is

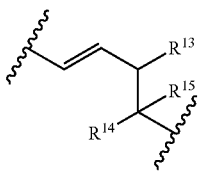

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$. In another aspect of this embodiment, $A^1$ is wherein each $R^{13}$ or $R^{14}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In one embodiment of the compound of Formula II, $A^2$ is

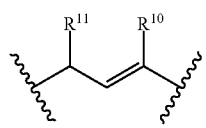

and $A^1$ is optionally substituted $(C_4)$alkylene or optionally substituted $(C_4)$alkenylene. In another aspect of this embodiment, $R^7$ optionally substituted $(C_1-C_8)$alkyl, optionally substituted aryl, or optionally substituted aryl$(C_1-C_4)$alkyl. In another aspect of this embodiment, $R^5$ is optionally substituted aryl$(C_1-C_4)$alkyl. In another aspect of this embodiment, $R^9$ is $OR^4$. In another aspect of this embodiment, $R^8$ is optionally substituted $(C_1-C_8)$alkyl. In another aspect of this embodiment, $A^1$ is

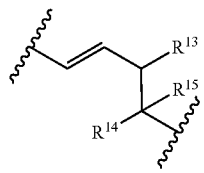

wherein each $R^{13}$, $R^{14}$ or $R^{15}$ is independently H, optionally substituted $(C_1-C_8)$alkyl or $OR^4$. In another aspect of this embodiment, $A^1$ is

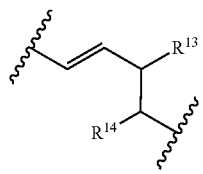

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In one embodiment of the compound of Formula II, $A^2$ is

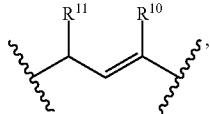

$A^1$ is optionally substituted $(C_4)$alkylene or optionally substituted $(C_4)$alkenylene and $R^7$ is optionally substituted $(C_1-C_8)$alkyl. In another aspect of this embodiment, $R^5$ is optionally substituted aryl$(C_1-C_4)$alkyl. In another aspect of this embodiment, $R^5$ is optionally substituted benzyl. In another aspect of this embodiment, $R^9$ is $OR^4$. In another aspect of this embodiment, $R^8$ is optionally substituted $(C_1-C_8)$alkyl. In another aspect of this embodiment, $R^9$ is $OR^4$ and $R^8$ is optionally substituted $(C_1-C_8)$alkyl. In another aspect of this embodiment, $R^{12}$ is H. In another aspect of this embodiment, $A^1$ is

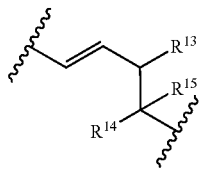

wherein each $R^{13}$, $R^{14}$ or $R^{15}$ is independently H, optionally substituted $(C_1-C_8)$alkyl or $OR^4$. In another aspect of this embodiment, $A^1$ is

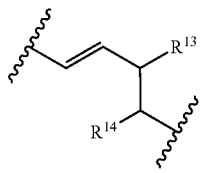

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H.

In one embodiment of the compound of Formula II, $A^2$ is

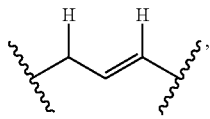 [SMILES: */C=C/C*]

$A^1$ is optionally substituted $(C_4)$alkylene or optionally substituted $(C_4)$alkenylene, $R^7$ is optionally substituted $(C_1-C_8)$ alkyl and $X^1$ is O or $NR^1$. In another aspect of this embodiment, $R^5$ is optionally substituted aryl$(C_1-C_4)$alkyl. In another aspect of this embodiment, $R^5$ is optionally substituted benzyl. In another aspect of this embodiment, $R^5$ is optionally substituted

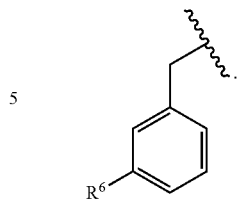

In another aspect of this embodiment, $R^9$ is $OR^4$. In another aspect of this embodiment, $R^8$ is optionally substituted $(C_1-C_8)$alkyl. In another aspect of this embodiment, $R^9$ is $OR^4$ and $R^8$ is optionally substituted $(C_1-C_8)$alkyl. In another aspect of this embodiment, $R^{12}$ is H. In another aspect of this embodiment, $A^1$ is

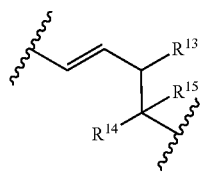

wherein each $R^{13}$, $R^{14}$ or $R^{15}$ is independently H, optionally substituted $(C_1-C_8)$alkyl or $OR^4$. In another aspect of this embodiment, $A^1$ is

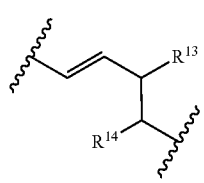

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In one embodiment of the compound of Formula II, $A^2$ is

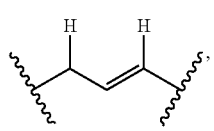 [SMILES: */C=C/C*]

$A^1$ is optionally substituted $(C_4)$alkylene or optionally substituted $(C_4)$alkenylene, $R^7$ is optionally substituted $(C_1-C_8)$ alkyl, $X^1$ is O or $NR^1$ and $R^5$ is optionally substituted

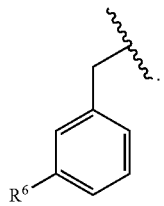

In another aspect of this embodiment, $R^6$ is $OR^4$, $CH_2OR^4$, $N(R^1)_2$, $NHCOR^1$, $NHC(O)OR^1$, $NHC(O)N(R^1)_2$, $NHC(NR^1)R^1$, $NHC(NR^1)N(R^1)_2$, $C(O)N(R^1)_2$, $S(O)_2N(R^1)_2$, $NHS(O)_2OR^1$, $NHS(O)_2R^{16}$ or $NHS(O)_2N(R^1)_2$. In another aspect of this embodiment, $R^6$ is OH. In another aspect of this embodiment, $R^9$ is $OR^4$. In another aspect of this embodiment, $R^8$ is optionally substituted $(C_1-C_8)$alkyl. In another aspect of this embodiment, $R^9$ is $OR^4$ and $R^8$ is optionally substituted $(C_1-C_8)$alkyl. In another aspect of this embodiment, $R^{12}$ is H. In another aspect of this embodiment, $A^1$ is

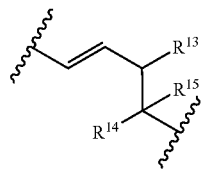

wherein each $R^{13}$, $R^{14}$ or $R^{15}$ is independently H, optionally substituted $(C_1-C_8)$alkyl or $OR^4$. In another aspect of this embodiment, $A^1$ is

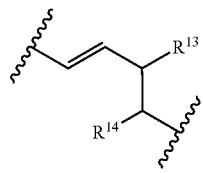

wherein each $R^{13}$ or $R^{14}$ is independently H, optionally substituted $(C_1-C_8)$alkyl or $OR^4$ and each $R^{8b}$ and $R^{9b}$ is H. In another aspect of this embodiment, $R^8$ is methyl. In another aspect of this embodiment, $R^8$ is methyl and each $R^{8a}$ and $R^{9a}$ is H. In another aspect of this embodiment, $R^{12}$ is H or optionally substituted $(C_1-C_4)$alkyl. In another aspect of this embodiment, $R^{12}$ is H or methyl.

In another embodiment, the compound of Formula I is

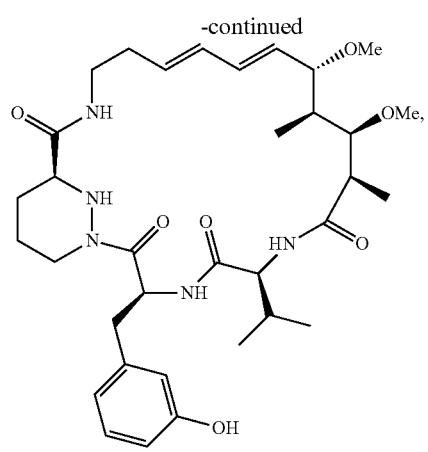

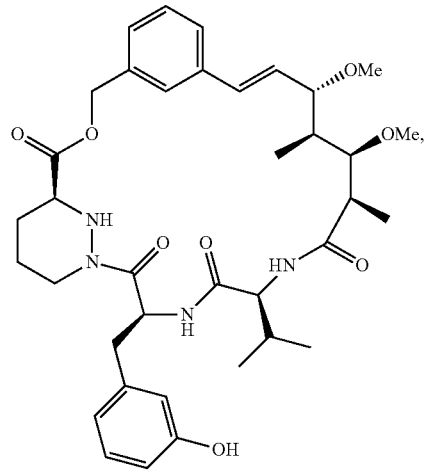

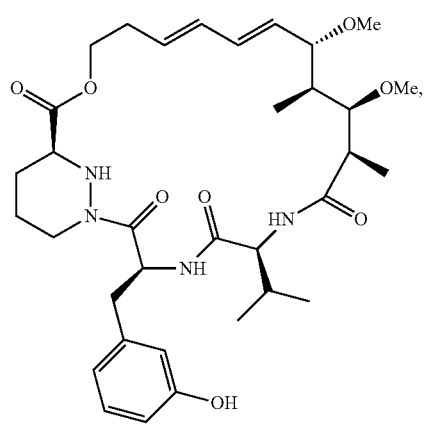

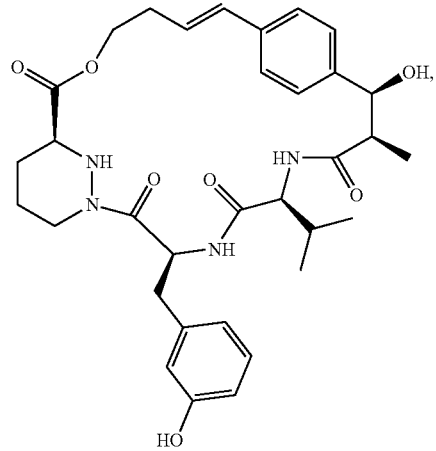

-continued

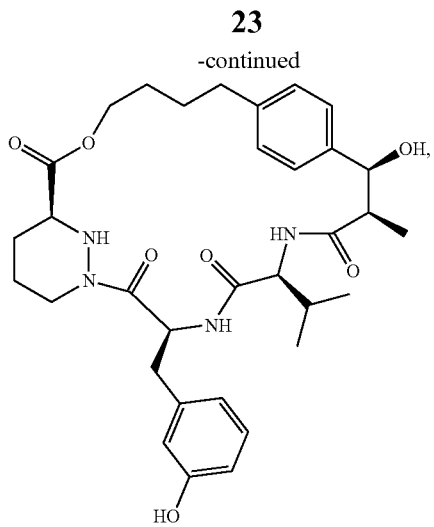

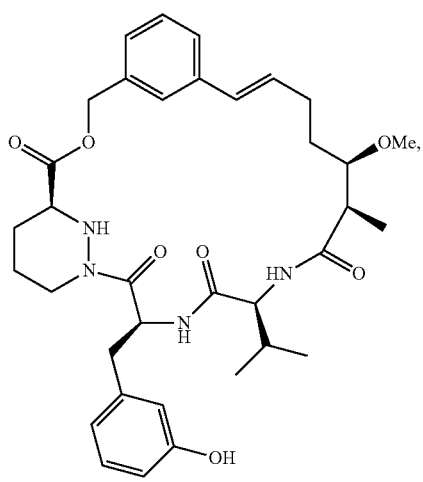

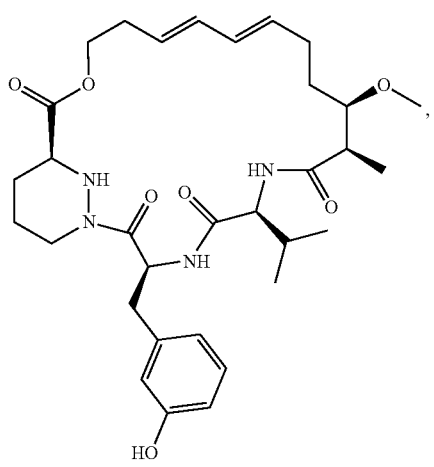

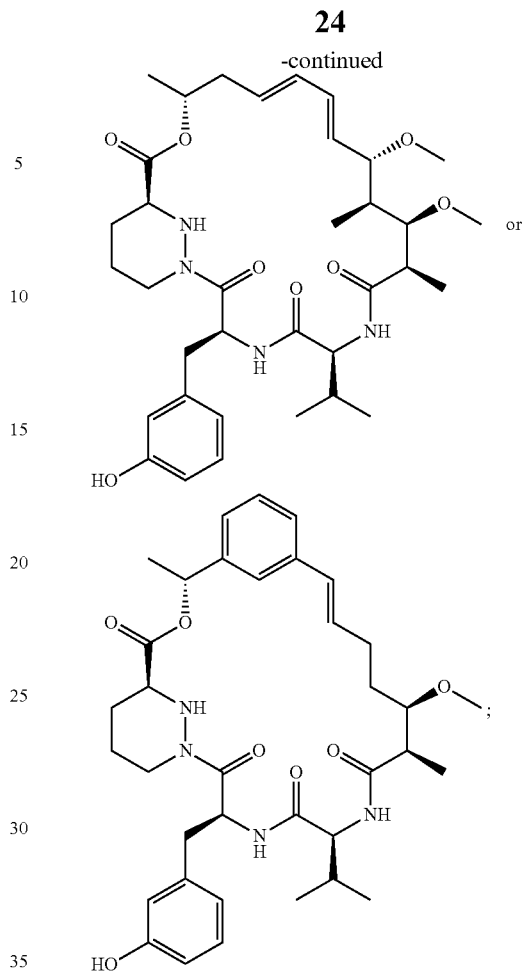

or a pharmaceutically acceptable salt or ester thereof.

Each document referenced herein is incorporated by reference in its entirety for all purposes.

DEFINITIONS

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms ($C_1$-$C_{12}$ alkoxy), or 1 to 6 carbon atoms (i.e., $C_1$-$C_6$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or -OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms ($C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —CF$_3$, —CHF$_2$, —CFH$_2$, —CH$_2$CF$_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain radical or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from two different carbon atoms of a parent aryl. Typical arylene radicals include, but are not limited to, phenylene and naphthylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkylene" refers to an arylalkyl as defined above having two monovalent radical centers derived by the removal of one hydrogen atom from the aryl radical and the other hydrogen removed from the alkyl radical of the group. Non-limiting examples of arylalkylene groups comprise:

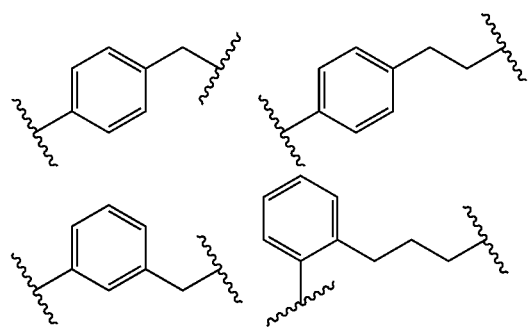

aryl($C_1$)alkylene aryl($C_2$)alkylene aryl($C_1$)alkylene aryl($C_3$)alkylene.

When an arylalkyl or arylalkylene group is described as aryl($C_0$-$C_n$)alkyl or aryl($C_0$-$C_n$)alkylene, respectively, then the meaning of aryl($C_0$)alkyl or aryl($C_0$)alkylene is the same as aryl or arylene, respectively.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 6 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic cycloalkyls include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl. Non-limiting examples of bicyclo cycloalkyls includes naphthyl, tetrahydronapthalene, decaline and bicyclo[3.1.0]hex-6-yl and the like.

"Cycloalkylene" refers to a cycloalkyl as defined above having two monovalent radical centers derived by the removal of two hydrogen atoms from the same or two different carbon atoms of a parent cycloalkyl. Typical cycloalkylene radicals include, but are not limited to, cyclopropylene, cyclobutylene, cyclopentylene and cyclohexylene.

"Halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

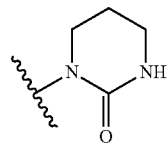

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

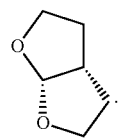

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclene" or "heterocyclylene" refers to a "heterocycle" or "heterocyclyl" as defined above having two monovalent radical centers derived by the removal of two hydrogen atoms from the same or two different carbon atoms of a parent heterocycle, the removal of two hydrogen atoms from two nitrogen atoms of a parent heterocycle, or the removal of a hydrogen atom from a nitrogen and the removal of a hydrogen atom from a carbon atom of a parent heterocycle. Non-limiting examples of heterocyclene or heterocyclylenes are:

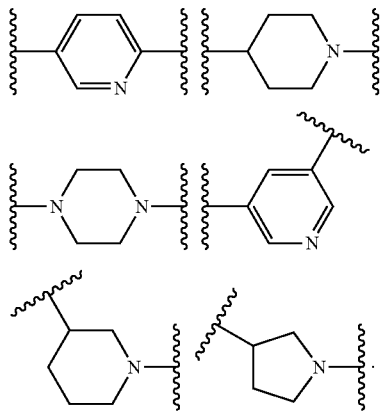

"Heteroaryl" refers to a monovalent aromatic heterocyclyl having at least one heteroatom in the ring. Thus, "heteroaryl" refers to an aromatic group of from 1 to 14 carbon atoms and 1 to 6 heteroatoms selected from oxygen, nitrogen, sulfur, or phosphorus. For multiple ring systems, by way of example, the term "heteroaryl" includes fused (e.g., bicyclic), bridged, and spiro ring systems having aromatic and non-aromatic rings. In one embodiment, the carbon, nitrogen, or sulfur ring atom(s) of the heteroaryl group may be oxidized to provide for C(=O), N-oxide, sulfinyl, or sulfonyl moieties. Non-limiting examples of heteroaryls include pyridinyl, quinolinyl, benzothiophenyl, benzofuranyl and the like.

"Heterarylene" refers to a "heteraryl" as defined above having two monovalent radical centers derived by the removal of two hydrogen atoms from the same or two different carbon atoms of a parent heteraryl group. Non-limiting examples of heteroarylene groups are:

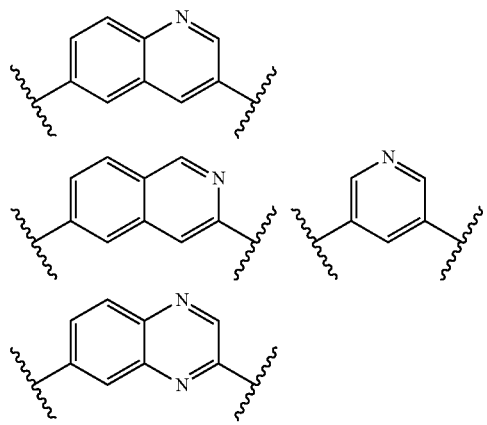

-continued

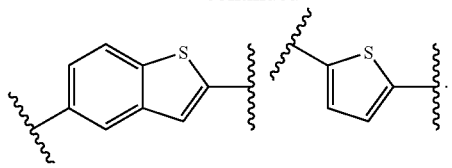

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms and 1-6 heteroatoms, e.g., the alkyl portion of the heterocyclylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, phosphorus, and/or nitrogen containing heterocycles such as pyrrolidiylmethyl, 2-tetrahydrofuranylylethan-1-yl, and the like, 6-membered sulfur, oxygen, and/or nitrogen containing heterocycles such as piperidinylmethyl, morpholinylmethyl, piperidinylethyl, teterahydropyranylethyl, and the like.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, and the like.

The term "heterocyclyloxy" represents a heterocyclyl group attached to the adjacent atom by an oxygen.

When there is a sulfur atom present, the sulfur atom can be at different oxidation levels, namely, S, SO, SO$_2$, or SO$_3$. All such oxidation levels are within the scope of the present invention.

The term "optionally substituted" in reference to a particular moiety of the compound of Formula I-II (e.g., an optionally substituted aryl group) refers to a moiety wherein all substituents are hydrogen or wherein one or more of the hydrogens of the moiety may be replaced by substituents such as those listed under the definition of "substituted" or as otherwise specified.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl", unless otherwise indicated, means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —$R^b$, —$O^-$, =O, —$OR^b$, —$SR^b$, —$S^-$, —$NR^b{}_2$, —$N^+R^b{}_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b{}_2$, —S(=O)$_2$—, —S(=O)$_2$OH, —S(=O)$_2R^b$, —OS(=O)$_2OR^b$, —S(=O)$_2$$NR^b{}_2$, —S(=O)$R^b$, —OP(=O)(O$R^b$)$_2$, —P(=O)(O$R^b$)$_2$, —P(=O)(O$^-$)$_2$, —P(=O)(OH)$_2$, —P(O)(O$R^b$)(O$^-$), —C(=O)$R^b$, —C(=O)X, —C(S)$R^b$, —C(O)O$R^b$, —C(O)O$^-$, —C(S)O$R^b$, —C(O)S$R^b$, —C(S)S$R^b$, —C(O)$NR^b{}_2$, —C(S)$NR^b{}_2$, —C(=$NR^b$)$NR^b{}_2$, where each X is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

As will be appreciated by those skilled in the art, the compounds of the present invention may exist in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention includes prodrug forms of the compound herein described.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

The compounds of Formula I and II feature variables such as A, $A^1$ and $A^2$ within ring structures. When structural representations are given for these variables, they should be represented in Formula II as presented in a clockwise direction, i.e., from left to right. By way of example and not by limitation, when $A^2$ of Formula II is represented by the moiety

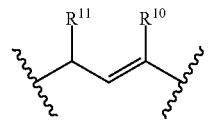

and $A^1$ is represented by the moiety

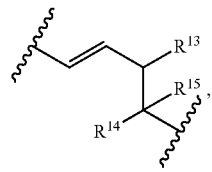

then the macrocyclic structure of Formula II is

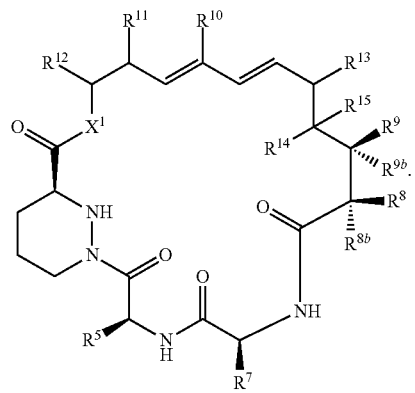

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. In addition, the scope of the present invention includes prodrug forms of the compound herein described.

A compound of Formula I-II and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-II and their pharmaceutically acceptable salts.

A compound of Formula I-II and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-II and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The definitions and substituents for various genus and subgenus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The modifier "about" used in connection with a quantity is inclusive of the stated value and has the meaning dictated by the context (e.g., includes the degree of error associated with measurement of the particular quantity).

Whenever a compound described herein is substituted with more than one of the same designated group, e.g., "R" or "R¹", then it will be understood that the groups may be the same or different, i.e., each group is independently selected. Wavy lines,

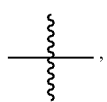

indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Selected substituents comprising the compounds of Formula I-II may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The compounds of Formula I-II also include molecules that incorporate isotopes of the atoms specified in the particular molecules. Non-limiting examples of these isotopes include D, T, $^{14}C$, $^{13}C$ and $^{15}N$.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

In yet another embodiment, the present application discloses pharmaceutical compositions comprising a compound of Formula I-II or a pharmaceutically acceptable salt thereof, and a pharmaceutically acceptable carrier or excipient.

Routes of Administration

One or more compounds of the invention (herein referred to as the active ingredients) are administered by any route appropriate to the condition to be treated. Suitable routes include oral, rectal, nasal, topical (including pulmonary, buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy, Including HCV and HIV Combination Therapy

In another embodiment, the compounds of the present invention may be combined with one or more active agent. Non-limiting examples of suitable combinations include combinations of one or more compounds of the present invention with one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), GS-6620 and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib)

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV, and combinations thereof.

Combinations of the compounds of Formula I-II and additional active therapeutic agents may be selected to treat patients infected with HCV and other additional conditions such as HIV infections. Accordingly, the compounds of Formula I-II may be combined with one or more compounds useful in treating HIV; for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), IDX184, PSI-7851, HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811, 19) pharmacokinetic enhancers, e.g., BAS-100, SPI-452, PF-4194477, TMC-41629, GS-9350, GS-9585, and roxythromycin, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. Non-limiting examples of the additional active agents include those disclosed above. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

As will be appreciated by those skilled in the art, when treating a Flaviviridae viral infection such as HCV, such treatment may be characterized in a variety of ways and measured by a variety of endpoints. The scope of the present invention is intended to encompass all such characterizations.

SYNTHETIC EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| Ac₂O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH⁺ | mass plus 1 |
| MH⁻ | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |

TABLE 1-continued

List of abbreviations and acronyms.

| Abbreviation | Meaning |
| --- | --- |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

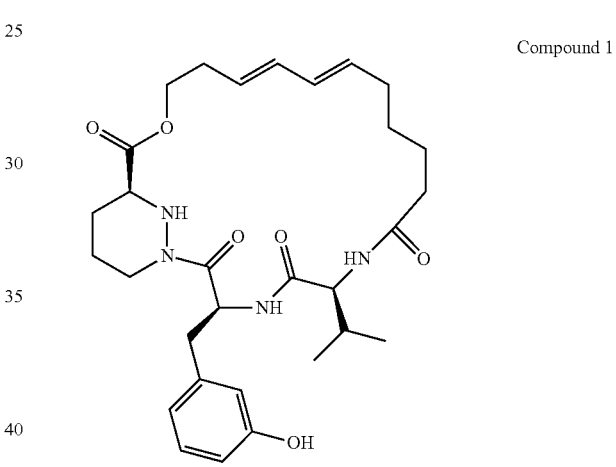

Compound 1

Example I

Compound 1: (13E,15E)-(3S,6S,21S)-3-(3-Hydroxy-benzyl)-6-isopropyl-19-oxa-1,4,7,25-tetraaza-bicyclo[19.3.1]pentacosa-13,15-diene-2,5,8,20-tetraone Prepared as described in J. Am. Chem. Soc. 2003, 125, 3849.

$^1$H NMR (300 MHz, d₆-DMSO) δ9.09 (s, 1H), 7.88 (d, J=7.9 Hz, 1H), 7.71 (d, J=8.4 Hz, 1H), 6.96 (app t, J=7.7 Hz, 1H), 6.65-6.51 (m, 3H), 6.00 (app pentet, J=13.0 Hz, 2H), 5.70-5.49 (m, 3H), 4.89 (d, J=11.5 Hz, 1H), 4.24-4.06 (m, 3H), 2.76-2.56 (m, 3H), 2.43-2.25 (m, 3H), 2.07-1.94 (m, 2H), 1.93-1.75 (m, 2H), 1.73-1.12 (m, 10H), 0.85 (d, J=6.9 Hz, 3H), 0.82 (d, J=6.9 Hz, 3H). LCMS (m/z) 555.3 [M+H], 577.1 [M+Na], Tr=4.45 min.

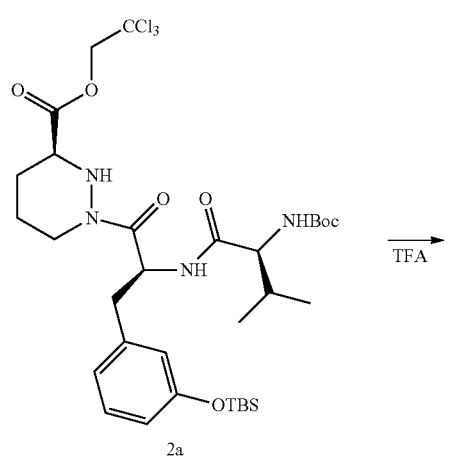

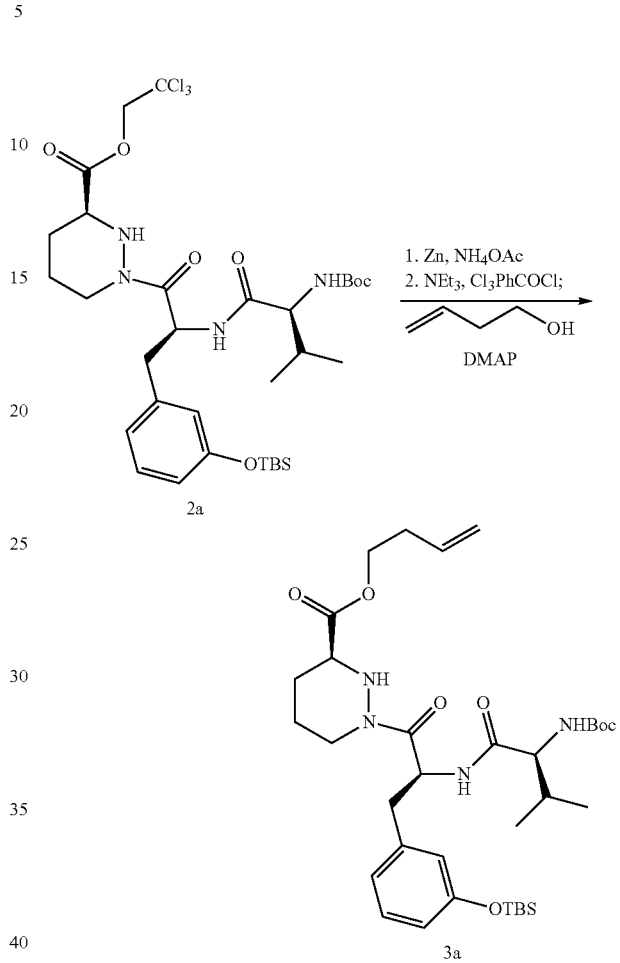

(S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid but-3-enyl Ester (3a)

A solution of tripeptide 2a (5.46 g, 7.4 mmol), prepared as described in *J. Am. Chem. Soc.* 2003, 125, 3849, in 50 mL anhydrous CH₂Cl₂ was cooled to 0° C. and treated with 10 mL TFA. After 24 h at 0° C., 30 mL of dry toluene was added to the reaction mixture and the volatiles were removed in vacuo. The TFA ammonium salt was isolated as a foam and used without further purification (Intermediate 2b)

Example III

Compound 3: (13E,15E)-(3S,6S,9R,10R,11S,12S,21S)-3-(3-Hydroxy-benzyl)-6-isopropyl-10,12-dimethoxy-9,11-dimethyl-19-oxa-1,4,7,25-tetraaza-bicyclo[19.3.1]pentacosa-13,15-diene-2,5,8,20-tetraone

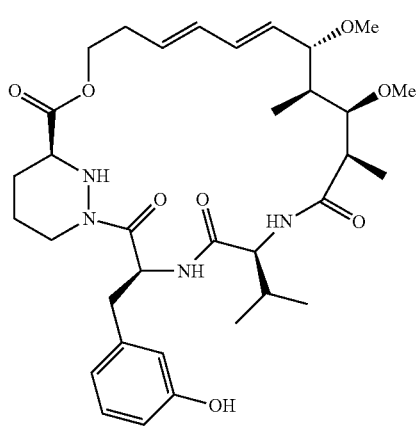

A solution of 2a (1.891 g, 2.562 mmol) in 50 mL THF was successively treated with Zinc (3.685 g, 56.368 mmol) and a solution of ammonium acetate (2.962 g, 38.430 mmol) in 10 mL water. After 24 h at RT, the mixture was filtered through a pad of Celite and rinsed with pH 4 solution (KHSO₄). The aqueous layer was extracted with EtOAc (3×50 mL) and the organics were combined, dried (Na₂SO₄) and filtered. The volatiles were removed in vacuo and the residual AcOH was azeotroped with toluene (3×50 mL). The acid 2f was isolated as a white solid and used without further purification. The acid 2f was partially dissolved in 20 mL anhydrous toluene. Upon the addition of triethylamine (540 μL, 3.843 mmol), the mixture became clear. The mixture was subsequently treated with 2,4,6-trichlorobenzoyl chloride (480 μL, 3.074 mmol). After 50 min at RT, a solution of allyl alcohol (330 μL, 3.843 mmol) and DMAP (469 mg, 3.843 mmol) in 20 mL toluene was added to the mixte anhydride. After stirring overnight at RT, the volatiles were removed in vacuo and the residue was purified by MPLC (50 g Isolute cartridge, continuous gradient, 100% hexanes→hexanes/EtOAc, 1:2) to provide the desired ester 3a (85 mg, 14% over 2 steps) as a white solid. ¹H NMR (300 MHz, CDCl₃) δ7.13 (app t, J=7.5 Hz, 1H), 6.81 (d, J=7.5 Hz, 1H), 6.74-6.64 (m, 2H), 6.48 (d, J=8.4 Hz, 1H), 5.90-5.68 (m, 2H), 5.18-5.08 (m, 2H), 5.08-5.01 (m, 1H), 4.34-4.25 (br d, J=13.9 Hz, 1H), 4.18 (app dp, J=4.4, 6.8 Hz, 2H), 4.00-3.90 (m, 1H), 3.52 (d, J=11.0 Hz, 1H), 2.93 (qd, J=6.0, 15.5 Hz, 2H), 2.81-2.70 (m, 1H), 2.59-2.48 (m, 1H), 2.41 (app q, J=6.8 Hz, 2H), 2.20-2.06 (m, 1H), 1.88-1.73 (m, 2H), 1.57-1.49 (m, 2H), 1.46 (s, 9H), 0.99 (s, 9H), 0.94 (d, J=6.8 Hz, 3H), 0.88 (d, J=6.8 Hz, 3H), 0.20 (s, 6H). LCMS (m/z) 661.6 [M+H], 683.5 [M+Na], Tr=5.79 min.

S)-1-{(S)-3-[3-(tert-Butyl-dimethyl-silanyloxy)-phenyl]-2-[(S)-2-((E)-(2R,3R,4S,5S)-3,5-dimethoxy-2,4-dimethyl-nona-6,8-dienoylamino)-3-methyl-butyrylamino]-propionyl}-hexahydro-pyridazine-3-carboxylic Acid but-3-enyl Ester (3d)

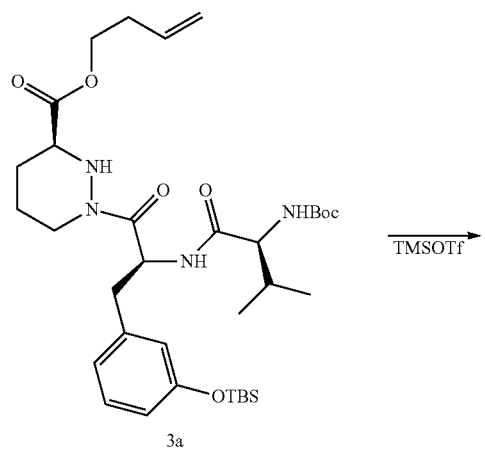

3a

TMSOTf →

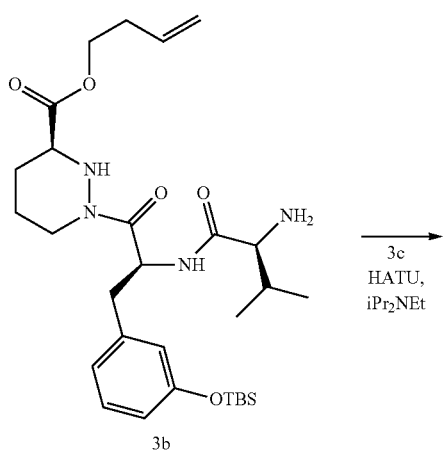

3b

3c
HATU, iPr₂NEt
→

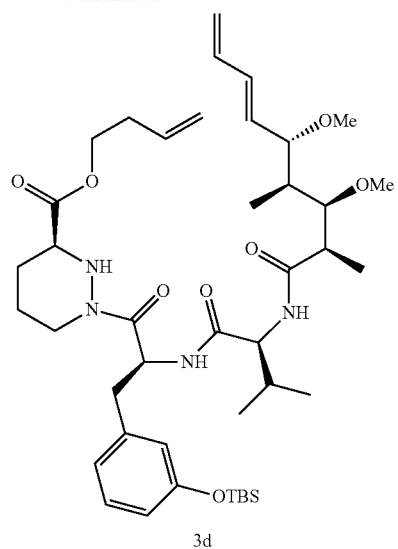

3d

A solution of 3a (328 mg, 0.500 mmol) in 15 mL anhydrous CH₂Cl₂ was cooled to 0° C. and treated with TMSOTf (140 μL, 0.750 mmol). After 1.5 h at 0° C., i-Pr₂NEt (0.3 mL, 2.000 mmol) was added and the volatiles were removed in vacuo. The free amine (Intermediate B) was isolated as a white solid and used without further purification.

A solution of (E)-(2R,3R,4S,5S)-3,5-Dimethoxy-2,4-dimethyl-nona-6,8-dienoic acid 3c (100 mg, 0.413 mmol) in 1 mL anhydrous DMF was cooled to 0° C. and successively treated with iPr₂NEt (290 μL, 1.652 mmol) and a solution of HATU (188 mg, 0.496 mmol) in 1 mL DMF. After 40 min at 0° C., the reaction mixture was treated with a solution of the freshly prepared amine in 2 mL DMF. The green solution was allowed to warm overnight to RT and then quenched with pH 7 buffer (10 mL). The aqueous layer was extracted with CH₂Cl₂ (3×10 mL) and the organics were combined, dried (Na₂SO₄), filtered and the volatiles were removed in vacuo. The residual DMF was azeotroped with toluene (2×30 mL) and the solid residue was purified by MPLC (25 g Isolute cartridge, continuous gradient 100% isohexane→isohexane/EtOAc, 1:1) to provide desired amide 3d (229 mg, 70%) as a white solid. ¹H NMR (300 MHz, CDCl₃) δ7.12 (app t, J=8.2 Hz, 1H), 6.80 (d, J=8.2 Hz, 1H), 6.74-6.63 (m, 2H), 6.50-6.32 (m, 2H), 6.27 (s, 1H), 6.25-6.16 (m, 1H), 5.90-5.67 (m, 2H), 5.47 (dd, J=8.8, 15.0 Hz, 1H), 5.25 (d, J=16.1 Hz, 1H), 5.18-5.08 (m, 3H), 4.29 (dd, J=6.0, 7.9 Hz, 2H), 4.18 (app dp, J=5.3, 6.6 Hz, 2H), 3.87 (dd, J=2.2, 9.1 Hz, 1H), 3.53 (d, J=11.1 Hz, 1H), 3.42 (app q, J=9.3 Hz, 1H), 3.40 (s, 3H), 3.25 (s, 3H), 2.99-2.85 (m, 2H), 2.78-2.69 (m, 1H), 2.62-2.50 (m, 1H), 2.46-2.32 (m, 3H), 2.22-2.08 (m, 1H), 1.89-1.67 (m, 2H), 1.53-1.40 (m, 1H), 1.31-1.25 (m, 2H), 1.07 (d, J=7.0 Hz, 3H), 0.99 (s, 9H), 0.98 (d, J=6.8 Hz, 3H), 0.96 (d, J=6.8 Hz, 3H), 0.77 (d, J=7.1 Hz, 3H), 0.19 (s, 6H). LCMS (m/z) 785.6 [M+H], 807.6 [M+Na], Tr=5.97 min.

51

(13E,15E)-(3S,6S,9R,10R,11S,12S,21S)-3-(3-Hy-droxy-benzyl)-6-isopropyl-10,12-dimethoxy-9,11-dimethyl-19-oxa-1,4,7,25-tetraaza-bicyclo[19.3.1]pentacosa-13,15-diene-2,5,8,20-tetraone (3)

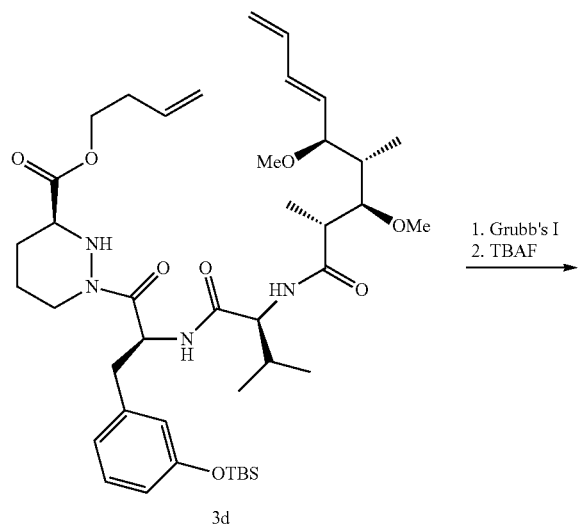

3d

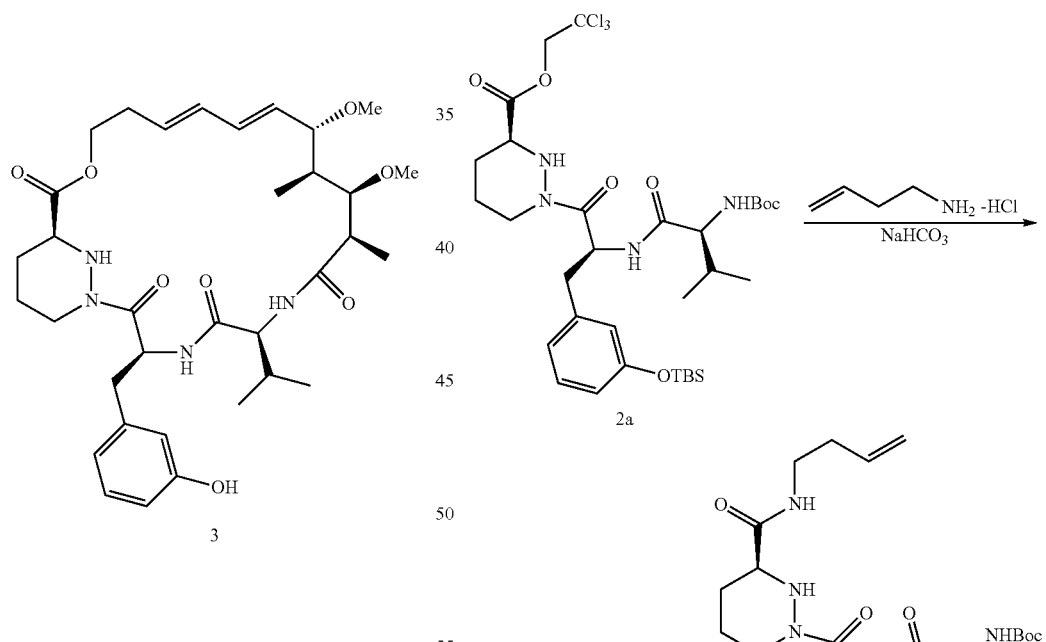

3

Compound 3 was prepared in the same manner as Compound 8 using 3d in place of 8c (See below). $^1$H NMR (300 MHz, d$_6$-DMSO) δ9.14 (s, 1H), 8.04 (d, J=7.3 Hz, 1H), 7.06-6.95 (m, 2H), 6.66-6.48 (m, 4H), 6.19-6.04 (m, 2H), 5.56-5.27 (m, 3H), 4.84 (d, J=11.3 Hz, 1H), 4.29-4.19 (m, 1H), 4.18-3.99 (m, 3H), 3.18 (s, 3H), 3.04 (s, 3H), 2.81-2.61 (m, 3H), 2.45-2.37 (m, 1H), 2.35-2.25 (m, 1H), 1.94-1.74 (m, 2H), 1.73-1.55 (m, 3H), 1.53-1.39 (m, 1H), 1.38-1.26 (m, 1H), 1.13 (d, J=7.7 Hz, 3H), 0.86 (d, J=6.8 Hz, 3H), 0.80 (d, J=6.8 Hz, 3H), 0.67 (d, J=6.8 Hz, 3H). LCMS (m/z) 665.4 [M+Na], Tr=4.78 min.

52

Example IV

Compound 4: (13E,15E)-(3S,6S,9R,10R,11S,12S,21S)-3-(3-Hydroxy-benzyl)-6-isopropyl-10,12-dimethoxy-9,11-dimethyl-1,4,7,19,25-pentaaza-bicyclo[19.3.1]pentacosa-13,15-diene-2,5,8,20-tetraone

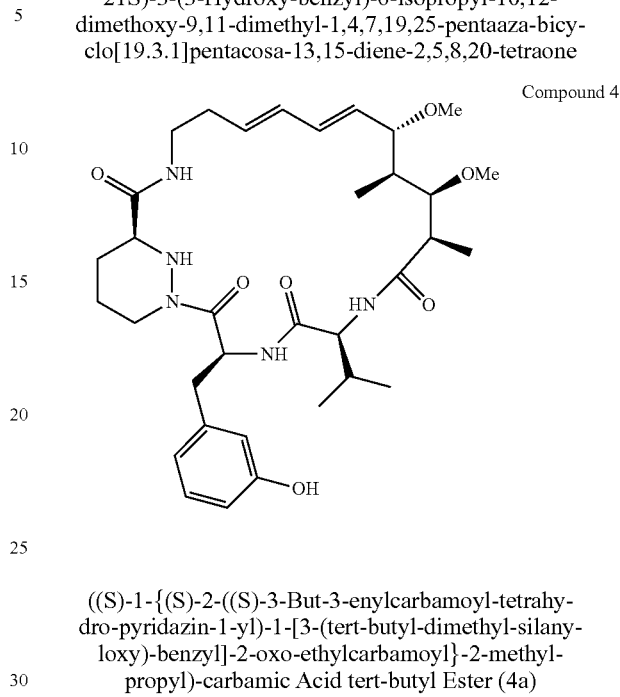

Compound 4

((S)-1-{(S)-2-((S)-3-But-3-enylcarbamoyl-tetrahydro-pyridazin-1-yl)-1-[3-(tert-butyl-dimethyl-silanyloxy)-benzyl]-2-oxo-ethylcarbamoyl}-2-methyl-propyl)-carbamic Acid tert-butyl Ester (4a)

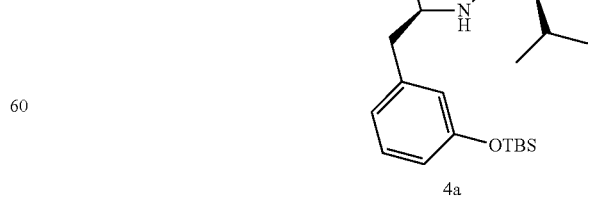

4a

A solution of 2a (1.370 g, 1.855 mmol) in 30 mL THF was treated with NaHCO$_3$ (623 mg, 7.420 mmol) and 3-buteny lamine hydrochloride (400 mg, 3.711 mmol). After overnight stirring, the reaction mixture was filtered through a pad of silica which was eluted with EtOAc. The volatiles were removed in vacuo to provide desired amide 4a (1.4 g, quant.) as a white solid. $^1$H NMR (300 MHz, d$_6$-DMSO) δ7.87 (t, J=5.5 Hz, 1H), 7.67 (d, J=8.6 Hz, 1H), 7.08 (app t, J=7.9 Hz, 1H), 6.81 (d, J=6.8 Hz, 1H), 6.79 (d, J=6.9 Hz, 1H), 6.70-6.57 (m, 3H), 5.84-5.69 (m, 1H), 5.43 (td, J=4.2, 8.8 Hz, 1H), 5.09-4.90 (m, 3H), 4.03 (d, J=6.8 Hz, 2H), 3.70 (app t, J=8.2 Hz, 1H), 3.25-3.11 (m, 3H), 2.90-2.76 (m, 2H), 2.63 (dd, J=9.1, 13.5 Hz, 1H), 2.18 (app q, J=7.5 Hz, 2H), 1.84 (app q, J=6.8 Hz, 2H), 1.79-1.70 (m, 2H), 1.37 (s, 9H), 0.94 (s, 9H), 0.71 (d, J=6.8 Hz, 3H), 0.67 (d, J=6.8 Hz, 3H), 0.15 (s, 6H). LCMS (m/z) 660.6 [M+H], 682.7 [M+Na], Tr=5.74 min.

Hz, 1H), 5.27 (dd, J=8.8, 15.5 Hz, 1H), 5.06 (d, J=17.0 Hz, 1H), 4.97-4.89 (m, 3H), 4.06-4.02 (m, 1H), 4.00 (app t, J=6.1 Hz, 1H), 3.62 (dd, J=2.6, 8.8 Hz, 1H), 3.27-3.19 (m, 2H), 3.21 (s, 3H), 3.13 (app octet, J=7.0 Hz, 2H), 3.06 (s, 3H), 2.79-2.69 (m, 2H), 2.56 (br t, J=12.3 Hz, 1H), 2.23-2.16 (m, 1H), 2.12 (q, J=7.0 Hz, 2H), 2.02-1.90 (m, 2H), 1.66-1.48 (m, 2H), 1.38-1.21 (m, 2H), 0.88 (d, J=7.0 Hz, 3H), 0.79 (s, 9H), 0.76 (d, J=7.0 Hz, 3H), 0.74 (d, J=7.0 Hz, 3H), 0.72-0.62 (m, 2H), 0.59 (d, J=7.0 Hz, 3H), 0.01 (s, 3H), 0.00 (s, 3H). LCMS (m/z) 806.6 [M+Na], Tr=5.86 min.

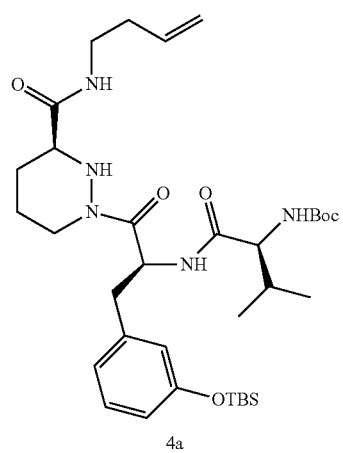

4a

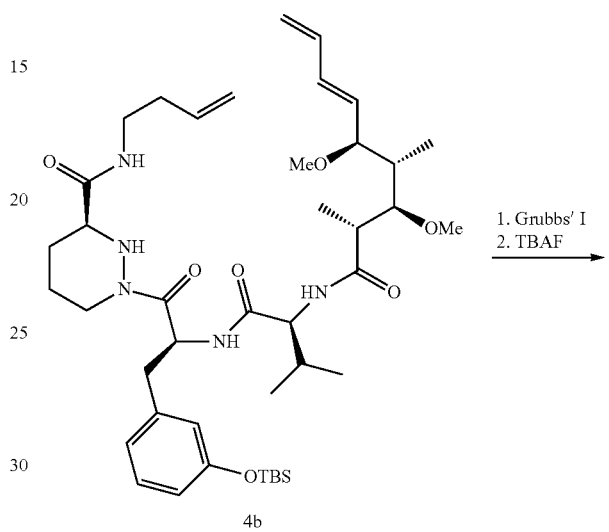

4b

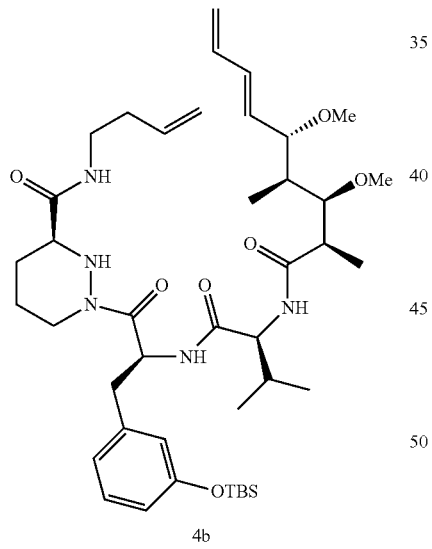

4b (S)-1-{(S)-3-[3-(tert-Butyl-dimethyl-silanyloxy)-phenyl]-2-[(S)-2-((E)-(2R,3R,4S,5S)-3,5-dimethoxy-2,4-dimethyl-nona-6,8-dienoylamino)-3-methyl-butyrylamino]-propionyl}-hexahydro-pyridazine-3-carboxylic Acid but-3-enylamide (4b)

Compound 4b was prepared in the same manner as 3d by substituting 4a for 3a. $^1$H NMR (400 MHz, CDCl$_3$) δ6.95 (app t, J=7.6 Hz, 1H), 6.66 (d, J=7.6 Hz, 1H), 6.56 (s, 1H), 6.53 (dd, J=2.0, 8.2 Hz, 1H), 6.26-6.14 (m, 2H), 6.07-5.99 (m, 2H), 5.61 (ddt, J=6.7, 10.2, 17.2 Hz, 1H), 5.51 (td, J=6.4, 8.8

(13E,15E)-(3S,6S,9R,10R,11S,12S,21S)-3-(3-Hydroxy-benzyl)-6-isopropyl-10,12-dimethoxy-9,11-dimethyl-1,4,7,19,25-pentaaza-bicyclo[19.3.1]pentacosa-13,15-diene-2,5,8,20-tetraone (4)

Compound 4 was prepared in the same manner as Compound 8d using 4b in place of 8c (See below). $^1$H NMR (400 MHz, d$_6$-DMSO) δ9.19 (br s, 1H), 8.06 (d, J=7.3 Hz, 1H), 7.19-7.10 (m, 2H), 7.03 (app t, J=8.5 Hz, 1H), 6.70-6.55 (m, 3H), 6.10-5.92 (m, 2H), 5.69-5.60 (m, 1H), 5.36-5.27 (m, 2H), 4.83 (d, J=12.0 Hz, 1H), 4.21-4.13 (m, 1H), 4.10-4.00 (m, 2H), 3.46-3.39 (m, 1H), 3.25 (s, 3H), 3.09 (s, 3H), 3.06-2.98 (m, 1H), 2.80-2.61 (m, 2H), 2.31-2.25 (m, 1H), 2.23-2.11 (m, 2H), 1.88-1.62 (m, 3H), 1.48-1.37 (m, 2H), 1.28-1.21 (m, 2H), 1.14 (d, J=7.0 Hz, 3H), 1.11-1.02 (m, 1H), 0.86

(d, J=7.0 Hz, 3H), 0.83 (d, J=7.0 Hz, 3H), 0.60 (d, J=7.0 Hz, 3H). LCMS (m/z) 664.5 [M+Na], Tr=4.46 min.

Preparation of (E)-(2R,3R,4S,5S)-3,5-Dimethoxy-2,4-dimethyl-nona-6,8-dienoic Acid (3c)

((E)-(2S,3S,4S,5S)-3,5-Dimethoxy-2,4-dimethyl-oct-6-enyloxymethyl)-benzene

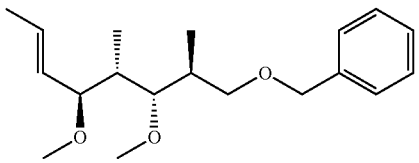 [SMILES: C/C=C/[C@H](OC)[C@H](C)[C@@H](OC)[C@@H](C)COCc1ccccc1]

To 18-crown-6 (3.8 g, 14.4 mmol) in anhydrous THF (90 ml) at 0° C. and under an atmosphere of nitrogen was added potassium hydride (30%, 6.7 g, 50.4 mmol) and the suspension stirred for 5 minutes. Methyl iodide (2.5 ml, 40.3 mmol) was then added at 0° C. and the reaction stirred for an additional 5 minutes. A solution of (E)-(2S,3S,4S,5S)-1-Benzyloxy-2,4-dimethyl-oct-6-ene-3,5-diol (2 g, 7.2 mmol) (Paterson, I. et al, J. Amer. Chem. Soc. 1994, 116, 11287-11314) in anhydrous THF (40 ml) was added dropwise and the reaction was allowed to warm to room temperature and stirred overnight. The reaction was carefully quenched with saturated ammonium chloride and extracted with diethyl ether (2×). The combined organic layers were dried over magnesium sulphate, filtered and concentrated in vacuo. The product was purified by flash chromatography (SiO$_2$, iHex/EtOAc, 25:1) to afford 2.0 g (91%) as a clear oil. $^1$H NMR (300 MHz, CDCl$_3$) δ 7.40-7.29 (m, 5H), 5.66 (dq, J=15.3 Hz, 6.4 Hz, 1H), 5.21 (ddd, J=15.3 Hz, 8.8 Hz, 1.6 Hz, 1H), 4.54 (s, 2H), 3.61 (dd, J=8.8 Hz, 3.3 Hz, 1H), 3.53-3.46 (m, 2H), 3.40 (s, 3H), 3.36 (t, J=9.7 Hz, 1H), 3.23 (s, 3H), 1.93 (m, 1H), 1.77 (dd, J=6.4 Hz, 1.6 Hz, 3H), 1.70 (m, 1H), 0.95 (d, J=6.9 Hz, 3H), 0.75 (d, J=6.9 Hz, 3H).

(E)-(2S,3S,4S,5S)-3,5-Dimethoxy-2,4-dimethyl-oct-6-en-1-ol

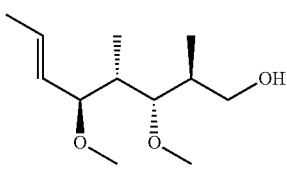

To ((E)-(2S,3S,4S,5S)-3,5-Dimethoxy-2,4-dimethyl-oct-6-enyloxymethyl)-benzene (5.5 g, 18.0 mmol) in anhydrous THF (180 ml) at −78° C. and under an atmosphere of nitrogen, was slowly added LiDBB until a dark green colour persisted. The temperature was maintained below −70° C. during the addition. The reaction was quenched with saturated ammonium chloride, allowed to warm to room temperature and extracted with diethyl ether (2×). The combined organic layers were dried over magnesium sulphate, filtered and concentrated in vacuo. The product was purified by flash chromatography (SiO$_2$, iHex/EtOAc, 50:1 then 1:1) to afford 3.6 g (93%) as a clear oil. $^1$H NMR (300 MHz, CDCl$_3$) δ 5.66 (dq, J=15.2 Hz, 6.4 Hz, 1H), 5.19 (dd, J=15.2 Hz, 8.8 Hz, 1H), 3.75-3.52 (m, 3H), 3.49 (s, 3H), 3.31 (t, J=9.1 Hz, 1H), 3.24 (s, 3H), 2.82 (dd, J=8.2 Hz, 2.9 Hz, 1H), 1.91 (m, 1H), 1.77 (d, J=6.4 Hz, 3H), 1.68 (m, 1H), 0.84 (d, J=6.9 Hz, 3H), 0.79 (d, J=7.1 Hz, 3H).

2,2-Dimethyl-propionic Acid (E)-(2S,3S,4S,5S)-3,5-dimethoxy-2,4-dimethyl-oct-6-enyl Ester

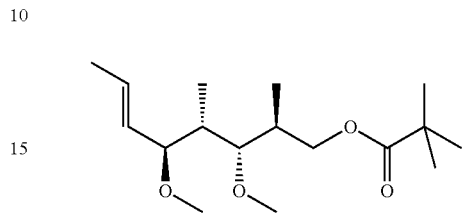

To (E)-(2S,3S,4S,5S)-3,5-Dimethoxy-2,4-dimethyl-oct-6-en-1-ol (1.5 g, 6.94 mmol) in anhydrous pyridine (20 ml) at 0° C. and under an atmosphere of nitrogen was added pivaloyl chloride (1.33 ml, 10.7 mmol). The reaction was warmed to room temperature and stirred for 2 hours, after which it was quenched with saturated ammonium chloride and extracted with dichloromethane (2×). The combined organic layers were dried by passing through a hydrophobic frit and concentrated in vacuo. The product was purified by flash chromatography (SiO$_2$, iHex/EtOAc, 20:1 then 1:1) to afford 2.0 g (100%) as a clear oil. $^1$H NMR (300 MHz, CDCl$_3$) δ 5.67 (dq, J=15.3 Hz, 6.6 Hz, 1H), 5.21 (m, 1H), 4.23 (dd, J=10.6 Hz, 3.3 Hz, 1H), 4.1 (dd, J=10.6 Hz, 6.0 Hz, 1H), 3.52 (dd, J=10.0 Hz, 2.0 Hz, 1H), 3.42 (s, 3H), 3.34 (t, J=9.3 Hz, 1H), 3.25 (s, 3H), 1.96 (m, 1H), 1.78 (dd, J=6.4 Hz, 1.5 Hz, 3H), 1.68 (m, 1H), 1.24 (s, 9H), 0.90 (d, J=7.1 Hz, 3H), 0.76 (d, J=7.1 Hz, 3H).

2,2-Dimethyl-propionic Acid (2S,3S,4R,5R)-3,5-dimethoxy-2,4-dimethyl-6-oxo-hexyl Ester

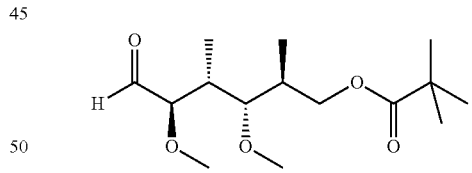

To (2,2-Dimethyl-propionic acid (E)-(2S,3S,4S,5S)-3,5-dimethoxy-2,4-dimethyl-oct-6-enyl ester (2.0 g, 6.94 mmol) in anhydrous dichloromethane (60 ml) at −78° C., ozone was bubbled through until a pale blue colour persisted. Nitrogen was then bubbled through until the solution turned colourless. Triphenylphosphine (2.7 g, 10.4 mmol) was added and the reaction was warmed to room temperature and stirred overnight. The reaction was concentrated in vacuo and the product purified by flash chromatography (SiO$_2$, iHex/EtOAc, 20:1 then 4:1) to afford 1.62 g (81%) as a yellow oil. $^1$H NMR (300 MHz, CDCl$_3$) δ 9.51 (d, J=4.1 Hz, 1H), 4.14 (dd, J=10.8 Hz, 3.3 Hz, 1H), 4.00 (dd, J=10.8 Hz, 5.9 Hz, 1H), 3.36-3.29 (m, 2H), 3.33 (s, 3H), 3.32 (s, 3H), 1.93 (m, 2H), 1.20 (s, 9H), 0.84 (d, J=7.0 Hz, 3H), 0.78 (d, J=7.0 Hz, 3H).

2,2-Dimethyl-propionic Acid (E)-(2S,3S,4S,5S)-3,5-dimethoxy-2,4-dimethyl-nona-6,8-dienyl Ester

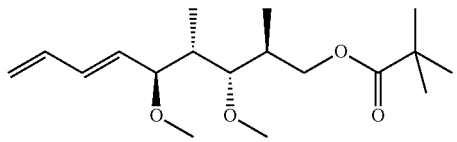 [SMILES: C=C/C=C/[C@H](OC)[C@H](C)[C@@H](OC)[C@@H](C)COC(=O)C(C)(C)C]

To diethylallylphosphonate (1.86 g, 10.4 mmol) in anhydrous THF (25 ml), at −78° C. and under an atmosphere of nitrogen, was slowly added n-Butyllithium (2.5M in hexanes, 4.2 ml, 10.4 mmol) maintaining the temperature below −78° C. The reaction was stirred at −78° C. for 30 minutes after which a solution of (2R,3R,4S,5S)-6-tert-Butoxy-2,4-dimethoxy-3,5-dimethyl-hexanal (2.0 g, 6.9 mmol) and DMPU (distilled over CaH$_2$, 1.7 ml, 13.9 mmol) in anhydrous THF (5 ml) was added. The reaction was allowed to stir at −78° C. for 1 h and then warmed to room temperature and stirred overnight. The reaction was diluted with saturated ammonium chloride and extracted with dichloromethane (2×). The combined organic layers were dried by passing through a hydrophobic frit and concentrated in vacuo. The product was purified by flash chromatography (SiO$_2$, iHex/EtOAc, 20/1) to afford 1.3 g (60%) as a clear oil. $^1$H NMR (300 MHz, CDCl$_3$) δ 6.41 (dt, J=16.8 Hz, 10.4 Hz, 10.2 Hz, 1H), 6.24 (dd, J=15.2 Hz, 10.4 Hz, 1H), 5.47 (dd, J=15.2 Hz, 8.6 Hz, 1H), 5.25 (dd, J=16.8 Hz, 1.5 Hz, 1H), 5.13 (dd, J=9.7 Hz, 1.5 Hz, 1H), 4.23 (dd, J=10.6 Hz, 3.3 Hz, 1H), 4.01 (dd, J=10.6 Hz, 6.0 Hz, 1H), 3.52 (dd, J=10.0 Hz, 2.0 Hz, 1H), 3.43 (s, 3H), 3.43 (m, 1H), 3.27 (s, 3H), 1.96 (m, 1H), 1.72 (m, 1H), 1.24 (s, 9H), 0.90 (d, J=6.9 Hz, 3H), 0.77 (d, J=7.1 Hz, 3H).

(E)-(2S,3S,4S,5S)-3,5-Dimethoxy-2,4-dimethyl-nona-6,8-dien-1-ol

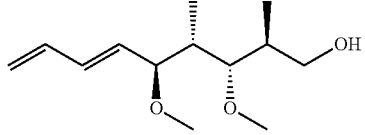 [SMILES: C=C/C=C/[C@H](OC)[C@H](C)[C@@H](OC)[C@@H](C)CO]

To (E)-(5S,6S,7S,8S)-9-tert-Butoxy-5,7-dimethoxy-6,8-dimethyl-nona-1,3-diene (1.3 g, 4.2 mmol) in anhydrous methanol (10 ml) at room temperature and under an atmosphere of nitrogen was added sodium methoxide (30% wt in MeOH, 3.7 ml, 20.8 mmol). The reaction was stirred overnight. A further amount of sodium methoxide (30% wt in MeOH, 3.7 ml, 20.8 mmol) was added and the reaction was stirred for a further 1 hour. The reaction was quenched with saturated ammonium chloride and extracted with dichloromethane (3×). The combined organic layers were dried by passing through a hydrophobic frit and concentrated in vacuo. The product was purified by flash chromatography (SiO$_2$, iHex/EtOAc, 10:1 then 2:1) to afford 2.0 g (100%) as a clear oil. $^1$H NMR (300 MHz, CDCl$_3$) δ 6.40 (dt, J=16.8 Hz, 10.4 Hz, 10.2 Hz, 1H), 6.23 (dd, J=15.2 Hz, 10.4 Hz, 1H), 5.46 (dd, J=15.2 Hz, 8.4 Hz, 1H), 5.26 (dd, J=17.0 Hz, 1.6 Hz, 1H), 5.14 (dd, J=10.2 Hz, 1.6 Hz, 1H), 3.77-3.53 (m, 3H), 3.51 (s, 3H), 3.42 (t, J=9.3 Hz, 1H), 3.27 (s, 3H), 2.75 (dd, J=8.4 Hz, 3.1 Hz, 1H), 1.91 (m, 1H), 1.72 (m, 1H), 0.85 (d, J=7.1 Hz, 3H), 0.80 (d, J=7.1 Hz, 3H).

(E)-(2R,3R,4S,5S)-3,5-Dimethoxy-2,4-dimethyl-nona-6,8-dienal

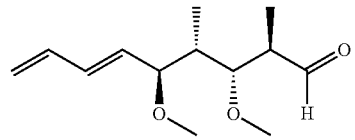 [SMILES: C=C/C=C/[C@H](OC)[C@H](C)[C@@H](OC)[C@@H](C)C=O]

To (E)-(2S,3S,4S,5S)-3,5-Dimethoxy-2,4-dimethyl-nona-6,8-dien-1-ol (1.3 g, 5.70 mmol) in anhydrous dichloromethane (58 ml) at room temperature and under an atmosphere of nitrogen was added activated 4$^A$ molecular sieves (1.3 g), N-methylmorpholine-N-oxide (2.0 g, 17.1 mmol) and TPAP (100 mg, 0.29 mmol). The reaction was stirred for 3 hours and filtered through a SiO$_2$ pad, and the pad washed well with diethyl ether. The filtrate was concentrated in vacuo to afford the product as a clear oil (1.2 g, 93%). $^1$H NMR (300 MHz, CDCl$_3$) δ 9.83 (d, J=2.7 Hz, 1H), 6.40 (dt, J=16.8 Hz, 10.2 Hz, 1H), 6.24 (dd, J=15.2 Hz, 10.6 Hz, 1H), 5.45 (dd, J=15.2 Hz, 8.8 Hz, 1H), 5.26 (dd, J=16.4 Hz, 1.3 Hz, 1H), 5.14 (dd, J=10.2 Hz, 1.6 Hz, 1H), 3.87 (dd, J=9.1 Hz, 2.4 Hz, 1H), 3.41 (m, 1H), 3.43 (s, 3H), 3.26 (s, 3H), 2.62 (m, 1H), 1.70 (m, 1H), 1.00 (d, J=7.1 Hz, 3H), 0.82 (d, J=7.1 Hz, 3H).

(E)-(2R,3R,4S,5S)-3,5-Dimethoxy-2,4-dimethyl-nona-6,8-dienoic Acid (3c)

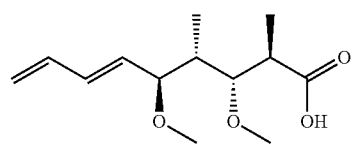

3c

To (E)-(2R,3R,4S,5S)-3,5-Dimethoxy-2,4-dimethyl-nona-6,8-dienal (1.2 g, 5.3 mmol) in tert-butanol (24 ml) and 2-methyl-2-butene (5.6 ml, 53.1 mmol) at room temperature, was added a solution of sodium chlorite (2.4 g, 26.5 mmol) and sodium dihydrogenphosphate (1.5 g, 10.6 mmol) in water (5 ml). The reaction was stirred vigorously for 1.5 hours, after which brine (10 ml) was added and the reaction acidified to pH5 with 2M hydrochloric acid. The reaction was extracted with dichloromethane (3×), the organics dried through a hydrophobic frit and concentrated in vacuo. The oily residue was left on a vacuum pump overnight to afford the product 3c as an orange solid (1.02 g, 79%). $^1$H NMR (300 MHz, CDCl$_3$) δ 6.39 (dt, J=16.7 Hz, 10.3 Hz, 10.0 Hz, 1H), 6.23 (dd, J=14.9 Hz, 10.5 Hz, 1H), 5.45 (dd, J=14.9 Hz, 8.7 Hz, 1H), 5.26 (d, J=16.3 Hz, 1H), 5.14 (d, J=10.3 Hz, 1H), 3.91 (dd, J=9.4 Hz, 1.8 Hz, 1H), 3.46 (s, 3H), 3.43 (m, 1H), 3.26 (s, 3H), 2.67 (m, 1H), 1.71 (m, 1H), 1.13 (d, J=7.1 Hz, 3H), 0.78 (d, J=7.1 Hz, 3H).

Example V

Compound 5: (E)-(5S,11S,14S,17R,18R,19S,20S)-11-(3-Hydroxy-benzyl)-14-isopropyl-18,20-dimethoxy-17,19-dimethyl-3-oxa-9,12,15,28-tetraaza-tricyclo[21.3.1.1*5,9*]octacosa-1(27),21,23,25-tetraene-4,10,13,16-tetraone

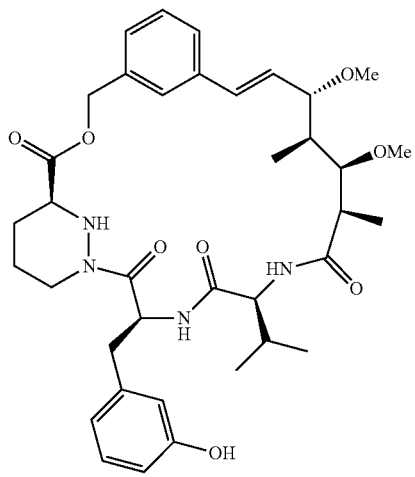

Compound 5

(S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid 3-iodo-benzyl Ester 5a

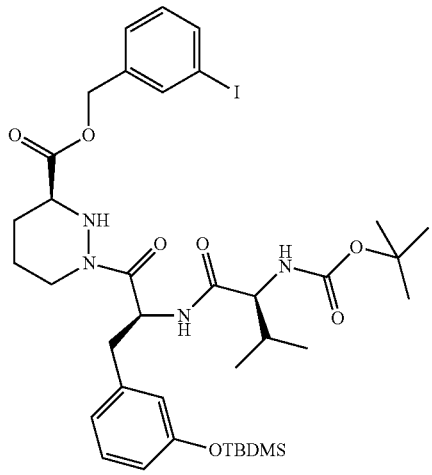

To 2a (1.0 g, 1.36 mmol) in THF (35 ml) at room temperature was added zinc dust (1.90 g, 29.8 mmol) and a solution of ammonium acetate (1.60 g, 20.3 mmol) in water (15 ml). The reaction was stirred for 24 hours and then filtered through celite and the filter pad washed with THF/water. The filtrate was extracted with ethyl acetate. The aqueous was acidified to pH 4-5 with 2M HCl and extracted further with ethyl acetate (2×). The combined organic extracts were dried over $Na_2SO_4$, filtered and concentrated in vacuo. This product was dissolved in dry toluene (30 ml) at room temperature and under an atmosphere of nitrogen was added triethylamine (0.28 ml, 2.03 mmol) followed by 2,4,6-Trichloro-benzoyl chloride (0.23 ml, 1.49 mmol). The reaction was stirred at room temperature for 0.5 hours and then a solution of 3-iodobenzyl alcohol (349 mg, 1.49 mmol) and DMAP (199 mg, 1.63 mmol) in anhydrous toluene (6 ml) was added. The reaction was stirred for 2 hours then brine was added and extracted with dichloromethane (3×). The combined organics were dried through a hydrophobic frit and concentrated in vacuo. The product was purified by flash chromatography ($SiO_2$, iHex/EtOAc, 3:1 then 2:1) to afford 5a 410 mg (37%) as a white solid. $^1$H NMR (300 MHz, $CDCl_3$) δ 7.51 (m, 2H), 7.13 (m, 1H), 6.95 (m, 1H), 6.87 (m, 1H), 6.63 (m, 1H), 6.56-6.46 (m, 2H), 6.33 (m, 1H), 5.57 (m, 1H), 4.94-4.83 (m, 3H), 4.09 (m, 1H), 3.77 (m, 1H), 3.36-3.19 (m, 1H), 2.85-2.54 (m, 3H), 2.28 (m, 1H), 1.95 (m, 1H), 1.69-1.52 (m, 2H), 1.33 (m, 1H), 1.26 (s, 9H), 0.83-0.64 (m, 15H), 0.03-0.02 (m, 6H). LCMS (m/z) 823.44 [M+H], Tr=6.01 min.

(S)-1-{(S)-3-[3-(tert-Butyl-dimethyl-silanyloxy)-phenyl]-2-[(S)-2-((E)-(2R,3R,4R,5R)-3,5-dimethoxy-2,4-dimethyl-7-tributylstannanyl-hept-6-enoylamino)-3-methylbutyrylamino]-propionyl}-hexahydro-pyridazine-3-carboxylic Acid 3-iodo-benzyl Ester (5c)

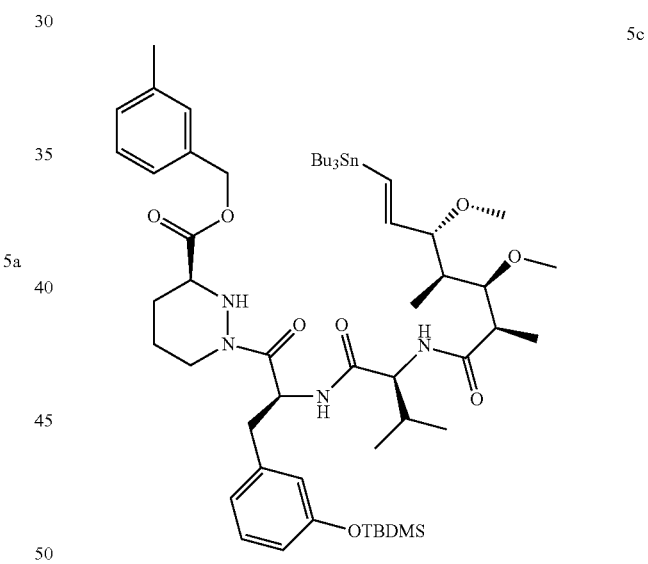

5c

To (E)-(2R,3R,4R,5R)-3,5-Dimethoxy-2,4-dimethyl-7-tributylstannanyl-hept-6-enoic acid (5b) (85 mg, 0.17 mmol) in anhydrous DMF (1.1 ml) at 0° C. and under an atmosphere of nitrogen was added Diisopropylethylamine (0.12 ml, 0.67 mmol), followed by HATU (64 mg, 0.17 mmol). The reaction was stirred for 1.5 hours after which a solution of (S)-1-{(S)-2-((S)-2-tert-Butoxycarbonylamino-3-methyl-butyrylamino)-3-[(tert-butyl-dimethyl-silanyloxy)-phenyl]-propionyl}-hexahydro-pyridazine-3-carboxylic acid 3-iodo-benzyl ester (134 mg, 0.19 mmol) in anhydrous DMF (1.1 ml) was added. The reaction was warmed to room temperature, stirred for 16 hours and quenched with pH7 buffer. The reaction was extracted with dichloromethane (3×), the organics dried through a hydrophobic frit and concentrated in vacuo. The product was purified by flash chromatography ($SiO_2$, iHex/EtOAc, 2:1) to afford 5c 100 mg (57%) as a viscous oil.

¹H NMR (300 MHz, CDCl₃) δ 7.52 (m, 2H), 7.14 (d, J=7.6 Hz, 1H), 6.96 (t, J=7.6 Hz, 1H), 6.87 (t, J=7.6 Hz, 1H), 6.63 (m, 1H), 6.51 (m, 3H), 6.31 (t, J=8.8 Hz, 1H), 6.08 (d, J=8.5 Hz, 1H), 5.96 (d, J=19 Hz, 1H), 5.56 (m, 1H), 5.50 (dd, J=19 Hz, 7.9 Hz, 1H), 4.89 (m, 2H), 4.12 (m, 2H), 3.68 (d, J=9.4 Hz, 1H), 3.34 (d, J=10.5 Hz, 1H), 3.22 (s, 3H), 3.14 (t, J=8.8 Hz, 1H), 3.07 (s, 3H), 2.83-2.60 (m, 3H), 2.30 (m, 1H), 2.20 (m, 1H), 1.97 (m, 1H), 1.71-1.47 (m, 4H), 1.33 (m, 6H), 1.15 (m, 6H), 0.89 (d, J=7.0 Hz, 3H), 0.82-0.69 (m, 30H), 0.60 (d, J=7.0 Hz, 3H), 0.006 (m, 6H). LCMS (m/z) 1211.48 [M+H], Tr=7.29 min.

(E)-(5S,11S,14S,17R,18R,19S,20S)-11-(3-Hydroxybenzyl)-14-isopropyl-18,20-dimethoxy-17,19-dimethyl-3-oxa-9,12,15,28-tetraaza-tricyclo[21.3.1.1*5,9*]octacosa-1(27),21,23,25-tetraene-4,10,13,16-tetraone (5)

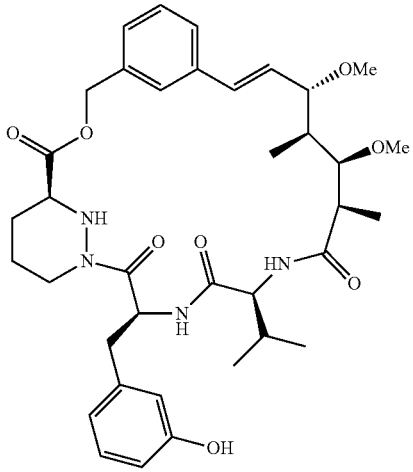

To 5c (100 mg, 0.1 mmol) in anhydrous DMF (57 ml) at room temperature and under an atmosphere of nitrogen was added diisopropylethylamine (0.17 ml, 1.0 mmol), triphenylarsine (22 mg, 0.07 mmol) and Pd₂(dba)₃.CHCl₃ (20 mg, 0.02 mmol). The solution was degassed by 2 freeze thawing cycles under vacuum. The reaction flask was covered with foil and allowed to stir for 48 hours. The reaction mixture was filtered through a short pad of silica and concentrated in vacuo. To the resulting residue was added anhydrous THF (5 ml) and cooled to 0° C. A solution of TBAF (0.5 ml, 0.49 mmol, 1.0 M in THF) was added and the reaction stirred at 0° C. for 0.5 hours and then room temperature for 1 hour. The reaction was concentrated in vacuo and the product purified by flash chromatography (SiO₂, iHex/EtOAc, 1:0 to 0:1). The product was further purified by preparative TLC (SiO₂, EtOAc) to afford 5 (10 mg). ¹H NMR (300 MHz, d₆-DMSO) δ9.16 (br s, 1H), 7.99 (d, J=8.2 Hz, 1H), 7.54 (s, 1H), 7.36 (d, J=4.7 Hz, 2H), 7.28-7.23 (m, 1H), 7.06 (d, J=8.7 Hz, 1H), 6.60-6.49 (m, 3H), 6.47-6.41 (m, 1H), 5.96 (dd, J=8.7, 15.6 Hz, 1H), 5.56 (app q, J=6.9 Hz, 1H), 5.17 (app q, J=16.5 Hz, 2H), 5.11 (dd, J=4.0, 11.4 Hz, 1H), 4.10 (app t, J=8.2 Hz, 1H), 3.65 (br d, J=4.9 Hz, 1H), 3.17 (s, 3H), 3.08 (s, 3H), 2.81-2.59 (m, 5H), 2.30-2.25 (m, 1H), 1.99-1.63 (m, 4H), 1.58-1.45 (m, 2H), 1.42-1.29 (m, 1H), 1.12 (d, J=7.6 Hz, 3H), 0.99-0.90 (m, 1H), 0.84 (d, J=6.7 Hz, 3H), 0.80 (d, J=6.7 Hz, 3H), 0.70 (d, J=6.9 Hz, 3H). LCMS (m/z) 701.44 [M+Na], Tr=5.05 min.

Preparation of (E)-(2R,3R,4R,5R)-3,5-Dimethoxy-2,4-dimethyl-7-tributylstannanyl-hept-6-enoic Acid (5b)

2,2-Dimethyl-propionic Acid (2S,3S,4R,5R)-3,5-dimethoxy-2,4-dimethyl-hept-6-ynyl Ester

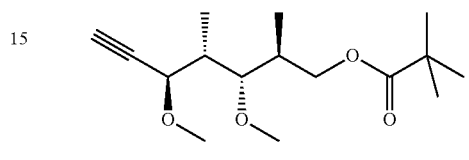

To 2,2-Dimethyl-propionic acid (2S,3S,4R,5R)-3,5-dimethoxy-2,4-dimethyl-6-oxo-hexyl ester (2.0 g, 6.94 mmol) in anhydrous methanol (100 ml) at 0° C. and under an atmosphere of nitrogen was added diethyl 1-diazo-2-oxopropylphosphonate (1.6 ml, 10.4 mmol) and potassium carbonate (1.44 g, 10.4 mmol). The reaction was stirred at 0° C. for 1 hour and then room temperature for 2 hours, after which it was quenched with saturated ammonium chloride and extracted with diethyl ether (3×). The combined organic layers were dried over magnesium sulphate, filtered and concentrated in vacuo. The product was purified by flash chromatography (SiO₂, iHex/EtOAc, 15:1) to afford 1.67 g (85%) as a clear oil. ¹H NMR (300 MHz, CDCl₃) δ 4.22 (dd, J=10.7 Hz, 3.6 Hz, 1H), 4.07 (dd, J=10.7 Hz, 5.8 Hz, 1H), 3.87 (dd, J=9.6 Hz, 2.0 Hz, 1H), 3.46 (s, 3H), 3.44 (m, 1H), 3.40 (s, 3H), 2.48 (d, J=2.0 Hz, 1H), 1.97 (m, 2H), 1.23 (s, 9H), 1.00 (d, J=6.9 Hz, 3H), 0.92 (d, J=6.9 Hz, 3H).

(2S,3S,4R,5R)-3,5-Dimethoxy-2,4-dimethyl-hept-6-yn-1-ol

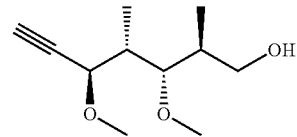

To 2,2-Dimethyl-propionic acid (2S,3S,4R,5R)-3,5-dimethoxy-2,4-dimethyl-hept-6-ynyl ester (750 mg, 2.64 mmol) in anhydrous methanol (10 ml) at room temperature and under an atmosphere of nitrogen was added sodium methoxide (30% wt in MeOH, 3.8 ml, 21.1 mmol). The reaction was stirred overnight, quenched with saturated ammonium chloride and extracted with dichloromethane (3×). The combined organic layers were dried by passing through a hydrophobic frit and concentrated in vacuo. The product was purified by flash chromatography (SiO₂, iHex/EtOAc, 6:1 then 2:1) to afford 500 mg (94%) as a clear oil. ¹H NMR (300 MHz, CDCl₃) δ 3.86 (dd, J=9.4 Hz, 2.1 Hz, 1H), 3.75-3.60 (m, 2H), 3.49 (s, 3H), 3.48 (m, 1H), 3.46 (s, 3H), 2.59 (m, 1H), 2.49 (d, J=2.1 Hz, 1H), 2.03-1.84 (m, 2H), 1.04 (d, J=7.0 Hz, 3H), 0.90 (d, J=7.0 Hz, 3H).

(E)-(2S,3S,4R,5R)-3,5-Dimethoxy-2,4-dimethyl-7-tributylstannanyl-hept-6-en-1-ol

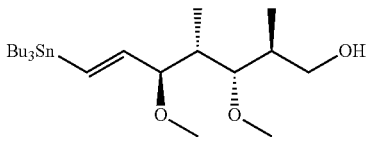

To (2S,3S,4R,5R)-3,5-Dimethoxy-2,4-dimethyl-hept-6-yn-1-ol (500 mg, 2.49 mmol) in dry dichloromethane (25 ml) at room temperature and under an atmosphere of nitrogen was added (PPh$_3$)$_2$PdCl$_2$ (887 mg, 0.12 mmol), followed by dropwise addition of tributyltinstannane (2.0 ml, 7.46 mmol) over 5 minutes. The reaction was stirred for 1 hour, concentrated in vacuo and the product was purified by flash chromatography (SiO$_2$, iHex/EtOAc, 40:1 then 4:1) to afford 812 mg (66%) as a yellow oil. $^1$H NMR (300 MHz, CDCl$_3$) δ 6.13 (d, J=19.3 Hz, 1H), 5.64 (dd, J=19.3 Hz, 8.2 Hz, 1H), 3.66 (m, 1H), 3.63-3.51 (m, 2H), 3.48 (s, 3H), 3.28 (m, 1H), 3.25 (s, 3H), 2.83 (m, 1H), 1.90 (m, 1H), 1.68 (m, 1H), 1.51 (m, 6H), 1.30 (m, 6H), 0.88

(E)-(2R,3R,4R,5R)-3,5-Dimethoxy-2,4-dimethyl-7-tributylstannanyl-hept-6-enal

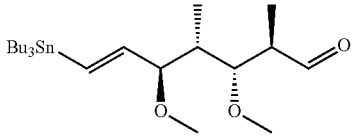

To (E)-(2S,3S,4R,5R)-3,5-Dimethoxy-2,4-dimethyl-7-tributylstannanyl-hept-6-en-1-ol (100 mg, 0.2 mmol) in anhydrous dichloromethane (2 ml) at room temperature and under an atmosphere of nitrogen was added activated 4$^A$ molecular sieves (50 mg), N-methylmorpholine-N-oxide (71 mg, 0.61 mmol) and TPAP (3.6 mg, 0.01 mmol). The reaction was stirred for 30 minutes and filtered through a SiO$_2$ pad, and the pad washed well with diethyl ether. The filtrate was concentrated in vacuo to afford the product as a clear oil (98 mg, 100%). $^1$H NMR (300 MHz, CDCl$_3$) δ 9.74 (d, J=2.6 Hz, 1H), 6.08 (d, J=19.0 Hz, 1H), 5.58 (dd, J=19.0 Hz, 8.2 Hz, 1H), 3.77 (dd, J=9.1 Hz, 2.3 Hz, 1H), 3.34 (s, 3H), 3.25 (t, J=9.3 Hz, 1H), 3.18 (s, 3H), 2.54 (m, 1H), 1.59 (m, 1H), 1.44 (m, 6H), 1.24 (m, 6H), 0.93 (d, J=7.0 Hz, 3H), 0.82 (m, 15H), 0.75 (d, J=7.0 Hz, 3H).

(E)-(2R,3R,4R,5R)-3,5-Dimethoxy-2,4-dimethyl-7-tributylstannanyl-hept-6-enoic Acid (5b)

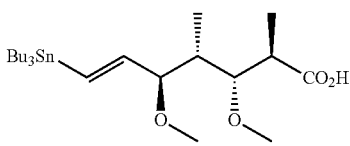

To (E)-(2R,3R,4R,5R)-3,5-Dimethoxy-2,4-dimethyl-7-tributylstannanyl-hept-6-enal (98 mg, 0.2 mmol) in tert-butanol (2 ml) and 2-methyl-2-butene (0.22 ml, 2.03 mmol) at room temperature, was added a solution of sodium chlorite (92 mg, 1.02 mmol) and sodium dihydrogenphosphate (58 mg, 0.41 mmol) in water (0.5 ml). The reaction was stirred vigorously overnight, after which brine was added and then extracted with dichloromethane (2x). The organics were dried through a hydrophobic frit and concentrated in vacuo. The oily residue was left on a vacuum pump overnight to afford the product 5b as a solid (91 mg, 90%). $^1$H NMR (300 MHz, CDCl$_3$) δ 6.05 (d, J=19.0 Hz, 1H), 5.58 (dd, J=19.0 Hz, 7.9 Hz, 1H), 3.72 (m, 1H), 3.38 (s, 3H), 3.23 (t, J=8.8 Hz, 1H), 3.16 (s, 3H), 2.52 (m, 1H), 1.61 (m, 1H), 1.43 (m, 6H), 1.24 (m, 6H), 1.01 (d, J=7.0 Hz, 3H), 0.82 (m, 15H), 0.71 (d, J=7.0 Hz, 3H).

Example VIII

Compound 8: (E)-(8S,14S,17S,20R,21S)-21-Hydroxy-14-(3-hydroxy-benzyl)-17-isopropyl-20-methyl-6-oxa-12,15,18,27-tetraaza-tricyclo[20.2.2.1*8,12*]heptacosa-1(25),2,22(26),23-tetraene-7,13,16,19-tetraone

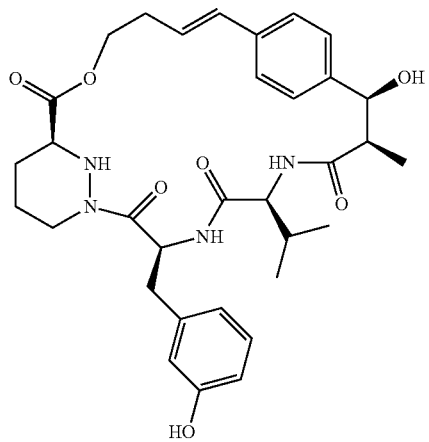

Compound 8

(2R,3S)-1-((R)-10,10-Dimethyl-3,3-dioxo-3-thia-4-aza-tricyclo[5.2.1]dec-4-yl)-3-(tert-butyl-dimethyl-silanyloxy)-2-methyl-3-(4-vinyl-phenyl)-propionamide (8a)

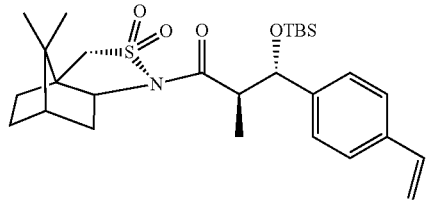

8a

A 1M solution of 4-vinyl-benzaldehyde in DCM (4.5 ml) was treated with calcium hydride (large spatula tip) and the resulting suspension was stirred at room temperature for 3 days (necessary to remove hydrate). To a separate flask containing a stirred solution of N-propionyl-sultam (750 mg, 2.76 mmol) in dry DCM (3 ml) was added calcium hydride (small spatula tip), triethylamine (462 µl, 3.3 mmol) and tert-butyldimethylsilyl trifluoromethanesulfonate (950 µl, 4.14 mmol). The resulting mixture was stirred for 20 h at room temperature before cooling to −40° C., whereupon the pre-dried 1M solution of 4-vinyl-benzaldehyde in DCM (3.3 ml) was added. Stirring was continued for 1 h at −40° C. before the reaction was quenched with a saturated solution of ammonium chloride (5 ml). The organic layer was separated and the aqueous layer washed with DCM (2×10 ml). The combined organics were dried ($MgSO_4$), filtered and concentrated. Flash-column chromatography (10 to 20% gradient of ethylacetate in iso-hexane) of the residue gave 8a (561 mg, 40% yield) as a syrup. LCMS (m/z) 540.3 [M−H], Tr=6.0 min. $^1$H NMR (300 MHz, $CDCl_3$) δ 7.37 and 7.29 (2×d, J=8.2 Hz, 4H), 6.71 (dd, J=10.8, 17.5 Hz, 1H), 5.75 (d, J=17.7 Hz, 1H), 5.25 (d, J=10.9 Hz, 1H), 4.83 (d, J=8.6 Hz, 1H), 3.92 (dd, J=7.5, 4.9 Hz, 1H), 3.51 (q, $J_{a,b}$=13.7 Hz, 2H), 3.39 (m, 1H), 2.23 (m, 1H), 2.11 (m, 1H), 1.90 (m, 3H), 1.40 (m, 2H), 1.22 and 1.99 (2×s, 6H), 0.90 (q, J=6.9 and 8.2 Hz, 3H), 0.80 (s, 9H), −0.05 and −0.26 (2×s, 6H).

(2R,3S)-3-(tert-Butyl-dimethyl-silanyloxy)-2-methyl-3-(4-vinyl-phenyl)-propionic Acid (8b)

To a solution of 8a (600 mg, 1.16 mmol) in THF (20 ml) was added 2M lithium hydroxide and the resulting biphasic mixture was stirred at 85° C. for 48 h. The THF layer was removed under a stream of nitrogen and the remaining aqueous layer was acidified to pH 1 with 2M HCl. The aqueous layer was extracted with ethylacetate (2×50 ml); the combined organic layers were dried ($MgSO_4$), filtered and concentrated. The syrup-like residue was treated with pentane, filtered and the filtrate was concentrated. Flash-column chromatography (20 to 30% gradient of ethylacetate in iso-hexane) of the residue gave 8b (86 mg, 23% yield) as a syrup. LCMS (m/z) 319.1 [M−H], Tr=5.7 min. $^1$H NMR (300 MHz, $CDCl_3$) δ 7.34 and 7.25 (2×d, J=8.3 Hz, 4H), 6.68 (dd, J=10.9, 17.6 Hz, 1H), 5.74 (d, J=17.6 Hz, 1H), 5.23 (d, J=10.9 Hz, 1H), 4.71 (d, J=8.9 Hz, 1H), 2.72 (m, 1H), 0.90 (d, J=6.9 Hz, 3H), 0.80 (s, 9H), 0.02 and −0.27 (2×s, 6H).

(S)-1-{(S)-2-{(S)-2-[(2R,3S)-3-(tert-Butyl-dimethyl-silanyloxy)-2-methyl-3-(4-vinyl-phenyl)-propionylamino]-3-methyl-butyrylamino}-3-[3-(tert-butyl-dimethyl-silanyloxy)-phenyl]-propionyl}-hexahydropyridazine-3-carboxylic Acid but-3-enyl Ester (8c)

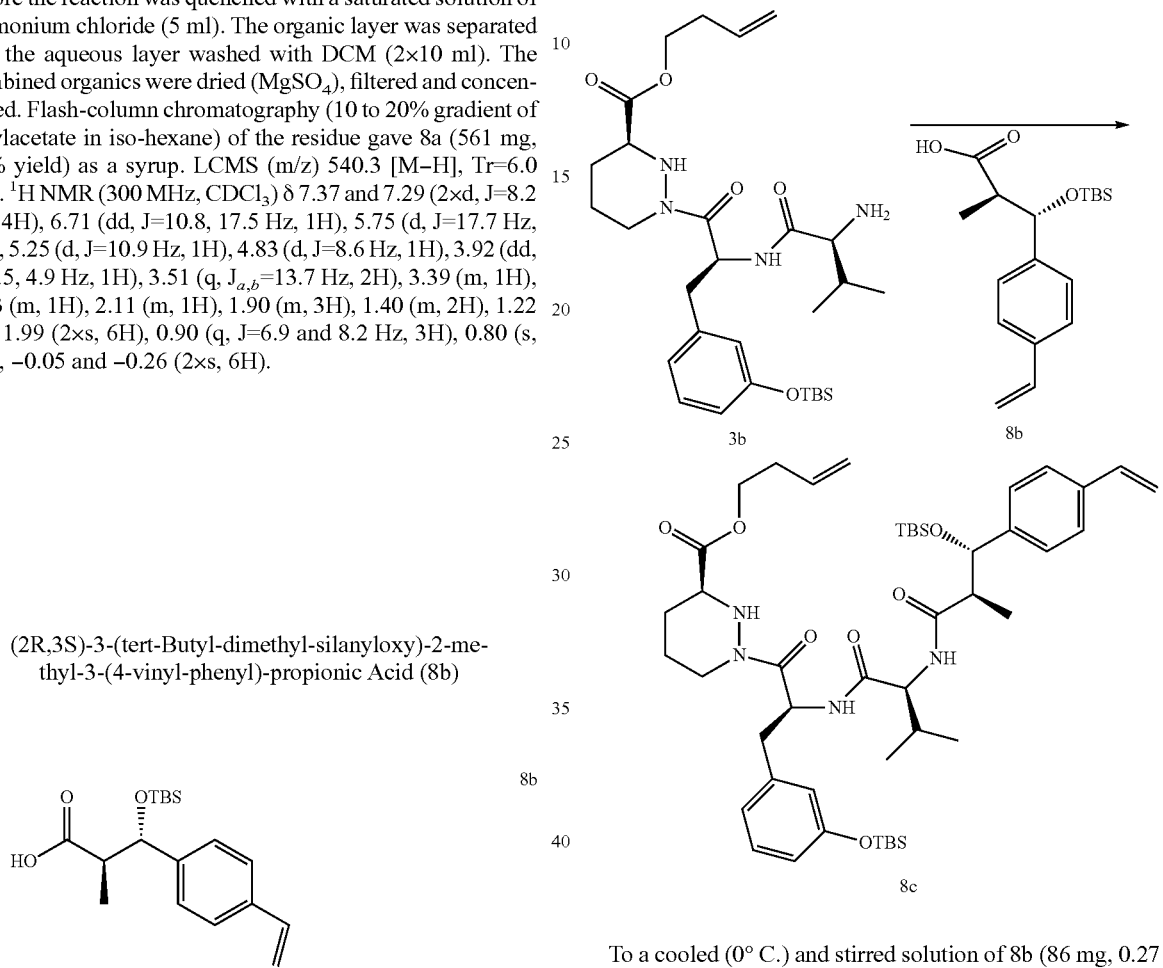

To a cooled (0° C.) and stirred solution of 8b (86 mg, 0.27 mmol) in DMF (2 ml) under nitrogen was added HATU (102 mg, 0.27 mmol) and DIPEA (209 µl, 1.2 mmol). The resulting solution was stirred at 0° C. for 20 min before a solution of 3b (0.3 mmol) in DMF (2 ml) was added and the resulting mixture was stirred at room temperature for 18 h. The reaction mixture was partitioned between 1M phosphate buffer (pH 7) (20 ml) and DCM (20 ml) and the aqueous layer extracted with DCM (4×10 ml). The combined organics were dried ($MgSO_4$), filtered and concentrated; toluene was evaporated (3×20 ml) from the residue to remove any remaining DMF. Flash-column chromatography (40 to 50% gradient of ethylacetate in iso-hexane) of the residue gave 8c (170 mg, 73% yield) as a foam. LCMS (m/z) 863.6 [M+H], Tr=6.3 min $^1$H NMR δ (300 MHz, $CDCl_3$) 7.16 and 7.09 (2×d, J=8.3 Hz, 4H), 6.92 (t, J=7.81 Hz, 1H), 6.60 (brd, J=7.6 Hz, 1H), 6.46 (m, 4H), 6.29 (d, J=8.0 Hz, 1H), 5.56 (m, 3H), 4.96 (m, 3H), 4.62 (d, J=6.7 Hz, 1H), 4.11 (brd, J=13.2 Hz, 1H), 3.99 (m, 3H), 3.37 (d, J=11.2 Hz, 1H), 2.75 (dd, J=12.9, 5.1 Hz, 1H), 2.63 (dd, J=12.9, 9.1 Hz, 1H), 2.55 (m, 1H), 2.35 (m, 1H), 2.22 (m, 2H), 1.90 (m, 1H), 1.60 (m, 2H), 1.27 (m, 2H), 1.10 (m, 1H), 0.85 (d, J=7.1 Hz, 3H), 0.80 (s, 18H), 0.70 (s, 6H), 0.00 (s, 6H), −0.14 and −0.35 (2×s, 6H).

(E)-(8S,14S,17S,20R,21S)-21-(t-Butyl-dimethyl-silanyloxy)-14-[3-(t-butyl-dimethyl-silanyloxy)-benzyl]-17-isopropyl-20-methyl-6-oxa-12,15,18,27-tetraaza-tricyclo[20.2.2.1*8,12*]heptacosa-1(25),2,22(26),23-tetraene-7,13,16,19-tetraone (8d)

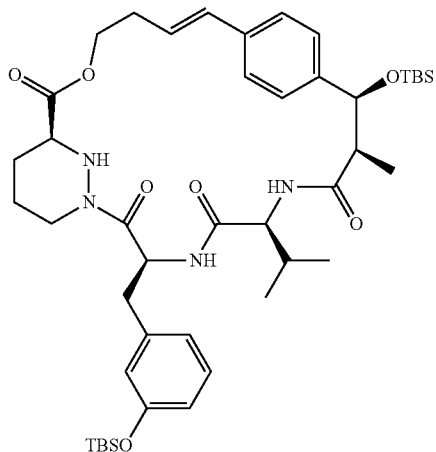

8d

A stirred solution of 8c (85 mg, 0.10 mmol.) in dichloromethane (45 ml) was prepared and Grubbs catalyst 1$^{st}$ generation (24.6 mg, 0.03 mmol.) was added. The reaction was heated at reflux for 40 hours then maintained at room temperature for 36 hours. Silica gel was added to the reaction, which was then evaporated to dryness. The material was loaded onto a silica column, which was eluted with 25% ethyl acetate, 75% hexane then 50% ethyl acetate 50% hexane to yield 8d as a brown gum (44 mg). LCMS (m/z) 855.62 [M+H] Tr=6.24 min $^1$H NMR δ (300 MHz NMR, CDCl$_3$) 0.00-0.02 (m, 12H), 0.65-0.85 (m, 18H), 0.95-1.33 (m, 2H), 1.41-1.96 (m, 8H) 2.04-2.18 (m, 1H), 2.20-2.52 (m, 6H), 2.55-2.70 (m, 1H), 3.43-3.78 (m, 2H), 3.85-3.95 (m, 1H), 4.25-4.38 (m, 1H), 4.42-4.55 (m, 1H), 4.98-5.08 (m, 1H) 5.78-5.92 (m, 1H), 6.15-6.20 (m, 1H) 6.23-6.58 (m, 5H) 6.88-7.13 (m, 8H).

(E)-(8S,14S,17S,20R,21S)-21-Hydroxy-14-(3-hydroxy-benzyl)-17-isopropyl-20-methyl-6-oxa-12,15,18,27-tetraaza-tricyclo[20.2.2.1*8,12*]heptacosa-1(25),2,22(26),23-tetraene-7,13,16,19-tetraone (8)

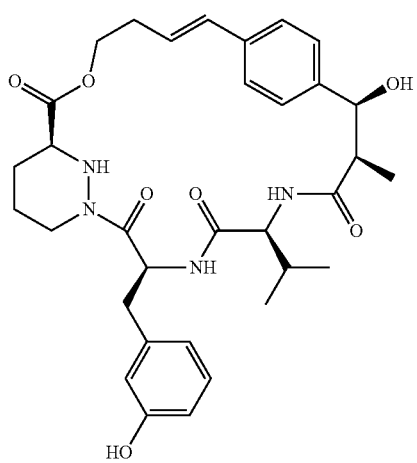

8

A stirred solution of 8d (90 mg, 0.108 mmol.) in anhydrous tetrahydrofuran (30 ml) was cooled over an ice bath before adding a solution of tetra-n-butylammonium fluoride (1M in tetrahydrofuran, 1.08 ml, 1.08 mmol.). The reaction was warmed to room temperature and stirred for 1 hour before adding saturated sodium bicarbonate solution (25 ml). The mixture was extracted with ethylacetate (2×25 ml). The extract was dried over anhydrous sodium sulfate, filtered and evaporated to give a brown gum. The gum was purified on a silica column eluting with ethyl acetate to yield 8 as a white solid (27 mg) LCMS. (m/z) 607.27 [M+H] Tr=4.21 min $^1$H NMR δ (300 MHz NMR, CDCl$_3$) 1.12-1.28 (m, 6H), 1.31-1.39 (d, 3H, J=7.1 Hz), 1.44-1.60 (m, 3H), 1.71-2.13 (m, 3H) 2.14-2.28 (m, 1H), 2.38-2.70 (m, 4H), 2.81-2.91 (m, 1H), 2.91-3.08 (m, 1H), 3.61-3.70 (d, 1H), 4.12-4.21 (m, 1H), 4.32-4.46 (m, 2H), 4.81-4.89 (s, 1H) 5.07-5.18 (q, 1H, J=6.5 Hz), 5.90-6.05 (m, 1H) 6.15-6.33 (m, 3H) 6.37-6.44 (d, 1H) 6.61-6.70 (m, 1H) 6.95-7.72 (m, 7H) 7.80-8.05 (bs, 1H).

Example IX

Compound 9: (8S,14S,17S,20R,21S)-21-Hydroxy-14-(3-hydroxy-benzyl)-17-isopropyl-20-methyl-6-oxa-12,15,18,27-tetraaza-tricyclo[20.2.2.1*8,12*]heptacosa-1(25),22(26),23-triene-7,13,16,19-tetraone

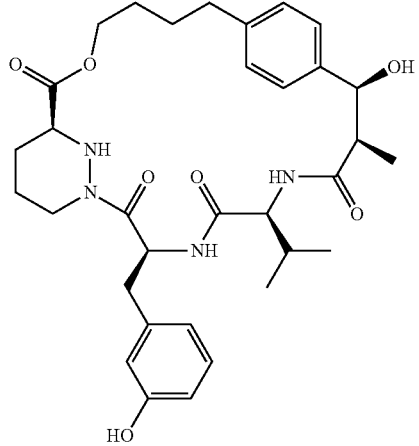

Compound 9

A solution of 8 (10 mg, 16.5 umol.) in ethanol (2 ml) was added to a flask containing 10% palladium on carbon (5 mg). The mixture was placed under a hydrogen atmosphere and stirred at room temperature for 2.5 hours. The mixture was filtered through hyflo-super-cel then evaporated to give a white solid. The solid was redissolved in ethyl acetate and filtered through a pad of silica. The solvent was evaporated and the resultant gum was dried under vacuum to yield 9 as an amorphous solid (6 mg). LCMS (m/z) 609.39 [M+H] Tr=4.25 min $^1$H NMR δ (300 MHz NMR, CDCl$_3$) 0.65-1.05 (m, 6H), 1.05-2.25 (m, 16H), 2.30-2.79 (m, 5H), 2.80-3.05 (m, 1H), 3.05-3.29 (m, 1H), 3.58-3.83 (m, 1H), 3.95-4.13 (m, 1H), 4.18-4.55 (m, 3H), 4.90-5.07 (s, 1H), 5.42-5.60 (m, 1H), 6.40-6.88 (m, 3H), 6.96-7.45 (m, 5H).

Example X

Compound 10: (E)-(5S,11S,14S,17R,18R)-11-(3-Hydroxy-benzyl)-14-isopropyl-18-methoxy-17-methyl-3-oxa-9,12,15,28-tetraaza-tricyclo[21.3.1.1*5,9*]octacosa-1(27),21,23,25-tetraene-4,10,13,16-tetraone Compound 10

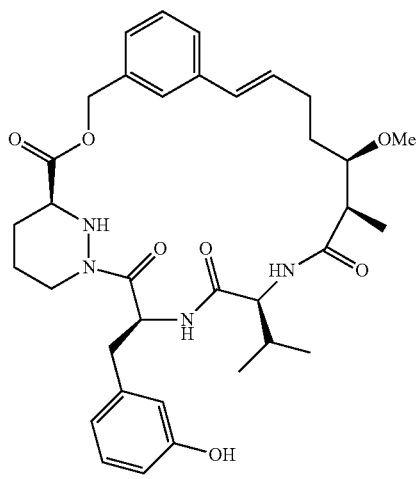

(S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid 3-vinyl-benzyl Ester (10a)

10a

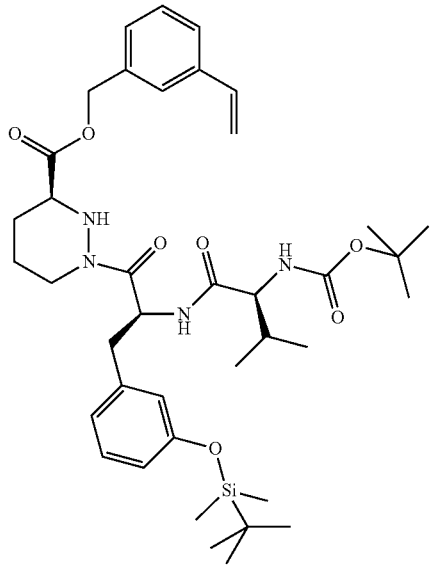

To (3-Vinyl-phenyl)-methanol (1.9 g, 14.2 mmol) in THF (12 ml) at room temperature and under an atmosphere of nitrogen was added 2a (2.6 g, 3.54 mmol), followed by sodium hydride (60%, 28 mg, 0.71 mmol). The reaction was warmed to 40° C. for 6 hours. After cooling to room temperature water was added and the reaction extracted with dichloromethane (×2). The combined organic layers were dried through a hydrophobic frit and concentrated in vacuo. The product was purified by flash chromatography (SiO$_2$, iHex/EtOAc, 2:1 then 1:2) to afford 10a 1.5 g (59%) as a viscous clear oil, that forms a white foam when placed under vacuum. $^1$H NMR (300 MHz, CDCl$_3$) δ 7.39 (m, 3H), 7.26 (m, 1H), 7.03 (m, 1H), 6.80 (m, 1H), 6.71 (m, 1H), 6.67 (m, 2H), 6.50 (m, 1H), 5.79 (d, J=17.4 Hz, 1H), 5.76 (m, 1H), 5.31 (d, J=10.7 Hz, 1H), 5.15 (m, 2H), 5.09 (m, 1H), 4.29 (m, 1H), 3.96 (m, 1H), 3.55 (m, 1H), 3.03-2.81 (m, 2H), 2.76 (m, 1H), 2.52 (m, 1H), 2.12 (m, 1H), 1.90-1.71 (m, 2H), 1.49 (m, 2H). 1.47 (s, 9H), 1.0-0.8 (m, 15H), 0.18 (s, 6H). LCMS (m/z) 723.48 [M+H], Tr=5.64 min (2R,3R)-1-((1R,5S)-10,10-Dimethyl-3,3-dioxo-3lambda*6*-thia-4-aza-tricyclo[5.2.1.0*1,5*]dec-4-yl)-3-hydroxy-2-methyl-hept-6-en-1-one (10b)

10b

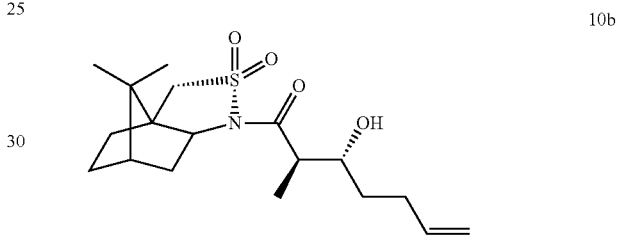

A solution of 1-((1R,5S)-10,10-dimethyl-3,3-dioxo-3lambda*6*-thia-4-aza-tricyclo[5.2.1.0*1,5*]dec-4-yl)-propan-1-one (3.95 g, 14.55 mmol.) in toluene (50 ml) was prepared, then evaporated to dryness. This process was repeated and then the resulting white solid was dissolved in anhydrous dichloromethane (16 ml). A small quantity of calcium hydride was added before adding tert-butyldimethylsilyl trifluoromethanesulfonate (3.83 ml, 14.5 mmol.), then anhydrous triethylamine (2.33 ml, 16.7 mmol.). The reaction mixture was stirred at room temperature under a nitrogen atmosphere for 15 hours. The resulting solution was evaporated to yield a thick paste, which was re-dissolved in anhydrous dichloromethane (15 ml) and added dropwise to a stirred solution of 4-pentenal (2.69 g, 32.0 mmol.) and titanium tetrachloride (1M in dichloromethane, 32 ml, 32 mmol.) in anhydrous dichloromethane (20 ml) at −78° C., under a nitrogen atmosphere. The reaction was stirred at −78° C. for 30 minutes before diluting with saturated aqueous ammonium chloride solution (100 ml). The layers were separated and the aqueous layer was extracted with further dichloromethane (2×50 ml). The combined extract was dried over sodium sulfate, filtered and evaporated to give a brown gum. This was purified on a silica column eluting with 20% ethyl acetate, 80% hexane to yield 10b as a colourless gum (3.09 g, 60%). $^1$H NMR δ (300 MHz NMR, CDCl$_3$) 0.98-1.00 (s, 3H), 1.18-1.20 (s, 3H), 1.23-1.27 (d, 3H J=6.7 Hz), 1.31-1.55 (m, 3H), 1.63-1.76 (m, 1H), 1.84-2.01 (m, 3H), 2.08-2.53 (m, 5H), 3.15-3.26 (m, 1H), 3.42-3.59 (dd, 2H J=13.8, 26.3), 3.61-3.73 (bs, 1H), 3.88-3.95 (dd, 1H, J=5.13, 7.59), 4.94-5.00 (m, 2H), 5.74-5.90 (m, 1H). LCMS (m/z) 356.17 [M+H] Tr=3.41 min.

(2R,3R)-1-((1R,5S)-10,10-Dimethyl-3,3-dioxo-3lambda*6*-thia-4-aza-tricyclo[5.2.1.0*1,5*]dec-4-yl)-3-methoxy-2-methyl-hept-6-en-1-one (10c)

(S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid 3-vinyl-benzyl Ester (10e)

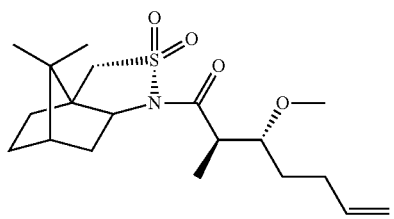

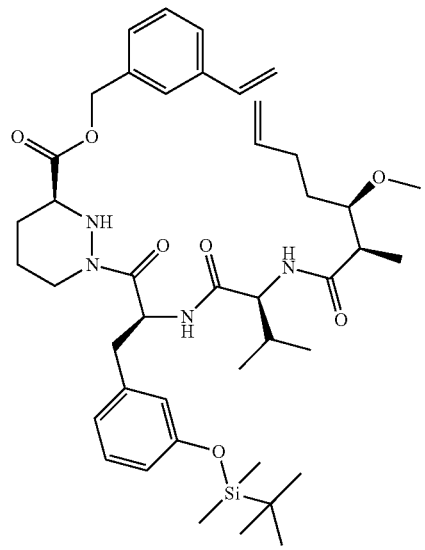

A solution of 10b (250 mg, 0.703 mmol.) in anhydrous dichloromethane (7 ml) was prepared and proton sponge (452 mg, 0.703 mmol.) was added in anhydrous dichloromethane (7 ml). Trimethyloxonium tetrafluoroborate (208 mg, 1.406 mmol.) was added. The reaction mixture was stirred at room temperature for 15 hours. The reaction mixture was the treated with methanol (1 ml), then 2M hydrochloric acid (20 ml) and saturated brine (20 ml). The mixture was extracted with ethyl acetate (3×15 ml) and the extract was dried over sodium sulfate, filtered and evaporated to give a yellow gum. The gum was purified on a silica column eluting with 25% ethyl acetate, 75% hexane to give 10c as a colourless gum (223 mg, 86%). $^1$H NMR δ (300 MHz NMR, CDCl$_3$) 0.96-0.98 (s, 3H), 1.07-1.12 (d, 3H, J=6.7 Hz), 1.17-1.20 (s, 3H), 1.30-1.45 (m, 2H) 1.48-1.60 (m, 2H), 1.81-1.98 (m, 4H), 2.00-2.27 (m, 5H), 3.31-3.34 (s, 1H), 3.34-3.56 (m, 4H), 3.86-3.92 (dd, 1H, J=5.13, 7.37), 4.91-5.06 (m, 2H), 5.70-5.86 (m, 1H). LCMS (m/z) 370.22 [M+H] Tr=3.69 min.

(2R,3R)-3-Methoxy-2-methylhept-6-enoic Acid (10d)

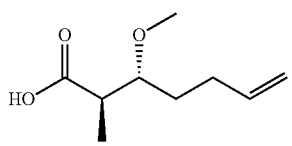

A solution of 2M lithium hydroxide in water (5 ml) was added to a stirred solution of 10c (223 mg, 0.60 mmol.) in tetrahydrofuran (15 ml). The stirred mixture was heated to 60° C. for 15 hours. The reaction mixture was partially evaporated before adding 2M hydrochloric acid (20 ml). The solution was extracted with ethyl acetate (3×15 ml). The extract was dried over sodium sulfate filtered and evaporated to give a yellow gum (209 mg). The gum was purified on a silica column eluting with 25% ethyl acetate, 75% hexane to yield 10d as a yellow gum (68 mg, 66%). $^1$H NMR δ (300 MHz NMR, CDCl$_3$) 1.15-1.19 (d, 3H), 1.57-1.67 (m, 2H), 2.11-2.23 (m, 2H), 2.74-2.85 (m, 1H), 3.39-3.42 (s, 3H), 3.45-3.53 (m, 1H), 4.97-5.10 (m, 2H), 5.76-5.91 (m, 1H).

To 10d (80 mg, 0.46 mmol) in anhydrous DMF (3 ml) at 0° C. and under an atmosphere of nitrogen was added Diisopropylethylamine (0.32 ml, 1.86 mmol), followed by HATU (177 mg, 0.46 mmol). The reaction was stirred for 0.5 hours after which a solution of (S)-1-{(S)-2-((S)-2-Amino-3-methyl-butyrylamino)-3-[3-(tert-butyl-dimethyl-silanyloxy)-phenyl]-propionyl}-hexahydro-pyridazine-3-carboxylic acid 3-vinyl-benzyl ester (from 10a)* (398 mg, 0.64 mmol) in anhydrous DMF (3 ml) was added. The reaction was warmed to room temperature, stirred for 16 hours and quenched with pH7 buffer. The reaction was extracted with dichloromethane (2×), the organics dried through a hydrophobic frit and concentrated in vacuo. The product was purified by flash chromatography (SiO$_2$, iHex/EtOAc, 2:1 then 1:1) to afford 10e 280 mg (78%). $^1$H NMR (300 MHz, CDCl$_3$) δ 7.39 (m, 3H), 7.26 (m, 1H), 7.03 (m, 1H), 6.83-6.62 (m, 4H), 6.55-6.46 (m, 2H), 5.91-5.70 (m, 2H), 5.79 (d, J=17.6 Hz, 1H), 5.31 (d, J=10.9 Hz, 1H), 5.15 (s, 2H), 5.05 (dd, J=1.6 Hz, 17.2 Hz, 1H), 4.97 (d, J=10.0 Hz, 1H), 4.31 (m, 2H), 3.55 (m, 1H), 3.40 (s, 3H), 3.37 (m, 1H), 3.00-2.80 (m, 2H), 2.75 (m, 1H), 2.48 (m, 2H), 2.15 (m, 3H), 1.90-1.63 (m, 4H), 1.47 (m, 2H), 1.18 (d, J=6.9 Hz, 3H), 1.00-0.88 (m, 6H), 0.97 (s, 9H), 0.17 (s, 6H). LCMS (m/z) 777.55 [M+H], Tr=4.35 min.

*(S)-1-{(S)-2-((S)-2-Amino-3-methyl-butyrylamino)-3-[3-(tert-butyl-dimethyl-silanyloxy)-phenyl]-propionyl}-hexahydro-pyridazine-3-carboxylic acid 3-vinyl-benzyl ester was prepared by adding TMS (OTf) (0.17 ml, 0.64 mmol) to a solution of 10a (400 mg, 0.49 mmol) in anhydrous dichloromethane (20 ml) at 0° C. The reaction was stirred for 2 hours at 0° C., quenched by adding iPr$_2$NEt (0.45 ml, 2.56 mmol) and concentrated in vacuo to yield a white solid.

(E)-(5S,11S,14S,17R,18R)-11-(3-Hydroxy-benzyl)-14-isopropyl-18-methoxy-17-methyl-3-oxa-9,12,15,28-tetraaza-tricyclo[21.3.1.1*5,9*]octacosa-1(27),21,23,25-tetraene-4,10,13,16-tetraone (10)

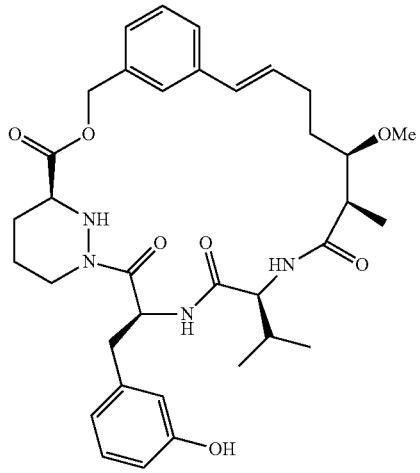

To 10e (280 mg, 0.36 mmol) in anhydrous dichloromethane (120 ml) was added Grubbs 1$^{st}$ generation catalyst (89 mg, 0.11 mmol). The reaction was heated to reflux and left for 16 hours. The reaction was cooled and concentrated in vacuo. The product was purified by flash chromatography (SiO$_2$, iHex/EtOAc, 1:1 then 1:2) to afford 213 mg (75%) of a brown oil that solidifies under vacuum. To the resulting residue (70 mg, 0.09 mmol), was added anhydrous THF (1 ml) and cooled to 0° C. A solution of TBAF (0.5 ml, 0.47 mmol, 1.0 M in THF) was added and the reaction stirred at 0° C. for 0.5 hours. The reaction was quenched with aqueous saturated ammonium chloride and extracted with dichloromethane (2×). The combined organic layers were dried through a hydrophobic frit and concentrated in vacuo. The product was purified by flash chromatography (SiO$_2$, iHex/EtOAc, 1:1 to 1:2) to afford 10 as a white solid (25 mg, 44%). $^1$H NMR (300 MHz, d$_6$-DMSO) δ 8.10 (br s, 1H), 7.41-7.21 (m, 3H), 7.18 (m, 1H), 7.08 (m, 1H), 6.91 (m, 1H), 6.80 (m, 1H), 6.66 (m, 2H), 6.46 (m, 1H), 6.06 (m, 2H), 5.73 (m, 1H), 5.21 (s, 2H), 4.57 (m, 1H), 4.22 (m, 1H), 3.67 (m, 1H), 3.50 (s, 3H), 2.84 (m, 2H), 2.65 (m, 2H) 2.26-1.91 (m, 5H), 1.82-1.55 (m, 6H), 1.37 (d, J=7.1 Hz, 3H), 1.00 (2d, J=2.7 Hz, 6H). LCMS (m/z) 635.42 [M+H], Tr=5.01 min Example XI Compound 11: (13E,15E)-(3S,6S,9R,10R,21S)-3-(3-Hydroxy-benzyl)-6-isopropyl-10-methoxy-9-methyl-19-oxa-1,4,7,25-tetraaza-bicyclo[19.3.1]pentacosa-13,15-diene-2,5,8,20-tetraone Compound 11

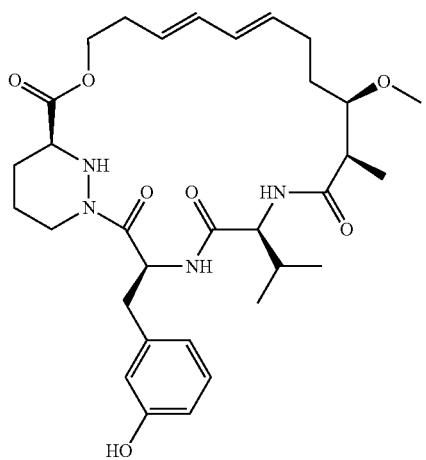

(S)-1-{(S)-3-(3-Hydroxy-phenyl)-2-[(S)-2-((2R,3R)-3-methoxy-2-methyl-hept-6-enoylamino)-3-methyl-butyrylamino]-propionyl}-hexahydro-pyridazine-3-carboxylic Acid (E)-hexa-3,5-dienyl Ester (11a)

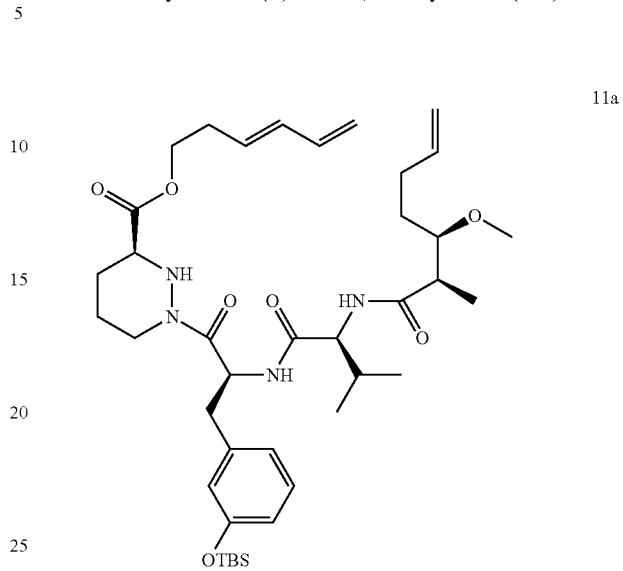

A solution of 10d (83.5 mg, 0.485 mmol.) in anhydrous dimethylformamide (4 ml) was cooled to 0° C. before adding N,N-diisopropylethylamine (340 uL, 1.94 mmol.) and 2-(1H-7-azabenzotriazol-1-yl)-1,1,3,3-tetramethyl uronium hexafluorophosphate methanaminium (185 mg, 0.485 mmol.) The reaction mixture was stirred at 0° C. for 20 minutes before addition of (S)-1-{(S)-2-((S)-2-amino-3-methylbutyryl amino)-3-[3-(tert-butyl-dimethyl-silanyloxy)-phenyl]-propionyl}-hexahydro-pyridazine-3-carboxylic acid (E)-hexa-3,5-dienyl ester (285 mg, 0.485 mmol.)* in anhydrous dimethylformamide (4 ml). The reaction mixture was stirred at room temperature for 15 hours. The reaction mixture was the diluted with pH7 phosphate buffer (0.5M, 20 ml) then extracted with ethyl acetate (3×20 ml). The combined extract was washed with brine (3×20 ml), dried over sodium sulfate, filtered and evaporated to give a brown gum. The gum was purified on a silica column eluting with 60% ethyl acetate, 40% hexane to yield 11a as a colourless solid (133 mg, 37%). $^1$H NMR δ (300 MHz NMR, CDCl$_3$) 0.17-0.21 (s, 6H), 0.87-0.96 (m, 6H) 0.96-1.01 (s, 9H), 1.14-1.20 (d, 3H, J=7.1 Hz), 1.35-1.85 (m, 7H), 2.08-2.21 (m, 3H), 2.39-2.53 (m, 3H), 2.65-3.01 (m, 3H), 3.31-3.45 (m, 4H), 3.50-3.57 (d, 1H, J=11.2), 4.09-4.35 (m, 5H), 4.93-5.20 (m, 3H), 5.57-5.90 (m, 3H), 6.08-6.19 (m, 1H), 6.25-6.40 (m, 1H), 6.45-6.59 (m, 2H), 6.64-6.75 (m, 2H), 6.78-6.85 (d, 1H, J=7.8 Hz), 7.07-7.15 (t, 1H, J=7.8 Hz). LCMS (m/z) 741.44 [M+H] Tr=5.72 min.

(S)-1-{(S)-2-((S)-2-amino-3-methylbutyryl amino)-3-[3-(tert-butyl-dimethyl-silanyloxy)-phenyl]-propionyl}-hexahydro-pyridazine-3-carboxylic acid (E)-hexa-3,5-dienyl ester was prepared from the corresponding BOC protected product ((S)-((E)-hexa-3,5-dienyl)1-((S)-2-((S)-2-(tert-butoxycarbonylamino)-3-methylbutanamido)-3-(3-(tert-butyldimethylsilyloxy)phenyl)propanoyl)piperazine-3-carboxylate) in a similar manner to that described for the preparation of 3b from 3a. In turn, (S)-((E)-hexa-3,5-dienyl)1-((S)-2-((S)-2-(tert-butoxycarbonylamino)-3-methylbutanamido)-3-(3-(tert-butyldimethylsilyloxy)phenyl)propanoyl)piperazine-3-carboxylate was prepared as described in the synthesis of 3a except substituting (E)-hexa-3,5-dien-1-ol for but-3-en-1-ol.

(13E,15E)-(3S,6S,9R,10R,21S)-3-[3-(tert-Butyl-dimethyl-silanyloxy)-benzyl]-6-isopropyl-10-methoxy-9-methyl-19-oxa-1,4,7,25-tetraaza-bicyclo[19.3.1]pentacosa-13,15-diene-2,5,8,20-tetraone (11b)

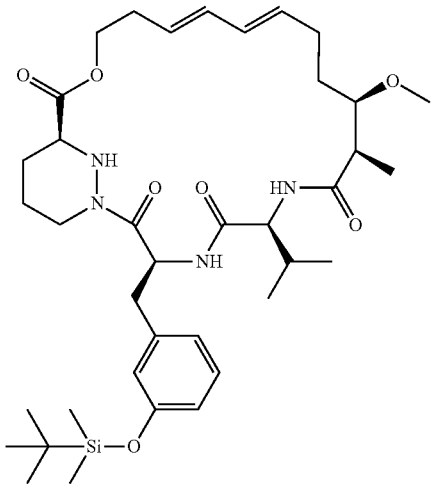

11b

A solution of 11a (133 mg, 0.180 mmol.) in dichloromethane (85 ml) was prepared and Grubbs 1$^{st}$ generation catalyst (45 mg, 0.054 mmol.) was added. The stirred reaction mixture was heated at reflux for 36 hours then cooled to room temperature. Silica gel was added and the mixture was evaporated to dryness. The residue was purified on a silica column eluting with a gradient from 100% hexane to 100% ethyl acetate. This yielded the title product as a dark brown solid (38 mg, 30%). $^{1}$H NMR δ (300 MHz NMR, CDCl$_3$) 0.17-0.21 (s, 6H), 0.92-0.97 (d, 3H, J=6.7 Hz) 0.97-1.01 (s, 9H), 1.20-1.38 (m, 4H), 1.39-1.88 (m, 6H), 1.94-2.28 (m, 4H), 2.29-2.70 (m, 4H), 2.72-2.96 (m, 2H), 3.09-3.41 (m, 2H), 3.45-3.49 (s, 1H), 3.49-3.54 (d, 1H, J=11.4 Hz), 3.57-3.66 (d, 1H, J=12.0 Hz), 4.02-4.19 (m, 2H), 4.20-4.41 (m, 2H), 4.44-4.55 (m, 1H), 5.49-5.80 (m, 3H), 5.98-6.20 (m, 2H), 6.42-6.51 (d, 1H, J=8.03 Hz), 6.52-6.74 (m, 3H).), 6.78-6.84 (d, 1H, J=7.6 Hz), 6.93-7.00 (d, 1H, J=9.1), 7.05-7.20 (m, 1H). LCMS (m/z) 713.40 [M+H] Tr=5.62 min.

(13E,15E)-(3S,6S,9R,10R,21S)-3-(3-Hydroxy-benzyl)-6-isopropyl-10-methoxy-9-methyl-19-oxa-1,4,7,25-tetraaza-bicyclo[19.3.1]pentacosa-13,15-diene-2,5,8,20-tetraone (11)

11

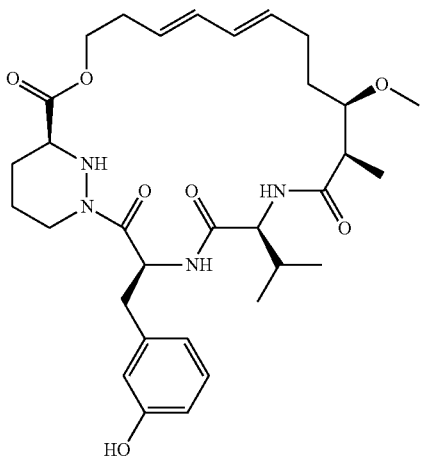

A stirred solution of 11b (38 mg, 0.053 mmol.) in anhydrous tetrahydrofuran (10 ml) was cooled to 0° C. under a nitrogen atmosphere before adding a 1M solution of tetrabutylammonium fluoride in tetrahydrofuran (265 ul, 0.265 mmol.). The reaction mixture was warmed to room temperature and was stirred under a nitrogen atmosphere for 2.5 hours. The reaction mixture was then treated with saturated aqueous sodium bicarbonate solution (20 ml) and the subsequent mixture was extracted with ethyl acetate (3×15 ml). The combined extract was dried over sodium sulfate, filtered and evaporated. The residue was purified on a silica column eluting with 50% ethyl acetate, 50% hexane then 100% ethyl acetate to yield 11 as a colourless solid (15 mg, 47%). $^{1}$H NMR δ (300 MHz NMR, CDCl$_3$) 0.81-0.92 (m, 3H) 0.93-1.01 (m, 4H), 1.34-1.39 (d, 3H, J=7.4 Hz), 1.45-2.10 (m, 6H), 2.18-2.20 (s, 1H), 2.38-2.53 (m, 2H), 2.55-2.71 (m, 2H), 2.75-2.92 (m, 2H), 3.18-3.30 (m, 2H), 3.51-3.53 (s, 3H), 3.54-3.60 (d, 1H, J=12.5 Hz), 4.09-4.40 (m, 4H), 4.50-4.60 (d, 1H, J=12.7 Hz), 5.43-5.69 (m, 3H), 5.91-6.00 (m, 3H), 6.51-6.58 (d, 1H, J=7.4 Hz), 6.68-6.78 (m, 2H), 6.80-6.90 (d, 1H J=8.7 Hz), 7.05-7.12 (t, 1H, J=7.7), 7.37-7.45 (d, 1H, J=9.6), 8.15-8.38 (bs, 1H). LCMS (m/z) 599.36 [M+H] Tr=4.59 min.

Example XII

Compound 12: (13E,15E)-(3S,6S,9R,10R,11S,12S,18R,21S)-3-(3-Hydroxy-benzyl)-6-isopropyl-10,12-dimethoxy-9,11,18-trimethyl-19-oxa-1,4,7,25-tetraaza-bicyclo[19.3.1]pentacosa-13,15-diene-2,5,8,20-tetraone Compound 12

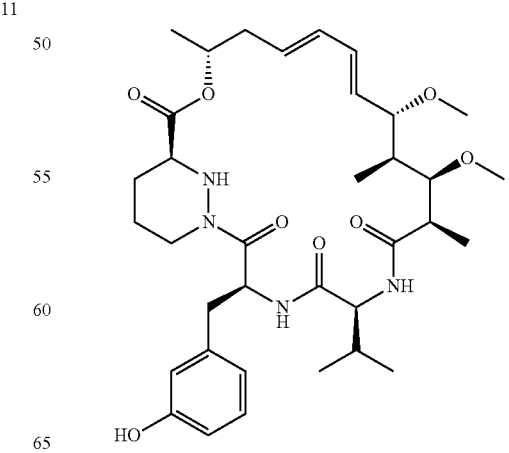

77

(S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid (R)-1-methyl-but-3-enyl Ester (12a)

78

(S)-1-{(S)-3-[3-(tert-Butyl-dimethyl-silanyloxy)-phenyl]-2-[(S)-2-((Z)-(2R,3R,4S,5S)-3,5-dimethoxy-2,4-dimethyl-nona-6,8-dienoylamino)-3-methyl-butyrylamino]-propionyl}-hexahydro-pyridazine-3-carboxylic Acid (R)-1-methyl-but-3-enyl Ester (12c)

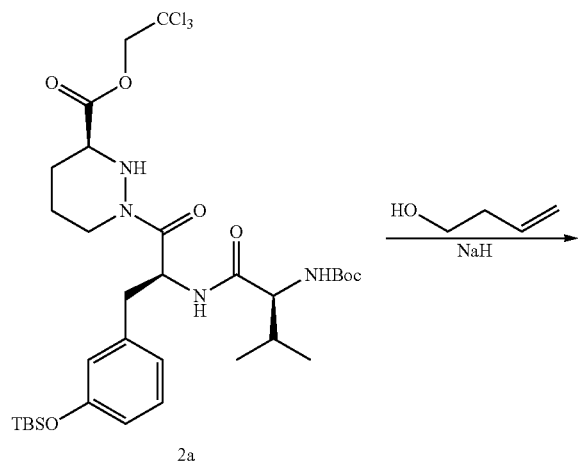

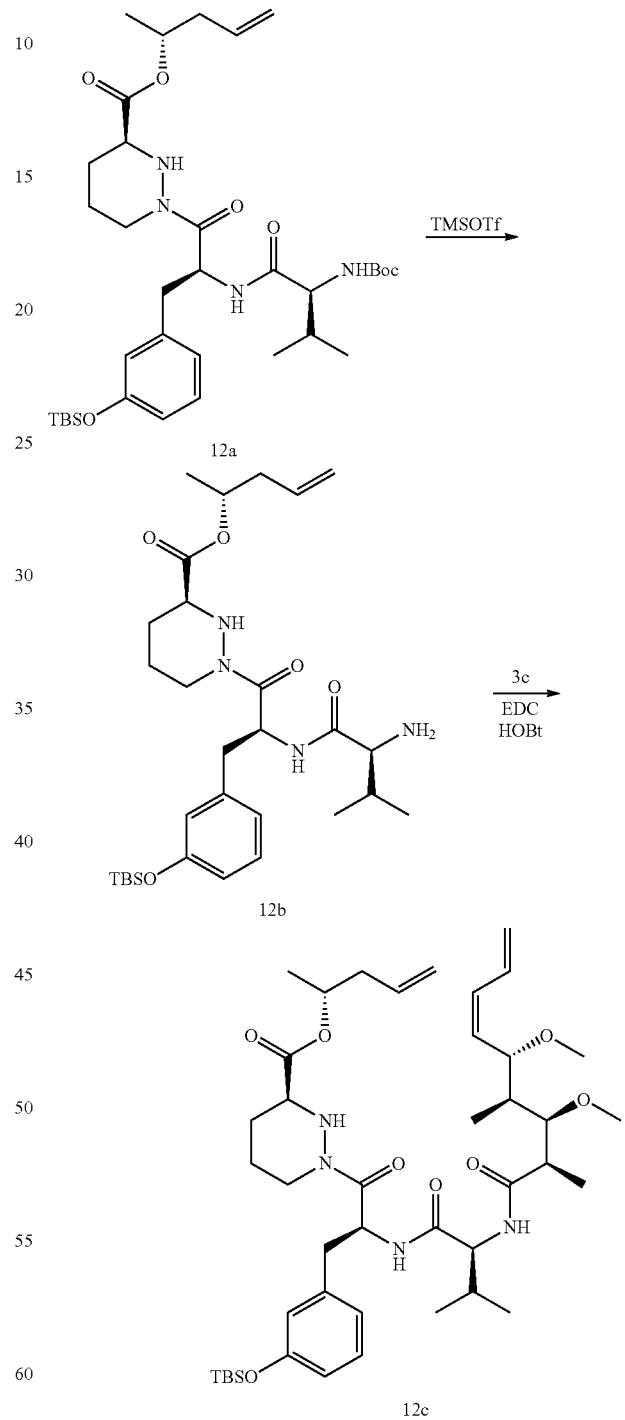

Sodium hydride (11 mg, 0.271 mmol) was added to a solution of 2a (1 g, 1.35 mmol) and 3-buten-1-ol (1.4 ml, 6.98 mmol) in tetrahydrofuran (10 ml) and the reaction stirred at 50° C. under $N_2$ for 3 h. The reaction was cooled and the mixture passed through a plug of $SiO_2$ (eluting with ethyl acetate, 2×50 ml) to afford a colourless oil. This was azeotroped with toluene (2×) to afford 12a as a colourless oil (767 mg, 84%). $^1$H NMR (300 MHz, $CDCl_3$) δ 7.15 (1H, m), 6.82 (1H, d, J=7.6 Hz), 6.65 (2H, m), 6.48 (1H, d, J=8.3 Hz), 5.72 (1H, m), 4.95-5.15 (4H, m), 4.32 (1H, m), 3.95 (1H, br s), 3.52 (1H, d, J=11 Hz), 2.95 (2H, m), 2.75 (1H, m), 2.60 (1H, m), 2.35 (2H, m), 2.12 (1H, m), 1.80 (2H, m), 1.62 (2H, m), 1.30 (1H, m), 1.22 (3H, d, J=6.3 Hz), 0.98 (9H, s), 0.95 (3H, d, J=6.7 Hz), 0.88 (3H, d, J=6.7 Hz), 0.18 (6H, s). LCMS (m/z) 675.43 [M+H], Tr=5.69 min.

Trimethylsilyltrifluoromethanesulfonate (371 uL, 1.205 mmol) was added dropwise to a solution of the 12a (767 mg, 1.14 mmol) in dichloromethane (15 ml) at 0° C. under $N_2$ and the reaction was stirred for 60 minutes. To this was added Hunig's base (793 uL, 4.55 mmol) and the reaction was warmed to room temperature. The volatiles were evaporated to afford 12b as a colourless foam which was used without further purification. 1-Hydroxybenzotriazole (96 mg, 0.57 mmol), followed by N-(3-dimethylaminopropyl)-N'-ethyl-carbodiimide hydrochloride (131 mg, 0.68 mmol) was added to a solution of 12b and 3c (138 mg, 0.57 mmol) in acetonitrile (10 ml) and the reaction was stirred at room temperature for 18 h. The solvent was evaporated and the residue was purified with a plug of $SiO_2$ (eluting with ethyl acetate/i-hexane, 1:1, 600 ml) to afford a solution which was washed with saturated sodium bicarbonate, dried ($Na_2SO_4$) and the volatiles evaporated to afford 12c as a yellow oil (242 mg, 53%). $^1$H NMR (300 MHz, $CDCl_3$) δ7.10 (1H, m), 6.60-6.85 (3H, m), 6.30-6.45 (2H, m), 6.25 (2H, m), 5.75 (2H, m), 5.45 (1H, dd, J=15.2, 8.9 Hz), 5.25 (1H, m), 5.12 (2H, m), 5.00 (1H, q, J=6.5 Hz), 4.30 (2H, m), 3.87 (1H, dd, J=9, 2.2 Hz), 3.53 (1H, m), 3.45 (1H, m), 3.50 (3H, s), 3.25 (3H, s), 2.90 (2H, m), 2.75 (1H, m), 2.60 (1H, m), 2.35 (3H, m), 2.15 (1H, m), 2.05 (1H, m), 1.65-1.90 (3H, m), 1.30-150 (5H, m), 1.25 (3H, m), 1.20 (3H, m), 1.05 (3H, d, J=6.9 Hz), 0.98 (9H, s), 0.75 (3H, d, J=6.9 Hz), 0.20 (6H, s). LCMS (m/z) 767.43 [M+H], Tr=5.98 min.

(13E,15E)-(3S,6S,9R,10R,11S,12S,18R,21S)-3-(3-Hydroxy-benzyl)-6-isopropyl-10,12-dimethoxy-9,11,18-trimethyl-19-oxa-1,4,7,25-tetraaza-bicyclo[19.3.1]pentacosa-13,15-diene-2,5,8,20-tetraone (12)

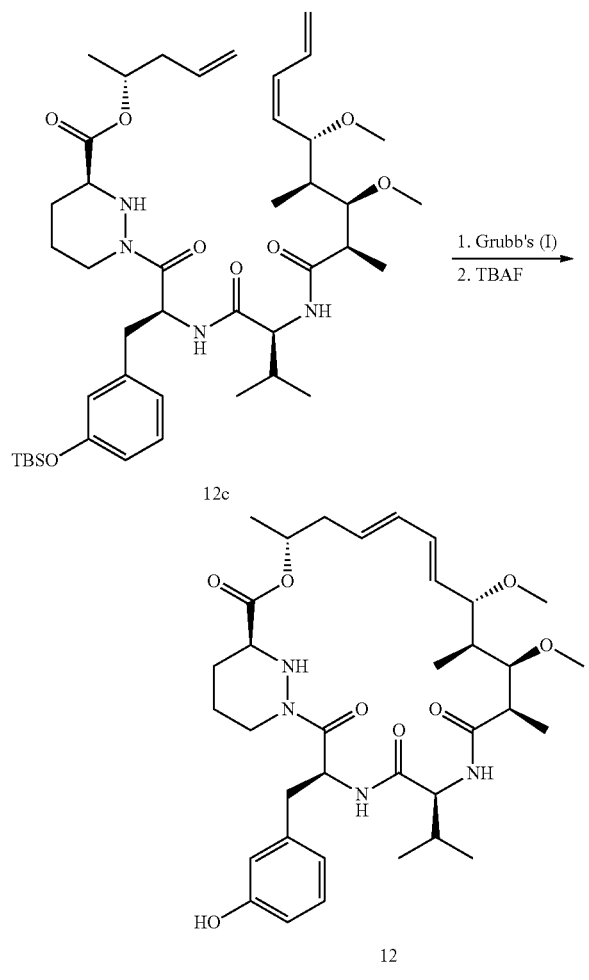

Grubbs (I) (33 mg, 0.04 mmol) was added to a solution of 12c (160 mg, 0.20 mmol) in dichloromethane (100 ml) and the reaction was heated at reflux under $N_2$ for 18 h. Grubbs (I) (33 mg, 0.04 mmol) was added and the reaction was continued at reflux for a further 24 h. The reaction was cooled and $SiO_2$ was added. The solvent was evaporated and the resultant residue purified by $SiO_2$ (2:1 to 4:1 ethyl acetate/i-hexane) to afford a brown oil (65 mg, 42%). The brown oil (65 mg, 0.084 mmol) was dissolved in THF (5 ml) and tetrabutylammonium fluoride (1.0M solution in THF) (422 uL, 0.422 mmol) was added. The reaction was stirred at room temperature for 1 h. $SiO_2$ was added and the solvent evaporated. The residue was purified by $SiO_2$ (3:1 to 4:1 ethyl acetate/i-hexane) and then repurified by $SiO_2$ (4:1 ethyl acetate/dichloromethane) to afford 12 as a colourless solid (20 mg, 36%). $^1$H NMR (300 MHz, MeCN-$d_3$) δ7.69 (1H, s), 6.90-7.17 (3H, m), 6.65 (2H, m), 5.95-6.20 (2H, m), 5.63 (1H, m), 5.40 (2H, m), 5.05 (1H, m), 4.33 (1H, m), 4.15 (1H, m), 3.95 (1H, m), 3.50-3.75 (2H, m), 3.48 (3H, s), 3.42 (1H, m), 3.24 (2H, m), 3.15 (3H, s), 2.83 (2H, m), 2.67 (1H, m), 2.35-2.60 (2H, m), 1.76 (3H, m), 1.48 (3H, m), 1.30 (3H, d, J=7.1 Hz), 1.23 (3H, d, J=6.2 Hz), 0.92 (6H, t, J=6.5 Hz), 0.72 (3H, d, J=7.1 Hz). LCMS (m/z) 657.37 [M+H], Tr=4.97 min.

Example XIII

Compound 13: (E)-(2R,5S,11S,14S,17R,18R)-11-(3-Hydroxy-benzyl)-14-isopropyl-18-methoxy-2,17-dimethyl-3-oxa-9,12,15,28-tetraaza-tricyclo[21.3.1.1*5,9*]octacosa-1(26),21,23(27),24-tetraene-4,10,13,16-tetraone

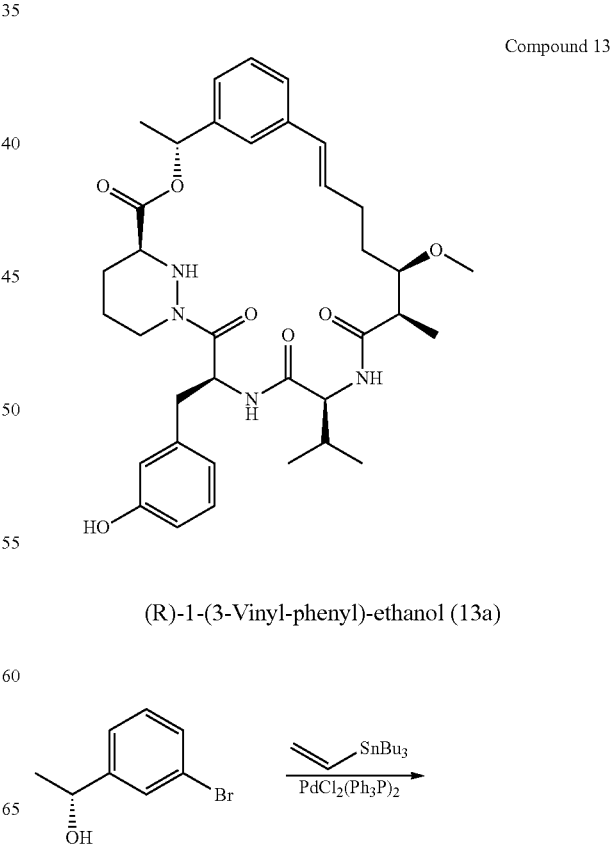

(R)-1-(3-Vinyl-phenyl)-ethanol (13a)

-continued

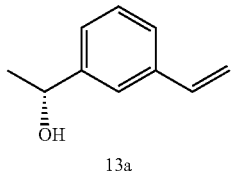
13a

Bis(triphenylphosphine)palladium(II) dichloride (360 mg, 0.512 mmol) was added to a degassed solution of (R)-1-(3-bromo-phenyl)-ethanol (1.03 g, 5.123 mmol) and tributyl(vinyl)tin (1.8 ml, 6.15 mmol) in toluene (10 ml) under $N_2$ and the reaction was stirred at 45° C. for 18 h. Tributyl(vinyl)tin (2.56 mmol, 750 uL) and bis(triphenylphosphine)palladium (II) dichloride (0.256 mmol, 180 mg) were added and stirring was continued for 18 h. The reaction was cooled and the solvent evaporated to afford a residue which was absorbed onto $SiO_2$. Purification by $SiO_2$ (3:1 i-hexane/ethyl acetate) afforded 13a as a yellow oil (675 mg, 89%). $^1$H NMR (300 MHz, $CDCl_3$) δ7.49 (1H, s), 7.33 (3H, m), 6.75 (1H, dd, J=17.6, 10.9 Hz), 5.80 (1H, d, J=17.6 Hz), 5.28 (1H, d, J=10.7 Hz), 4.93 (1H, m), 1.81 (1H, d, J=3.1 Hz), 1.52 (3H, d, J=6.5 Hz).

(S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid (R)-1-(3-vinyl-phenyl)-ethyl Ester (13b)

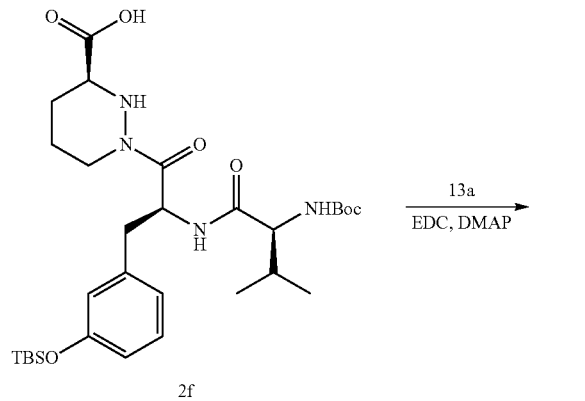

chloride (2.16 mmol), 414 mg) was added to a solution of 2f (818 mg, 1.35 mmol) and 13a (300 mg, 2.025 mmol) in dichloromethane (20 ml) and the reaction was stirred at room temperature for 18 h. The mixture was washed with citric acid, saturated sodium bicarbonate, dried ($Na_2SO_4$) and the solvent evaporated to afford a brown oil. Purification, $SiO_2$ (2:1 to 1:1 i-hexane/ethyl acetate) afforded the 13b as a colourless oil (537 mg, 54%). $^1$H NMR (300 MHz, $CDCl_3$) δ7.37 (2H, m), 6.93 (1H, t, J=9.1 Hz), 6.65-6.85 93H, m), 6.62 (2H, m), 6.47 (1H, d, J=7.6 Hz), 5.65-5.95 (3H, m), 5.30 (1H, m), 5.05 (1H, br d, J=7.4 Hz), 4.33 (1H, m), 3.96 (1H, br s), 3.53 (1H, d, J=11.2 Hz), 2.80-3.05 (3H, m), 2.73 (1H, m), 2.48 (1H, m), 2.12 (1H, q, J=5.8 Hz), 1.89 (1H, m), 1.81 (1H, m), 1.55 (3H, d, J=6.9 Hz), 1.46 (9H, s), 1.15-1.40 (2H, m), 0.98 (9H, s), 0.94 (3H, d, J=6.7 Hz), 0.88 (3H, d, J=6.9 Hz), 0.18 (6H, s). LCMS (m/z) 737.35 [M+H], Tr=5.95 min.

(S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid (R)-1-(3-vinyl-phenyl)-ethyl Ester (13d)

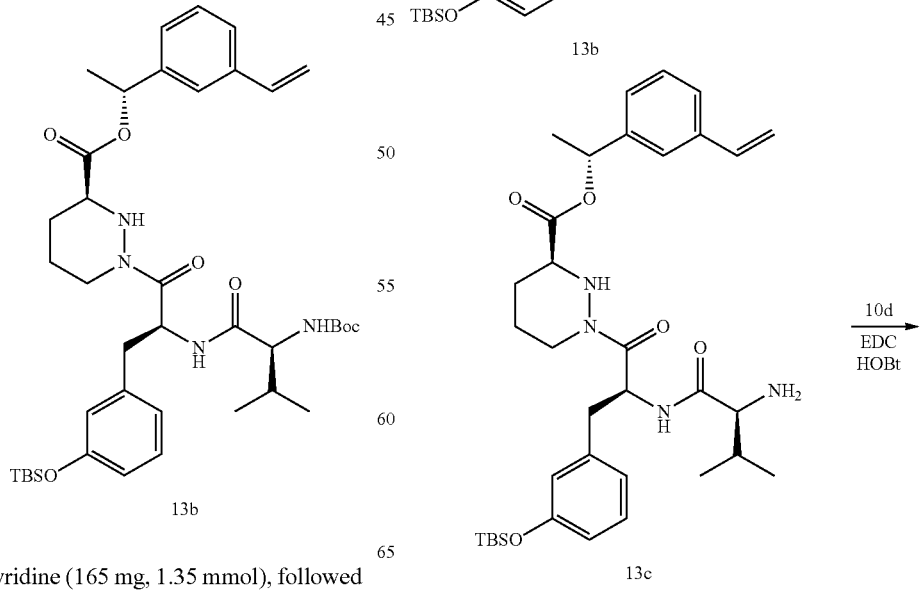

83

-continued

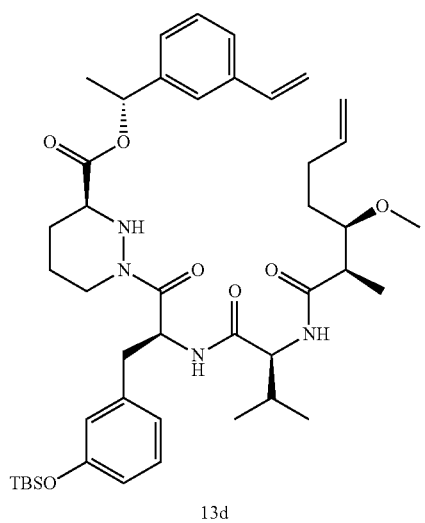

13d

Trimethylsilyltrifluoromethanesulfonate (198 uL, 1.093 mmol) was added dropwise to a solution of the 13b (537 mg, 0.729 mmol) in dichloromethane (10 ml) at 0° C. under $N_2$ and the reaction was stirred for 60 minutes. To this was added Hunig's base (508 uL, 2.92 mmol) and the reaction was warmed to room temperature. The volatiles were evaporated to afford 13c as a waxy solid which was used without further purification. 1-Hydroxybenzotriazole (123 mg, 0.729 mmol), followed by N-(3-dimethylaminopropyl)-N'-ethylcarbodiimide hydrochloride (196 mg, 1.02 mmol) was added to a solution of 13c and 10d (125 mg, 0.729 mmol) in acetonitrile (10 ml) and the reaction was stirred at room temperature for 18 h. The solvent was evaporated and the residue partitioned between water and ethyl acetate. The organic layer was dried ($Na_2SO_4$) and the solvent evaporated. Purification, $SiO_2$ (3:1 ethyl acetate/i-hexane) afforded 13d as a colourless foam (318 mg, 55%). $^1$H NMR (300 MHz, $CDCl_3$) δ7.74 (1H, d, J=9.2 Hz), 7.57 (1H, m), 7.25-7.48 (4H, m), 5.83 (3H, m), 7.47 (1H, q, J=7.4 Hz), 5.25 (2H, m), 4.98 (2H, m), 4.12 (1H, m), 4.02 (1H, m), 3.20 (3H, s), 3.00 (1H, m), 2.84 (1H, m), 2.67 (2H, m), 2.00 (4H, m), 1.83 (1H, m), 1.67 (1H, m), 1.55 (2H, m), 1.46 (3H, d, J=6.7 Hz), 0.92 (3H, d, J=8 Hz), 0.92 (9H, s), 0.87 (3H, d, J=6.9 Hz), 0.77 (3H, d, J=6.7 Hz), 0.13 (6H, s). LCMS (m/z) 791.41 [M+H], Tr=6.00 min.

84

(E)-(2R,5S,11S,14S,17R,18R)-11-(3-Hydroxy-benzyl)-14-isopropyl-18-methoxy-2,17-dimethyl-3-oxa-9,12,15,28-tetraaza-tricyclo[21.3.1.1*5,9*]octacosa-1(26),21,23(27),24-tetraene-4,10,13,16-tetraone (13)

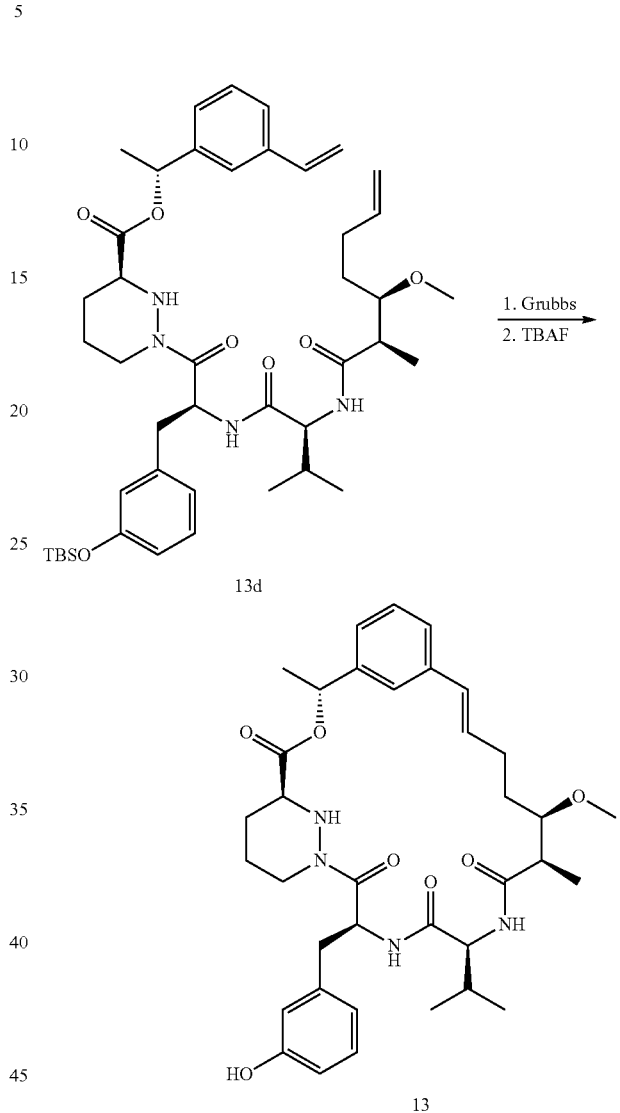

Grubbs/Hoveyda $2^{nd}$ generation (25 mg, 0.04 mmol) was added to a solution of 13d (318 mg, 0.402 mmol) in dichloroethane (150 ml) and the reaction was heated at reflux under $N_2$ for 3 h. The reaction was cooled and $SiO_2$ was added. The solvent was evaporated and the resultant residue purified by $SiO_2$ (2:1 ethyl acetate/i-hexane) to afford a brown foam (214 mg, 70%). The brown oil (214 mg, 0.28 mmol) was dissolved in THF (10 ml) and tetrabutylammonium fluoride (1.0M solution in THF) (449 uL, 0.449 mmol) was added. The reaction was stirred at room temperature for 1 h. $SiO_2$ was added and the solvent evaporated. The residue was purified by $SiO_2$ (2:1 to 3:1 ethyl acetate/i-hexane) and then repurified by preparative TLC (3:1 ethyl acetate/i-hexane) to afford 13 as a colourless solid (115 mg, 63%). $^1$H NMR (300 MHz, MeCN-$d_3$) δ8.25 (1H, s), 7.34 (1H, d, J=8.0 Hz), 7.22 (3H, m), 7.05 (3H, m), 6.96 (2H, m), 6.65 (1H, m), 6.03 (1H, m), 5.75 (2H, m), 5.48 (1H, dt, J=9.2, 6.2 Hz), 4.36 (1H, br d, J=13.4 Hz), 4.20 (1H, t, J=8.5 Hz), 3.97 (1H, d, J=12.3 Hz), 3.65 (1H, dt, J=3.1, 11.8 Hz), 3.45 (3H, s), 3.35 (1H, m), 2.89 (2H, d, J=6.3 Hz), 2.66 (2H, m), 1.60-2.10 (9H, m), 1.57 (3H, d, J=6.7 Hz), 1.31 (3H, d, J=7.4 Hz), 0.97 (3H, d, J=6.7 Hz), 0.96 (3H, d, J=6.9 Hz).
LCMS (m/z) 649.35 [M+H], Tr=4.96 min.

Example 14

Compound 14a: 3-Chloro-6-(1-ethoxy-vinyl)-isoquinoline

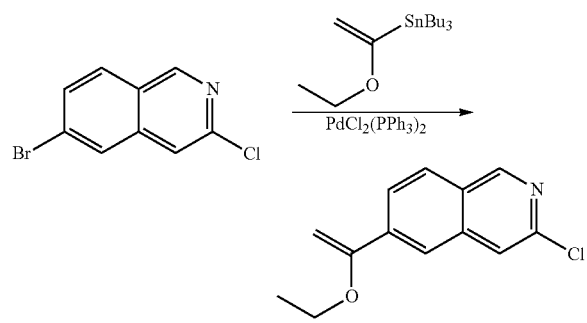

A solution of 6-bromo-3-chloro-isoquinoline (972 mg, 4 mmol) and tributyl-(1-ethoxy-vinyl)-stannane (2.5 g, 2.5 mL, 7 mmol) in toluene (12 mL) was degassed with nitrogen for 30 minutes. Bis(triphenylphosphine)palladium(II) dichloride (280 mg, 0.4 mmol) was added and the reaction mixture was heated at 50° C. for 18 h. The reaction mixture was cooled to room temperature and the mixture was purified by silica gel chromatography using a gradient of iso-hexanes/ethyl acetate 20:1 to 10:1 to afford the title compound (964 mg). $^1$H NMR (300 MHz, CDCl$_3$) δ1.51 (t, J=7.0 Hz, 3H), 4.01 (q, J=7.0 Hz, 2H), 4.45 (d, J=2.8 Hz, 1H), 4.90 (d, J=2.8 Hz, 1H), 7.76 (s, 1H), 7.85-7.97 (m, 2H), 8.04 (s, 1H), 0.94 (s, 1H). LCMS (m/z) 234/236 [M+H], Tr=5.40 min.

Compound 14b: 1-(3-Chloro-isoquinolin-6-yl)-ethanone

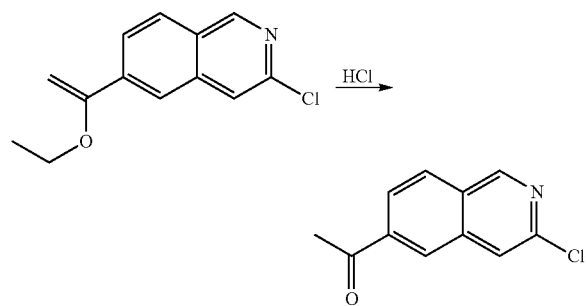

A solution of 3-chloro-6-(1-ethoxy-vinyl)-isoquinoline (934 mg, 4 mmol) in 1,4-dioxane (10 mL) and hydrochloric acid (2 M, 5 mL) was stirred at room temperature for 30 minutes. The solvent was evaporated and the residue was partitioned between ethyl acetate and water. The organic extracts were combined, washed with water and brine, dried over sodium sulfate, filtered and evaporated. The residue was purified by silica gel chromatography using a gradient of iso-hexanes/ethyl acetate 9:1 to 4:1 to afford the title compound (732 mg, 89%) as a white solid. $^1$H NMR (300 MHz, CDCl$_3$) δ2.77 (s, 3H), 7.88 (s, 1H), 8.05 (d, J=8.5 Hz, 1H), 8.15 (dd, J=8.5, 1.4 Hz, 1H), 8.37 (br s, H), 9.17 (s, 1H). LCMS (m/z) 206/208 [M+H], Tr=4.40 min.

Compound 14c: (R)-1-(3-Chloro-isoquinolin-6-yl)-ethanol

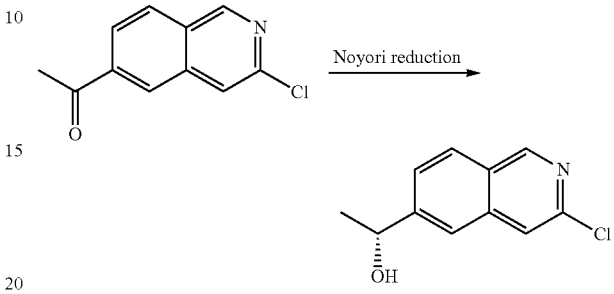

Dichloro(p-cymene)ruthenium(II) dimer (3 mg, 0.005 mmol) and (1R,2R)-(−)-N-p-tosyl-1,2-diphenylethylenediamine (4.4 mg, 0.012 mmol) was suspended in degassed water (2 mL) and the mixture was degassed with nitrogen for 15 minutes. The mixture was stirred at 70° C. under nitrogen for 90 minutes. The resulting yellow solution was cooled to room temperature. 1-(3-Chloro-isoquinolin-6-yl)-ethanone (206 mg, 1 mmol), sodium formate (340 mg, 5 mmol) and degassed tetrahydrofuran (1 mL) were added and the reaction mixture was degassed with nitrogen for 5 minutes. The reaction mixture was vigorously stirred at 40° C. for 2.5 hours. The reaction mixture was cooled to room temperature and was extracted with ethyl acetate. The organic layer was separated, washed with water and brine, dried over sodium sulfate, filtered and evaporated. The residue was purified by silica gel chromatography using a gradient of iso-hexanes/ethyl acetate 4:1 to 2:1 to afford the title compound (193 mg, 92%) as a white solid. $^1$H NMR (300 MHz, CDCl$_3$) δ1.60 (d, J=5.9 Hz, 3H), 2.14 (d, J=3.1 Hz, 1H), 5.08-5.16 (m, 1H), 7.63 (dd, J=8.6, 1.6 Hz, 1H), 7.72 (s, 1H), 7.77 (br s, 1H), 7.96 (d, J=8.6 Hz, 1H), 9.04 (s, 1H). LCMS (m/z) 208/210 [M+H], Tr=4.25 min.

Compound 14d: (R)-1-(3-Vinyl-isoquinolin-6-yl)-ethanol

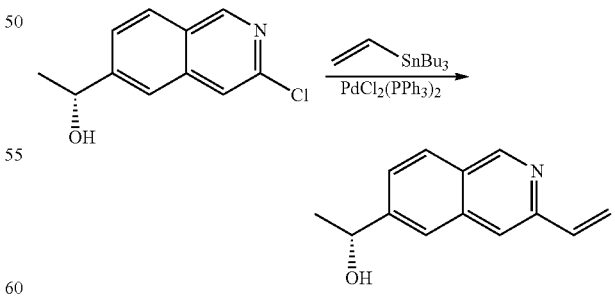

1,4-Dioxane (5 mL) was degassed with nitrogen, (R)-1-(3-chloro-isoquinolin-6-yl)-ethanol (208 mg, 1 mmol), tributyl (vinyl)tin (951 mg, 0.9 mL, 3 mmol) and bis(triphenylphosphine)palladium(II) dichloride (70 mg, 0.1 mmol) were added and the reaction mixture was heated at 150° C. in a microwave reactor for 1 hour. Additional tributyl(vinyl)tin (0.3 mL, 1 mmol) and bis(triphenylphosphine)palladium(II) dichloride (70 mg, 0.1 mmol) was added and the reaction mixture was heated at 150° C. in a microwave reactor for 1 hour. The reaction mixture was cooled to room temperature and the mixture was filtered thorough filter aid and the filter pad was washed with ethyl acetate. The filtrate was evaporated and the residue was purified by silica gel chromatography using a gradient of iso-hexanes/ethyl acetate 4:1 to 2:1 followed by silica gel chromatography using iso-hexanes/ethyl acetate 3:1 to afford the title compound (100 mg, 50%) as a white solid. $^1$H NMR (300 MHz, CDCl$_3$) δ1.60 (d, J=6.5 Hz, 3H), 2.11 (br s, 1H), 5.10 (q, J=6.5 Hz, 1H), 5.52 (dd, J=10.6, 1.6 Hz, 1H), 6.40 (dd, J=17.2, 1.6 Hz, 1H), 6.95 (dd, J=17.2, 10.7 Hz, 1H), 7.57 (s, 1H), 7.58 (dd, J=8.5, 1.6 Hz, 1H), 7.78 (br s, 1H), 7.94 (d, J=8.5 Hz, 1H), 9.19 (s, 1H). LCMS (m/z) 200 [M+H], Tr=1.50 min.

Compound 14e: (S)-1-[(S)-3-[3-(tert-Butyl-dimethyl-silanyloxy)-phenyl]-2-((S)-3-methyl-2-pent-4-enoylamino-butyrylamino)-propionyl]-hexahydro-pyridazine-3-carboxylic Acid 2,2,2-trichloro-ethyl Ester

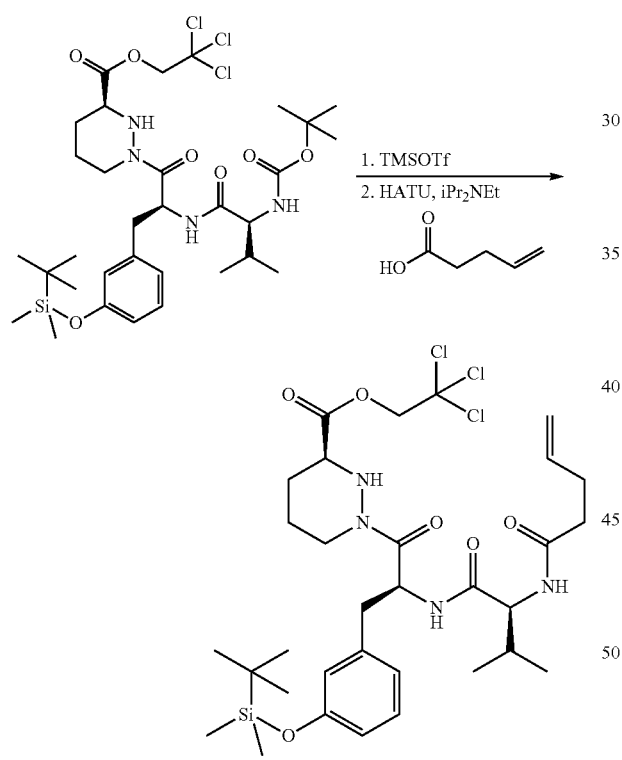

A solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid 2,2,2-trichloro-ethyl ester (2.21 g, 3 mmol) in dichloromethane (30 mL) was stirred at 0° C. under nitrogen. Trimethylsilyl trifluoromethanesulfonate (1.00 g, 0.82 mL, 4.5 mmol) was added and the reaction mixture was stirred at 0° C. for 40 minutes. N,N-Diisopropylethylamine (1.55 g, 2.1 mL, 12 mmol) was added and the solvent was evaporated to afford (S)-1-{(S)-2-((S)-2-amino-3-methyl-butyrylamino)-3-[3-(tert-butyl-dimethyl-silanyloxy)-phenyl]-propionyl}-hexahydro-pyridazine-3-carboxylic acid 2,2,2-trichloro-ethyl ester (3 mmol), which was used crude in the next step. A mixture of crude (S)-1-{(S)-2-((S)-2-amino-3-methyl-butyrylamino)-3-[3-(tert-butyl-dimethyl-silanyloxy)-phenyl]-propionyl}-hexahydro-pyridazine-3-carboxylic acid 2,2,2-trichloro-ethyl ester (3 mmol) in acetonitrile (30 mL) was stirred at 0° C. under nitrogen. 4-Pentenoic acid (330 mg, 3.3 mmol) and N,N-diisopropylethylamine (1.55 g, 2.1 mL, 12 mmol) was added followed by 2-(1H-7-azabenzotriazol-1-yl)-1,1,3,3-tetramethyl uronium hexafluorophosphate methanaminium (1.6 g, 4.2 mmol) and the reaction mixture was stirred at room temperature for 3 hours. The solvent was evaporated and the residue was partitioned between ethyl acetate and water. The organic extract was separated, washed with brine, dried over anhydrous sodium sulfate and evaporated. The residue was purified by silica gel chromatography using a gradient of iso-hexanes/ethyl acetate 3:1 to 1:3 to afford the title compound (1.46 g, 68%) as a gum. $^1$H NMR (300 MHz, CDCl$_3$) δ0.20 (s, 6H), 0.92 (d, J=6.2 Hz, 3H), 0.94 (d, J=6.3 Hz, 3H), 0.99 (s, 9H), 1.50-2.50 (m, 10H), 2.80-3.02 (m, 3H), 3.50 (d, J=10.7 Hz, 1H), 4.20-4.26 (m, 1H), 4.31 (dd, J=8.5, 6.0 Hz, 1H), 4.62 (d, J=12.0 Hz, 1H), 4.92 (d, J=12.0 Hz, 1H), 5.03 (dd, J=10.2, 1.5 Hz, 1H), 5.10 (dd, J=17.2, 1.5 Hz, 1H), 5.70-5.90 (m, 2H), 6.10 (d, J=8.5 Hz, 1H), 6.43 (d, J=8.3 Hz, 1H), 6.68-6.74 (m, 2H), 6.82 (d, J=7.6 Hz, 1H), 7.16 (t, J=7.8 Hz, 1H). LCMS (m/z) 719/721 [M+H], Tr=3.89 min.

Example 16

Compound 16

(E)-(2R,5S,11S,14S,17R,18R)-11-(3-Hydroxy-benzyl)-14-isopropyl-18-methoxy-2,17-dimethyl-3,9,12,15,28-pentaaza-tricyclo[21.3.1.1*5,9*]octacosa-1(27),21,23,25-tetraene-4,10,13,16-tetraone

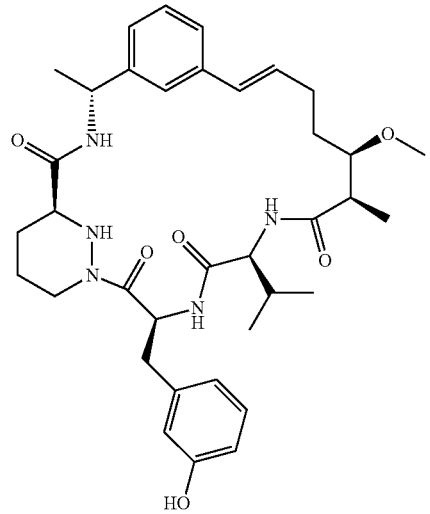 [SMILES: CO[C@@H]1CC/C=C/c2cccc(c2)[C@@H](C)NC(=O)[C@@H]2CCCN(N2)C(=O)[C@H](Cc2cccc(O)c2)NC(=O)[C@H](C(C)C)NC(=O)[C@@H]1C]

Compound 16a: [(R)-1-(3-Bromo-phenyl)-ethyl]-carbamic Acid tert-butyl Ester

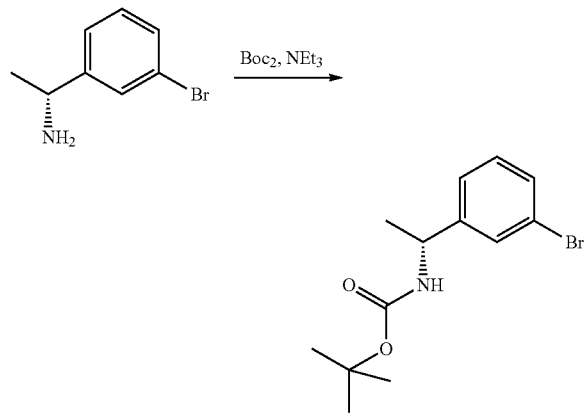

A solution of (R)-bromo-α-methylbenzylamine (1.023 g, 5.112 mmol) in dichloromethane (20 mL) was subsequently treated with triethylamine (720 µL, 5.112 mmol) and di-tert-butyl dicarbonate (1.784 g, 8.179 mmol). After overnight stirring at room temperature, the volatiles were removed in vacuo and the residue was purified by silica gel chromatography using a 50 g Isolute cartridge eluted with a continuous gradient of iso-hexanes/Et$_2$O 1:0 to 4:1 to afford the title compound (1.552 g, 100%) as a white solid. $^1$H NMR (300 MHz, CDCl$_3$) δ1.43 (br s, 12H), 4.77 (br s, 2H), 7.16-7.26 (m, 2H), 7.39 (dt, J=2.0, 7.1 Hz, 1H), 7.46 (s, 1H).

Compound 16b: [(R)-1-(3-Vinyl-phenyl)-ethyl]-carbamic Acid tert-butyl Ester

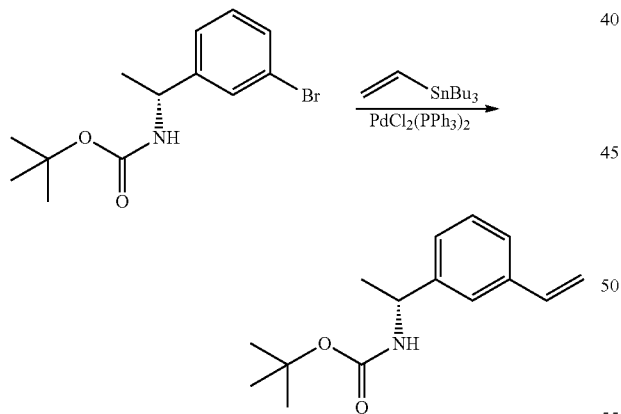

A solution of [(R)-1-(3-bromo-phenyl)-ethyl]-carbamic acid tert-butyl ester (10.26 g, 0.0342 mol.) and tributyl(vinyl)stannane (32.5 g, 30 mL, 0.103 mol.) in toluene (175 mL) was purged with nitrogen for 30 minutes before addition of bis(triphenylphosphine palladium II chloride (2.38 g, 0.0034 mol.). The stirred mixture was heated to 60° C. for 16 hours before cooling to room temperature. The reaction mixture was filtered through hyflo-supercel then evaporated to give a dark coloured oil. The oil was purified by silica gel chromatography using iso-hexanes/ethyl acetate 19:1 to yield the title compound (6.95 g, 82%) as a yellow oil. $^1$H NMR (300 MHz, CDCl$_3$) δ1.39-1.51 (m, 12H), 4.80 (br s, 2H), 5.24-5.32 (m, 1H), 5.77 (d, J=17.6 Hz, 1H), 6.73 (dd, J=17.6, 10.9 Hz, 1H), 7.18-7.36 (m, 4H).

Compound 16c: (R)-1-(3-Vinylphenyl)ethylamine Hydrochloride

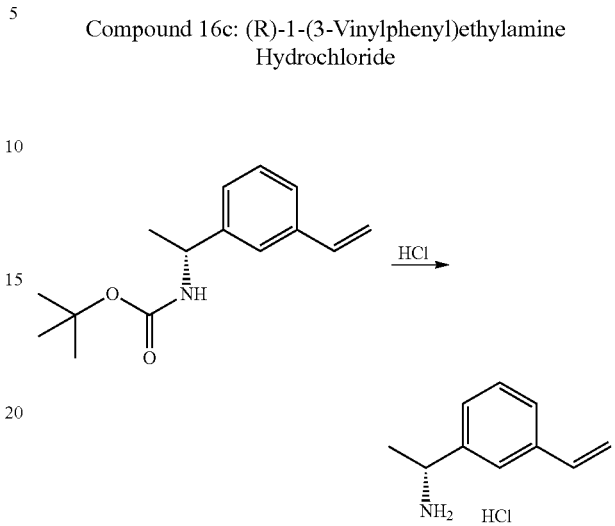

A solution of [(R)-1-(3-vinyl-phenyl)-ethyl]-carbamic acid tert-butyl ester (6.95 g, 28.1 mmol) in 1,4-dioxane (30 mL) was prepared and a solution of hydrogen chloride in 1,4 dioxane (4M, 60 mL) was added. The reaction mixture was stirred at room temperature for 2 hours then evaporated to dryness. The resultant solid was re-dissolved in toluene and evaporated. The solid was triturated with diethyl ether, which was removed by decanting. The solid was then dried under vacuum to give the title compound (4.96 g, 96%) as an off-white solid. $^1$H NMR (300 MHz, d$_6$-DMSO) δ1.52 (d, J=6.7 Hz, 3H), 4.32-4.44 (m, 1H), 5.32 (d, J=10.9 Hz, 2H), 5.91 (d, J=17.6 Hz, 1H), 6.74 (dd, J=17.6, 10.9 Hz, 1H), 7.35-7.48 (m, 3H), 7.70 (s, 1H), 8.60 (br s, 3H)

Compound 16d: (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid 2,2,2-trichloro-ethyl Ester

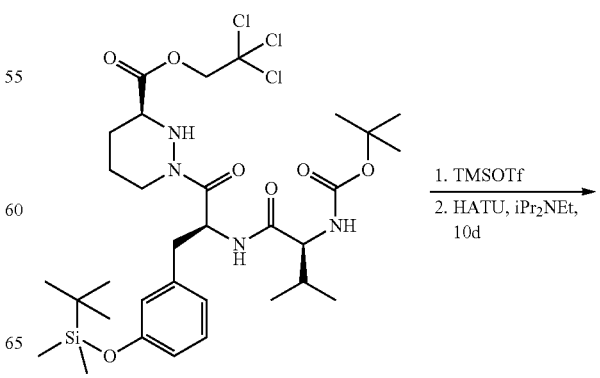

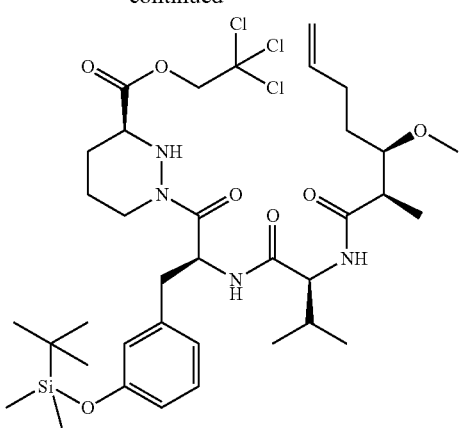

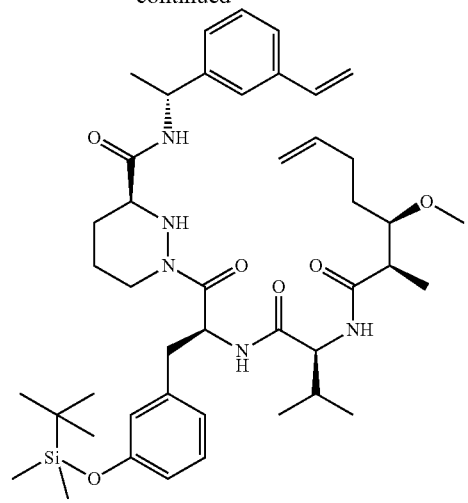

Compound 16d was prepared in the same manner as compound 14e using (2R,3R)-3-methoxy-2-methylhept-6-enoic acid 10d instead of 4-pentenoic acid in 76% yield. $^1$H NMR (300 MHz, CDCl$_3$) δ 0.20 (s, 6H), 0.93 (d, J=6.9 Hz, 3H), 0.96 (d, J=6.9 Hz, 3H), 0.99 (s, 9H), 1.18 (d, J=7.1 Hz, 3H), 1.52 (m, 2H), 1.62-1.96 (m, 4H), 2.10-2.23 (m, 3H), 2.34-2.54 (m, 2H), 2.83 (m, 2H), 2.99 (m, 1H), 3.35 (q, J=6.0 Hz, 1H), 3.41 (s, 3H), 3.51 (m, 1H), 4.26-4.31 (m, 2H), 4.63 (d, J=11.8 Hz, 1H), 4.92 (d, J=12.1 Hz, 1H), 4.98 (dd, J=10.3, 1.8 Hz, 1H), 5.06 (dd, J=17.2, 1.8 Hz, 1H), 5.71-5.91 (m, 2H), 6.52 (m, 2H), 6.71 (m, 2H), 6.84 (d, J=7.6 Hz, 1H), 7.15 (t, J=8.0 Hz, 1H). LCMS (m/z) 791/793 [M+H], Tr=6.04 min Compound 16e: (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid [(R)-1-(3-vinyl-phenyl)-ethyl]-amide

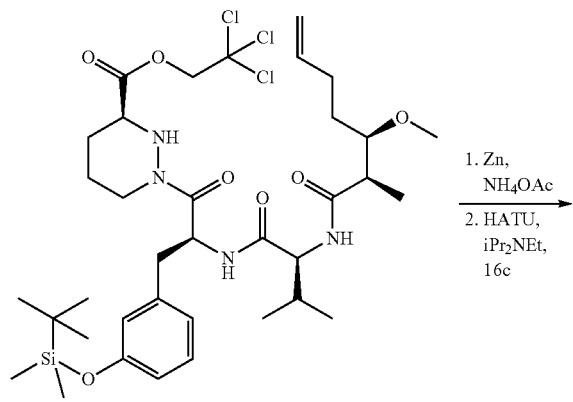

To a solution of (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic acid 2,2,2-trichloro-ethyl ester (560 mg, 0.71 mmol) in tetrahydrofuran (16 mL) was added zinc dust (1.0 g, 15.6 mmol) followed by a solution of ammonium acetate (817 mg, 10.6 mmol) in water (7 mL). The reaction mixture was stirred vigorously at room temperature for 24 hours. The reaction mixture was filtered through celite and the filter pad was washed with dichloromethane. The aqueous layer was acidified to pH 4-5 with 2 M hydrochloric acid and the mixture was extracted with dichloromethane. The organic layers were combined and dried by passing through a hydrophobic frit. The solvent was evaporated and dried to afford (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic acid (480 mg) which was used crude in the next step. LCMS (m/z) 661 [M+H], Tr=5.46 min.

A mixture of (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic acid (480 mg, 0.72 mmol), (R)-1-(3-vinylphenyl)ethylamine hydrochloride (159 mg, 0.86 mmol) and N,N-diisopropylethylamine (372 mg, 0.5 mL, 2.88 mmol) in acetonitrile (20 mL) was stirred at room temperature under nitrogen. 2-(1H-7-Azabenzotriazol-1-yl)-1,1,3,3-tetramethyl uronium hexafluorophosphate methanaminium (380 mg, 1 mmol) was added and the reaction mixture was stirred at room temperature for 24 hours. Ethyl acetate and water were added. The aqueous layer was separated and extracted with ethyl acetate. The organic extracts were combined, washed with water and brine, dried over anhydrous sodium sulfate, filtered and evaporated. The residue was purified by silica gel chromatography using a gradient of iso-hexanes/ethyl acetate 1:1 to neat ethyl acetate to afford the title compound (331 mg, 58%) as a white foam. $^1$H NMR (300 MHz, CD$_3$CN) δ0.20 (s, 6H), 0.81 (d, J=6.9 Hz, 3H), 0.82 (d, J=6.7 Hz, 3H), 0.99 (m, 9H), 1.03 (d, J=6.9 Hz, 3H), 1.40 (d, J=7.1 Hz, 3H), 1.45-2.20 (m, 7H), 2.50-2.70 (m, 2H), 2.75-2.85 (m, 1H), 2.95-3.15 (m, 2H), 3.30 (s, 3H), 3.30-3.35 (m, 1H), 3.95-4.15 (m, 2H), 4.25-4.35 (m, 1H), 4.93-5.10 (m, 4H), 5.25 (dd, J=10.9, 0.9 Hz, 1H), 5.28 (dd, J=10.9, 0.9 Hz, 1H), 5.49-5.58 (m, 1H), 5.81 (dd, J=17.6, 0.9

Hz, 1H), 5.83 (dd, J=17.6, 0.9 Hz, 1H), 6.54-6.61 (m, 1H), 6.70-6.84 (m, 5H), 7.10 (t, J=7.6 Hz, 1H), 7.24-7.43 (m, 6H). LCMS (m/z) 790 [M+H], Tr=5.91 min.

Example 16

Compound 16

(E)-(2R,5S,11S,14S,17R,18R)-11-(3-Hydroxy-benzyl)-14-isopropyl-18-methoxy-2,17-dimethyl-3,9,12,15,28-pentaaza-tricyclo[21.3.1.1*5,9*]octacosa-1(27),21,23,25-tetraene-4,10,13,16-tetraone

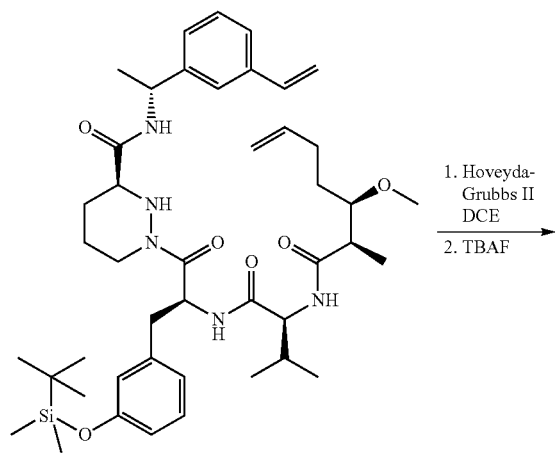

gradient of iso-hexanes/ethyl acetate 1:1 to neat ethyl acetate to afford (E)-2R,5S,11S,14S,17R,18R)-11-[3-(tert-butyl-dimethyl-silanyloxy)-benzyl]-14-isopropyl-18-methoxy-2,17-dimethyl-3,9,12,15,28-pentaaza-tricyclo[21.3.1.1*5,9*] octacosa-1(27),21,23,25-tetraene-4,10,13,16-tetraone (59 mg, 22%) as a gum. LCMS (m/z) 762 [M+H], Tr=5.01 min. A solution of (E)-(2R,5S,11S,14S,17R,18R)-11-[3-(tert-butyl-dimethyl-silanyloxy)-benzyl]-14-isopropyl-18-methoxy-2,17-dimethyl-3,9,12,15,28-penta-azaricyclo[21.3.1.1*5,9*] octacosa-1(27),21,23,25-tetraene-4,10,13,16-tetraone (59 mg, 0.077 mmol) in tetrahydrofuran (5 mL) was stirred at 0° C. under nitrogen. A solution of tetra-N-butylammonium fluoride (1 M in tetrahydrofuran, 0.12 mL, 0.123 mmol) was added and the reaction mixture was stirred at 0° C. for 10 minutes. Silica gel was added and the solvent was evaporated. The residue was purified by silica gel chromatography using a gradient of iso-hexanes/ethyl acetate 1:3 to neat ethyl acetate. The residue was triturated with ether and the resulting solid was collected, washed with ether and dried to afford the title compound (30 mg, 60%) as a white solid. $^1$H NMR (300 MHz, CD$_3$CN) δ0.94 (d, J=6.7 Hz, 3H), 0.95 (d, J=6.7 Hz, 3H), 1.30 (d, J=7.1 Hz, 3H), 1.45 (d, J=6.9 Hz, 3H), 1.55-2.20 (m, 9H), 2.62-2.68 (m, 2H), 2.81-2.98 (m, 2H), 3.26-3.38 (m, 2H), 3.45 (s, 3H), 3.96 (d, J=12.2 Hz, 1H), 4.17 (t, J=8.0 Hz, 1H), 4.34-4.39 (m, 1H), 4.80-4.90 (m, 1H), 5.50-5.56 (m, 1H), 5.85 (d, J=15.8 Hz, 1H), 6.01-6.08 (m, 1H), 6.66-6.69 (m, 1H), 6.86-7.30 (m, 10H), 8.15-8.25 (br s, 1H). LCMS (m/z) 648 [M+H], Tr=4.30 min.

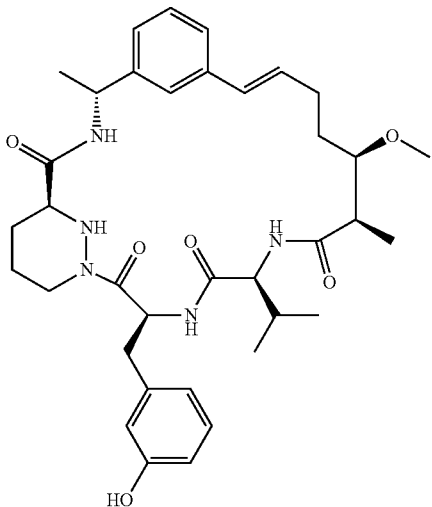

Hoveyda-Grubbs 2nd generation catalyst (22 mg, 0.035 mmol) was added to a stirred solution of (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-prop ionyl}-hexahydro-pyridazine-3-carboxylic acid [(R)-1-(3-vinyl-phenyl)-ethyl]-amide (276 mg, 0.35 mmol) in 1,2-dichloroethane (135 mL) and the reaction mixture was heated at 80° C. under nitrogen for 3 hours. The reaction mixture was cooled to room temperature, silica gel was added and the reaction mixture was evaporated. The residue was purified by silica gel chromatography using a Example 17

Compound 17

(E)-(1S,14R,15R,18S,21S)-21-(3-Hydroxy-benzyl)-18-isopropyl-14-methoxy-15-methyl-3-oxa-6,17,20,23,27-pentaaza-tricyclo[21.3.1.1*5,9*]octacosa-5,7,9(28),10-tetraene-2,16,19,22-tetraone

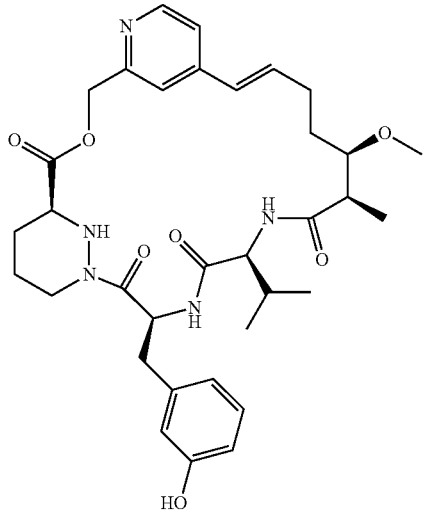 [SMILES: CO[C@@H]1CC/C=C/c2ccnc(c2)COC(=O)[C@@H]2CCCN(N2)C(=O)[C@H](Cc2cccc(O)c2)NC(=O)[C@H](C(C)C)NC(=O)[C@@H]1C]

Compound 17a: (4-Bromo-pyridin-2-yl)-methanol

Sodium borohydride (763 mg, 20.17 mmol) was added portionwise to a solution of 4-bromo-pyridine-2-carboxylic acid methyl ester (1.98 g, 9.166 mmol) in ethanol (50 mL) under nitrogen and the reaction mixture was stirred at room temperature for 18 hours. The reaction was quenched by the addition of acetone (10 mL) and the reaction was stirred for 15 minutes. The solvent was evaporated and the residue partitioned between water and ethyl acetate. The aqueous layer was extracted with ethyl acetate and the combined organics were collected, dried over anhydrous sodium sulfate and the solvent evaporated to afford the title compound (1.61 g, 94%) as a yellow oil. $^1$H NMR (300 MHz, CDCl$_3$) δ3.4-3.5 (br s, 1H), 4.80 (s, 2H), 7.40 (dd, J=5.4, 1.8 Hz, 1H), 7.50 (br m, 1H), 8.39 (d, J=5.4 Hz, 1H). LCMS (m/z) 188/200 [M+H], Tr=1.55 min.

Compound 17b: (4-Vinyl-pyridin-2-yl)-methanol

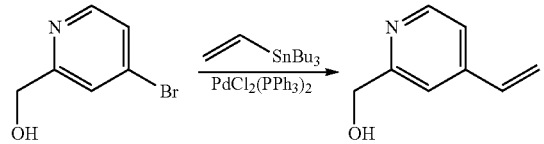

Bis(triphenylphosphine)palladium(II) dichloride (94 mg, 0.134 mmol) was added to a degassed solution of (4-bromo-pyridin-2-yl)-methanol (252 mg, 1.34 mmol) and tributyl (vinyl)tin (0.588 mL, 2.01 mmol) in toluene (10 mL) under nitrogen and the reaction mixture was stirred at 50° C. for 18 hours. Additional tributyl(vinyl)tin (0.176 mL, 0.67 mmol) and bis(triphenylphosphine)palladium(II) dichloride (47 mg, 0.067 mmol) were added and stirring was continued for 18 hours at 80° C. under nitrogen. The reaction mixture was cooled to room temperature and silica gel was added. The solvent was evaporated and the residue was purified by silica gel chromatography using a gradient of iso-hexanes/ethyl acetate 1:2 to 1:4 to afford the title compound (282 mg, 1.34 mmol) as a yellow oil. $^1$H NMR (300 MHz, CDCl$_3$) δ3.60-3.80 (br s, 1H), 4.78 (s, 2H), 5.52 (d, J=10.9 Hz, 1H), 6.01 (d, J=17.6 Hz, 1H), 6.69 (dd, J=17.6, 10.9 Hz, 1H), 7.22 (d, J=5.4 Hz, 1H), 7.27 (s, 1H), 8.52 (d, J=5.4 Hz, 1H).

Compound 17c: (S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid 4-vinyl-pyridin-2-ylmethyl Ester

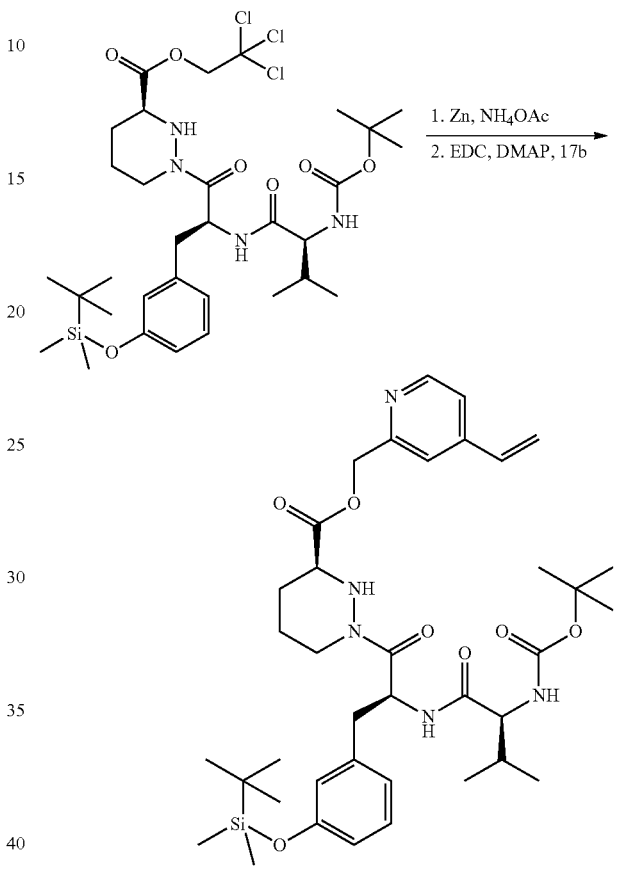

Ammonium acetate (548 mg, 7.11 mmol) was added to a mixture of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid 2,2,2-trichloro-ethyl ester (750 mg, 1.016 mmol) and zinc dust (664 mg, 10.16 mmol) in tetrahydrofuran (20 mL) and water (7 mL) and the reaction mixture was stirred for 3 days at room temperature. The mixture was filtered through celite and the residue was washed with ethyl acetate. The organic layer was washed with an aqueous citric acid solution and water, dried over anhydrous sodium sulfate and the solvent evaporated to afford (S)-1-[(S)-3-[3-(tert-butyl-dimethyl-silanyloxy)-phenyl]-2-((S)-3-methyl-2-pent-4-enoylamino-butyrylamino)-propionyl]-hexahydro-pyridazine-3-carboxylic acid (599 mg, 97%) as a colourless foam which was used crude in the next step. N-(3-Dimethylaminopropyl)-N'-ethylcarbodiimide hydrochloride (265 mg, 1.38 mmol) and 4-dimethylaminopyridine (60 mg, 0.494 mmol) was added to a solution of (S)-1-[(S)-3-[3-(tert-butyl-dimethyl-silanyloxy)-phenyl]-2-((S)-3-methyl-2-pent-4-enoylamino-butyrylamino)-propionyl]-hexahydro-pyridazine-3-carboxylic acid (599 mg, 0.987 mmol) and (4-vinyl-pyridin-2-yl)-methanol (1.34 mmol) in dichloromethane (10 mL) and the reaction mixture was stirred at room temperature for 18 hours. The solution was washed with aqueous citric acid and saturated sodium hydrogen carbonate solution, dried over anhydrous sodium sulfate and the solvent evaporated. The residue was purified by silica gel chromatography using iso-hexanes/ethyl acetate 1:4 to afford the title compound (386 mg, 54%) as a colourless foam. $^1$H NMR (300 MHz, CDCl$_3$) δ0.20 (s, 6H), 0.88 (d, J=6.9 Hz, 3H), 0.94 (d, J=6.9 Hz, 3H), 0.97 (s, 9H), 1.46 (s, 9H), 1.5-2.2 (m, 7H), 2.6-3.1 (m, 3H), 3.55-3.65 (m, 1H), 3.92-3.98 (m, 1H), 4.25-4.35 (m, 1H), 5.07 (d, J=8.7 Hz, 1H), 5.27-5.31 (m, 2H), 5.57 (d, J=10.9 Hz, 1H), 5.72-5.80 (m, 1H), 6.03 (d, J=17.6 Hz, 1H), 6.50 (d, J=8.0 Hz, 1H), 6.67-6.82 (m, 4H), 7.05-7.10 (m, 1H), 7.37 (s, 1H), 8.56 (d, J=5.1 Hz, 1H). LCMS (m/z) 724 [M+H], Tr=5.75 min.

Compound 17d: (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid 4-vinyl-pyridin-2-ylmethyl Ester

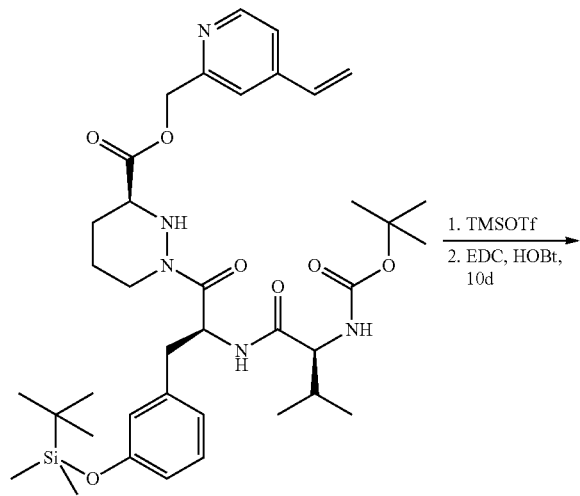

A solution of (S)-1-{(S)-2-((S)-2-tert-butoxycarbonylamino-3-methyl-butyrylamino)-3-[3-(tert-butyl-dimethylsilanyloxy)-phenyl]-propionyl}-hexahydro-pyridazine-3-carboxylic acid 4-vinyl-pyridin-2-ylmethyl ester (377 mg, 0.52 mmol) in dichloromethane (10 mL) was stirred at 0° C. under nitrogen. Trimethylsilyl trifluoromethanesulfonate (173 mg, 0.14 mL, 0.78 mmol) was added and the reaction mixture was stirred at 0° C. for 1 hour. N,N-Diisopropylethylamine (268 mg, 0.36 mL, 2.08 mmol) was added and the reaction mixture was warmed to room temperature. The solvent was evaporated to afford (S)-1-[(S)-3-[3-(tert-butyl-dimethyl-silanyloxy)-phenyl]-2-((S)-2-formylamino-3-methyl-butyrylamino)-propionyl]-hexahydro-pyridazine-3-carboxylic acid 4-vinyl-pyridin-2-ylmethyl ester (0.52 mmol), which was used crude in the next step. LCMS (m/z) 624 [M+H], Tr=4.30 min.

A mixture of crude (S)-1-[(S)-3-[3-(tert-butyl-dimethyl-silanyloxy)-phenyl]-2-((S)-2-formylamino-3-methyl-butyrylamino)-propionyl]-hexahydro-pyridazine-3-carboxylic acid 4-vinyl-pyridin-2-ylmethyl ester (0.52 mmol) and (2R,3R)-3-methoxy-2-methylhept-6-enoic acid 10d (90 mg, 0.52 mmol) in acetonitrile (10 mL) was stirred at room temperature. N-(3-Dimethylaminopropyl)-N'-ethylcarbodiimide hydrochloride (140 mg, 0.73 mmol) and 1-hydroxybenzotriazole hydrate (containing 20% water, 85 mg, 0.52 mmol) was added and the reaction mixture was stirred at room temperature for 4 hours. The solvent was evaporated and the residue was partitioned between ethyl acetate and water. The organic extract was separated, washed with brine, dried over anhydrous sodium sulfate and evaporated. The residue was purified by silica gel chromatography using a gradient of iso-hexanes/ethyl acetate 1:3 to neat ethyl acetate to afford the title compound (271 mg, 67%) as a gum. $^1$H NMR (300 MHz, CDCl$_3$) δ 0.17 (s, 6H), 0.86-0.98 (m, 15H), 1.17 (d, J=7.1 Hz, 3H), 1.5-2.2 (m, 11H), 2.45-3.00 (m, 5H), 3.33-3.44 (m, 1H), 3.40 (s, 3H), 3.60 (d, J=10.9 Hz, 1H), 4.27-4.33 (m, 2H), 4.97 (dd, J=10.2, 1.7 Hz, 1H), 5.05 (dd, J=17.2, 1.7 Hz, 1H), 5.28 (d, J=7.3 Hz, 1H), 5.56 (d, J=10.7 Hz, 1H), 5.73-5.87 (m, 2H), 6.03 (d, J=17.6 Hz, 1H), 6.50 (d, J=8.2 Hz, 2H), 6.66-6.82 (m, 4H), 7.04-7.10 (m, 1H), 7.31 (s, 1H), 8.56 (d, J=5.1 Hz, 1H). LCMS (m/z) 778 [M+H], Tr=5.78 min.

Example 17

Compound 17

(E)-(1S,14R,15R,18S,21S)-21-(3-Hydroxy-benzyl)-18-isopropyl-14-methoxy-15-methyl-3-oxa-6,17,20,23,27-pentaaza-tricyclo[21.3.1.1*5,9*]octacosa-5,7,9(28),10-tetraene-2,16,19,22-tetraone

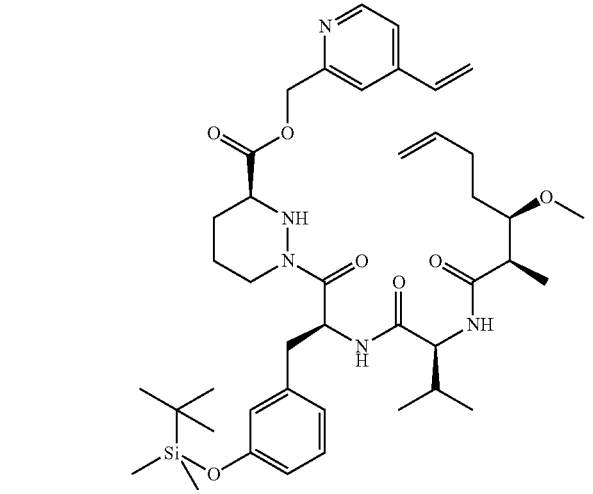

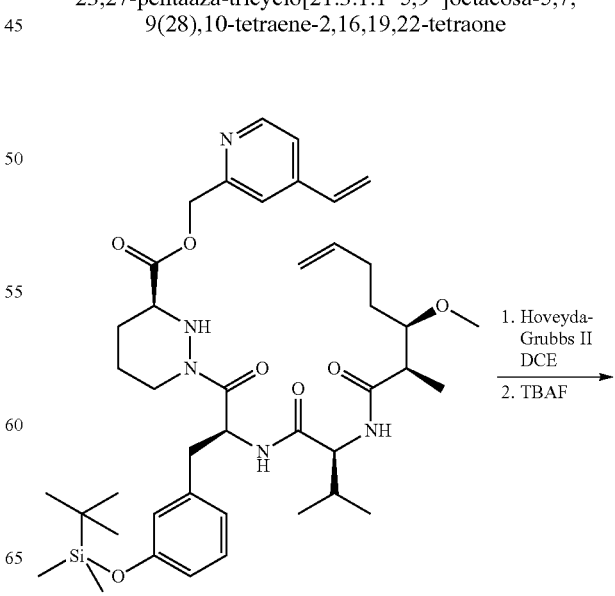

99
-continued

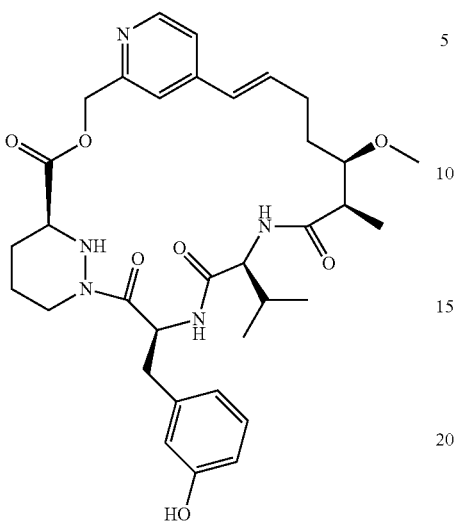

Hoveyda-Grubbs 2nd generation catalyst (22 mg, 0.035 mmol) was added to a stirred solution of (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic acid 4-vinyl-pyridin-2-ylmethyl ester (276 mg, 0.35 mmol) in 1,2-dichloroethane (130 mL) and the reaction mixture was heated at 80° C. under nitrogen for 3 hours. The reaction mixture was cooled to room temperature, silica gel was added and the solvent was evaporated. The residue was purified by silica gel chromatography using a gradient of iso-hexanes/ethyl acetate 1:1 to neat ethyl acetate to afford (E)-(1S,14R,15R,18S,21S)-21-[3-(tert-butyl-dimethyl-silanyloxy)-benzyl]-18-isopropyl-14-methoxy-15-methyl-3-oxa-6,17,20,23,27-pentaaza-tricyclo[21.3.1.1*5,9*]octacosa-5(28),6,8,10-tetraene-2,16,19,22-tetraone (160 mg, 61%) as a white solid. LCMS (m/z) 750 [M+H], Tr=5.58 min.

A solution of (E)-(1S,14R,15R,18S,21S)-21-[3-(tert-butyl-dimethyl-silanyloxy)-benzyl]-18-isopropyl-14-methoxy-15-methyl-3-oxa-6,17,20,23,27-pentaaza-tricyclo[21.3.1.1*5,9*]octacosa-5(28),6,8,10-tetraene-2,16,19,22-tetraone (160 mg, 0.21 mmol) in tetrahydrofuran (10 mL) was stirred at 0° C. under nitrogen. A solution of tetra-N-butylammonium fluoride (1 M in tetrahydrofuran, 0.34 mL, 0.34 mmol) was added and the reaction mixture was stirred at 0° C. for 15 minutes and then at room temperature for 15 minutes. Silica gel was added and the solvent was evaporated. The residue was purified by silica gel chromatography using a gradient of ethyl acetate to ethyl acetate/acetone 9:1 to afford the title compound (88 mg, 65%) as a white solid. $^1$H NMR (300 MHz, CD$_3$CN) δ0.97 (d, J=7.1 Hz, 3H), 0.99 (d, J=7.1 Hz, 3H), 1.32 (d, J=7.4 Hz, 3H), 1.60-2.20 (m, 9H), 2.55-2.89 (m, 4H), 3.28-3.34 (m, 1H), 3.46 (s, 3H), 3.62-3.69 (m, 1H), 4.19-4.41 (m, 3H), 5.19 (d, J=14.5 Hz, 1H), 5.35 (d, J=14.5 Hz, 1H), 5.58-5.65 (m, 1H), 5.83 (d, J=15.8 Hz, 1H), 6.30-6.39 (m, 1H), 6.51 (dd, J=7.9, 1.6 Hz, 1H), 6.67 (d, J=7.6 Hz, 1H), 6.75-6.81 (m, 1H), 7.01-7.07 (m, 3H), 7.22-7.28 (m, 2H), 8.02 (s, 1H), 8.39 (d, J=5.1 Hz, 1H)
LCMS (m/z) 636 [M+H], Tr=4.18 min. .

100
Example 18

Compound 18

(E)-(1S,14R,15R,18S,21S)-21-(3-Hydroxy-benzyl)-18-isopropyl-14-methoxy-15-methyl-3-oxa-8,17,20,23,27-pentaaza-tricyclo[21.3.1.1*5,9*]octacosa-,7,9(28),10-tetraene-2,16,19,22-tetraone

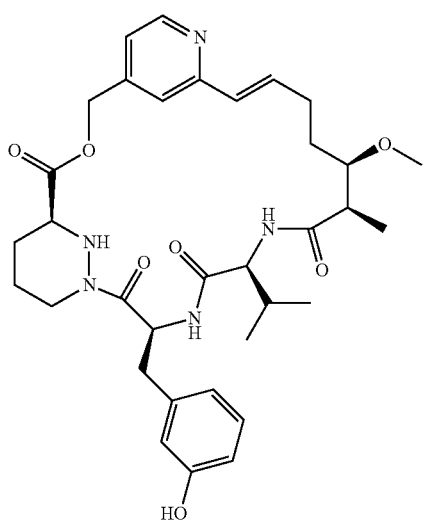 [SMILES: CO[C@@H]1CC/C=C/c2cc(ccn2)COC(=O)[C@@H]2CCCN(N2)C(=O)[C@H](Cc2cccc(O)c2)NC(=O)[C@H](C(C)C)NC(=O)[C@@H]1C]

Compound 18a: (2-Bromo-pyridin-4-yl)-methanol

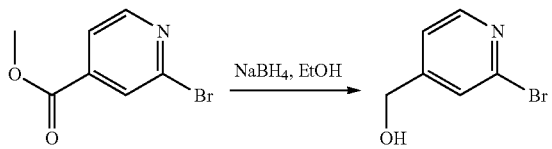

Compound 18a was prepared in the same manner as compound 17a, using 2-bromo-isonicotinic acid methyl ester instead of 4-bromo-pyridine-2-carboxylic acid methyl ester, in 87% yield. $^1$H NMR (300 MHz, CDCl$_3$) δ2.00-2.30 (br s, 1H), 4.76 (s, 2H), 7.26 (dd, J=5.0, 0.6 Hz, 1H), 7.54 (d, J=0.6 Hz, 1H), 8.33 (d, J=5.0 Hz, 1H).

Compound 18b: (2-Vinyl-pyridin-4-yl)-methanol

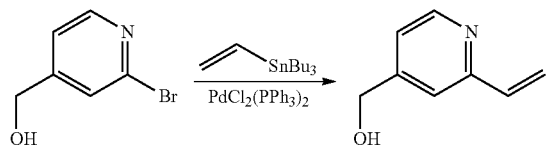

Compound 18b was prepared in the same manner as compound 17b, using compound 18a instead of compound 17a, in 72% yield. $^1$H NMR (300 MHz, d$_6$-DMSO) δ4.53 (d, J=5.8 Hz, 2H), 5.41-5.47 (m, 2H), 6.21 (dd, J=17.4, 1.6 Hz, 1H), 6.80 (dd, J=17.4, 10.7 Hz, 1H), 7.20 (d, J=5.1 Hz, 1H), 7.41 (s, 1H), 8.46 (d, J=5.1 Hz, 1H). LCMS (m/z) 136 [M+H], Tr=0.75 min.

Compound 18c: (S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid 2-vinyl-pyridin-4-ylmethyl Ester 6.52 (d, J=8.2 Hz, 1H), 6.67-6.90 (m, 4H), 7.05-7.14 (m, 2H), 8.60 (d, J=4.9 Hz, 1H). LCMS (m/z) 724 [M+H], Tr=5.30 min.

Compound 18d: (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid 2-vinyl-pyridin-4-ylmethyl Ester

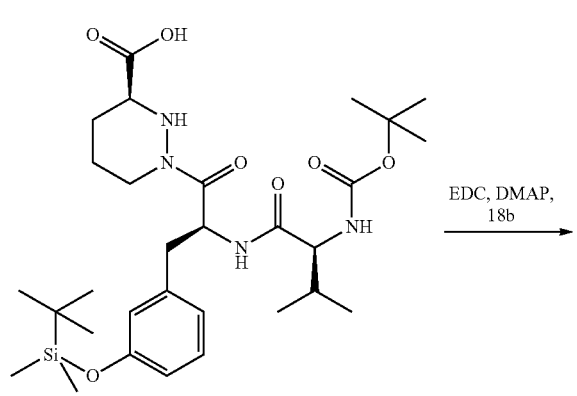

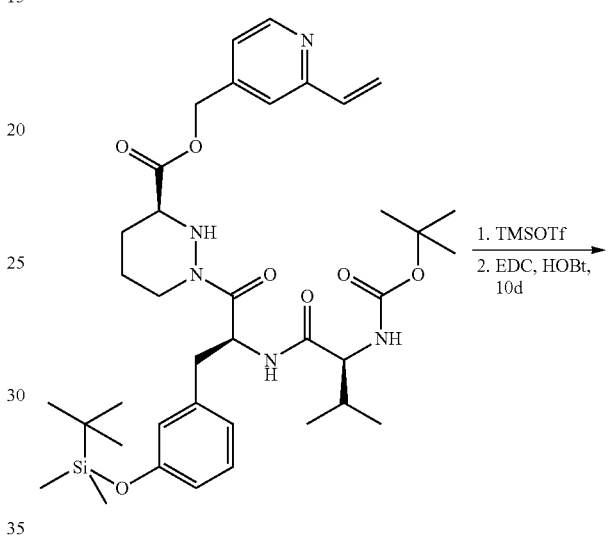

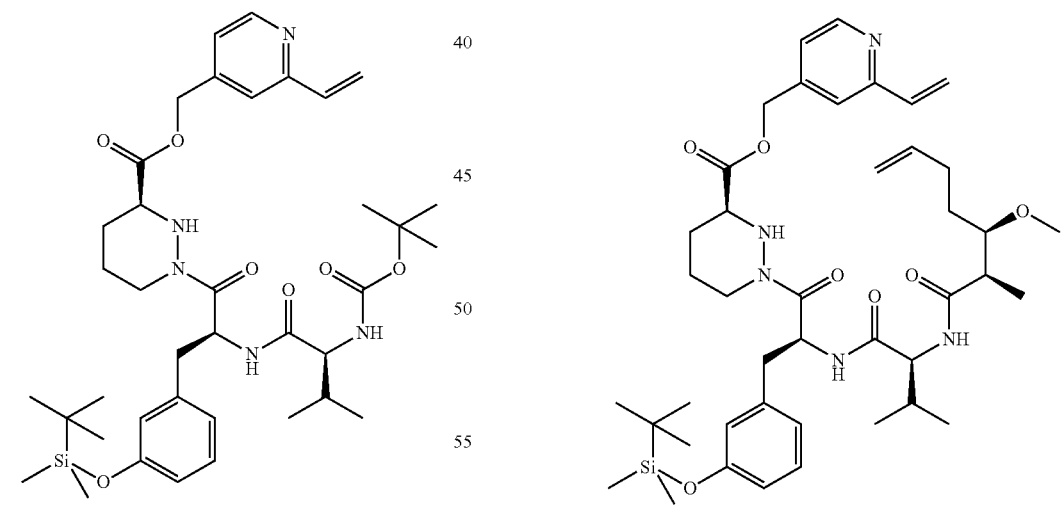

Compound 18c was prepared in the same manner as compound 17c, using compound 18b instead of compound 17b, in 44% yield. $^1$H NMR (300 MHz, CDCl$_3$) δ0.18 (s, 6H), 0.88 (d, J=6.9 Hz, 3H), 0.95 (d, J=7.1 Hz, 3H), 0.97 (s, 9H), 1.46 (s, 9H), 1.50-2.60 (m, 7H), 2.80-3.05 (m, 3H), 3.48-3.52 (m, 1H), 3.94-3.98 (m, 1H), 4.20-4.28 (m, 1H), 5.05 (d, J=8.5 Hz, 1H), 5.10 (d, J=13.4 Hz, 1H), 5.19 (d, J=13.4 Hz, 1H), 5.54 (d, J=10.7 Hz, 1H), 5.75-5.83 (m, 1H), 6.25 (d, J=17.6 Hz, 1H), Compound 18d was prepared in the same manner as compound 17d, using compound 18c instead of compound 17c, in 84% yield. $^1$H NMR (300 MHz, CDCl$_3$) δ 0.17 (s, 6H), 0.91 (d, J=6.9 Hz, 3H), 0.94-0.97 (m, 12H), 1.18 (d, J=6.9 Hz, 3H), 1.45-2.20 (m, 11H), 2.45-3.01 (m, 5H), 3.31-3.37 (m, 1H), 3.41 (s, 3H), 3.51 (d, J=10.7 Hz, 1H), 4.20-4.33 (m, 2H), 4.95-5.21 (m, 4H), 5.54 (d, J=10.7 Hz, 1H), 5.73-5.90 (m, 2H), 6.26 (d, J=17.4 Hz, 1H), 6.50-6.55 (m, 1H), 6.69 (br s, 2H), 6.80-6.90 (m, 2H), 7.04-7.13 (m, 2H), 8.60 (d, J=5.1 Hz, 1H). LCMS (m/z) 778 [M+H], Tr=5.65 min.

Example 18

Compound 18

(E)-(1S,14R,15R,18S,21S)-21-(3-Hydroxy-benzyl)-18-isopropyl-14-methoxy-15-methyl-3-oxa-8,17,20,23,27-pentaaza-tricyclo[21.3.1.1*5,9*]octacosa-,7,9(28),10-tetraene-2,16,19,22-tetraone

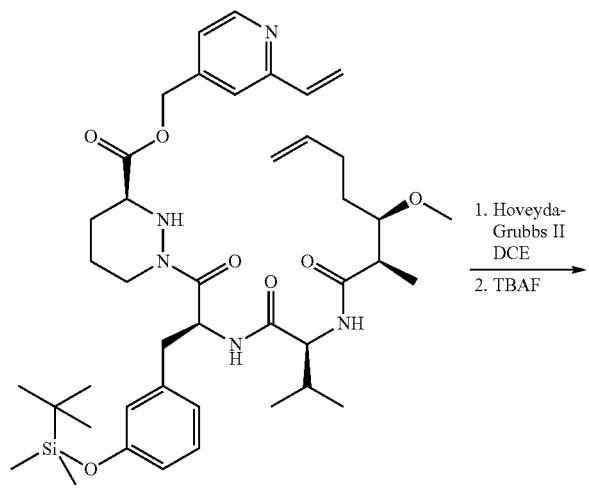

Compound 18 was prepared in the same manner as compound 17 using compound 18d instead of compound 17d in 32% yield. $^1$H NMR (300 MHz, CD$_3$CN) δ0.97 (d, J=6.9 Hz, 3H), 0.99 (d, J=6.7 Hz, 3H), 1.32 (d, J=7.4 Hz, 3H), 1.60-2.20 (m, 9H), 2.55-2.90 (m, 4H), 3.28-3.34 (m, 1H), 3.47 (s, 3H), 3.60-3.66 (m, 1H), 4.20-4.40 (m, 3H), 5.16 (d, J=14.5 Hz, 1H), 5.30 (d, J=14.5 Hz, 1H), 5.57-5.65 (m, 1H), 5.92 (d, J=15.6 Hz, 1H), 6.53 (dd, J=8.0, 1.6 Hz, 1H), 6.61-6.71 (m, 2H), 6.77-6.82 (m, 1H), 7.00-7.06 (m, 4H), 7.28 (d, J=8.7 Hz, 1H), 8.04 (s, 1H), 8.41 (d, J=4.9 Hz, 1H). LCMS (m/z) 636 [M+H], Tr=3.20 min.

Example 19

Compound 19

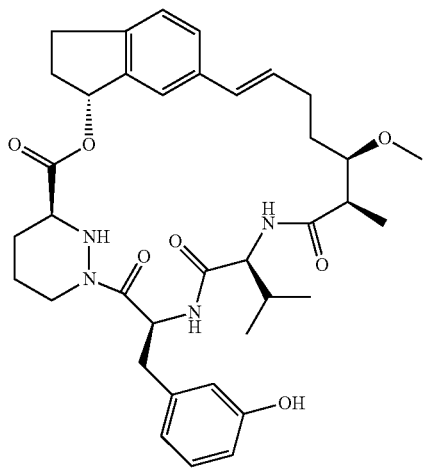 [SMILES: CO[C@@H]1CC/C=C/c2ccc3c(c2)[C@@H](CC3)OC(=O)[C@@H]2CCCN(N2)C(=O)[C@H](Cc2cccc(O)c2)NC(=O)[C@H](C(C)C)NC(=O)[C@@H]1C]

Compound 19a: (R)-6-Bromo-indan-1-ol

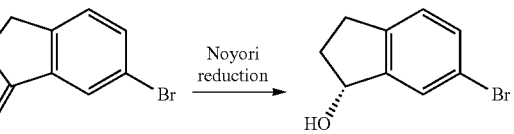

Compound 19a was prepared in the same manner as compound 14c using 3-bromoindanone instead of 1-(3-chloro-isoquinolin-6-yl)-ethanone 14b in 95% yield. $^1$H NMR (300 MHz, CDCl$_3$) δ1.76 (d, J=6.9 Hz, 1H), 1.97 (dddd, J=5.6, 6.9, 8.5, 12.7 Hz, 1H), 2.53 (dddd, J=4.4, 6.9, 8.0, 12.9 Hz, 1H), 3.01 (ddd, J=4.5, 8.7, 16.0 Hz, 1H), 2.84 (m, 1H), 5.24 (app q, J=6.2 Hz, 1H), 7.14 (d, J=8.0 Hz, 1H), 7.39 (dd, J=1.8, 8.2 Hz, 1H), 7.56 (d, J=0.9 Hz, 1H).

Compound 19b: (R)-6-Vinyl-indan-1-ol

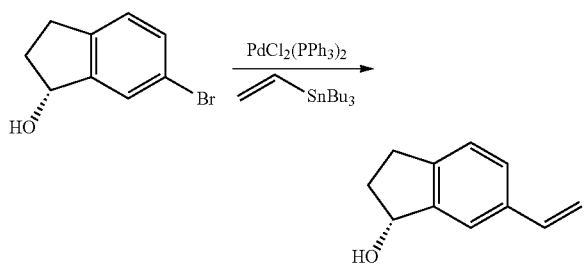

Compound 19b was prepared in the same manner as compound 14d using (R)-6-bromo-indan-1-ol (19a) instead of (R)-1-(3-chloro-isoquinolin-6-yl)-ethanol (14c) in 30% yield. ¹H NMR (300 MHz, CDCl₃) δ1.65 (br s, 1H), 1.98 (dddd, J=5.4, 6.7, 8.5, 13.8 Hz, 1H), 2.53 (dddd, J=4.7, 6.7, 8.2, 13.1 Hz, 1H), 2.89 (m, 1H), 3.06 (ddd, J=4.7, 8.7, 16.0 Hz, 1H), 5.30 (m, 2H), 5.75 (d, J=17.6 Hz, 1H), 6.75 (dd, J=10.7, 17.6 Hz, 1H), 7.23 (d, J=7.8 Hz, 1H), 7.33 (dd, J=1.6, 7.8 Hz, 1H), 7.50 (s, 1H).

Compound 19c: (S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid (R)-6-vinyl-indan-1-yl Ester

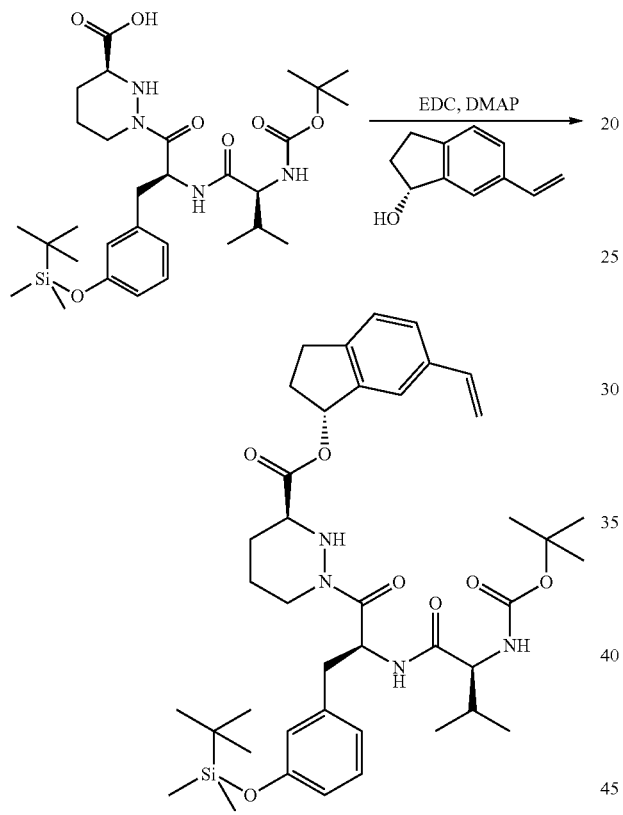

A solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid (658 mg, 1.086 mmol) 2f, prepared as described earlier, (R)-6-vinyl-indan-1-ol (208.7 mg, 1.303 mmol) and 4-dimethylaminopyridine (132.7 mg, 1.086 mmol) in anhydrous dichloromethane (20 mL) was treated with 1-ethyl-3-(3-dimethylaminopropyl)carbodiimide (340.6 mg, 1.738 mmol). After overnight stirring at room temperature the volatiles were removed in vacuo and the residue was purified by silica gel chromatography using a 50 g Isolute cartridge eluted with a continuous gradient of isohexanes/ethyl acetate 1:0 to 1:1 to afford the title compound (762 mg, 95%) as a white solid. ¹H NMR (300 MHz, CDCl₃) δ0.13-0.22 (m, 6H), 0.86-0.99 (m, 15H), 1.47 (s, 10H), 1.72-1.91 (m, 3H), 1.99-2.20 (m, 2H), 2.43-2.60 (m, 2H), 2.66-2.78 (m, 1H), 2.81-3.01 (m, 3H), 3.04-3.17 (m, 1H), 3.91-4.01 (m, 1H), 4.33 (br d, J=12.7 Hz, 1H), 5.03-5.11 (m, 1H), 5.22-5.33 (m, 1H), 5.70-5.82 (m, 2H), 6.21 (dd, J=3.6, 6.9 Hz, 1H), 6.49 (d, J=8.5 Hz, 1H), 6.57-6.65 (m, 2H), 6.68-6.74 (m, 1H), 6.75-6.85 (m, 2H), 6.92 (app t, J=7.6 Hz, 1H), 7.26 (d, J=7.8 Hz, 1H), 7.41 (d, J=7.8 Hz, 1H), 7.48 (s, 1H). LCMS (m/z) 771.4 [M+Na], Tr=6.05 min.

Compound 19d: (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid (R)-6-vinyl-indan-1-yl Ester

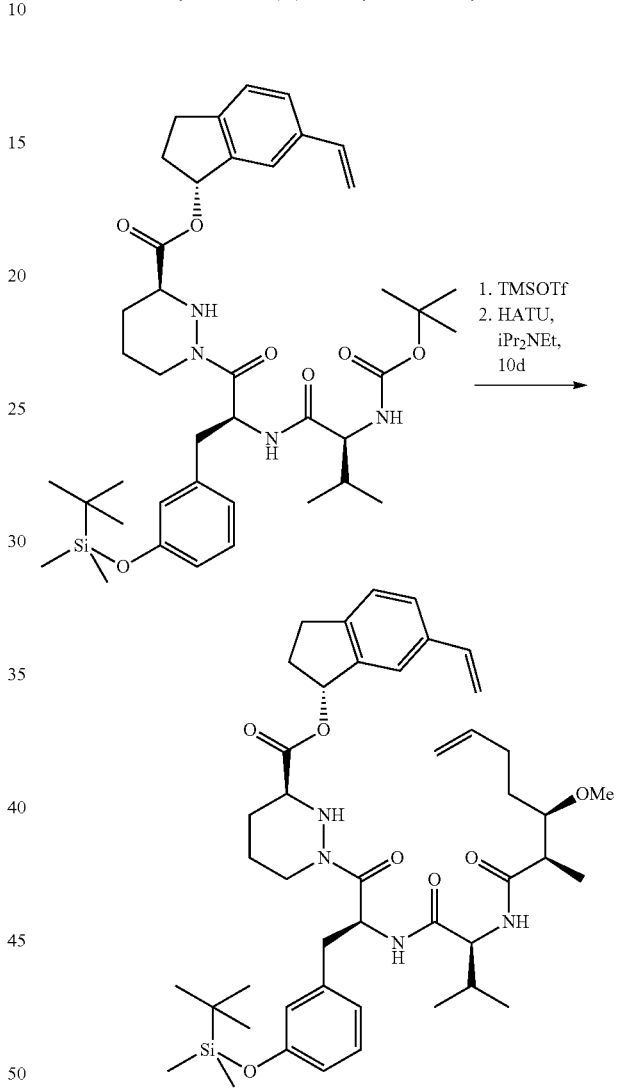

A cooled (0° C.) solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid (R)-6-vinyl-indan-1-yl ester (761.6 mg, 1.017 mmol) in anhydrous dichloromethane (20 mL) was treated with trimethylsilyl trifluoromethanesulfonate (370 µL, 2.033 mmol). After 1 h at 0° C., the reaction mixture was treated with N,N-diisopropylethylamine (710 µL, 4.068 mmol) and the volatiles were removed in vacuo to afford the corresponding amine as a yellow solid. To this crude amine was added (2R,3R)-3-methoxy-2-methyl-hept-6-enoic acid 10d (175.1 mg, 1.017 mmol), N,N-diisopropylethylamine (710 µL, 4.068 mmol) and acetonitrile (20 mL). The reaction mixture was cooled to 0° C. and treated with 2-(1H-7-azabenzotriazol-1-yl)-1,1,3,3-tetramethyl uronium hexafluorophosphate methanaminium (541.4 mg, 1.424 mmol). After overnight stirring at room temperature the volatiles were removed in vacuo and the residue was purified by silica gel chromatography using a 50 g Isolute cartridge eluted with a continuous gradient of iso-hexanes/ethyl acetate 1:0 to 1:2 to afford the title compound (507 mg, 62%) as a white solid. $^1$H NMR (300 MHz, CDCl$_3$) δ 0.14-0.21 (m, 6H), 0.89-1.00 (m, 15H), 1.18 (d, J=6.9 Hz, 3H), 1.34-1.56 (m, 2H), 1.62-1.91 (m, 4H), 2.10-2.23 (m, 3H), 2.40-2.61 (m, 3H), 2.63-2.77 (m, 1H), 2.84-3.01 (m, 4H), 3.03-3.17 (m, 1H), 3.32-3.45 (m, 2H), 3.40 (s, 3H), 3.58 (d, J=11.4 Hz, 1H), 4.31 (dd, J=5.6, 8.9 Hz, 2H), 4.97 (d, J=10.9 Hz, 1H), 5.05 (d, J=17.2 Hz, 1H), 5.27 (d, J=10.9 Hz, 1H), 5.69-5.90 (m, 3H), 6.21 (dd, J=3.6, 6.9 Hz, 1H), 6.50 (app t, J=7.3 Hz, 2H), 6.60 (s, 1H), 6.67-6.74 (m, 1H), 6.75-6.81 (m, 2H), 6.91 (app t, J=7.8 Hz, 1H), 7.41 (dd, J=1.6, 7.8 Hz, 1H), 7.48 (s, 1H). LCMS (m/z) 825.4 [M+Na], Tr=6.08 min.

Example 19

Compound 19

A solution of (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic acid (R)-6-vinyl-indan-1-yl ester (507 mg, 0.631 mmol) in dichloroethane (200 mL) was treated with Hoveyda-Grubbs' 2$^{nd}$ generation catalyst (40 mg, 0.063 mmol). After stirring for 2 h at reflux, more catalyst (40 mg, 0.063 mmol) was added to the reaction mixture. After 4 h at reflux, the mixture was cooled to room temperature. A few scoops of silica gel were added and the volatiles were removed in vacuo. The macrocycle was purified by silica gel chromatography using a 25 g Isolute cartridge eluted with a continuous gradient of iso-hexanes/ethyl acetate 1:0 to 1:2 to afford the macrocycle in a mixture that was immediately dissolved in anhydrous tetrahydrofuran (10 mL), cooled to 0° C. and treated with tetra-N-butylammonium fluoride (1 M in tetrahydrofuran, 1.1 mL, 1.066 mmol). After 1.5 h the volatiles were removed in vacuo and the residue was purified by silica chromatography using a 25 g Isolute cartridge eluted with a continuous gradient of iso-hexanes/ethyl acetate 1:0 to 0:1 to afford the title compound (60 mg, 14%) as a white solid. $^1$H NMR (300 MHz, d$_6$-DMSO) δ 0.74-0.91 (m, 10H), 1.15 (d, J=7.1 Hz, 3H), 1.25-1.45 (m, 2H), 1.50-1.76 (m, 5H), 1.84-2.12 (m, 2H), 2.17-2.32 (m, 1H), 2.54-2.65 (m, 3H), 2.68-3.04 (m, 5H), 4.11-4.25 (m, 2H), 5.14 (d, J=10.9 Hz, 1H), 5.59-5.73 (m, 1H), 6.09-6.24 (m, 2H), 6.30-6.48 (m, 5H), 6.99 (d, J=9.1 Hz, 1H), 7.21-7.37 (m, 3H), 8.02 (d, J=7.8 Hz, 1H), 9.04 (s, 1H). LCMS (m/z) 661.4 [M+H], 684.4 [M+Na], Tr=5.26 min.

Example 20

Compound 20

(2R,5S,11S,14S,17R,18R)-11-(3-Hydroxy-benzyl)-14-isopropyl-18-methoxy-2,17-dimethyl-3-oxa-9,12,15,28-tetraaza-tricyclo[21.3.1.1*5,9*]octacosa-1(27),23,25-triene-4,10,13,16-tetraone

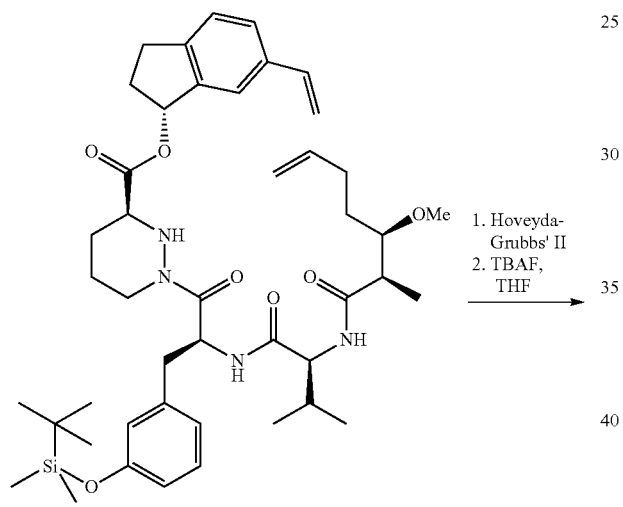

1. Hoveyda-Grubbs' II
2. TBAF, THF

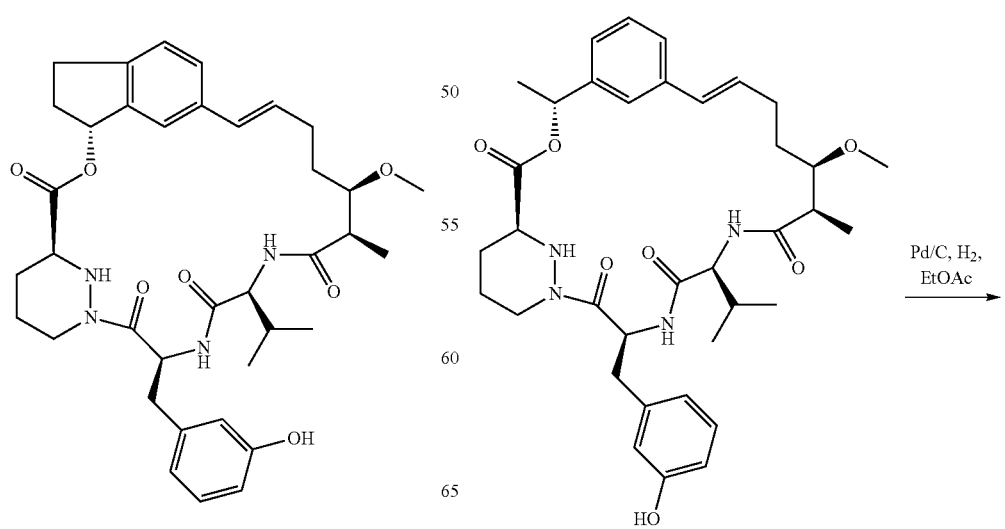

Pd/C, H$_2$, EtOAc

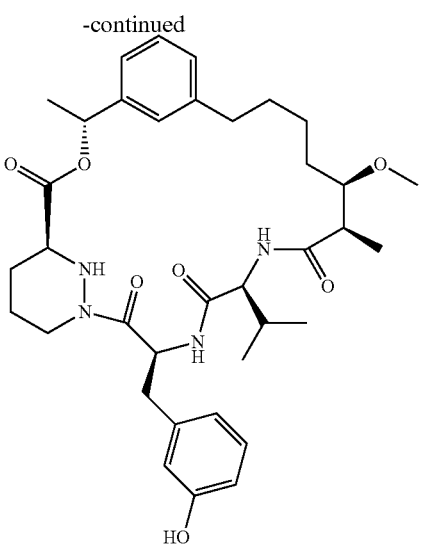

A solution of (E)-(2R,5S,11S,14S,17R,18R)-11-(3-hydroxy-benzyl)-14-isopropyl-18-methoxy-2,17-dimethyl-3-oxa-9,12,15,28-tetraaza-tricyclo[21.3.1.1*5,9*]octacosa-1(27),21,23,25-tetraene-4,10,13,16-tetraone (12 mg, 0.0185 mmol) in ethyl acetate (2 mL) containing 10% palladium on carbon (10 mg) was hydrogenated at room temperature and pressure for 1 hour. The reaction mixture was filtered through filter aid and the filter pad was washed with ethyl acetate. The filtrate was evaporated and the residue was purified by silica gel chromatography using iso-hexanes/ethyl acetate 4:6 to afford the title compound (5.6 mg, 47%) as a white solid. $^1$H NMR (300 MHz, CD$_3$CN) δ0.95 (d, J=6.7 Hz, 6H), 1.28 (d, J=7.4 Hz, 3H), 1.54 (d, J=6.7 Hz, 3H), 1.30-2.30 (m, 13H), 2.55-2.60 (m, 1H), 2.75-2.91 (m, 3H), 3.26-3.32 (m, 1H), 3.44 (s, 3H), 3.50-3.57 (m, 1H), 4.00 (d, J=11.4 Hz, 1H), 4.17-4.30 (m, 2H), 5.48-5.56 (m, 1H), 5.77 (q, J=6.5 Hz, 1H), 6.66 (dd, J=8.0, 1.6 Hz, 1H), 6.88 (d, J=7.6 Hz, 1H), 7.02-7.15 (m, 7H), 7.22 (d, J=7.6 Hz, 1H), 7.95-8.05 (br s, 1H). LCMS (m/z) 651 [M+H], Tr=5.20 min.

Example 21

Compound 21

(13E,15E)-(3S,6S,9R,10R,11S,12S,21S)-3-(3-Hydroxy-benzyl)-10,12-dimethoxy-6-(4-methoxy-benzyl)-9,11-dimethyl-19-oxa-1,4,7,25-tetraazabicyclo[19.3.1]pentacosa-13,15-diene-2,5,8,20-tetraone

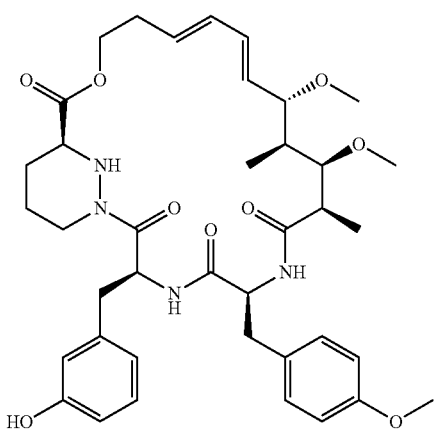 [SMILES: COc1ccc(C[C@@H]2NC(=O)[C@H](C)[C@H](OC)[C@@H](C)[C@@H](OC)/C=C/C=C/CCOC(=O)[C@@H]3CCCN(N3)C(=O)[C@H](Cc3cccc(O)c3)NC2=O)cc1]

Compound 21a: (S)-1-{(S)-2-tert-Butoxycarbonylamino-3-[3-(tert-butyl-dimethyl-silanyloxy)-phenyl]-propionyl}-hexahydro-pyridazine-3-carboxylic Acid 2,2,2-trichloro-ethyl Ester

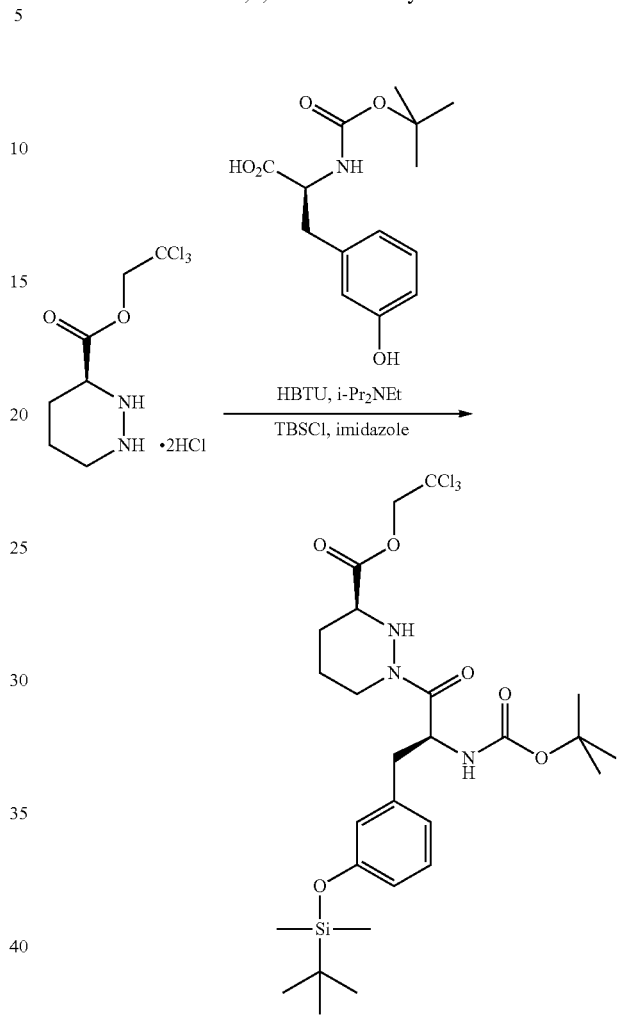

(S)-2-tert-Butoxycarbonylamino-3-(3-hydroxy-phenyl)-propionic acid (618 mg, 2.20 mmol) and N,N-diisopropyl-ethylamine (1.6 mL, 9.15 mmol) were dissolved in acetonitrile (12 ml). To this solution was added O-benzotriazole-N,N,N',N'-tetramethyl-uronium-hexafluoro-phosphate (902 mg, 2.38 mmol). (S)-Hexahydro-pyridazine-3-carboxylic acid 2,2,2-trichloro-ethyl ester (612 mg, 1.83 mmol) (JACS 2003, 125, p. 3849) was dissolved in acetonitrile (8 mL) and added to the reaction mixture. The reaction was allowed to stir at room temperature for 18 h. The solvent was evaporated and the residue partitioned between ethyl acetate and water. The phases were separated, the organic layer was dried over anhydrous sodium sulfate and the solvent evaporated to afford an oil. This was purified by silica gel chromatography, eluting with a gradient of iso-hexanes/ethyl acetate (2:1-1:1) to afford a pale yellow oil (726 mg, 76%). This oil was dissolved in acetone (10 mL) and imidazole (151 mg, 2.2 mmol) and tert-butyldimethylsilyl chloride (271 mg, 1.8 mmol) were added. The reaction was stirred at room temperature for 24 hours. The solvent was evaporated and the residue partitioned between diethyl ether and water. The layers were separated, the organic layer was dried over anhydrous sodium sulfate and the solvent evaporated to afford an oil. This was purified by silica gel chromatography, eluting with iso-hexanes/ethyl acetate 3:1 to afford the title compound (670 mg, 76%) as a colourless solid. ¹H NMR (300 MHz, CDCl₃) δ0.20 (s, 3H), 0.21 (s, 3H), 0.99 (s, 9H), 1.44 (s, 9H), 1.78-1.88 (m, 1H), 1.90-2.00 (m, 1H), 2.46-2.57 (m, 1H), 2.68-2.80 (m, 1H), 2.82-2.96 (m, 2H), 3.57-3.65 (m, 1H), 4.38-4.44 (m, 1H), 4.67 (d, J=12.0 Hz, 1H), 4.90 (d, J=12.0 Hz, 1H), 5.19-5.24 (m, 1H), 5.44-5.55 (m, 1H), 6.67-6.74 (m, 2H), 6.84 (d, J=7.6 Hz, 1H), 7.16 (app t, J=7.8 Hz, 1H).

Compound 21b: (S)-1-{(S)-2-[(S)-2-tert-Butoxycarbonylamino-3-(4-methoxy-phenyl)-propionylamino]-3-[3-(tert-butyl-dimethyl-silanyloxy)-phenyl]-propionyl}-hexahydro-pyridazine-3-carboxylic Acid 2,2,2-trichloro-ethyl Ester

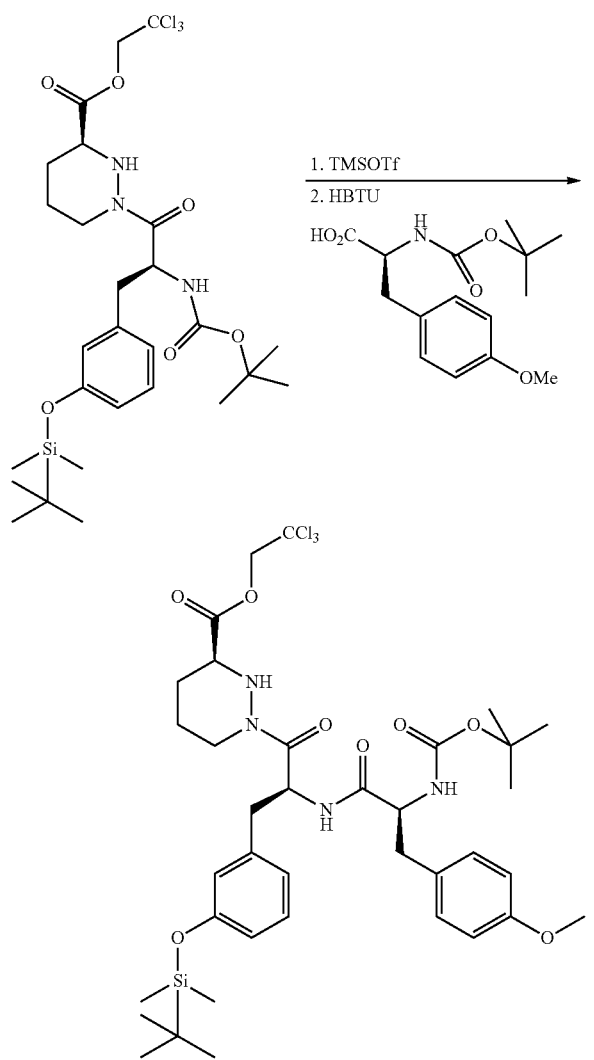

Trimethylsilyltrifluoromethanesulfonate (341 µL, 1.89 mmol) was added dropwise to a solution of the (S)-1-{(S)-2-tert-butoxycarbonylamino-3-[3-(tert-butyl-dimethyl-silanyloxy)-phenyl]-propionyl}-hexahydro-pyridazine-3-carboxylic acid 2,2,2-trichloro-ethyl ester (670 mg, 1.05 mmol) in dichloromethane (15 mL) at 0° C. under N₂ and the reaction was stirred for 85 minutes. To this was added N,N-diisopropylethylamine (730 µL, 4.19 mmol) and the reaction was warmed to room temperature. The volatiles were evaporated to afford a colourless foam which was dissolved in acetonitrile (15 mL). To this solution was added O-benzotriazole-N,N,N',N'-tetramethyl-uronium-hexafluoro-phosphate (477 mg, 1.26 mmol), (S)-2-tert-butoxycarbonylamino-3-(4-methoxy-phenyl)-propionic acid (340 mg, 1.15 mmol) and N,N-diisopropylethylamine (730 µL, 4.19 mmol) and the reaction was stirred for 18 h. The volatiles were evaporated and the residue partitioned between pH=7 buffer and ethyl acetate. The organic layer was dried over anhydrous sodium sulfate and the volatiles evaporated. The residue was purified by silica chromatography using a gradient of iso-hexanes/ethyl acetate 3:1 to 1:1 to afford the title compound (570 mg, 67%) as a colourless foam. ¹H NMR (300 MHz, CDCl₃) δ0.18 (s, 6H), 1.00 (s, 9H), 1.43 (s, 9H), 1.45-1.60 (m, 2H) 1.73-1.83 (m, 1H), 1.85-1.95 (m, 1H), 2.30 (br s, 1H), 2.65-3.00 (m, 5H), 3.50 (d, J=11.2 Hz, 1H), 3.80 (s, 3H), 4.24-4.37 (m, 2H), 4.65 (d, J=11.8 Hz, 1H), 4.95 (d, J=11.8 Hz, 1H), 4.96-5.04 (m, 1H), 5.62-5.75 (m, 1H), 6.45 (d, J=8.3 Hz, 1H), 6.64-6.75 (m, 2H), 6.78-6.86 (m, 3H), 7.07-7.16 (m, 3H). LCMS (m/z) 817.3 [M+H], Tr=5.89 min.

Compound 21c: (S)-1-{(S)-2-[(S)-2-tert-Butoxycarbonylamino-3-(4-methoxy-phenyl)-propionylamino]-3-[3-(tert-butyl-dimethyl-silanyloxy)-phenyl]-propionyl}-hexahydro-pyridazine-3-carboxylic Acid but-3-enyl Ester

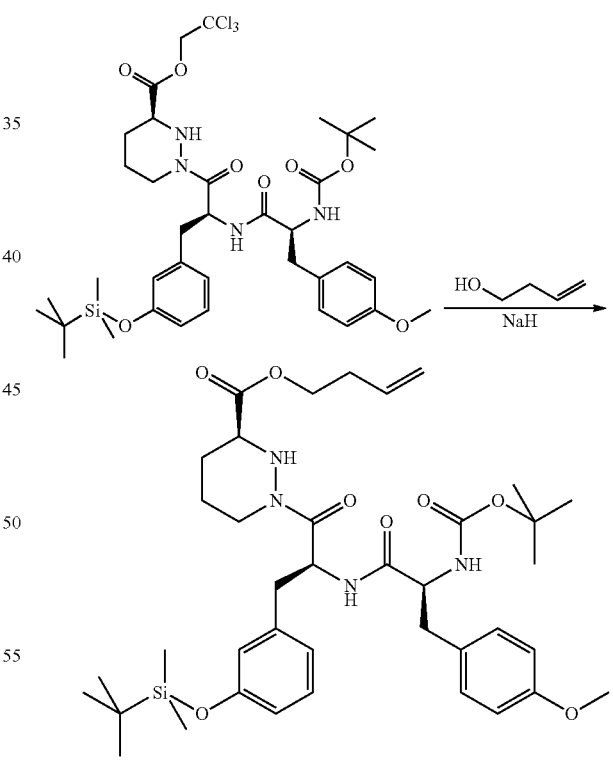

Sodium hydride (6 mg, 0.139 mmol) was added to a solution of (S)-1-{(S)-2-[(S)-2-tert-butoxycarbonylamino-3-(4-methoxy-phenyl)-propionylamino]-3-[3-(tert-butyl-dimethyl-silanyloxy)-phenyl]-propionyl}-hexahydro-pyridazine-3-carboxylic acid 2,2,2-trichloro-ethyl ester (570 mg, 0.698 mmol) and 3-buten-1-ol (601 µL, 6.98 mmol) in tetrahydrofuran (10 mL) and the reaction stirred at 50° C.

under nitrogen for 18 h. The reaction was cooled and the mixture passed through a plug of silica gel (eluting twice with ethyl acetate, 50 mL) to afford the title compound (438 mg, 85%) as a colourless oil (438 mg, 85%). ¹H NMR (300 MHz, CDCl₃) δ0.20 (s, 6H), 1.00 (s, 9H), 1.10-140 (m, 2H), 1.40 (s, 9H), 1.72-1.86 (m, 2H), 2.33-2.46 (m, 3H), 2.60-3.05 (m, 5H), 3.50 (d, 11.4 Hz, 1H), 3.80 (s, 3H), 4.15-4.35 (m, 4H), 4.95 (br s, 1H), 5.09-5.19 (m, 2H), 5.60-5.70 (m, 1H), 5.71-5.87 (m, 1H), 6.42 (d, J=8.0 Hz, 1H), 6.62-6.80 (m, 3H), 6.82 (d, J=8.7 Hz, 2H), 7.07-7.16 (m, 3H). LCMS (m/z) 739.40 [M+H], Tr=5.82 min.

Compound 21d: (S)-1-{(S)-3-[3-(tert-Butyl-dimethyl-silanyloxy)-phenyl]-2-[(S)-2-((Z)-(2R,3R,4S,5S)-3,5-dimethoxy-2,4-dimethyl-nona-6,8-dienoylamino)-3-(4-methoxy-phenyl)-propionylamino]-propionyl}-hexahydro-pyridazine-3-carboxylic Acid but-3-enyl Ester

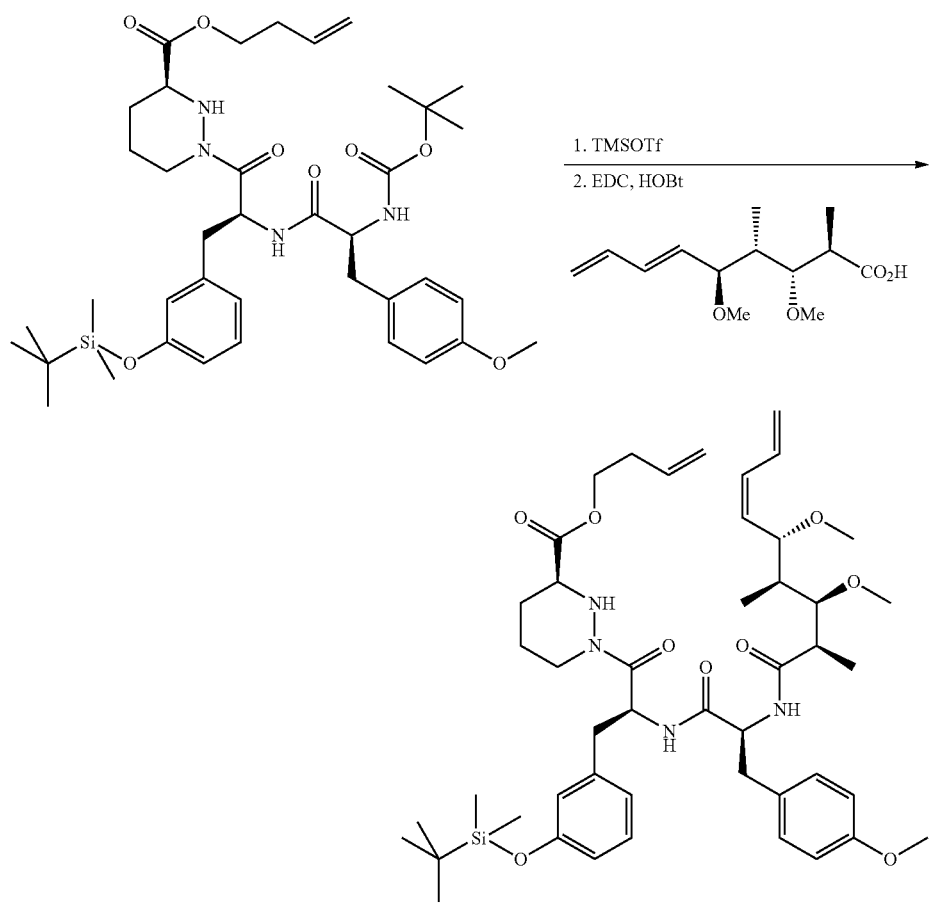

Trimethylsilyltrifluoromethanesulfonate (193 μL, 1.07 mmol) was added dropwise to a solution of (S)-1-{(S)-2-[(S)-2-tert-butoxycarbonylamino-3-(4-methoxy-phenyl)-propionylamino]-3-[3-(tert-butyl-dimethyl-silanyloxy)-phenyl]-propionyl}-hexahydro-pyridazine-3-carboxylic acid but-3-enyl ester (438 mg, 0.59 mmol) in dichloromethane (10 mL) at 0° C. under nitrogen and the reaction was stirred for 60 minutes. To this was added N,N-diisopropylethylamine (412 μL, 2.37 mmol) and the reaction was warmed to room temperature. The volatiles were evaporated to afford a colourless foam which dissolved in acetonitrile (10 mL). 1-Hydroxybenzotriazole (100 mg, 0.59 mmol) was added, followed by N-(3-dimethylaminopropyl)-N'-ethylcarbodiimide hydrochloride (136 mg, 0.71 mmol) and (E)-(2R,3R,4S,5S)-3,5-dimethoxy-2,4-dimethyl-nona-6,8-dienoic acid (144 mg, 0.59 mmol) and the reaction was stirred at room temperature for 18 h. The solvent was evaporated and the residue was suspended in ethyl acetate. This was washed with saturated ammonium chloride, saturated sodium bicarbonate, dried over anhydrous sodium sulfate and the solvent evaporated. The residue was purified by eluting through a plug of silica gel (eluting with ethyl acetate) to afford the title compound as a yellow oil (326 mg, 64%). ¹H NMR (300 MHz, CDCl₃) δ0.18 (s, 6H), 0.75 (d, J=6.9 Hz, 2H), 0.98 (s, 9H), 1.02 (d, J=6.9 Hz, 2H), 1.36-1.50 (m, 3H), 1.65-1.86 (m, 3H), 2.27-2.36 (m, 1H), 2.42 (app q, J=6.7 Hz, 2H), 2.60-3.00 (m, 4H), 3.13 (dd, J=6.2, 13.4 Hz, 1H), 3.25 (s, 3H), 3.33 (s, 3H), 3.37-3.52 (m, 2H), 3.80 (s, 3H), 3.78-3.85 (m, 1H), 4.11-4.23 (m, 2H), 4.27-4.37 (m, 1H), 4.63 (app q, J=6.0 Hz, 1H), 5.09-5.30 (m, 4H), 5.46 (dd, J=8.7, 15.4 Hz, 1H), 5.54-5.64 (m, 1H), 5.71-5.86 (m, 1H), 6.17-6.48 (m, 4H), 6.60-6.64 (m, 1H), 6.68 (dd, J=1.6, 8.2 Hz, 1H), 6.74 (d, J=7.6 Hz, 1H), 6.83 (d, J=8.5 Hz, 2H), 7.10 (t, J=7.8 Hz, 1H), 7.18 (d, J=8.5 Hz, 1H).

Example 21

Compound 21: (13E,15E)-(3S,6S,9R,10R,11S,12S,21S)-3-(3-Hydroxy-benzyl)-10,12-dimethoxy-6-(4-methoxy-benzyl)-9,11-dimethyl-19-oxa-1,4,7,25-tetraazabicyclo[19.3.1]pentacosa-13,15-diene-2,5,8,20-tetraone

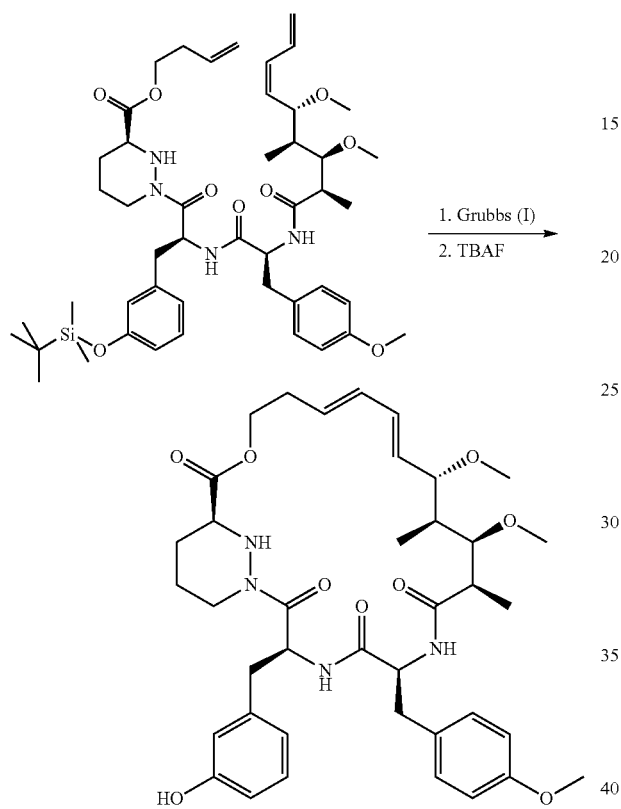

Grubbs' 1st generation catalyst (62 mg, 0.076 mmol) was added to a solution of (S)-1-{(S)-3-[3-(tert-butyl-dimethyl-silanyloxy)-phenyl]-2-[(S)-2-((Z)-(2R,3R,4S,5S)-3,5-dimethoxy-2,4-dimethyl-nona-6,8-dienoylamino)-3-(4-methoxy-phenyl)-propionylamino]-propionyl}-hexahydro-pyridazine-3-carboxylic acid but-3-enyl ester (326 mg, 0.378 mmol) in dichloromethane (150 mL) and the reaction was heated at reflux under nitrogen for 24 h. The reaction was cooled and silica gel was added. The solvent was evaporated and the resultant residue purified by silica gel chromatography eluting with a gradient of ethyl acetate/iso-hexanes (2:1 to 4:1) to afford a brown oil (107 mg, 34%). The brown oil (107 mg, 0.128 mmol) was dissolved in tetrahydrofuran (5 mL) and tetra-N-butylammonium fluoride (1.0 M solution in tetrahydrofuran) (256 µL, 0.256 mmol) was added. The reaction was stirred at room temperature for 1 h. Silica gel was added and the solvent evaporated. The residue was purified by silica gel chromatography eluting with a gradient of ethyl acetate/iso-hexanes 3:1 to 4:1 to afford the title compound (62 mg, 67%) as a colourless solid. $^1$H NMR (500 MHz, d$_6$DMSO) δ 0.72-0.89 (m, 6H), 0.92-1.02 (m, 3H), 1.12-1.20 (m, 1H), 1.21-1.32 (m, 2H), 1.38-1.54 (m, 2H), 1.62-1.73 (m, 2H), 1.77-1.84 (m, 0.5H), 1.86-1.93 (m, 0.5H), 2.63-2.92 (m, 4H), 2.98-3.05 (m, 1.5H), 3.07-3.12 (m, 1H), 3.13-3.19 (m, 3H), 3.35-3.44 (m, 1H), 3.48-3.59 (m, 1H), 3.71 (s, 3H), 3.98-4.21 (m, 2H), 4.26-4.38 (m, 0.5H), 4.42-4.50 (m, 0.5H), 4.84-4.96 (m. 0.5H), 5.01-5.15 (m, 0.5H), 5.32-5.42 (m, 1H), 5.44-5.56 (m, 1H), 5.57-5.64 (m, 0.5H), 5.74-5.85 (m, 0.5H), 6.03-6.16 (m, 1H), 6.18-6.27 (m, 0.5H), 6.35-6.46 (m, 0.5H), 6.50-6.67 (m, 3H), 6.75-6.85 (m, 2H), 6.93-7.11 (m, 2H), 7.13-7.27 (m, 1.5H), 7.51-7.66 (m, 0.5H), 7.85-8.01 (m, 0.5H), 8.05-8.17 (m, 0.5H), 8.31 (s, 0.5H), 9.12-9.28 (m, 1H). LCMS (m/z) 721.32 [M+H], Tr=4.91 min.

Example 22

Compound 22: (E)-(2R,5S,11S,14S,18R)-11-(3-Hydroxy-benzyl)-14-isopropyl-18-methoxy-2-methyl-3-oxa-9,12,15,28-tetraaza-tricyclo[21.3.1.1*5,9*]octacosa-1(26),21,23(27),24-tetraene-4,10,13,16-tetraone

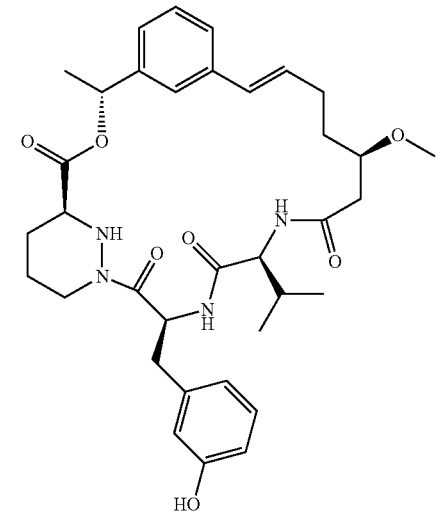 [SMILES: CO[C@@H]1CC/C=C/c2cccc(c2)[C@@H](C)OC(=O)[C@@H]2CCCN(N2)C(=O)[C@H](Cc2cccc(O)c2)NC(=O)[C@H](C(C)C)NC(=O)C1]

Compound 22a: (R)-3-Methoxy-hept-6-enoic Acid Methyl Ester

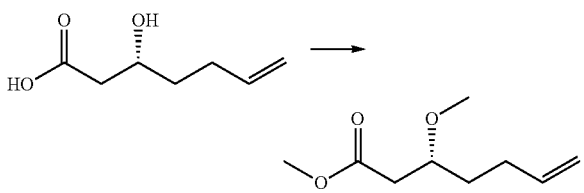

A stirred solution of (R)-3-hydroxy-hept-6-enoic acid (*J.C.S. Chem. Commun.* 1983, 599-600, 0.4 g, 2.77 mmol) in anhydrous dichloromethane (20 mL) was treated with trimethyloxonium tetrafluoroborate (1.64 g, 11.08 mmol) and 1,8-bis(dimethylamino)naphthalene (3.56 g, 16.62 mmol). The reaction was stirred at room temperature under a nitrogen atmosphere for 16 hours then treated with 2 M hydrochloric acid (30 mL) and ethyl acetate (50 mL). The mixture was filtered to remove an insoluble solid before separating the two layers. The aqueous layer was extracted with further ethyl acetate (30 mL). The combined organic layers were dried over anhydrous sodium sulfate, filtered and evaporated to give a yellow gum which was purified by silica gel chromatography using iso-hexanes/ethyl acetate 17:3 to give the title compound (225 mg, 47%) as a colourless oil. $^1$H NMR (300 MHz, CDCl$_3$) δ1.51-1.75 (m, 2H), 2.07-2.25 (m, 2H), 2.38-2.62 (m, 2H), 3.36 (s, 3H), 3.58-3.75 (m, 1H), 3.71 (s, 3H) 4.91-5.10 (m, 2H), 5.73-5.90 (m, 1H).

Compound 22b: (R)-3-Methoxy-hept-6-enoic Acid

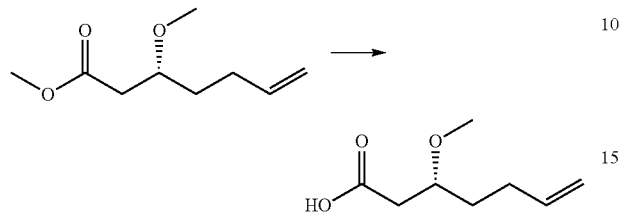

A stirred solution of (R)-3-methoxy-hept-6-enoic acid methyl ester (224 mg, 1.3 mmol) in tetrahydrofuran (5 mL) was prepared. A solution of lithium hydroxide (62 mg, 2.6 mmol) in water (2 mL) was added. The reaction mixture was stirred at room temperature for 2.5 hours then 2 M hydrochloric acid was added. The mixture was extracted ethyl acetate (15 mL×2). The extract was dried over anhydrous sodium sulfate, filtered and evaporated to give the title product (263 mg, 100%) as a colourless oil. $^1$H NMR (300 MHz, CDCl$_3$) δ1.55-1.80 (m, 2H), 2.09-2.21 (m, 2H), 2.46-2.65 (m, 2H), 3.40 (s, 3H), 3.61-3.72 (m, 1H), 4.96-5.11 (m, 2H), 5.74-5.90 (m, 1H).

Compound 22c: (S)-1-{(S)-3-[3-(tert-Butyl-dimethyl-silanyloxy)-phenyl]-2-[(S)-2-((R)-3-methoxy-hept-6-enoylamino)-3-methyl-butyrylamino]-propionyl}-hexahydro-pyridazine-3-carboxylic Acid (R)-1-(3-vinyl-phenyl)-ethyl Ester

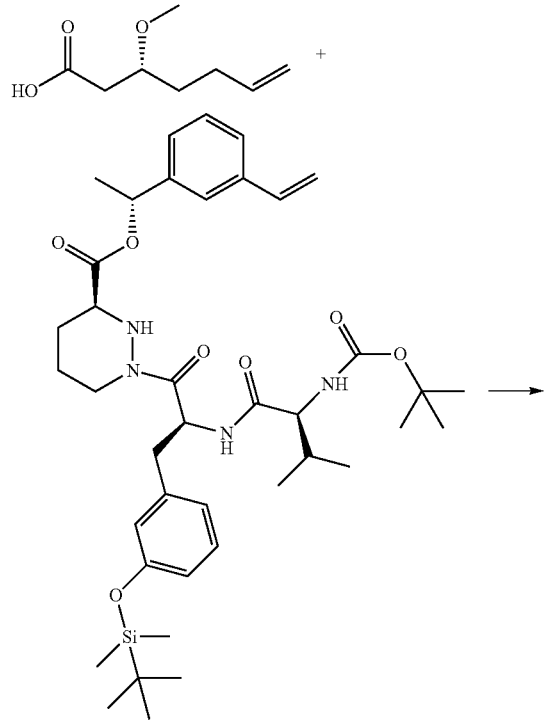

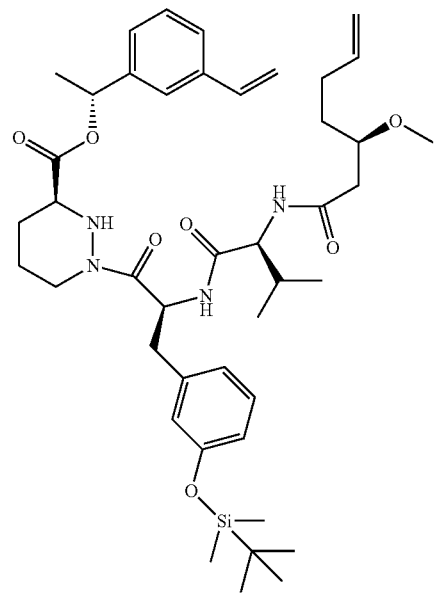

A stirred solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid (R)-1-(3-vinyl-phenyl)-ethyl ester (367 mg, 0.50 mmol) in anhydrous dichloromethane (10 mL) was cooled to 0° C. then treated with trimethylsilyl trimethanesulfonate (135 μL, 2.0 mmol). The reaction mixture was stirred at 0° C. for 1.5 hours, then N,N-diisopropylethylamine (350 μL, 2.0 mmol) was added and the mixture was evaporated. The residue was dissolved in acetonitrile (5 mL) and (R)-3-methoxy-hept-6-enoic acid was added followed by 1-ethyl-3-(3-dimethylaminopropyl)carbodiimide (134 mg, 0.70 mmol) and hydroxybenzotriazole (81 mg, 0.50 mmol). The reaction was stirred at room temperature under a nitrogen atmosphere for 16 hours. It was then evaporated to dryness before partitioning between ethyl acetate (20 mL) and water (20 mL). The aqueous was extracted with further ethyl acetate (20 mL), the organic layers were combined, dried over anhydrous sodium sulfate, filtered and evaporated. The residue was purified by silica gel chromatography using ethyl acetate/iso-hexanes 13:7 to give the title compound (123 mg, 32%) as a colourless solid. $^1$H NMR (300 MHz, CDCl$_3$) δ 0.16 (s, 6H), 0.80-1.00 (m, 17H), 1.34-1.94 (m, 12H), 2.00-2.20 (m, 5H), 2.34-2.53 (m, 3H), 2.63-3.03 (m, 3H), 3.38 (s, 3H), 3.52-3.70 (m, 2H), 4.27-4.38 (m, 2H), 4.92-5.10 (m, 2H), 5.29 (d, J=10.9 Hz, 1H), 5.64-5.98 (m, 2H), 6.52-6.99 (m, 4H), 7.22-7.42 (m, 2H). LCMS (m/z) 777.0 [M+H] Tr=5.96 min.

119

Compound 22d: (E)-(2R,5S,11S,14S,18R)-11-[3-(tert-Butyl-dimethyl-silanyloxy)-benzyl]-14-isopropyl-18-methoxy-2-methyl-3-oxa-9,12,15,28-tetraaza-tricyclo[21.3.1.1*5,9*]octacosa-1(26),21,23(27),24-tetraene-4,10,13,16-tetraone

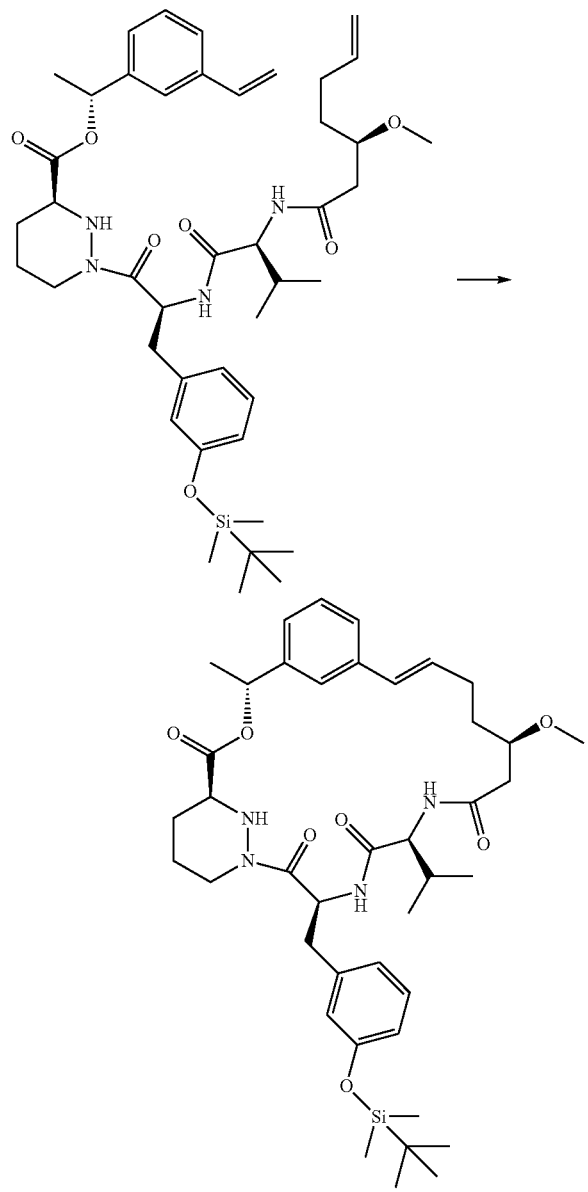

A stirred solution of (S)-1-{(S)-3-[3-(tert-butyl-dimethyl-silanyloxy)-phenyl]-2-[(S)-2-((R)-3-methoxy-hept-6-enoylamino)-3-methyl-butyrylamino]-propionyl}-hexahydro-pyridazine-3-carboxylic acid (R)-1-(3-vinyl-phenyl)-ethyl ester (123 mg, 0.158 mmol) and Hoveyda-Grubbs $2^{nd}$ generation catalyst (10 mg, 0.0158 mmol) in 1,2-dichloroethane (60 mL) was heated at 80° C. for 1.5 hours. The reaction mixture was cooled before adding silica gel. The mixture was evaporated then purified by silica gel chromatography using ethyl acetate to give the title compound (54 mg, 46%) as a pale brown solid. $^1$H NMR (300 MHz, CDCl$_3$) δ 0.16 (s, 6H), 0.80-1.00 (m, 17H), 1.34-1.94 (m, 12H), 2.00-2.20 (m, 5H), 2.34-2.53 (m, 3H), 2.63-3.03 (m, 3H), 3.38 (s, 3H), 3.52-3.70 (m, 2H), 4.27-4.38 (m, 2H), 4.92-5.10 (m, 2H), 5.29 (d, J=10.9 Hz, 1H), 5.64-5.98 (m, 2H), 6.52-6.99 (m, 4H), 7.22-7.42 (m, 2H). LCMS (m/z) 749.3 [M+H] Tr=5.91 min.

120

Example 22

Compound 22: (E)-(2R,5S,11S,14S,18R)-11-(3-Hydroxy-benzyl)-14-isopropyl-18-methoxy-2-methyl-3-oxa-9,12,15,28-tetraaza-tricyclo[21.3.1.1*5,9*]octacosa-1(26),21,23(27),24-tetraene-4,10,13,16-tetraone

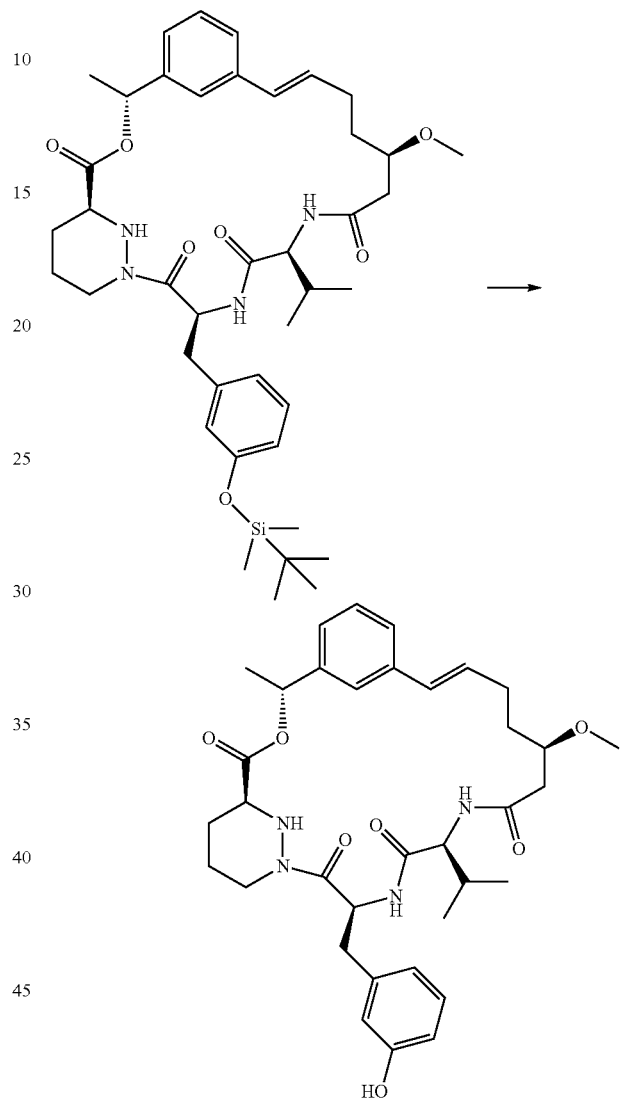

A solution of (E)-(2R,5S,11S,14S,18R)-11-[3-(tert-butyl-dimethyl-silanyloxy)-benzyl]-14-isopropyl-18-methoxy-2-methyl-3-oxa-9,12,15,28-tetraaza-tricyclo[21.3.1.1*5,9*]octacosa-1(26),21,23(27),24-tetraene-4,10,13,16-tetraone (54 mg, 0.072 mmol) in anhydrous tetrahydrofuran (10 mL) was cooled over an ice bath before addition of tetra-N-butylammonium fluoride (1M, 108 μL, 0.108 mmol). The reaction mixture was stirred at room temperature for 1.5 hours and then saturated aqueous sodium bicarbonate solution (20 mL) was added. The mixture was extracted with ethyl acetate (3×15 mL). The extract was dried over anhydrous sodium sulfate, filtered and evaporated to give a brown gum (56 mg). The gum was purified by silica gel chromatography using ethyl acetate/iso-hexanes 3:1 to give a colourless gum (23 mg) which crystallised on standing. The solid was further purified by preparative thin layer chromatography on silica plates using ethyl acetate to yield the title compound (12 mg, 26%) as a colourless solid. $^1$H NMR (300 MHz, CDCl$_3$)

121

δ 0.97 (d, J=6.9 Hz, 3H), 0.98 (d, J=6.7 Hz, 3H), 1.63 (d, J=6.5 Hz, 3H), 1.66-1.82 (m, 5H), 1.85-2.04 (m, 3H), 2.16-2.35 (m, 1H), 2.53-2.73 (m, 3H), 2.88 (d, J=6.0 Hz, 2H), 3.43 (s, 3H), 3.47-3.60 (m, 3H), 4.24-4.33 (m, 1H), 4.56 (d, J=11.6 Hz, 1H), 5.59-5.70 (m, 1H), 5.79-5.95 (m, 2H), 5.98-6.12 (m, 1H), 6.69-6.85 (m, 3H), 6.97 (s, 1H), 7.02-7.36 (m, 6H), 8.18 (s, 1H). LCMS (m/z) 635.3 [M+H] Tr=5.42 min.

Example 23

Compound 23: (E)-(3S,6S,9R,10R,21S)-3-(3-Hydroxy-benzyl)-6-isopropyl-10-methoxy-9-methyl-19-oxa-1,4,7,25-tetraaza-bicyclo[19.3.1]pentacos-13-ene-2,5,8,20-tetraone

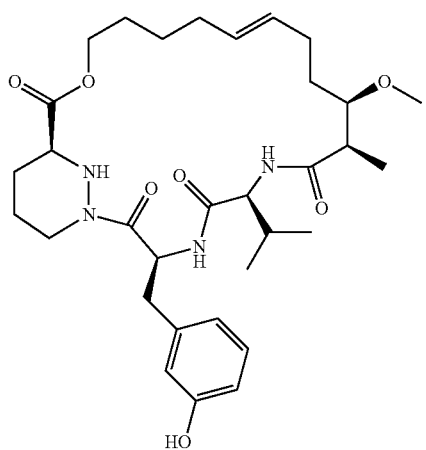 [SMILES: CO[C@@H]1CC/C=C/CCCCOC(=O)[C@@H]2CCCN(N2)C(=O)[C@H](Cc2cccc(O)c2)NC(=O)[C@H](C(C)C)NC(=O)[C@@H]1C]

Compound 23a: (S)-1-{(S)-2-((S)-2-tert-Butoxycarbonylamino-3-methyl-butyrylamino)-3-[3-(tert-butyl-dimethylsilanyloxy)-phenyl]-propionyl}-hexahydro-pyridazine-3-carboxylic Acid hex-5-enyl Ester

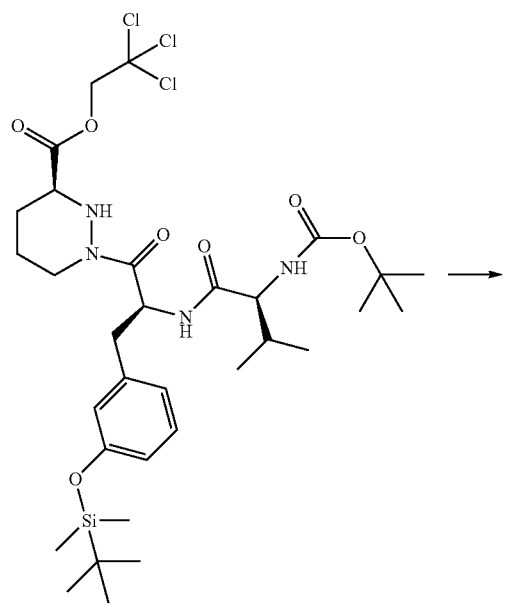

122

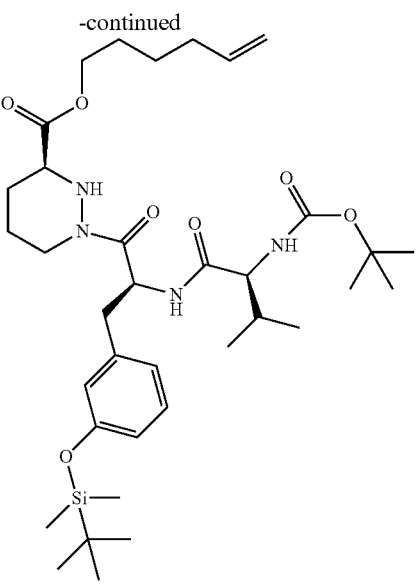

A stirred solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid 2,2,2-trichloro-ethyl ester (2.95 g, 4.0 mmol) and 5-hexen-1-ol (4.8 mL, 40 mmol) in anhydrous tetrahydrofuran (25 mL) was prepared and sodium hydride (60%, 32 mg, 0.8 mmol) was added. The stirred solution was heated to 50° C. under a nitrogen atmosphere for 16 hours. The solution was cooled and filtered through a pad of silica gel, eluting with ethyl acetate. The solution was evaporated to give an oil, which was dried further under vacuum then dissolved in toluene and re-evaporated to yield the title product (1.926 g, 70%) as a white amorphous solid. $^1$H NMR (300 MHz, CDCl$_3$) δ 0.20 (s, 6H), 0.88 (d, J=6.7 Hz, 3H), 0.94 (d, J=6.7 Hz, 3H), 0.98 (s, 9H), 1.46 (s, 9H), 1.39-1.90 (m, 7H), 2.01-2.29 (m, 2H), 2.43-3.77 (m, 4H), 3.89-4.20 (m, 1H), 4.50-4.22 (m, 3H), 4.33 (d, J=13.6 Hz, 1H), 4.95-5.13 (m, 4H), 5.68-5.92 (m, 2H), 6.51 (d, J=8.0 Hz, 1H), 6.64-6.87 (m, 3H), 7.12 (t, J=7.8 Hz, 1H). LCMS (m/z) 689.4 [M+H] Tr=5.94 min.

Compound 23b: (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid hex-5-enyl Ester

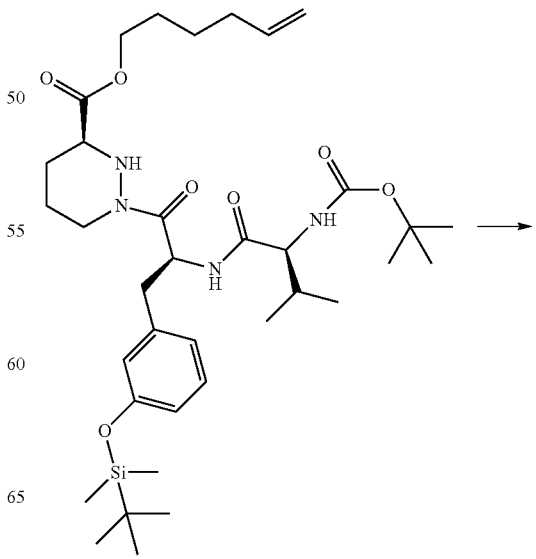

123
-continued

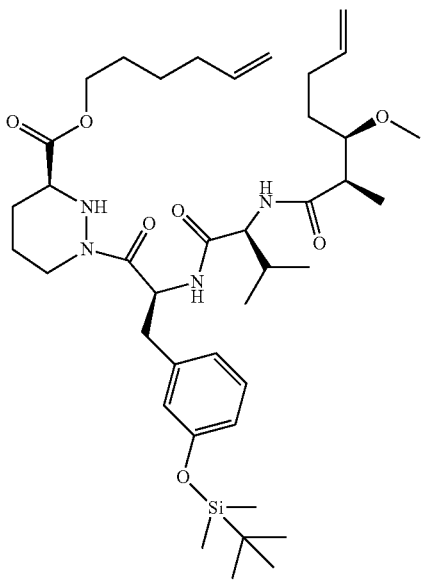

A solution of (S)-1-{(S)-2-((S)-2-tert-butoxycarbonylamino-3-methyl-butyrylamino)-3-[3-(tert-butyl-dimethylsilanyloxy)-phenyl]-propionyl}-hexahydro-pyridazine-3-carboxylic acid hex-5-enyl ester in anhydrous dichloromethane (12 mL) was cooled to 0° C. before adding trimethylsilyl trifluoromethanesulfonate (242 µL, 1.088 mmol). The reaction mixture was stirred at 0° C. under a nitrogen atmosphere for 3.5 hours, then N,N-diisopropylethylamine (480 µL, 2.903 mmol) was added. The reaction mixture was evaporated to give the crude amine as a colourless gum. A solution of (2S,3S)-3-methoxy-2-methyl-hept-6-enoic acid in anhydrous N,N-dimethylformamide (6 mL) was cooled to 0° C., before adding 2-(7-aza-1H-benzotriazole-1-yl)-1,1,3,3-tetramethyluronium hexafluorophosphate (276 mg, 0.726 mmol) and N,N-diisopropylethylamine (480 µL, 2.903 mmol). It was stirred at 0° C. for 20 minutes before adding a solution of the crude amine in N,N-dimethylformamide (10 mL). The reaction mixture was stirred at room temperature for 16 hours then diluted with brine (20 mL) and extracted with ethyl acetate (3×15 mL). The extract was further washed with brine (2×15 mL) then dried over anhydrous sodium sulfate and evaporated to give a brown oil. The oil was purified by silica gel chromatography using ethyl acetate/iso-hexanes 1:1, then ethyl acetate/iso-hexanes 7:3 to give the title compound (187 mg, 35%) as a white solid. $^1$H NMR (300 MHz, CDCl$_3$) δ 0.19 (s, 6H), 0.83-1.00 (m, 7H), 0.98 (s, 9H), 1.16 (d, J=7.1 Hz, 3H), 1.20-1.30 (m, 3H), 1.36-1.55 (m, 3H), 1.58-1.72 (m, 3H), 1.73-1.90 (m, 2H), 2.03-2.24 (m, 4H), 2.41-2.55 (m, 1H), 2.65-3.00 (m, 3H), 3.31-3.44 (m, 1H), 3.39 (s, 3H), 3.57 (d, J=11.4 Hz, 1H), 4.05-4.19 (m, 2H), 4.25-4.40 (m, 2H), 4.92-5.10 (m, 4H), 5.65-5.90 (m, 3H), 6.41-6.57 (m, 2H), 6.65 (s, 1H), 6.69 (d, J=8.0 Hz, 1H), 6.81 (d, J=6.9 Hz, 1H), 7.11 (t, J=7.8 Hz, 1H). LCMS (m/z) 743.46 [M+H] Tr=5.97 min.

124

Compound 23c: (E)-(3S,6S,9R,10R,21S)-3-[3-(tert-Butyl-dimethyl-silanyloxy)-benzyl]-6-Isopropyl-10-methoxy-9-methyl-19-oxa-1,4,7,25-tetraaza-bicyclo[19.3.1]pentacos-13-ene-2,5,8,20-tetraone

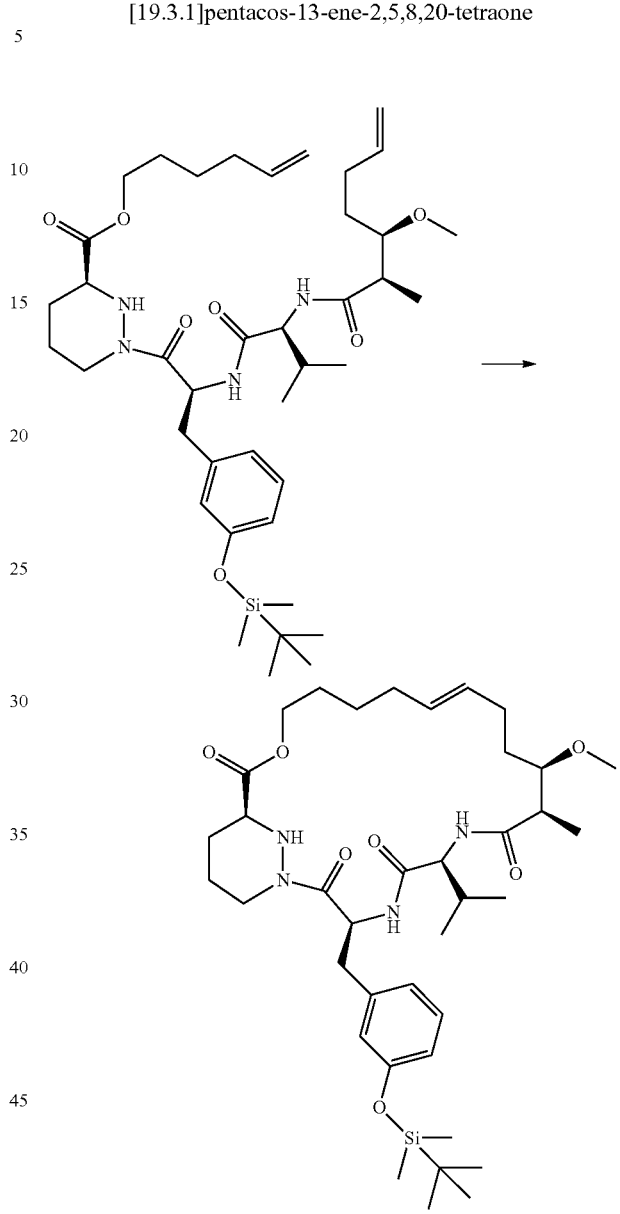

A stirred solution of (S)-1-{(S)-3-[3-(tert-butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic acid hex-5-enyl ester (187 mg, 0.251 mmol) in 1,2-dichloroethane (83 mL) was prepared and Grubbs 2$^{nd}$ generation catalyst (19 mg, 0.025 mmol) was added. The stirred solution was heated to reflux for 3 hours then cooled to room temperature before adding silica gel. The mixture was evaporated to dryness and the residue was purified by silica gel chromatography using ethyl acetate to give the title compound (85.5 mg, 48%) as a brown gum. $^1$H NMR (300 MHz, CDCl$_3$) δ 0.19 (s, 6H), 0.87-1.00 (m, 6H), 0.97 (s, 9H), 1.22-1.38 (m, 5H), 1.39-2.25 (m, 13H), 2.31-2.45 (m, 1H), 2.55-2.64 (m, 1H), 2.82-3.03 (m, 2H), 3.14-3.29 (m, 1H), 3.40-3.65 (m, 1H), 3.64 (s, 3H), 4.04-4.19 (m, 3H), 4.37-4.48 (m, 1H), 4.92-5.10 (m, 1H), 5.29-5.61 (m, 2H), 5.64-5.85 (m, 1H), 6.37 (d J=7.6 Hz, 1H), 6.62-6.75 (m, 2H), 6.82 (d, J=7.6 Hz, 1H), 6.99 (d, J=8.9 Hz, 1H), 7.06-7.20 (m, 1H). LCMS (m/z) 715.4 [M+H] Tr=5.81 min.

Example 23

Compound 23: (E)-(3S,6S,9R,10R,21S)-3-(3-Hydroxy-benzyl)-6-isopropyl-10-methoxy-9-methyl-19-oxa-1,4,7,25-tetraaza-bicyclo[19.3.1]pentacos-13-ene-2,5,8,20-tetraone

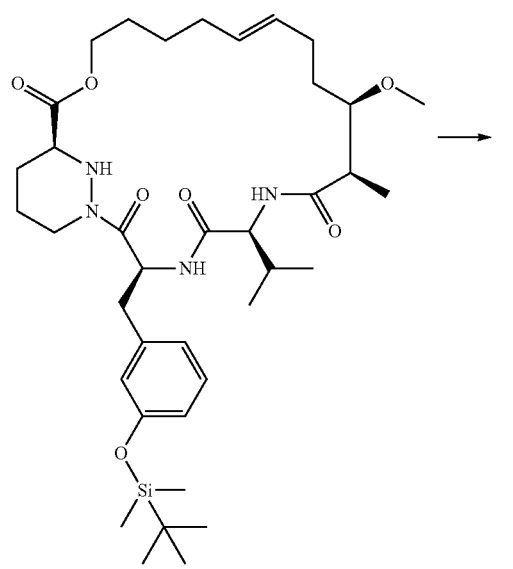

A stirred solution of (E)-(3S,6S,9R,10R,21S)-3-[3-(tert-butyl-dimethyl-silanyloxy)-benzyl]-6-isopropyl-10-methoxy-9-methyl-19-oxa-1,4,7,25-tetraaza-bicyclo[19.3.1]pentacos-13-ene-2,5,8,20-tetraone in anhydrous tetrahydrofuran (15 mL) was cooled to 0° C. under a nitrogen atmosphere before adding a solution of tetra-N-butylammonium fluoride in tetrahydrofuran (1 M, 0.6 mL, 0.6 mmol). The reaction mixture was allowed to warm to room temperature and was then stirred for 1.5 hours. The reaction mixture was treated with a saturated sodium bicarbonate solution (25 mL) and extracted with ethyl acetate (2×20 mL). The extract was dried over anhydrous sodium sulfate, filtered and evaporated to give a brown gum (73 mg), which was purified by silica gel chromatography using ethyl acetate/iso-hexanes 1:1 then ethyl acetate/iso-hexanes 3:1 to give a colourless gum (22 mg). The gum was further purified by preparative thin layer chromatography using ethyl acetate to yield the title product (9 mg, 12%) as a colourless solid. $^1$H NMR (300 MHz, CD$_3$CN) δ0.94 (d, J=6.5 Hz, 3H), 0.96 (d, J=6.0 Hz, 3H), 1.22-1.45 (m, 3H), 1.28 (d, J=7.4 Hz, 3H), 1.50-1.70 (m, 5H), 1.76-2.08 (m, 7H), 2.47-2.60 (m, 1H), 2.68-2.92 (m, 2H), 2.82 (d, J=6.3 Hz, 1H), 3.21-3.29 (m, 2H), 3.32-3.65 (m, 1H), 3.45 (s, 3H), 4.00-4.37 (m, 4H), 5.10-5.38 (m, 2H), 5.40-5.52 (m, 1H), 6.59-6.70 (m, 2H), 6.78-6.92 (m, 2H), 7.09 (t, J=7.8 Hz, 1H), 7.16 (d, J=9.1 Hz, 1H), 7.80 (s, 1H). LCMS (m/z) 601.4 [M+H] Tr=4.41 min.

Compound 24: (E)-(5S,11S,14S,17R,18R)-18-Ethoxy-11-(3-hydroxy-benzyl)-14-isopropyl-17-methyl-3-oxa-9,12,15,28-tetraaza-tricyclo[21.3.1.1*5,9*]octacosa-1(26),21,23(27),24-tetraene-4,10,13,16-tetraone

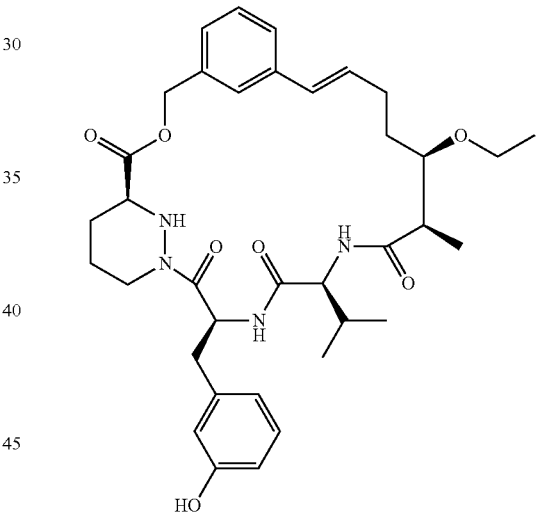

Compound 24a: (2R,3R)-1-((1R,5S)-10,10-Dimethyl-3,3-dioxo-3lambda*6*-thia-4-aza-tricyclo[5.2.1.0*1,5*]dec-4-yl)-3-ethoxy-2-methyl-hept-6-en-1-one

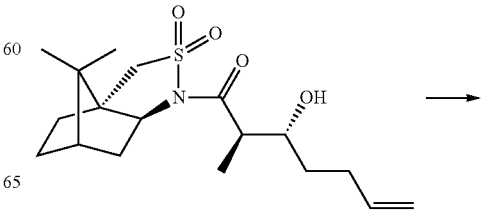

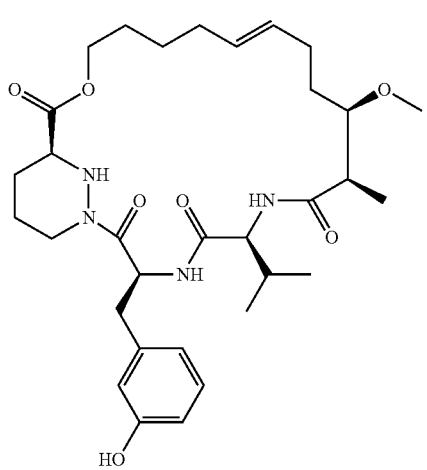

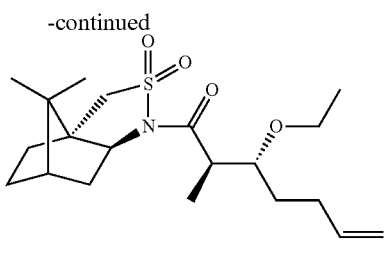

A solution of (2R,3R)-1-((1R,5S)-10,10-dimethyl-3,3-dioxo-3lambda*6*-thia-4-aza-tricyclo[5.2.1.0*1,5*]dec-4-yl)-3-hydroxy-2-methyl-hept-6-en-1-one 10b (1.04 g, 2.92 mmol) in anhydrous dichloromethane (20 mL) was prepared and 1,8-bis(dimethylamino)naphthalene (1.88 g, 8.76 mmol) was added followed by a solution of triethyloxonium tetrafluoroborate (1 M in dichloromethane, 5.85 mL, 5.85 mmol). The reaction mixture was stirred at room temperature under a nitrogen atmosphere for 2.5 hours. A further quantity of triethyloxonium tetrafluoroborate (1M in dichloromethane, 5.85 mL, 5.85 mmol) was added and the reaction was stirred for a further 16 hours at room temperature. A further quantity of triethyloxonium tetrafluoroborate (1M in dichloromethane, 5.85 mL, 5.85 mmol) was added and the reaction was stirred for a further 24 hours at room temperature. The reaction mixture was treated with 2 M hydrochloric acid (20 mL). The layers were separated and the aqueous layer was extracted with ethyl acetate (3×20 mL). The combined organic layers were dried over anhydrous sodium sulfate, filtered and evaporated to give an orange paste (1.56 g). The paste was purified by silica gel chromatography using iso-hexanes/ethyl acetate 3:1 to give the title compound (245 mg, 22%) as a pale yellow solid. $^1$H NMR (300 MHz, CDCl$_3$) δ 0.86-0.98 (m, 1H), 0.99 (s, 3H), 1.09-1.31 (m, 5H), 1.21 (s, 3H), 1.32-1.47 (m, 2H), 1.50-1.62 (m, 3H), 1.83-2.29 (m, 6H), 3.34-3.58 (m, 5H), 3.60-3.70 (m, 1H), 3.87-3.95 (m, 1H), 4.91-5.08 (m, 2H), 5.72-5.88 (m, 1H). LCMS (m/z) 384.1 [M+H] Tr=3.62 min.

Compound 24b:
(2R,3R)-3-Ethoxy-2-methyl-hept-6-enoic Acid

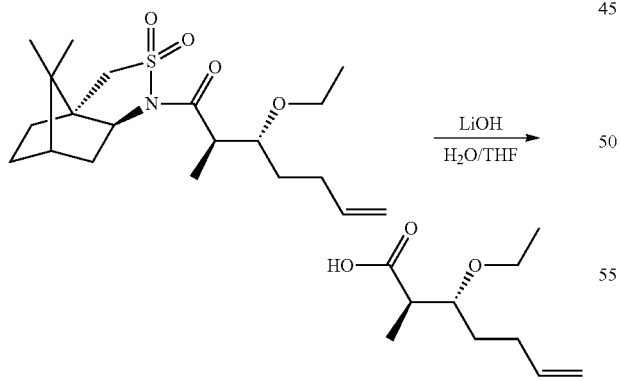

To a solution of (2R,3R)-1-((1R,5S)-10,10-dimethyl-3,3-dioxo-3lambda*6*-thia-4-aza-tricyclo[5.2.1.0*1,5*]dec-4-yl)-3-ethoxy-2-methyl-hept-6-en-1-one (245 mg, 0.64 mmol) in tetrahydrofuran (12 mL) was added a lithium hydroxide solution (2 M aqueous, 5 mL). The mixture was heated to reflux for 16 hours then cooled to room temperature and acidified to pH 1 with 2 M hydrochloric acid (15 mL). The aqueous layer was extracted with ethyl acetate. The extract was dried over anhydrous sodium sulfate, filtered and evaporated to give a colourless gum, which was purified by silica gel chromatography using iso-hexanes/ether 1:1 to give the title compound (78 mg, 65%) as a colourless gum. $^1$H NMR (300 MHz, CDCl$_3$) δ 1.17 (d, J=7.1 Hz, 3H), 1.20 (t, J=7.5 Hz, 3H), 1.55-1.65 (m, 2H), 2.05-2.30 (m, 2H), 2.72-2.83 (m, 1H), 3.52-3.62 (m, 3H), 4.95-5.10 (m, 2H), 5.75-5.90 (m, 1H).

Compound 24c: (S)-1-{(S)-3-[3-(tert-Butyl-dimethyl-silanyloxy)-phenyl]-2-[(S)-2-((2R,3R)-3-ethoxy-2-methyl-hept-6-enoylamino)-3-methyl-butyrylamino]-propionyl}-hexahydro-pyridazine-3-carboxylic Acid 3-vinyl-benzyl Ester

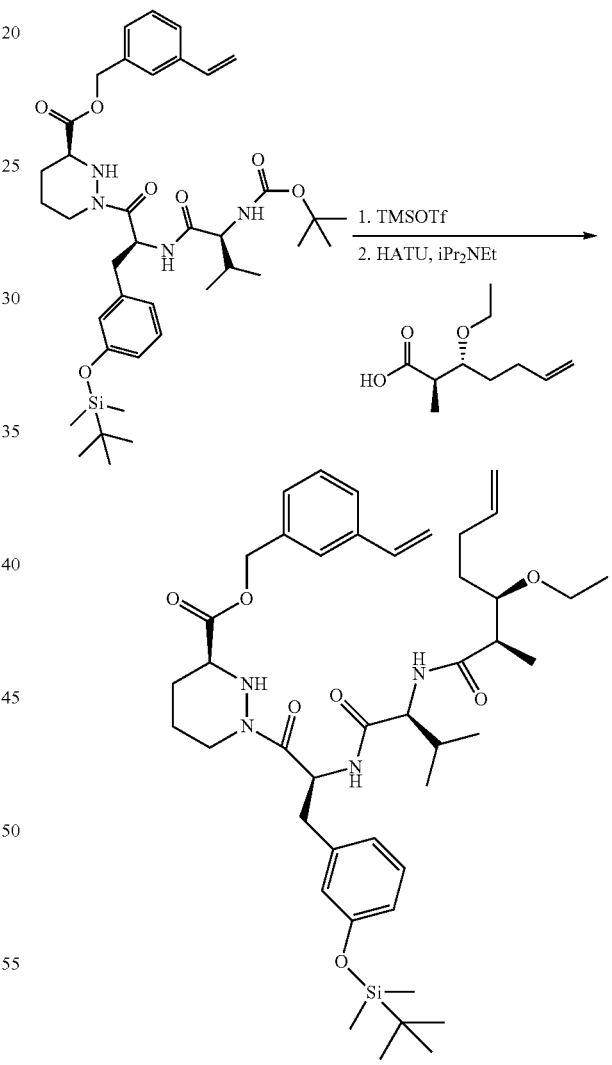

A solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid 3-vinyl-benzyl ester (300 mg, 0.42 mmol) in anhydrous dichloromethane (9 mL) was treated with trimethylsilyl trifluoromethanesulfonate (114 µL, 0.63 mmol). The reaction mixture was stirred at room temperature for 1.5 hours then N,N-diisopropylethylamine (293 μL, 1.68 mmol) was added. The reaction mixture was evaporated to give the crude amine as a colourless solid. A solution of (2R,3R)-3-ethoxy-2-methyl-hept-6-enoic acid (78 mg, 0.42 mmol) in anhydrous dichloromethane (8 mL) was cooled to 0° C. before adding N,N-diisopropylethylamine (293 μL, 1.68 mmol) and 2-(7-aza-1H-benzotriazole-1-yl)-1,1,3,3-tetramethyluronium hexafluorophosphate (160 mg, 0.42 mmol). The mixture was stirred at 0° C. for 20 minutes before adding a solution of the crude amine in dichloromethane (8 mL). The reaction mixture was allowed to warm to room temperature and was stirred under a nitrogen atmosphere for 16 hours. The reaction mixture was evaporated and purified by silica gel chromatography using iso-hexanes/ethyl acetate 1:1 to yield the title compound (200 mg, 60%) as a colourless solid. $^1$H NMR (300 MHz, CDCl$_3$) δ0.17 (s, 6H), 0.88-0.99 (m, 6H), 0.97 (s, 9H), 1.08-1.30 (m, 8H), 1.34-1.60 (m, 3H), 1.61-1.87 (m, 4H), 2.09-2.26 (m, 3H), 2.38-2.55 (m, 2H), 3.39-3.72 (m, 4H), 4.24-4.36 (m, 2H), 4.91-5.19 (m, 4H), 5.30 (d, J=10.9 Hz, 1H), 5.70-5.90 (m, 3H), 6.53-6.84 (m, 6H), 6.97-7.50 (m, 1H), 7.21-7.44 (m, 4H). LCMS (m/z) 791.4 [M+H] Tr=6.01 min.

Compound 24d: (E)-(5S,11S,14S,17R,18R)-11-[3-(tert-Butyl-dimethyl-silanyloxy)-benzyl]-18-ethoxy-14-isopropyl-17-methyl-3-oxa-9,12,15,28-tetraaza-tricyclo[21.3.1.1*5,9*]octacosa-1(26),21,23(27),24-tetraene-4,10,13,16-tetraone

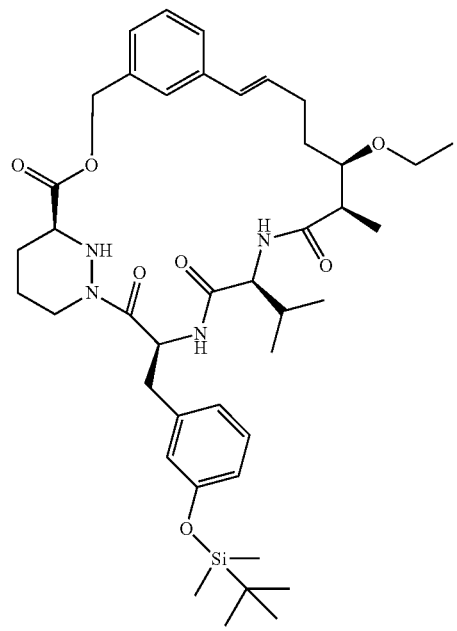

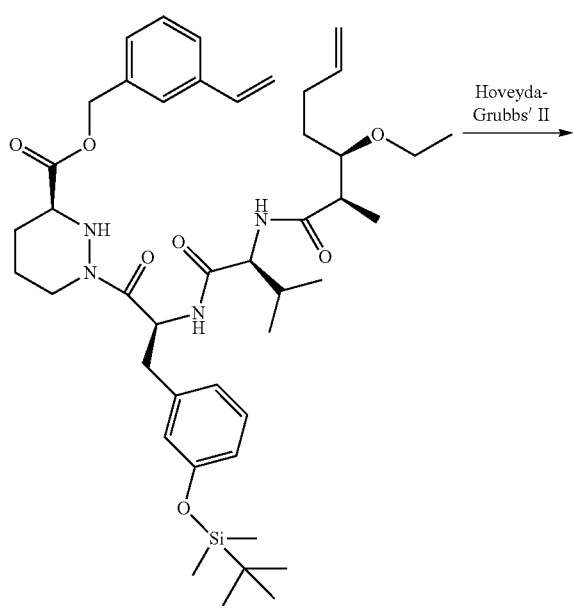

A solution of (S)-1-{(S)-3-[3-(tert-butyl-dimethyl-silanyloxy)-phenyl]-2-[(S)-2-((2R,3R)-3-ethoxy-2-methyl-hept-6-enoylamino)-3-methyl-butyrylamino]-propionyl}-hexahydro-pyridazine-3-carboxylic acid 3-vinyl-benzyl ester (200 mg, 0.253 mmol) in 1,2-dichloroethane (100 mL) was prepared and Hoveyda-Grubbs 2$^{nd}$ generation catalyst (16 mg, 0.025 mmol) was added. The stirred solution was heated at reflux for 1.5 hours then cooled to room temperature before adding silica gel. The mixture was evaporated to dryness and the resultant solid was extracted with ethyl acetate (6×15 mL). The extract was evaporated to give a brown gum which was purified by silica gel chromatography using ethyl acetate/iso-hexanes 1:1, then ethyl acetate/iso-hexanes 3:1 to yield the title compound (128 mg, 66%) as a brown solid. $^1$H NMR (300 MHz, CDCl$_3$) δ0.14 (s, 3H), 0.15 (s, 3H), 0.91-1.01 (m, 5H), 0.94 (s, 9H), 1.20-1.37 (m, 6H), 1.30-1.57 (m, 3H), 1.63-2.00 (m, 5H), 2.10-2.40 (m, 4H), 2.44-2.75 (m, 3H), 2.77-2.99 (m, 2H), 3.34-3.49 (m, 1H), 3.53-3.78 (m, 3H), 4.02-4.14 (m, 2H), 4.43-4.57 (m, 1H), 5.05-5.33 (m, 2H), 5.81-5.95 (m, 1H), 6.23-6.53 (m, 2H), 6.57-6.72 (m, 3H), 6.76-6.86 (m, 1H), 6.99-7.13 (m, 3H). LCMS (m/z) 763.4 [M+H] Tr=5.95 min.

Example 24

Compound 24: (E)-(5S,11S,14S,17R,18R)-18-Ethoxy-11-(3-hydroxy-benzyl)-14-isopropyl-17-methyl-3-oxa-9,12,15,28-tetraaza-tricyclo[21.3.1.1*5,9*]octacosa-1(26),21,23(27),24-tetraene-4,10,13,16-tetraone

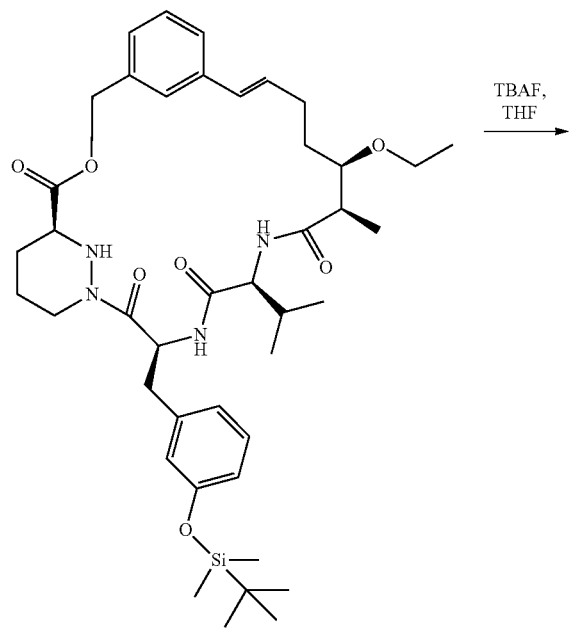

TBAF, THF →

A solution of tetra-N-butylammonium fluoride (1 M, 0.25 mL, 0.25 mmol) was added to a stirred solution of (E)-(5S,11S,14S,17R,18R)-11-[3-(tert-butyl-dimethyl-silanyloxy)-benzyl]-18-ethoxy-14-isopropyl-17-methyl-3-oxa-9,12,15,28-tetraaza-tricyclo[21.3.1.1*5,9*]octacosa-1(26),21,23(27),24-tetraene-4,10,13,16-tetraone (128 mg, 0.168 mmol) in anhydrous tetrahydrofuran (20 mL). The mixture was stirred under a nitrogen atmosphere at room temperature for 1 hour then diluted with a saturated aqueous solution of sodium bicarbonate (30 mL). The mixture was extracted with ethyl acetate (3×15 mL). The extract was dried over anhydrous sodium sulfate, filtered and evaporated to give a brown gum (122 mg) which was purified by silica gel chromatography using ethyl acetate/iso-hexanes 1:1 then ethyl acetate/iso-hexanes 3:1 to yield the title compound (58 mg, 53%) as a white solid. $^1$H NMR (300 MHz, CDCl$_3$) δ0.80-0.95 (m, 3H), 1.00 (d, J=6.7 Hz, 3H), 1.01 (d, J=6.7 Hz, 3H), 1.25 (t, J=6.9 Hz, 3H), 1.36 (d, J=7.1 Hz, 3H), 1.51-1.96 (m, 6H), 1.98-2.12 (m, 2H), 2.13-2.30 (m, 1H), 2.56-2.70 (m, 2H), 2.75-2.89 (m, 2H), 3.00-3.20 (m, 1H), 3.32-3.42 (m, 1H), 3.45-3.63 (m, 1H), 4.26-4.35 (m, 1H), 4.57 (d, J=12.5 Hz, 1H), 5.75-5.86 (m, 1H), 6.09-6.15 (m, 1H), 6.42 (d, J=7.4 Hz, 1H), 6.60-6.72 (m, 2H), 6.92 (s, 1H), 7.08 (d, J=7.6 Hz, 2H), 7.21-7.35 (m, 3H), 7.58 (d, J=8.9 Hz, 1H), 8.32 (br s, 1H). LCMS (m/z) 649.3 [M+H] Tr=5.00 min.

Example 25

Compound 25: (5S,11S,14S,17R,18R,19S,20S)-11-(3-Hydroxy-benzyl)-14-isopropyl-18,20-dimethoxy-17,19-dimethyl-3,9,12,15,28-pentaaza-tricyclo[21.3.1.1*5,9*]octacosa-1(27),23,25-triene-4,10,13,16-tetraone

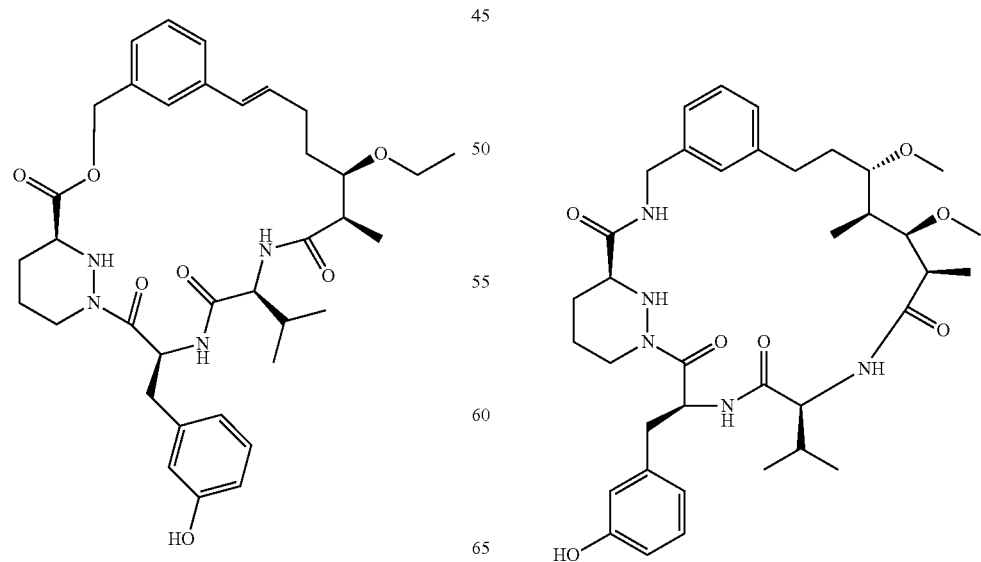

Example 25a ((S)-1-{(S)-1-[3-(tert-Butyl-dimethyl-silanyloxy)-benzyl]-2-[(S)-3-(3-iodo-benzylcarbamoyl)-tetrahydro-pyridazin-1-yl]-2-oxo-ethylcarbamoyl}-2-methyl-propyl)-carbamic Acid tert-butyl Ester

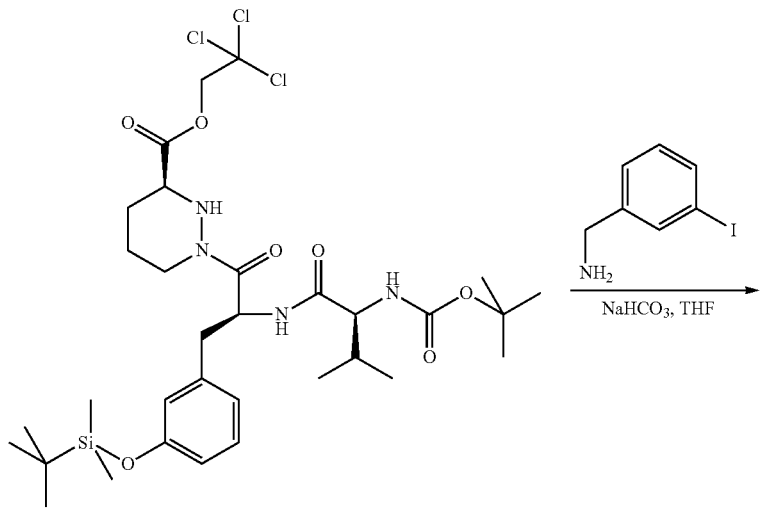

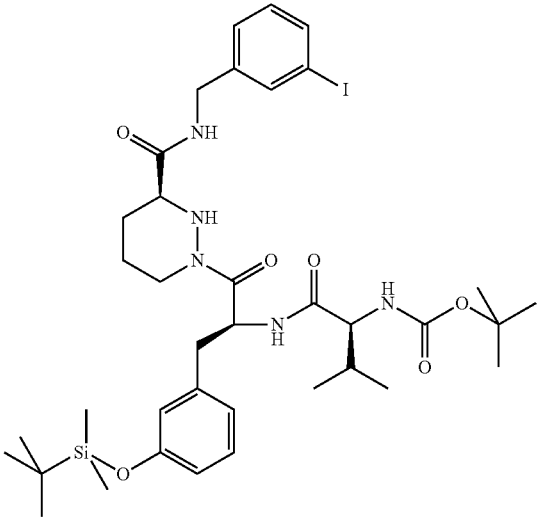

A solution of (S)-1-{(S)-2-((S)-2-tert-butoxycarbonylamino-3-methyl-butyrylamino)-3-[3-(tert-butyl-dimethyl-silanyloxy)-phenyl]-propionyl}-hexahydro-pyridazine-3-carboxylic acid 2,2,2-trichloro-ethyl ester (987 mg, 1.337 mmol) in tetrahydrofuran (20 mL) was treated with sodium bicarbonate (337 mg, 4.011 mmol) and 3-Iodo-benzylamine (467 mg, 2.005 mmol). After overnight stirring, ethyl acetate and silica were added and the volatiles removed in vacuo. The product was purified by silica gel chromatography using isohexanes/ethyl acetate, 1:0 then 1:2 to afford the title compound (374 mg, 34%) as a white solid. $^1$H NMR (300 MHz, CDCl$_3$) δ0.17 (s, 3H), 0.18 (s 3H), 0.81 (d, J=6.9 Hz, 3H), 0.86 (d, J=7.1 Hz, 3H), 0.97 (s, 9H), 1.46 (s, 9H), 1.61-1.70 (m, 2H), 1.73-1.83 (m, 1H), 1.84-1.94 (m, 1H), 1.96-2.05 (m, 1H), 2.53-2.66 (m, 1H), 2.81-3.01 (m, 3H), 3.34-3.45 (m, 1H), 3.74 (t, J=6.0 Hz, 1H), 3.98-4.09 (m, 1H), 4.31-4.51 (m, 2H), 4.79-4.88 (m, 1H), 5.75 (q, J=8.7 Hz, 1H), 6.38-6.49 (m, 1H), 6.67-6.73 (m, 1H), 6.74-6.78 (m, 1H), 6.84 (d, J=7.6 Hz, 1H), 7.03-7.15 (m, 2H), 7.31 (s, 1H), 7.33-7.43 (m, 1H), 7.60 (d, J=7.6 Hz, 1H), 7.67 (s, 1H).

Example 25b
(S)-1-{(S)-3-[3-(tert-Butyl-dimethyl-silanyloxy)-phenyl]-2-[(S)-2-((E)-(2R,3R,4R,5R)-3,5-dimethoxy-2,4-dimethyl-7-tributylstannanyl-hept-6-enoylamino)-3-methyl-butyrylamino]-propionyl}-hexahydro-pyridazine-3-carboxylic Acid 3-iodo-benzylamide
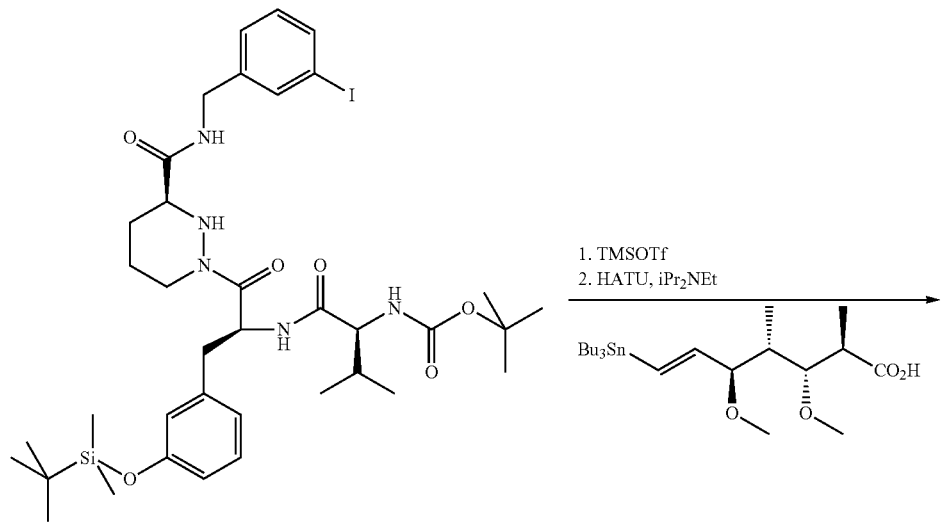
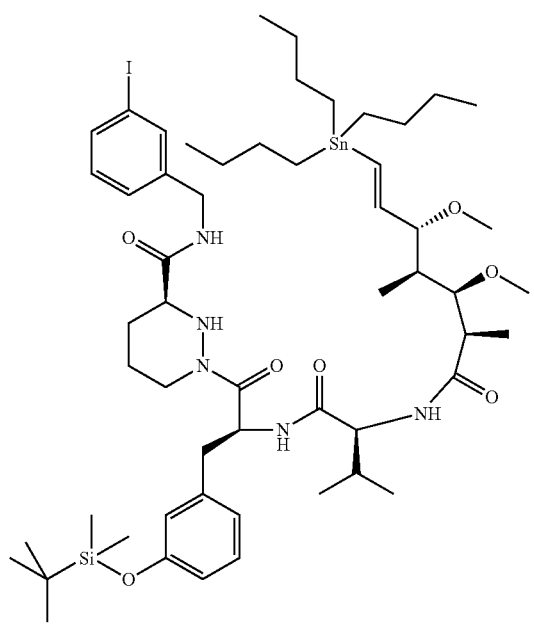
Compound 25b was prepared in the same manner as 3d substituting 3a for 25a (374 mg, 0.46 mmol) and 3c with 5b (292 mg, 0.40 mmol) to afford the title compound (150 mg, 27%, 2 steps). LCMS (m/z) 1210.5 [M+H], Tr=7.02 min.

Example 25

Compound 25: (5S,11S,14S,17R,18R,19S,20S)-11-(3-Hydroxy-benzyl)-14-isopropyl-18,20-dimethoxy-17,19-dimethyl-3,9,12,15,28-pentaaza-tricyclo[21.3.1.1*5,9*]octacosa-1(27),23,25-triene-4,10,13,16-tetraone

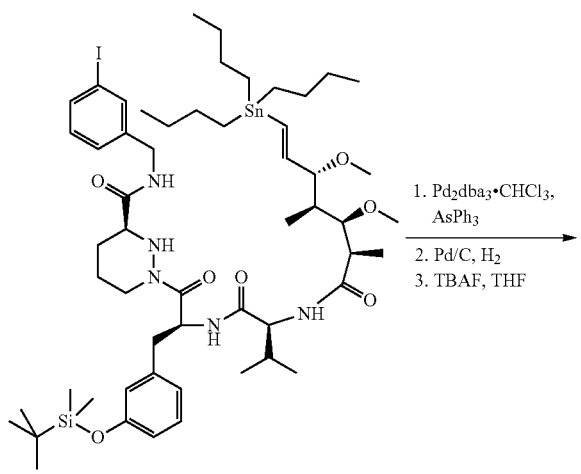

A solution of (S)-1-{(S)-3-[3-(tert-butyl-dimethyl-silanyloxy)-phenyl]-2-[(S)-2-((E)-(2R,3R,4R,5R)-3,5-dimethoxy-2,4-dimethyl-7-tributylstannanyl-hept-6-enoylamino)-3-methyl-butyrylamino]-propionyl}-hexahydro-pyridazine-3-carboxylic acid 3-iodo-benzylamide (150 mg, 0.124 mmol) in anhydrous N,N-dimethylformamide (62 mL) at room temperature and under an atmosphere of nitrogen, was treated with N,N-diisopropylethylamine (0.22 mL, 1.24 mmol), triphenylarsine (28 mg, 0.09 mmol) and tris(dibenzylideneacetone)dipalladium(0)-chloroform adduct (26 mg, 0.02 mmol). The reaction was degassed three times by freeze thawing under vacuum. The reaction flask was covered with aluminium foil and stirred at room temperature for 2 days, after which the volatiles were removed in vacuo. The product was purified by silica gel chromatography using iso-hexanes/ethyl acetate, 2:1 then ethyl acetate/2% methanol to afford the title compound (32 mg) as a red oil. LCMS (m/z) 792.61 [M+H] 814.54 [M+Na], Tr=5.66 min. The oil was dissolved in anhydrous ethanol (1 mL) at room temperature and treated with 10% palladium on carbon (30 mg). The reaction flask was purged with hydrogen and the reaction stirred vigorously for 8 h. The reaction was filtered through celite. The filtrate was treated with palladium hydroxide (30 mg) and the flask purged with hydrogen. Following a further 30 minutes of stirring the reaction was filtered through celite and the filtrate concentrated in vacuo to yield a viscous oil (30 mg). LCMS (m/z) 794.60 [M+H] 816.55 [M+Na], Tr=5.76 min. The ensuing oil was dissolved in anhydrous tetrahydrofuran (0.2 mL), cooled to 0° C. and treated with 1.0 M solution of tetra-N-butylammonium fluoride in tetrahydrofuran (0.2 mL, 0.2 mmol). Following stirring at 0° C. for 1 hour the reaction was warmed to room temperature and stirred for 15 minutes, before being quenched with a saturated solution of ammonium chloride. The reaction was extracted twice with dichloromethane, the organics dried through a hydrophobic frit and concentrated in vacuo. The product was purified by silica gel chromatography using neat ethyl acetate then ethyl acetate/methanol 98:2 to afford the title compound (8 mg, 10%, 3 steps) as a colourless viscous oil. $^1$H NMR (300 MHz, CDCl$_3$) δ0.94-1.03 (m, 9H), 1.37 (d, J=7.4 Hz, 3H), 1.48-1.96 (m, 9H), 2.13-2.24 (m, 1H), 2.61-2.74 (m, 1H), 2.74-2.94 (m, 5H), 2.94-3.15 (m, 2H), 3.21 (s, 3H), 3.35-3.42 (m, 1H), 3.42-3.48 (m, 1H), 3.55 (s, 3H), 4.28 (dd, J=15.0, 4.9 Hz, 1H), 4.44-4.56 (m, 2H), 6.00-6.13 (m, 1H), 6.22 (d, J=7.1 Hz, 1H), 6.35-6.44 (m, 1H), 6.62-6.75 (m, 2H), 6.89-6.99 (m, 1H), 7.07-7.26 (m, 3H), 7.31-7.38 (m, 1H), 8.13 (br s, 1H), 9.06 (br s, 1H). LCMS (m/z) 680.5 [M+H], 702.48 [M+Na], Tr=4.89 min.

Example 26

Compound 26: (E)-(1S,13R,14R,17S,20S)-20-(3-Hydroxy-benzyl)-17-isopropyl-13-methoxy-14-methyl-3-oxa-27-thia-16,19,22,26-tetraaza-tricyclo[20.3.1.1*5,8*]heptacosa-5,7,9-triene-2,15,18,21-tetraone

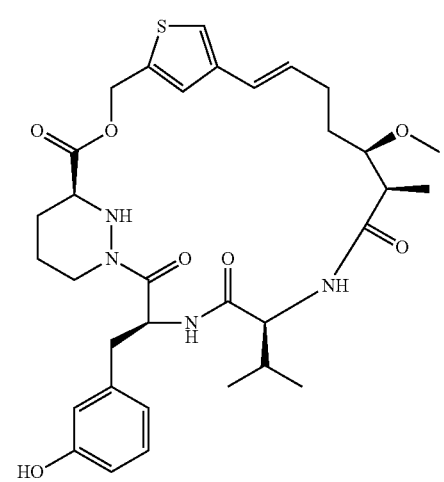 [SMILES: CO[C@@H]1CC/C=C/c2csc(c2)COC(=O)[C@@H]2CCCN(N2)C(=O)[C@H](Cc2cccc(O)c2)NC(=O)[C@H](C(C)C)NC(=O)[C@@H]1C]

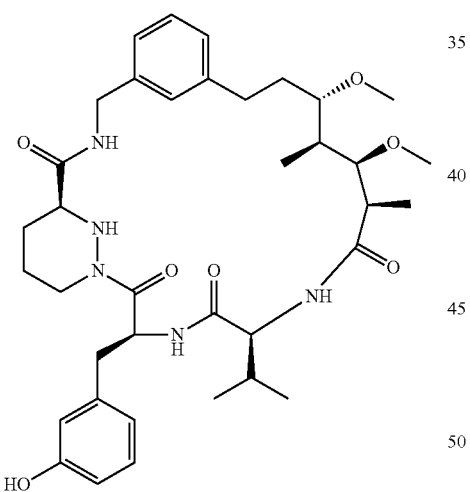

Example 26a

5-Vinyl-thiophene-2-carbaldehyde

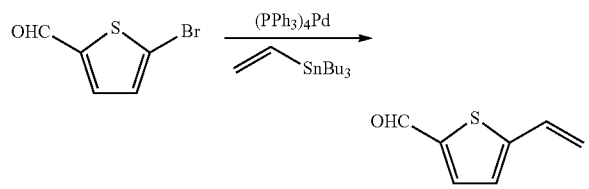

A solution of 5-bromo-thiophene-2-carbaldehyde (1 g, 5.23 mmol) in anhydrous toluene (20 mL), at room temperature and under an atmosphere of nitrogen, was treated with tetrakis(triphenylphosphine)palladium(0) (121 mg, 0.1 mmol) and tributylvinyltin (2.3 mL, 7.85 mmol). The reaction was heated to reflux for 1 hour, after which it was cooled and the volatiles removed in vacuo. The product was purified by silica gel chromatography using iso-hexanes/ethyl acetate 10:1 to afford the title compound (623 mg, 85%) as a yellow oil. $^1$H NMR (300 MHz, CDCl$_3$) δ 5.42 (d, J=10.9 Hz, 1H), 5.84 (d, J=17.4 Hz, 1H), 6.84 (dd, J=17.4, 10.9 Hz, 1H), 7.09 (d, J=4.0 Hz, 1H), 7.66 (d, J=3.8 Hz, 1H), 9.88 (s, 1H).

Example 26b (5-Vinyl-thiophen-2-yl)-methanol

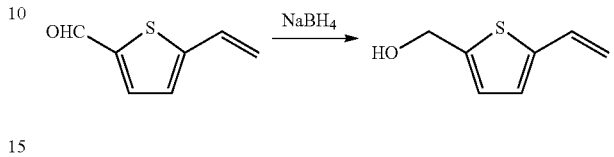

A solution of 5-vinyl-thiophene-2-carbaldehyde (900 mg, 6.4 mmol) in anhydrous methanol (20 mL) was cooled to 0° C. under an atmosphere of nitrogen and treated with sodium borohydride (268 mg, 7.1 mmol). The reaction was stirred at 0° C. for 5 minutes and then at room temperature for 5 minutes, before being quenched with water and concentrated in vacuo. The aqueous layer was extracted twice with dichloromethane, the combined organics dried through a hydrophobic frit and concentrated in vacuo. The product was purified by silica gel chromatography using iso-hexanes/ethyl acetate 7:1 then 2:1 to afford the title compound (800 mg, 88%) as a colourless oil. $^1$H NMR (300 MHz, CDCl$_3$) δ1.76 (t, J=6.0 Hz, 1H), 4.80 (d, J=6.3 Hz, 2H), 5.15 (d, J=10.7 Hz, 1H), 5.55 (d, J=17.4 Hz, 1H), 6.78 (dd, J=17.4, 10.7 Hz, 1H), 6.85 (d, J=3.6 Hz, 1H), 6.88 (d, J=3.6 Hz, 1H).

Example 26c (S)-1-{(S)-2-((S)-2-tert-Butoxycarbonylamino-3-methyl-butyrylamino)-3-[3-(tert-butyl-dimethyl-silanyloxy)-phenyl]-propionyl}-hexahydro-pyridazine-3-carboxylic Acid 5-vinyl-thiophen-2-ylmethyl Ester

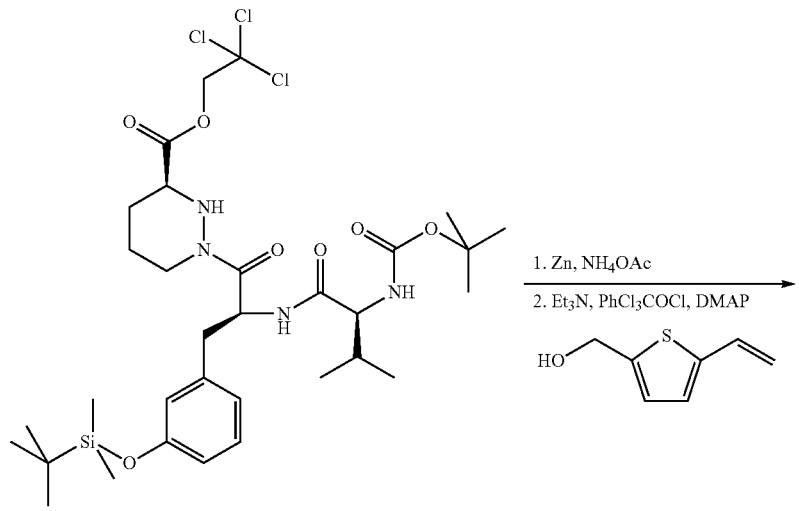

-continued

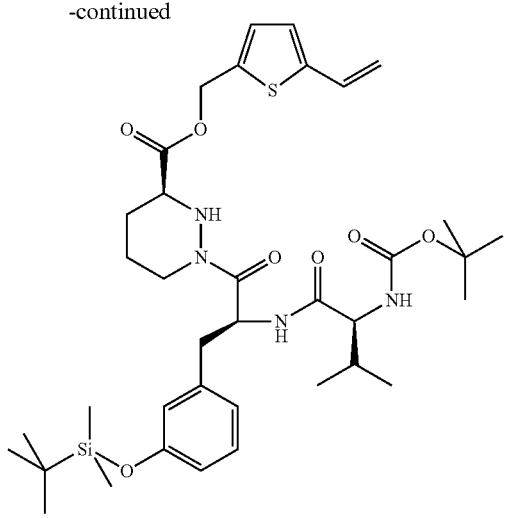

Compound 26c was prepared in the same manner as 3a substituting allyl alcohol with 26b (317 mg, 2.23 mmol) to afford the title compound (600 mg, 41%) as a viscous clear oil. $^1$H NMR (300 MHz, CDCl$_3$) δ 0.16-0.22 (m, 6H), 0.86-0.92 (m, 6H), 0.98 (s, 9H), 1.42-1.46 (m, 1H), 1.46 (s, 9H), 1.69-1.89 (m, 3H), 2.08-2.19 (m, 1H), 2.41-2.54 (m, 1H), 2.73-3.04 (m, 3H), 3.39-3.58 (m, 1H), 3.90-4.03 (m, 1H), 4.19-4.32 (m, 1H), 4.48 (dq, J=11.8, 6.2 Hz, 1H), 5.04-5.15 (m, 1H), 5.18 (d, J=10.7 Hz, 1H), 5.24 (ABq, Δδ$_{AB}$=0.04, J$_{AB}$=12.9 Hz, 2H), 5.58 (d, J=17.2 Hz, 1H), 5.71-5.83 (m, 1H), 6.54-6.64 (m, 1H), 6.64-6.73 (m, 2H), 6.75-6.84 (m, 2H), 6.86 (d, J=3.6 Hz, 1H), 6.96 (d, J=3.6 Hz, 1H), 7.05 (t, J=7.6 Hz, 1H). LCMS (m/z) 729.41 [M+H], Tr=5.93 min.

Example 26d (S)-1-{(S)-3-[3-(tert-Butyl-dimethyl-silanyloxy)-phenyl]-2-[(S)-2-((2R,3R)-3-methoxy-2-methyl-hept-6-enoylamino)-3-methyl-butyrylamino]-propionyl}-hexahydro-pyridazine-3-carboxylic Acid 5-vinyl-thiophen-2-ylmethyl Ester

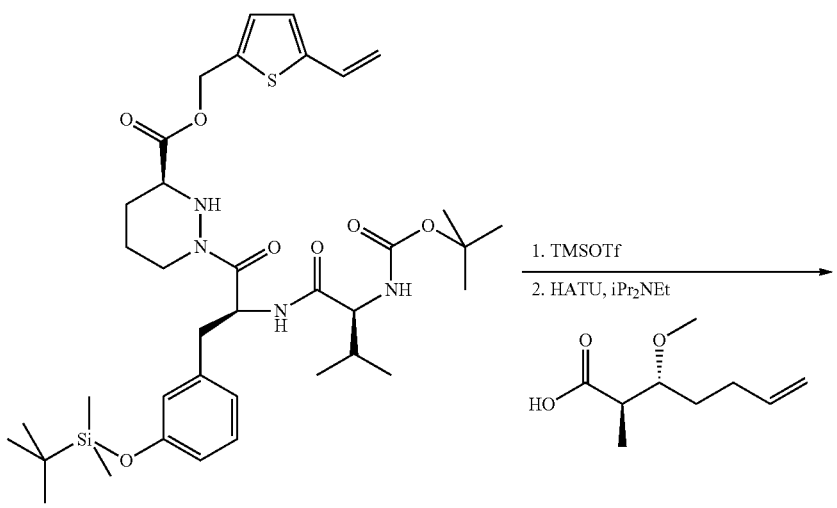

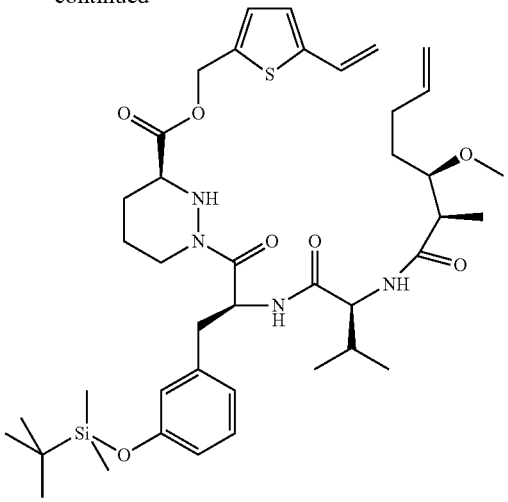

Compound 26d was prepared in the same manner as 10e substituting 10a with 26c (500 mg, 0.69 mmol) to afford the title compound (160 mg, 30% 2 steps) as a clear viscous oil. $^1$H NMR (300 MHz, CDCl$_3$) δ0.19 (2×s, 6H), 0.92 (d, J=6.9 Hz, 3H), 0.96 (d, J=7.4 Hz, 3H), 0.97-1.01 (m, 9H), 1.18 (d, J=6.7 Hz, 3H), 1.39-1.59 (m, 2H), 1.60-1.88 (m, 4H), 2.10-2.24 (m, 3H), 2.41-2.55 (m, 2H), 2.74-3.03 (m, 3H), 3.30-3.39 (m, 1H), 3.39-3.45 (m, 3H), 3.46-3.56 (m, 1H), 4.26-4.36 (m, 1H), 4.48 (dq, J=11.8, 6.2 Hz, 1H), 4.98 (d, J=10.2 Hz, 1H), 5.05 (dd, J=17.2, 1.3 Hz, 1H), 5.19 (d, J=10.9 Hz, 1H), 5.24 (ABq, Δδ$_{AB}$=0.04 J$_{AB}$=12.9 Hz, 2H), 5.58 (d, J=17.4 Hz, 1H), 5.70-5.91 (m, 2H), 6.49-6.74 (m, 4H), 6.76-6.84 (m, 2H), 6.86 (d, J=3.6 Hz, 1H), 6.96 (d, J=3.6 Hz, 1H), 7.01-7.17 (m, 1H). LCMS (m/z) 783.42 [M+H], 806.48 [M+Na], Tr=5.86 min.

Example 26

Compound 26: (E)-(1S,13R,14R,17S,20S)-20-(3-Hydroxy-benzyl)-17-isopropyl-13-methoxy-14-methyl-3-oxa-6-thia-16,19,22,26-tetraaza-tricyclo[20.3.1.1*5,8*]heptacosa-5(27),7,9-triene-2,15,18,21-tetraone

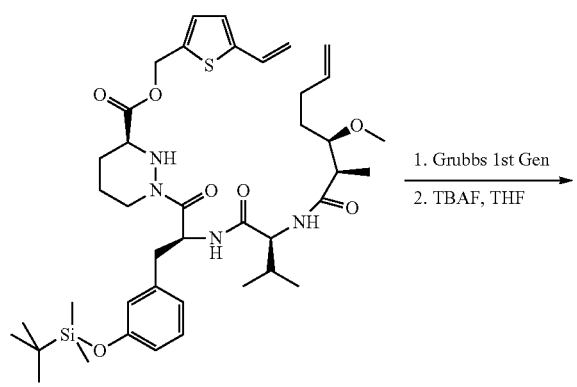

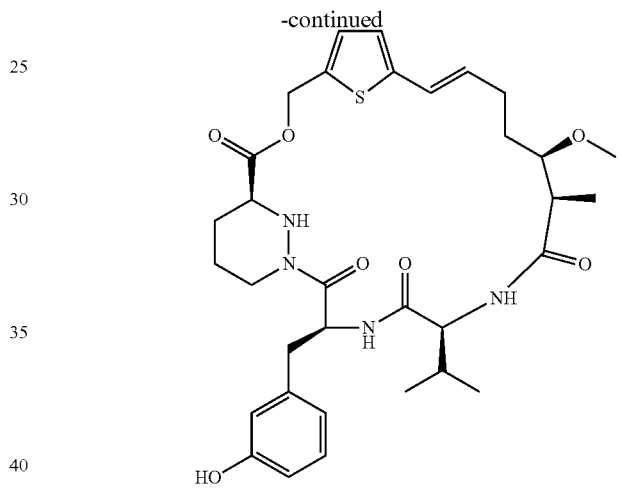

Compound 26 was prepared in the same manner as 10 substituting 10e with 26d (150 mg, 0.19 mmol) to afford the title compound (5 mg, 4% 2 steps) as a viscous light brown oil. $^1$H NMR (300 MHz, CDCl$_3$) δ0.82-0.89 (m, 6H), 0.99 (d, J=6.7 Hz, 3H), 1.62-1.78 (m, 4H), 1.92-2.10 (m, 4H), 2.19-2.38 (m, 2H), 2.58-2.83 (m, 3H), 3.13-3.30 (m, 2H), 3.35-3.45 (m, 1H), 3.51 (s, 3H), 3.72 (d, J=12.3 Hz, 1H), 4.18-4.27 (m, 1H), 4.51-4.62 (m, 1H), 5.40 (ABq, Δδ$_{AB}$=0.15 J$_{AB}$=12.1 Hz, 2H), 5.64-5.85 (m, 2H), 6.34 (d, J=16.3 Hz, 1H), 6.39 (d, J=8.0 Hz, 1H), 6.62 (d, J=3.6 Hz, 1H), 6.63-6.73 (m, 2H), 6.84 (d, J=3.6 Hz, 1H), 6.89 (t, J=7.6 Hz, 1H), 7.32 (d, J=9.4 Hz, 1H). LCMS (m/z) 641.41 [M+H], 663.36 [M+Na], Tr=4.74 min.

Biological Examples

Inhibition of Peptidyl-Prolyl Isomerase (PPIase) Activity

The PPIase assay was based on the procedure reported by Janowski et al. (*Anal. Biochem.* 1997, 252, 299). Assay buffer (1980 µL of a solution containing 35 mM HEPES pH 7.8, 50 µM DTT, and 0.01% NP40) was pre-equilibrated to 10° C. in a quartz cuvette equipped with an overhead stirrer. To this solution was added 10 µL of compound in DMSO (final concentration: 0.5% DMSO), followed by 5 µL of a 2 µM stock solution of cyclophilin A (final concentration: 5 nM). The reaction was initiated with the addition of 5 µL of 40 mM of the tetrapeptide Succ-AAPF-pNA (100 µM final concentration) dissolved in a solution of 0.5 M LiCl in trifluoroethanol. Upon the initiation of the reaction, the absorbance of the peptide substrate was monitored at 330 nm for five minutes using a Beckman Coulter DU800 spectrophotometer. Progress curves were fit with a single-exponential decay model to calculate rates. The $IC_{50}$ values were calculated with a four-parameter logistic fit using GraphPad Prism software.

Cyclophilin A TR-FRET Competitive Binding Assay

Inhibitor potency was measured using a competitive binding assay with a time-resolved fluorescence resonance energy transfer (TR-FRET) readout. To a reaction buffer consisting of 35 mM HEPES pH 7.8, 100 mM NaCl, 0.01% NP-40 (Pierce), 1 mM DTT, and 1% DMSO were added the following: 5 nM of cyclophilin A modified at the N-terminus with an 8× histidine affinity tag (CypA); 150 nM of cyclosporin A modified with a linker attached to a Cy5 fluorophore (CsA-Cy5); 1 nM Eu-labeled anti-(6×His) antibody (Perkin-Elmer); and test compound at one of various concentrations. The total volume of the assay solution was 100 µL. After a two-hour incubation, the TR-FRET was measured using a Perkin Elmer Envision plate reader (excitation at 340 nm, emission measured at 590 nm and 665 nm). The signal was calculated as the ratio of the emission at 665 nm to that at 590 nm. An $IC_{50}$ value was calculated using a four-parameter logistic fit.

When tested, certain compounds of this invention were found to inhibit cyclophilin binding as listed in Table 1 below. The $IC_{50}$'s are presented as ranges wherein A is $\leq 100$ nM, B is 101 to 1000 nM and C is 1001 to 10,000 nM.

TABLE 1

| Compound No. | $IC_{50}$, nM |
|---|---|
| 3 | A |
| 4 | A |
| 5 | A |
| 8 | B |
| 9 | C |
| 10 | A |
| 11 | A |
| 12 | A |
| 13 | A |
| 16 | A |
| 17 | A |
| 18 | A |
| 19 | A |
| 20 | A |
| 21 | B |
| 22 | A |
| 23 | B |
| 24 | A |
| 25 | B |
| 26 | B |

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-Based Flavivirus Immunodetection Assay

BHK21 or A549 cells are trypsinized, counted and diluted to $2\times10^5$ cells/mL in Hams F-12 media (A549 cells) or RPMI-1640 media (BHK21 cells) supplemented with 2% fetal bovine serum (FBS) and 1% penicillin/streptomycin. $2\times10^4$ cells are dispensed in a clear 96-well tissue culture plates per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 microliters of 3,3',5,5'-tetramethylbenzidine (TMB) substrate solution (Sigma) is added to each well for two minutes. The reaction is stopped by addition of 0.5 M sulfuric acid. The plates are read at 450 nm absorbance for viral load quantification. After measurement, the cells are washed three times with PBS followed by incubation with propidium iodide for 5 min. The plate is read in a Tecan Safire™ reader (excitation 537 nm, emission 617 nm) for cell number quantification. Dose response curves are plotted from the mean absorbance versus the log of the concentration of test compounds. The $EC_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of $4\times10^5$ cells/mL in RPMI-1640 media supplemented with 2% FBS and 1% penicillin/streptomycin. For testing against dengue virus, Huh7 cells are trypsinized and diluted to a concentration of $4\times10^5$ cells/mL in DMEM media supplemented with 5% FBS and 1% penicillin/streptomycin. A 50 microliter of cell suspension ($2\times10^4$ cells) is dispensed per well in a 96-well optical bottom PIT polymer-based plates (Nunc). Cells are grown overnight in culture medium at 37° C., 5% $CO_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 hours. At the end of incubation, 100 microliters of CellTiter-Glo™ reagent is added into each well. Contents are mixed for 2 minutes on an orbital shaker to induce cell lysis. The plates are incubated at room temperature for 10 minutes to stabilize luminescent signal. Luminescence reading is recorded using a plate reader. A positive control such as N-nonyl-deoxynojirimycin may be used.

Antiviral Activity in a Mouse Model of Dengue Infection.

Compounds are tested in vivo in a mouse model of dengue virus infection (Schul et al. J. Infectious Dis. 2007; 195:665-74). Six to ten week old AG129 mice (B&K Universal Ltd, HII, UK) are housed in individually ventilated cages. Mice are injected intraperitoneally with 0.4 mL TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water; or 6N HCl (1.5 eq):1N NaOH (pH adjusted to 3.5): 100 mM citrate buffer pH 3.5 (0.9% v/v:2.5% v/v:96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anaesthesia. Plasma is obtained from each blood sample by centrifugation and snap frozen in liquid nitrogen for plague assay analysis. The collected plasma samples are analyzed by plague assay as described in Schul et al. Cytokines are also analysed as described by Schul. NS1 protein levels are analysed using a Platelia™ kit (BioRad Laboratories). An antiviral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV Assay Protocol

The anti-HCV activity of the compounds of this invention was tested in a human hepatoma Huh-7 cell line harboring a HCV replicon. The assay comprised the following steps:

Step 1: Compound Preparation and Serial Dilution.

Serial dilution was performed in 100% DMSO in a 384-well plate. A solution containing a compound at 225-fold concentration of the starting final serial dilution concentration was prepared in 100% DMSO and 15 uL added to the pre-specified wells in column 3 or 13 of a polypropylene 384-well plate. The rest of the 384-well plate was filled with 10 uL 100% DMSO except for columns 23 and 24, where 10 uL of 500 uM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2: Cell Culture Plate Preparation and Compound Addition

To each well of a black polypropylene 384-well plate, 90 μL of cell media containing 1600 suspended Huh-7 HCV replicon cells was added with a Biotek uFlow Workstation. A volume of 0.4 μL of the compound solution was transferred from the serial dilution plate to the cell culture plate on a Biomek FX Workstation. The DMSO concentration in the final assay condition was 0.44%. The plates were incubated for 3 days at 37° C. with 5% CO2 and 85% humidity.

Step 3: Detection of Cytotoxicity and Inhibition of Viral Replication a) Assessment of cytotoxicity: The media in the 384-well cell culture plate was aspirated with a Biotek EL405 plate-washer. A volume of 50 μL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 μL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 μL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4: Calculation

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\%/[(EC_{50}/[I])^b + 1]$$

Where b is Hill's coefficient. See, for reference, Hill, A. V., *The Possible Effects of the Aggregation of the Molecules of Hemoglobin on its Dissociation Curves*, J. Physiol. 40: iv-vii. (1910).

% inhibition values at a specific concentration, for example 2 µM, can also be derived from the formula above.

When tested, certain compounds of this invention were found to inhibit viral replication as listed in Table 2. The $EC_{50}$'s are presented as ranges wherein A is ≦1 µM, B is 1.1 to 10 µm and C is 10.1 to 100 µM.

TABLE 2

| Compound No. | $EC_{50}$, µM |
|---|---|
| 3 | A |
| 4 | B |
| 5 | A |
| 9 | C |
| 11 | A |
| 12 | A |
| 13 | A |
| 16 | A |
| 17 | A |
| 18 | A |
| 19 | A |
| 20 | A |
| 21 | B |
| 22 | A |
| 23 | A |
| 24 | A |
| 25 | B |
| 26 | C |

When tested, certain compounds of this invention were found to inhibit viral replication as listed in Table 3. The $EC_{50}$'s are presented as a % inhibition.

TABLE 3

| Compound No. | % inhibition at 1 µM |
|---|---|
| 3 | 59 |
| 4 | 10 |
| 5 | 67 |
| 8 | 13 |
| 9 | 4 |
| 10 | 59 |
| 11 | 67 |
| 12 | 82 |
| 13 | 93 |
| 16 | 75 |
| 17 | 56 |
| 18 | 54 |
| 19 | 70 |
| 20 | 92 |
| 21 | 18 |
| 22 | 70 |
| 23 | 41 |
| 24 | 65 |
| 25 | 34 |
| 26 | 9 |

Non-limiting but preferred compounds of the invention include 3, 5, 11 and 12.

The specific pharmacological and biochemical responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:
1. A compound of Formula I:

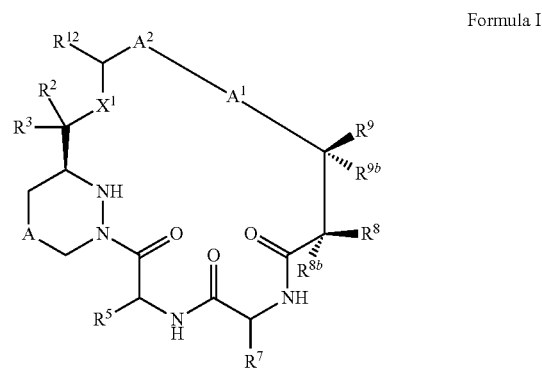

Formula I or a pharmaceutically acceptable salt thereof,
wherein:
$X^1$ is O, S, or $NR^1$;
each $R^1$ is independently H, optionally substituted ($C_1$-$C_4$)alkyl, optionally substituted ($C_2$-$C_4$)alkenyl or optionally substituted ($C_2$-$C_4$)alkynyl;
each $R^2$ or $R^3$ is independently H, optionally substituted ($C_1$-$C_4$)alkyl, optionally substituted ($C_2$-$C_4$)alkenyl, optionally substituted ($C_2$-$C_4$)alkynyl, halogen, cyano, $C(O)R^1$, $C(O)OR^1$ or $CON(R^1)_2$; or $R^2$ and $R^3$ when taken together with the carbon to which they are both attached form —C(═O)—, —C(═S)— or —C(═$NR^1$)—;
A is O, $S(O)_n$, $NR^4$ or optionally substituted ($C_1$-$C_2$) alkylene;
each n is independently 0, 1 or 2;
each $R^4$ is independently H, optionally substituted ($C_1$-$C_4$)alkyl, optionally substituted ($C_2$-$C_4$)alkenyl, optionally substituted ($C_2$-$C_4$)alkynyl, cyano, $C(O)R^7$, $C(O)OR^7$, $CON(R^7)_2$, $S(O)R^{16}$, $S(O)_2R^{16}$, $S(O)_2OR^7$ or $S(O)_2N(R^7)_2$;
$R^5$ is optionally substituted aryl($C_0$-$C_4$)alkyl, optionally substituted heterocyclyl($C_0$-$C_4$)alkyl, optionally substituted cycloalkyl($C_0$-$C_4$)alkyl or optionally substituted ($C_1$-$C_8$)alkyl wherein each optionally substituted aryl($C_0$-$C_4$)alkyl, optionally substituted cycloalkyl($C_0$-$C_4$)alkyl or optionally substituted ($C_1$-$C_8$)alkyl is substituted with one or more $R^6$;
each $R^6$ is independently halo, $CF_3$, $OR^4$, $CH_2OR^4$, $SR^4$, $S(O)R^{16}$, $S(O)_2R^{16}$, $N(R^1)_2$, $NHCOR^1$, $NHC(O)OR^1$, $NHC(O)N(R^1)_2$, $NHC(NR^1)R^1$, $NHC(NR^1)N(R^1)_2$, $C(O)R^1$, $C(O)N(R^1)_2$, $CO_2R^1$, $S(O)_2OR^1$, $S(O)_2 N(R^1)_2$, $NHS(O)_2OR^1$, $NHS(O)_2R^{16}$, $NHS(O)_2 N(R^1)_2$, $P(O)(OR^1)_2$, $P(O)(OR^1)(N(R^1)_2)$, $P(O)(R^7)(OR^1)$, $OP(O)(OR^1)_2$, $OP(O)(OR^1)(N(R^1)_2)$, $NHP(O)(OR^1)_2$ or $NHP(O)(OR^1)(N(R^1)_2)$;
each $R^7$ is H, optionally substituted ($C_1$-$C_8$)alkyl, optionally substituted ($C_2$-$C_8$)alkenyl, optionally substituted ($C_2$-$C_8$)alkynyl, optionally substituted aryl, optionally substituted heterocyclyl, optionally substituted cycloalkyl, optionally substituted aryl($C_1$-$C_4$)alkyl, optionally substituted cycloalkyl($C_1$-$C_4$) alkyl or optionally substituted heterocyclyl($C_1$-$C_4$) alkyl;

each $R^{16}$ is optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl or optionally substituted heterocyclyl$(C_1-C_4)$alkyl;

each $R^8$, $R^{8b}$, $R^9$ or $R^{9b}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$ or $N(R^4)_2$;

provided that each $R^8$, $R^{8b}$, $R^9$ and $R^{9b}$ is not H; and
provided that when $R^9$ is OH and each $R^{8b}$ and $R^{9b}$ are H, then $R^8$ is not

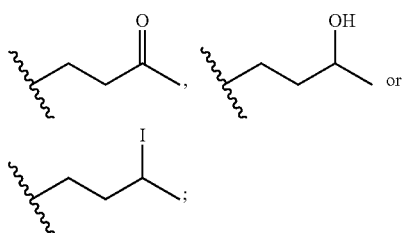

$A^1$ is optionally substituted $(C_2-C_5)$alkylene, optionally substituted $(C_2-C_5)$alkenylene or optionally substituted $(C_2-C_5)$alkynylene, wherein a sp$^3$ carbon atom of said optionally substituted $(C_2-C_5)$alkylene, optionally substituted $(C_2-C_5)$alkenylene, or optionally substituted $(C_2-C_5)$alkynylene, is optionally replaced by O, $S(O)_n$ or $NR^4$, and $A^2$ is optionally substituted arylene, optionally substituted heteroarylene, optionally substituted heterocyclene or optionally substituted cycloalkylene, or $A^1$ is optionally substituted aryl$(C_0-C_2)$alkylene, optionally substituted cycloalkyl$(C_0-C_2)$alkylene or optionally substituted heterocyclyl$(C_0-C_2)$alkylene, wherein a sp$^3$ carbon atom of said optionally substituted aryl$(C_0-C_2)$alkylene, optionally substituted cycloalkyl$(C_0-C_2)$alkylene or optionally substituted heterocyclyl$(C_0-C_2)$alkylene is optionally replaced by O, $S(O)_n$ or $NR^4$, and $A^2$ is optionally substituted $(C_1-C_3)$alkylene, optionally substituted $(C_2-C_3)$alkenylene or optionally substituted $(C_2-C_3)$alkynylene;

$R^{12}$ is H, optionally substituted $(C_1-C_4)$alkyl, optionally substituted $(C_2-C_4)$alkenyl or optionally substituted $(C_2-C_4)$alkynyl;

each $R^a$ is independently H, $(C_1-C_8)$alkyl, $(C_2-C_8)$alkenyl, $(C_2-C_8)$alkynyl, aryl, heterocyclyl, aryl$(C_1-C_8)$alkyl, cycloalkyl or cycloalkyl$(C_1-C_8)$alkyl and wherein when $R^1$, $R^2$, $R^3$, $R^4$, $R^7$, $R^8$, $R^9$, $R^{8b}$, $R^{9b}$, $R^{10}$, $R^{11}$, $R^{12}$, $R^{13}$, $R^{14}$, $R^{15}$, $R^{16}$, A, $A^1$ or $A^2$ is substituted, the substitutent is, independently, one or more substituents selected from the group consisting of halo, CN, $CF_3$, $N_3$, $N(R^a)_2$, $SR^a$, $OR^a$, $R^a$, $NHCOR^a$, NHC(O)$OR^a$, NHC(O)N($R^a)_2$, NHC(NR$^a$)R$^a$, NHC(NR$^a$) N($R^a)_2$, C(O)$R^a$, C(O)N($R^a)_2$, CO$_2R^a$, S(O)$_2OR^a$, S(O)$_2$N($R^a)_2$, NHS(O)$_2OR^a$, NHS(O)$_2$N($R^a)_2$, OP(O)(O$R^a)_2$, OP(O)(O$R^a$)(N($R^a)_2$), NHP(O)(O$R^a)_2$ and NHP(O)(O$R^a$)(N($R^a)_2$).

2. The compound of claim 1 represented by Formula II

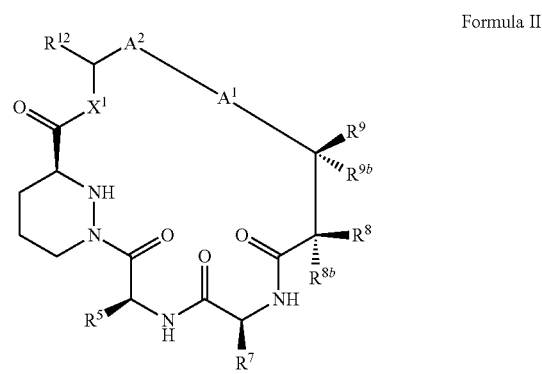

or a pharmaceutically acceptable salt thereof.

3. The compound of claim 2 wherein each $R^{8b}$ and $R^{9b}$ is H.

4. The compound of claim 3 wherein $R^8$ is methyl.

5. The compound of claim 2 wherein $A^1$ is optionally substituted $(C_4)$alkylene or optionally substituted $(C_4)$alkenylene.

6. The compound of claim 5 wherein $A^1$ is

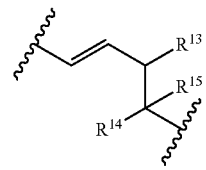

wherein each $R^{13}$, $R^{14}$ or $R^{15}$ is independently H, optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl, optionally substituted heterocyclyl$(C_1-C_4)$alkyl, $OR^4$, $SR^4$, $S(O)R^{16}$, $S(O)_2R^{16}$, or $N(R^4)_2$.

7. The compound of claim 6 wherein $R^{15}$ is H.

8. The compound of claim 2 wherein $A^2$ is optionally substituted arylene.

9. The compound of claim 8 wherein $A^2$ is

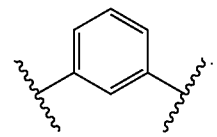 [SMILES: *c1cccc(*)c1]

10. The compound of claim 2 wherein $A^2$ is

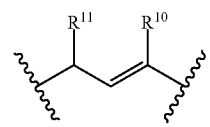

wherein:
each $R^{10}$ or $R^{11}$, independently, is H, optionally substituted $(C_1-C_4)$alkyl, optionally substituted $(C_2-C_4)$alkenyl, optionally substituted $(C_2-C_4)$alkynyl, halogen, cyano, $C(O)R^1$, $C(O)OR^1$ or $CON(R^1)_2$, or $R^{11}$ and $R^{10}$ taken together with the atoms to which they are attached form an optionally substituted $(C_5-C_7)$cycloalkenylene ring wherein a sp$^3$ carbon atom of said optionally substituted $(C_5-C_7)$cycloalkenylene ring is optionally replaced by O, $S(O)_n$ or $NR^4$.

11. The compound of claim 10 wherein each $R^{10}$ or $R^{11}$ is independently H, optionally substituted $(C_1-C_4)$alkyl or halogen.

12. The compound of claim 11 wherein each $R^{10}$ and $R^{11}$ is H.

13. The compound of claim 2 wherein $R^7$ is optionally substituted $(C_1-C_8)$alkyl, optionally substituted aryl, or optionally substituted aryl$(C_1-C_4)$alkyl.

14. The compound of claim 13 wherein $R^7$ is optionally substituted $(C_1-C_8)$alkyl.

15. The compound of claim 2 wherein $R^5$ is optionally substituted aryl$(C_0-C_4)$alkyl.

16. The compound of claim 15 wherein $R^5$ is optionally substituted benzyl.

17. The compound of claim 16 wherein $R^5$ is optionally substituted

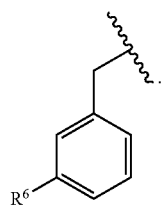

18. The compound of claim 17 wherein $R^6$ is $OR^4$, $CH_2OR^4$, $N(R^1)_2$, $NHCOR^1$, $NHC(O)OR^1$, $NHC(O)N(R^1)_2$, $NHC(NR^1)R^1$, $NHC(NR^1)N(R^1)_2$, $C(O)N(R^1)_2$, $S(O)_2N(R^1)_2$, $NHS(O)_2OR^1$, $NHS(O)_2R^{16}$ or $NHS(O)_2N(R^1)_2$.

19. The compound of claim 18 wherein $R^6$ is OH.

20. The compound of claim 2 wherein $R^7$ is isopropyl and $R^5$ is

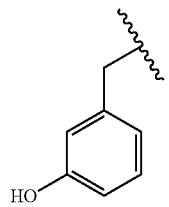

21. The compound of claim 20 wherein $R^9$ is $O(C_1-C_4)$alkyl.

22. The compound of claim 21 wherein $R^8$ is $(C_1-C_4)$alkyl.

23. The compound of claim 2 or a pharmaceutically acceptable salt thereof,
wherein:
$X^1$ is O or $NR^1$;
each $R^1$ is independently H, optionally substituted $(C_1-C_4)$alkyl, optionally substituted $(C_2-C_4)$alkenyl or optionally substituted $(C_2-C_4)$alkynyl;
each $R^4$ is independently H, optionally substituted $(C_1-C_4)$alkyl, optionally substituted $(C_2-C_4)$alkenyl, optionally substituted $(C_2-C_4)$alkynyl, cyano, $C(O)R^7$, $C(O)OR^7$, $CON(R^7)_2$, $S(O)R^{16}$, $S(O)_2R^{16}$, $S(O)_2OR^7$ or $S(O)_2N(R^7)_2$;

$R^5$ is aryl$(C_0-C_4)$alkyl, optionally substituted with one or more $R^6$;

each $R^6$ is independently halo, $CF_3$, $OR^4$, $CH_2OR^4$, $SR^4$, $S(O)R^{16}$, $S(O)_2R^{16}$, $N(R^1)_2$, $NHCOR^1$, $NHC(O)OR^1$, $NHC(O)N(R^1)_2$, $NHC(NR^1)R^1$, $NHC(NR^1)N(R^1)_2$, $C(O)R^1$, $C(O)N(R^1)_2$, $CO_2R^1$, $S(O)_2OR^1$, $S(O)_2N(R^1)_2$, $NHS(O)_2OR^1$, $NHS(O)_2R^{16}$, $NHS(O)_2N(R^1)_2$, $P(O)(OR^1)_2$, $P(O)(OR^1)(N(R^1)_2)$, $P(O)(R^7)(OR^1)$, $OP(O)(OR^1)_2$, $OP(O)(OR^1)(N(R^1)_2)$, $NHP(O)(OR^1)_2$ or $NHP(O)(OR^1)(N(R^1)_2)$;

each $R^{16}$ is optionally substituted $(C_1-C_8)$alkyl, optionally substituted $(C_2-C_8)$alkenyl, optionally substituted $(C_2-C_8)$alkynyl, optionally substituted aryl, optionally substituted heterocyclyl, optionally substituted cycloalkyl, optionally substituted aryl$(C_1-C_4)$alkyl, optionally substituted cycloalkyl$(C_1-C_4)$alkyl or optionally substituted heterocyclyl$(C_1-C_4)$alkyl;

each $R^7$ is optionally substituted $(C_1-C_8)$alkyl or optionally substituted aryl$(C_1-C_4)$alkyl;

each $R^8$, $R^{8b}$, $R^9$ or $R^{9b}$ is independently H, optionally substituted $(C_1-C_8)$alkyl, or $OR^4$;

$A^1$ is optionally substituted $(C_2-C_5)$alkylene or optionally substituted $(C_2-C_5)$alkenylene, and $A^2$ is optionally substituted arylene or optionally substituted heteroarylene, or $A^1$ is aryl$(C_0-C_2)$alkylene and $A^2$ is optionally substituted $(C_1-C_3)$alkylene or optionally substituted $(C_2-C_3)$alkenylene;

$R^{12}$ is H or optionally substituted $(C_1-C_4)$alkyl;

each $R^a$ is independently H, $(C_1-C_8)$alkyl, $(C_2-C_8)$alkenyl, $(C_2-C_8)$alkynyl, aryl, heterocyclyl, aryl$(C_1-C_8)$alkyl, cycloalkyl or cycloalkyl$(C_1-C_8)$alkyl; and wherein when $R^1$, $R^4$, $R^7$, $R^8$, $R^9$, $R^{8b}$, $R^{9b}$, $R^{12}$, $R^{16}$, $A^1$ or $A^2$ is substituted, the substituent is, independently, one or more substituents selected from the group consisting of halo, CN, $CF_3$, $N_3$, $N(R^a)_2$, $SR^a$, $OR^a$, $R^a$, $NHCOR^a$, $NHC(O)OR^a$, $NHC(O)N(R^a)_2$, $NHC(NR^a)R^a$, $NHC(NR^a)N(R^a)_2$, $C(O)R^a$, $C(O)N(R^a)_2$, $CO_2R^a$, $S(O)_2OR^a$, $S(O)_2N(R^a)_2$, $NHS(O)_2OR^a$, $NHS(O)_2N(R^a)_2$, $OP(O)(OR^a)_2$, $OP(O)(OR^a)(N(R^a)_2)$, $NHP(O)(OR^a)_2$ and $NHP(O)(OR^a)(N(R^a)_2)$.

24. The compound of claim 2 or a pharmaceutically acceptable salt thereof,
wherein:
$X^1$ is O or NH;
$R^5$ is

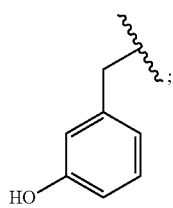 [SMILES: *Cc1cccc(O)c1]

$R^7$ is $(C_1-C_4)$alkyl or

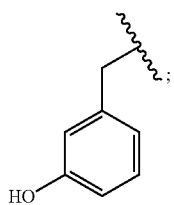

each $R^8$, $R^{8b}$, $R^9$ or $R^{9b}$ is independently H, $(C_1-C_4)$ alkyl, OH or $O(C_1-C_4)$alkyl;

$A^1$ is $(C_2-C_5)$alkylene or $(C_2-C_5)$alkenylene, wherein the alkylene or alkenylene groups are each optionally substituted with OH or $O(C_1-C_4)$alkyl and $A^2$ is phenylene, pyridinylene or thienylene; or $A^1$ is phenylene and $A^2$ is $(C_1-C_3)$alkylene or $(C_2-C_3)$ alkenylene; and $R^{12}$ is H or $(C_1-C_4)$alkyl.

25. A compound selected from the group consisting of

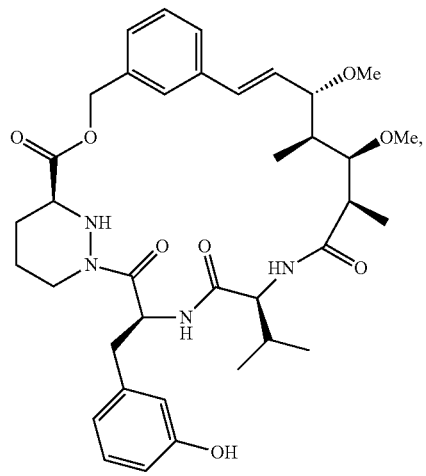 [SMILES: CO[C@@H]1[C@@H](C)[C@@H](OC)/C=C/c2cccc(c2)COC(=O)[C@@H]2CCCN(N2)C(=O)[C@H](Cc2cccc(O)c2)NC(=O)[C@H](C(C)C)NC(=O)[C@@H]1C]

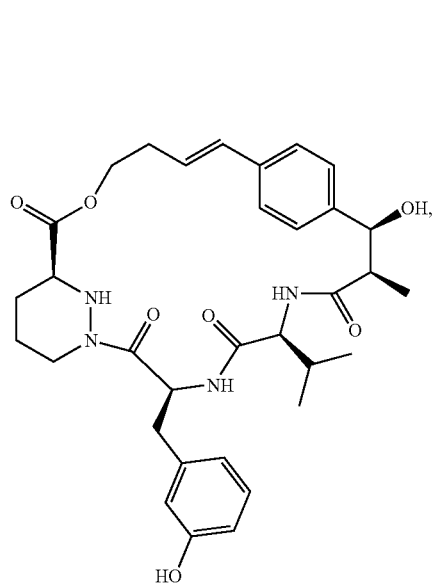

-continued

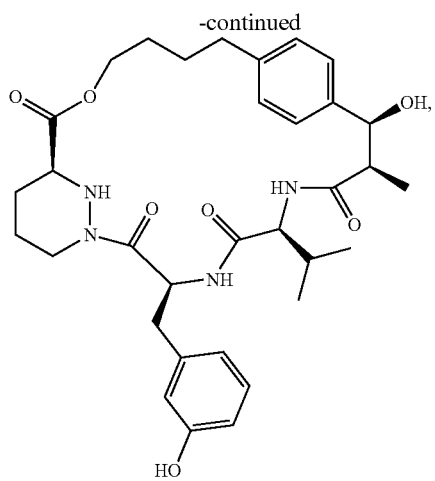

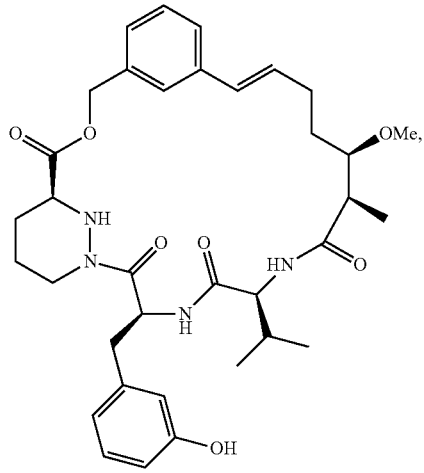

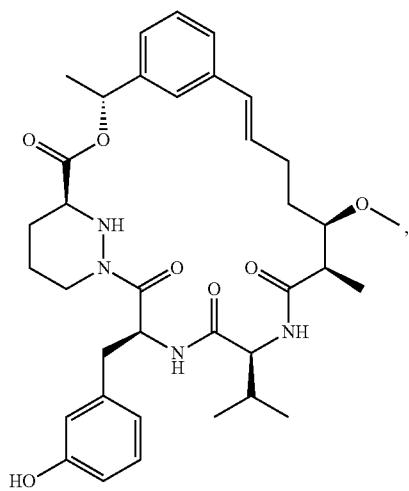 [SMILES: CO[C@@H]1CC/C=C/c2cccc(c2)[C@@H](C)OC(=O)[C@@H]2CCCN(N2)C(=O)[C@H](Cc2cccc(O)c2)NC(=O)[C@H](C(C)C)NC(=O)[C@@H]1C]

157
-continued
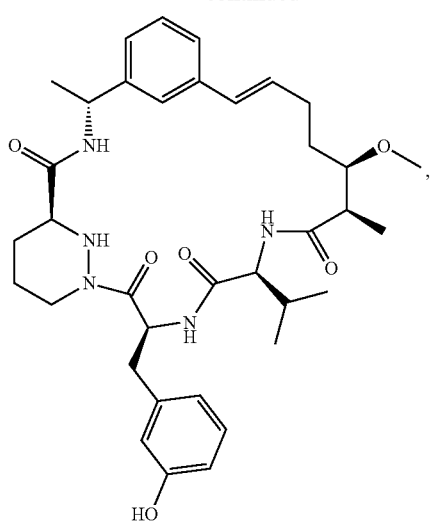
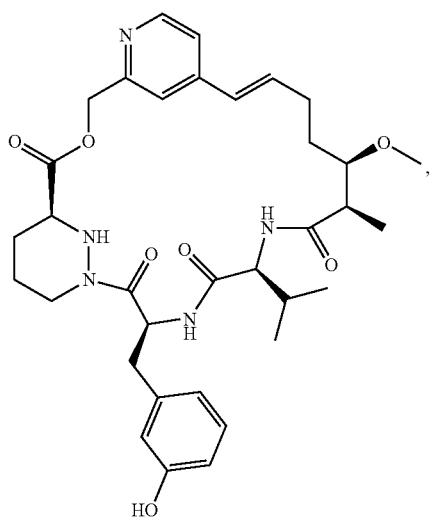
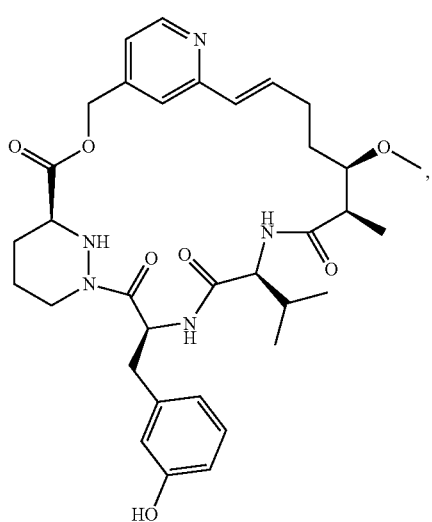
158
-continued
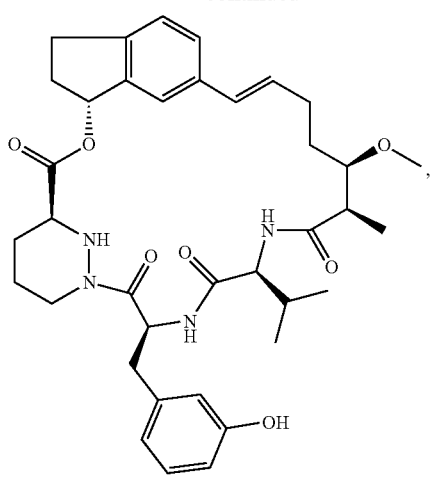
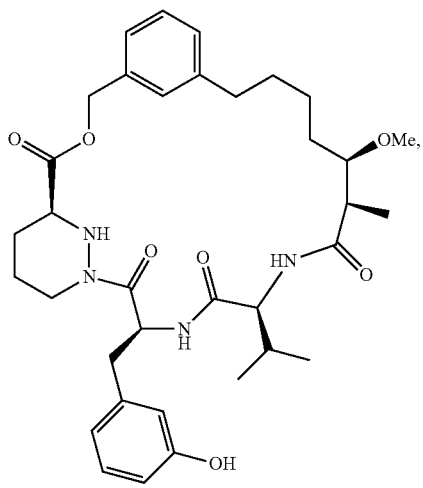
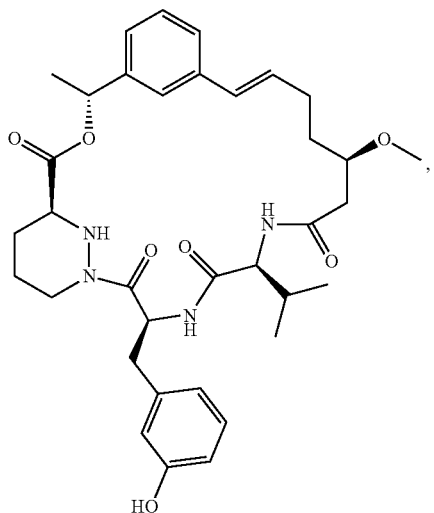

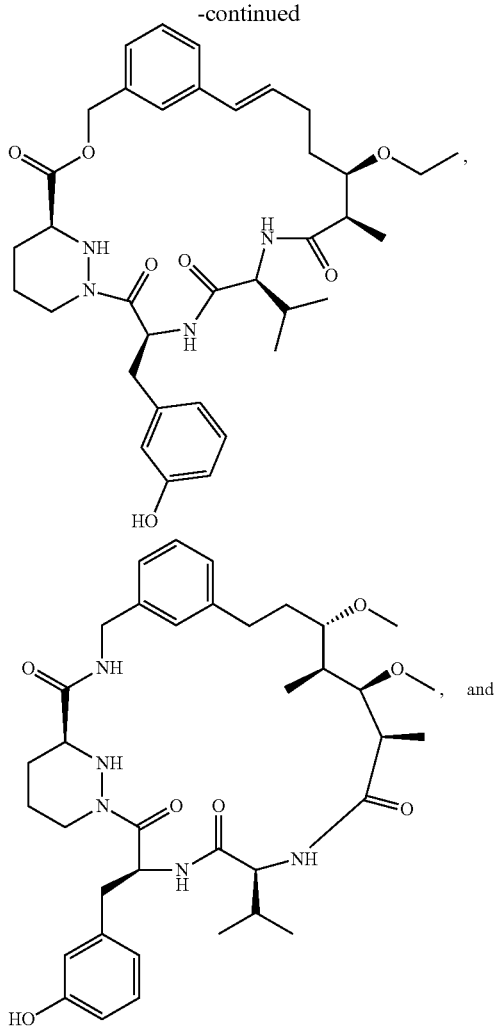

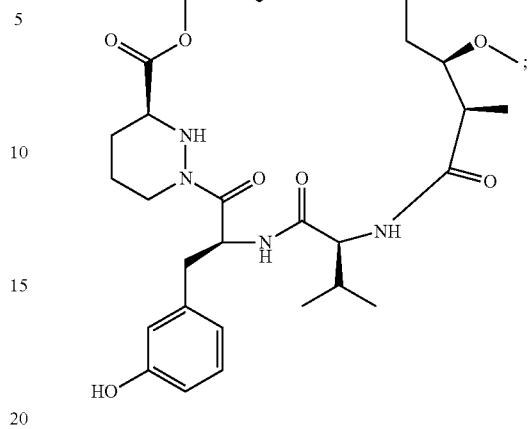

or a pharmaceutically acceptable salt thereof.

26. A pharmaceutical composition comprising a therapeutically effective amount of a compound of claims 1 or 25 and a pharmaceutically acceptable carrier or excipient.

27. The pharmaceutical composition of claim 26, further comprising at least one additional therapeutic agent selected from the group consisting of interferons, ribavirin or its analogs, HCV NS3 protease inhibitors, HCV NS5a inhibitors, nucleoside or nucleotide inhibitors of HCV NS5B polymerase, non-nucleoside inhibitors of HCV NS5B polymerase, and TLR-7 agonists; or mixtures thereof.

* * * * *

UNITED STATES PATENT AND TRADEMARK OFFICE
CERTIFICATE OF CORRECTION

PATENT NO. : 8,513,184 B2
APPLICATION NO. : 13/315069
DATED : August 20, 2013
INVENTOR(S) : Todd Appleby et al.

Page 1 of 1

It is certified that error appears in the above-identified patent and that said Letters Patent is hereby corrected as shown below:

IN THE CLAIMS

In column 150, line 51, claim 1, delete "is substituted" and replace with --is optionally substituted--.

In column 151, line 18, claim 1, delete "and each $R^{8b}$ and $R^{9b}$" and replace with --and both $R^{8b}$ and $R^{9b}$--.

In column 151, lines 58 to 59, claim 1, delete "$R^8$, $R^9$, $R^{8b}$, $R^{9b}$, $R^{10}$, $R^{11}$, $R^{12}$, $R^{13}$, $R^{14}$, $R^{15}$, $R^{16}$" and replace with --$R^8$, $R^9$, $R^{8b}$, $R^{9b}$, $R^{12}$, $R^{16}$--.

In column 152, line 45, claim 6, delete "$N(R^4)_2$." and replace with --$N(R^4)_2$, wherein when $R^{13}$, $R^{14}$ or $R^{15}$ is substituted, the substitutent is, independently, one or more substituents selected from the group consisting of halo, CN, $CF_3$, $N_3$, $N(R^a)_2$, $SR^a$, $OR^a$, $R^a$, $NHCOR^a$, $NHC(O)OR^a$, $NHC(O)N(R^a)_2$, $NHC(NR^a)R^a$, $NHC(NR^a)N(R^a)_2$, $C(O)R^a$, $C(O)N(R^a)_2$, $CO_2R^a$, $S(O)_2OR^a$, $S(O)_2N(R^a)_2$, $NHS(O)_2OR^a$, $NHS(O)_2N(R^a)_2$, $OP(O)(OR^a)_2$, $OP(O)(OR^a)(N(R^a)_2)$, $NHP(O)(OR^a)_2$ and $NHP(O)(OR^a)(N(R^a)_2)$.--.

In column 153, line 10, claim 10, delete "$NR^4$." and replace with --$NR^4$, wherein when $R^{10}$ or $R^{11}$ is substituted, the substitutent is, independently, one or more substituents selected from the group consisting of halo, CN, $CF_3$, $N_3$, $N(R^a)_2$, $SR^a$, $OR^a$, $R^a$, $NHCOR^a$, $NHC(O)OR^a$, $NHC(O)N(R^a)_2$, $NHC(NR^a)R^a$, $NHC(NR^a)N(R^a)_2$, $C(O)R^a$, $C(O)N(R^a)_2$, $CO_2R^a$, $S(O)_2OR^a$, $S(O)_2N(R^a)_2$, $NHS(O)_2OR^a$, $NHS(O)_2N(R^a)_2$, $OP(O)(OR^a)_2$, $OP(O)(OR^a)(N(R^a)_2)$, $NHP(O)(OR^a)_2$ and $NHP(O)(OR^a)(N(R^a)_2)$.--.

Signed and Sealed this
Fourth Day of November, 2014

Michelle K. Lee
*Deputy Director of the United States Patent and Trademark Office*